United States Patent
Cadilla et al.

(10) Patent No.: US 7,319,104 B2
(45) Date of Patent: Jan. 15, 2008

(54) HPPARS ACTIVATORS

(75) Inventors: Rodolfo Cadilla, Durham, NC (US); Brad Richard Henke, Durham, NC (US); Millard H. Lambert, III, Durham, NC (US); Guangcheng Kevin Liu, San Diego, CA (US); Jennifer Susan Smith, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 352 days.

(21) Appl. No.: 10/505,333

(22) PCT Filed: Feb. 25, 2003

(86) PCT No.: PCT/US03/05953

§ 371 (c)(1), (2), (4) Date: Aug. 23, 2004

(87) PCT Pub. No.: WO03/074495

PCT Pub. Date: Sep. 12, 2003

(65) Prior Publication Data

US 2005/0137212 A1 Jun. 23, 2005

Related U.S. Application Data

(60) Provisional application No. 60/360,975, filed on Mar. 1, 2002.

(51) Int. Cl.
- A61K 31/505 (2006.01)
- A61K 31/42 (2006.01)
- A61K 31/445 (2006.01)
- A61K 31/425 (2006.01)
- C07D 239/02 (2006.01)

(52) U.S. Cl. ............... 514/275; 514/324; 514/374; 514/331; 514/365; 544/323; 548/187; 548/235

(58) Field of Classification Search .......... 546/187; 514/331, 365, 374, 275, 324; 548/187, 235; 544/324, 323
See application file for complete search history.

(56) References Cited

U.S. PATENT DOCUMENTS 4,214,094 A * 7/1980 Kamiya et al. ............. 560/42
5,935,985 A * 8/1999 Hamanaka et al. ......... 514/399

FOREIGN PATENT DOCUMENTS

| WO | WO97/25042 | 7/1997 |
|---|---|---|
| WO | WO 01/00603 | 1/2001 |
| WO | WO 01/40207 | 6/2001 |
| WO | WO 02/46176 | 6/2002 |

OTHER PUBLICATIONS

Hcaplus 134:125379.*
Thiemermann, C., "Ligands of the peroxisome proliferator-activated receptor- y and heart failure", British Journal of Pharmacology (2004) 141 (1), 1-3.*
Schriffin, Ernesto, "Peroxisome proliferator-activated receptors and cardiovascular remodeling", American Journal of Physiology—Heart and Circulatory Physiology 288:1037-1043, 2005.*
Brown, Peter J., et al. "Generation of secondary alkyl amines on solid support by borane reduction. Application to the parallel synthesis of PPAR ligands." Synthesis (1997), (7), pp. 778-782.
Wilson, T.M., et al. "The PPARS: From Orphan Receptors to Drug Discovery." Journal of Medicinal Chemistry, American Chemical Society. Washington, US, vol. 43, No. 4., pp. 530, 540.
Lewis, D.F.V., et al. "Molecular modeling of the rat peroxisome proliferators-activated receptor -alpha (rPPARalpha) by homology with the human retinoic acid X receptor alpha (hRXRalpha) and investigation of ligand binding interactions I: QSARs." Toxicology In Vitro, Elsevier Science, GB, vol. 12, No. 6, Dec. 1998 pp. 619-632.
Brown, P.J., et al. "Identification of Peroxisome Proliferator-Activated Receptor Ligands from a Biased Chemical Library." Chemistry and Biology, Currently Biology, London, GB., vol. 4, No. 12, Dec. 1997, p. 910.
Brown, P.J. et al. "Identification of a Subtype Selective Human PPARalpha Agonist Through Parallel-Array Synthesis." Bioorganic & Medicinal Chemistry Letters, Oxford, GB, vol. 11, Mar. 12, 2001, pp. 1225-1227.
Liu, Kevin G., et al. "Identification of a Series of PPAR.gamma./.delta. dual agonists via solid-Phase parallel synthesis." Bioorganic & Medicinal Chemistry Letters, 2001, 11(22), pp. 2959-2962.

* cited by examiner

Primary Examiner—Janet L. Andres
Assistant Examiner—Binta Robinson
(74) Attorney, Agent, or Firm—Jennifer L. Fox

(57) ABSTRACT

Compounds of formula (1) or a pharmaceutically acceptable salt, solvate, acid isostere, or hydrolyzable ester thereof, are disclosed. Methods of making and using the compounds are also disclosed. In particular methods for treating diseases or conditions associated with one or more of human PPAR alpha, gamma, or delta ("hPPARs") comprising administration of a therapeutically effective amount of a compound of formula (1), are disclosed

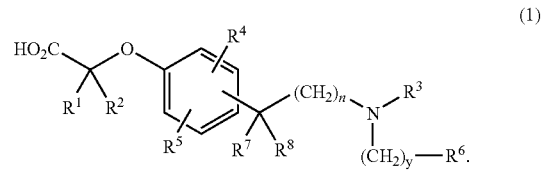

(1)

18 Claims, No Drawings

HPPARS ACTIVATORS

This application is filed pursuant to 35 U.S.C. § 371 as a United States National Phase Application of International Application No. PCT/US03/05953 filed Feb. 25, 2003, which claims priority from 60/360,975 filed Mar. 1, 2002.

The present invention relates to certain novel compounds. In particular, the present invention relates to compounds that activate human peroxisome proliferator activated receptors ("hPPARs"). The present invention also relates to method for preparing the compounds, their use in medicine, pharmaceutical compositions containing them and methods for the prevention or treatment of PPAR mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e. currently there are no drugs on the market that are useful for raising HDL-c). (Bisgaier, C. L.; Pape, M. E. *Curr. Pharm. Des.* 1998, 4, 53–70).

Syndrome X (including metabolic syndrome) is loosely defined as a collection of abnormalities including hyperinsulemia, obesity, elevated levels of triglycerides, uric acid, fibrinogen, small dense LDL particles, and plasminogen activator inhibitor 1 (PAI-1), and decreased levels of HDL-c.

NIDDM is described as insulin resistance which in turn causes anomalous glucose output and a decrease in glucose uptake by skeletal muscle. These factors eventually lead to impaired glucose tolerance (IGT) and hyperinsulinemia.

Peroxisome Proliferator Activated Receptors (PPARs) are orphan receptors belonging to the steroid/retinoid receptor superfamily of ligand-activated transcription factors. See, for example Willson T. M. and Wahli, W., *Curr. Opin. Chem. Biol.* (1997) Vol 1 pp 235–241 and Willson T. M. et. al., *J. Med. Chem.* (2000) Vol 43 p 527–549. The binding of agonist ligands to the receptor results in changes in the expression level of mRNAs encoded by PPAR target genes.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, *Trends Endoodn. Met.* 291–296, 4 (1993)).

It has been reported that thiazolidinediones are potent and selective activators of PPAR-gamma and bind directly to the PPAR-gamma receptor (J. M. Lehmann et. al., *J. Biol. Chem.* 12953–12956, 270 (1995)), providing evidence that PPAR-gamma is a possible target for the therapeutic actions of the thiazolidinediones.

Activators of the nuclear receptor PPARγ, for example troglitazone, have been shown in the clinic to enhance insulin-action, reduce serum glucose and have small but significant effects on reducing serum triglyceride levels in patients with Type 2 diabetes. See, for example, D. E. Kelly et al., *Curr. Opin. Endocrinol. Diabetes*, 90–96, 5 (2), (1998); M. D. Johnson et al., *Ann. Pharmacother.*, 337–348, 32 (3), (1997); and M. Leutenegger et al., *Curr. Ther. Res.*, 403–416, 58 (7), (1997).

The mechanism for this triglyceride lowering effect appears to be predominantly increased clearance of very low density lipoproteins (VLDL) through induction of lipoprotein lipase (LPL) gene expression. See, for example, B. Staels et al., *Arterioscler. Thromb., Vasc. Biol.*, 1756–1764, 17 (9), (1997).

Fibrates are a class of drugs which may lower serum triglycerides 20–50%, lower LDLc 10–15%, shift the LDL particle size from the more atherogenic small dense to normal dense LDL, and increase HDLc 10–15%. Experimental evidence indicates that the effects of fibrates on serum lipids are mediated through activation of PPARα. See, for example, B. Staels et al., *Curr. Pharm. Des.*, 1–14, 3 (1), (1997). Activation of PPARα results in transcription of enzymes that increase fatty acid catabolism and decrease de-novo fatty acid synthesis in the liver resulting in decreased triglyceride synthesis and VLDL production/secretion. In addition, PPARα activation decreases production of apoC-III. Reduction in apoC-III, an inhibitor of LPL activity, increases clearance of VLDL. See, for example, J. Auwerx et al., *Atherosclerosis*, (Shannon, Irel.), S29–S37, 124 (Suppl), (1996).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO 97/28149 (Leibowitz et al.) and WO99/04815 (Shimokawa et al.). In a recent report (Berger et al., *J. Biol. Chem.* 1999), vol. 274, pp. 6718–6725) it was stated that PPARδ activation does not appear to modulate glucose or triglyceride levels.

In one aspect, the present invention provides compounds of formula (1) and pharmaceutically acceptable salts, solvates, acid isosteres, and hydrolyzable esters thereof;

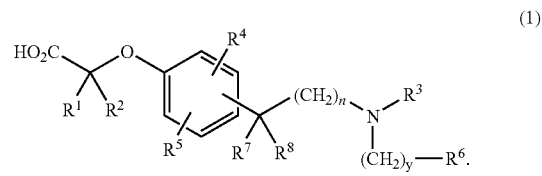

wherein $R^1$ and $R^2$ are independently hydrogen, F, $CF_3$, $C_{1-3}$alkyl, or $R^1$ and $R^2$ may together with the carbon atom to which they are attached form a 3 to 6-membered cycloakyl ring;

$R^4$ and $R^5$ are independently hydrogen, $C_{1-6}$alkyl, perfluoro$C_{1-6}$alkyl, —$OC_{1-3}$alkyl, perfluoro$OC_{1-6}$alkyl, halogen, or cyano;

$R^7$ and $R^8$ are independently H, F, $CF_3$, or $C_{1-3}$alkyl, and the carbon to which $R^7$ and $R^8$ are bonded is attached to the benzene ring either meta or para to the depicted oxygen;

n is 1 or 2;

y is 1 or 2;

$R^6$ is phenyl or a 5- or 6-membered heteroaryl group, where the phenyl or heteroaryl group is optionally substituted with 1, 2, or 3 moieties selected from the group consisting of $C_{1-6}$alkyl, halogen, perfluoro$C_{1-3}$alkyl, O$C_{1-3}$alkyl, perfluoroO$C_{1-3}$alkyl, S$C_{1-3}$alkyl, SO$_2C_{1-3}$alkyl, SO$_2C_{1-3}$perfluoroalkyl, SO$C_{1-3}$perfluoroalkyl, SO$C_{1-3}$alkyl, perfluoroS$C_{1-3}$alkyl, CN, phenyl (optionally substituted with one or two groups selected from halogen, $C_{1-3}$alkyl, O$C_{1-3}$alkyl, acetyl, CN, and perfluoro$C_{1-3}$alkyl), and 5- or 6-membered heteroaryl (optionally substituted with one group selected from $C_{1-3}$alkyl, $C_{3-6}$cycloalkyl, perfluoro$C_{1-3}$alkyl, NH$C_{1-3}$alkyl, and N($C_{1-3}$alkyl)$_2$); and $R^3$ is a 5- or 6-membered heteroaryl group optionally substituted by 1 or 2 moieties selected from the group consisting of halogen, $C_{1-6}$alkyl, perfluoro$C_{1-6}$alkyl, O$C_{1-3}$alkyl, phenyl (optionally substituted with one or two moieties selected from $C_{1-3}$alkyl, halogen, O$C_{1-3}$alkyl, acetyl, CN, Operfluoro$C_{1-3}$alkyl, and perfluoro$C_{1-3}$alkyl), 5- or 6-membered heteroaryl (optionally substituted with one or two moieties selected from $C_{1-3}$alkyl, halogen, O$C_{1-3}$alkyl, acetyl, CN, and perfluoro$C_{1-3}$alkyl), hydroxy$C_{1-3}$alkyl, $C_{3-7}$cycloalkyl, cyano$C_{1-3}$alkyl, acetyl, nitro, N(CH$_3$)$_2$, NHR$^{21}$ (where R$^{21}$ is $C_{1-3}$alkyl, —C(O)$C_{1-3}$alkyl, —C(O)O$C_{1-3}$alkyl, or SO$_2$CH$_3$), piperidin-4-yl (substituted at nitrogen with a moiety selected from $C_{1-5}$alkyl, benzyl, acetyl, C(O)O$C_{1-5}$alkyl, C(O)Obenzyl, C(O)NH$_2$, C(O)NH$C_{1-3}$alkyl, SO$_2$CH$_3$), 4-(4-fluorophenyl)piperazin-1-ylmethyl, morpholin-4-ylmethyl, tetrahydrofuran-3-yl, or two adjacent carbon atoms in the heteroaryl could be substituted to form a benzene ring thus forming a fused bicycle and wherein the resulting benzene ring is optionally substituted with one or two moieties selected from $C_{1-3}$alkyl, halogen, and perfluoro$C_{1-3}$alkyl.

In another aspect, the present invention discloses a method for prevention or treatment of a disease or condition mediated by one or more human PPAR alpha, gamma or delta ("hPPARs") comprising administration of a therapeutically effective amount of a compound of this invention. hPPAR mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, epithelial hyperproliferative diseases including eczema and psoriasis and conditions associated with the lung and gut and regulation of appetite and food intake in subjects suffering from disorders such as obesity, anorexia bulimia, and anorexia nervosa. In particular, the compounds of this invention are useful in the treatment and prevention of diabetes and cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

As used herein, "a compound of the invention" means a compound of formula (1) or a pharmaceutically acceptable salts, solvates, acid isosteres, and hydrolyzable esters thereof.

As used herein an "acid isostere thereof" means that the depicted CO$_2$H group in formula (1) may be replaced with a group that is generally recognized as being functionally equivalent to a carboxylic acid group. The preferred acid isostere is tetrazole.

As used herein "alkyl" and terms containing alkyl such as "perfluooroalkyl" mean straight or branched unless otherwise indicated.

Preferably R$^1$ and R$^2$ are independently hydrogen or $C_{1-3}$alkyl. More preferably R$^1$ and R$^2$ are both hydrogen or both methyl.

Preferably R$^4$ and R$^5$ are independently hydrogen, $C_{1-3}$alkyl, perfluoro$C_{1-3}$alkyl, —O$C_{1-3}$alkyl, perfluoroO$C_{1-3}$alkyl, halogen, or cyano. Most preferably at least one of R$^4$ and R$^5$ are hydrogen, and when one of R$^4$ and R$^5$ is hydrogen and the other is not then the one that is not hydrogen is preferably ortho to the depicted oxygen.

Preferably R$^7$ and R$^8$ are independently hydrogen or methyl. More preferably R$^7$ and R$^8$ are both hydrogen or both methyl.

Preferably y is 1.

Preferably R$^6$ is phenyl. More preferably R$^6$ is phenyl optionally substituted with 1 or 2 moieties selected from the group consisting of F, Cl, CF$_3$, OCF$_3$, 5-membered nitrogen-containing heteroaryl (optionally substituted with one group selected from $C_{1-3}$alkyl, $C_{3-6}$cycloalkyl, perfluoro$C_{1-3}$alkyl, NH$C_{1-3}$alkyl, and N($C_{1-3}$alkyl)$_2$).

Preferably the heteroaryl group in R$^3$ is selected from the group consisting of pyrimidine, pyridine, pyridazine, pyrazine, 1,2,4-oxadiazole, oxazole, and thiazole; and is optionally substituted by a moiety selected from the group consisting of halogen, $C_{1-6}$alkyl, perfluoro$C_{1-6}$alkyl, phenyl (optionally substituted with one or two moieties selected from $C_{1-3}$alkyl, halogen, O$C_{1-3}$alkyl, acetyl, CN, and perfluoro$C_{1-3}$alkyl), 5- or 6-membered heteroaryl (optionally substituted with one or two moieties selected from $C_{1-3}$alkyl, halogen, O$C_{1-3}$alkyl, acetyl, CN, and perfluoro$C_{1-3}$alkyl), hydroxy$C_{1-3}$alkyl, and $C_{3-7}$cycloalkyl, or R$^3$ may be substituted to form a fused bicycle selected from benzoxazole and benzothiazole. More preferably the heteroaryl group in R$^3$ is a thiazole, a pyrimidine, or a pyridine; and is optionally substituted by a moiety selected from the group consisting of halogen, $C_{1-6}$alkyl, perfluoro$C_{1-6}$alkyl, phenyl (optionally substituted with one or two moieties selected from $C_{1-3}$alkyl, halogen, O$C_{1-3}$alkyl, acetyl, CN, and perfluoro$C_{1-3}$alkyl), 5- or 6-membered heteroaryl, hydroxy$C_{1-3}$alkyl, and $C_{3-7}$cycloalkyl.

Preferably, the compounds of formula (1) are hPPAR agonists. The hPPAR agonists of formula (1) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 6.0 preferably at least 7.0 to the relevant PPAR, for example hPPARδ in the binding assay described below, and which achieve at least 50% activation of the relevant PPAR relative to the appropriate indicated positive control in the transfection assay described below at concentrations of $10^{-5}$ M or less. More preferably, the compounds of this invention achieve 50% activation of at least one human PPAR in the relevant transfection assay at concentrations of $10^{-6}$ M or less. More preferably the compounds of the invention achieve 50% activation of at least one human PPAR in the relevant transfection assay at concentrations of $10^{-7}$ M or less.

It will also be appreciated by those skilled in the art that the compounds of the present invention may also be utilized in the form of a pharmaceutically acceptable salt or solvate thereof. The physiologically acceptable salts of the compounds of formula (1) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvents". For example, a complex with water is known as a "hydrate". Solvates of the compound of formula (1) are within the scope of the invention. References hereinafter to a compound according to the invention include both compounds of formula (1) and their pharmaceutically acceptable salts and solvates.

Those skilled in the art will recognize that stereocenters exist in compounds of formula (1). Accordingly, the present invention includes all possible stereoisomers and geometric isomers of formula (1) and includes not only racemic compounds but also the optically active isomers as well. When a compound of formula (1) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (McGraw Hill, 1962) and *Tables of Resolving Agents* by S. H. Wilen. Additionally, in situations where tautomers of the compounds of formula (1) are possible, the present invention is intended to include all tautomeric forms of the compounds.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (1) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (1) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma, PPAR alpha or PPAR alpha/gamma agonists (for example thiazolidinediones such as e.g. Pioglitazone and Rosiglitazone). The compounds may also be used in combination with antihypertensive agents such as angistensin antagonists e.g. telmisartan, calcium channel antagonists e.g. lacidipine and ACE inhibitors e.g. enalapril. The invention thus provides in a further aspect the use of a combination comprising a compound of formula (1) with a further therapeutic agent in the treatment of a hPPAR mediated disease.

When the compounds of formula (1) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (1) is used in combination with a second therapeutic agent active against the same hPPAR mediated disease, the dose of each compound may differ from that when the compound is used alone. Appropriate doses will be readily appreciated by those skilled in the art.

There is further provided processes for the preparation of compounds of formula (1). Unless otherwise indicated all definitions are as above.

Compounds of this invention may be conveniently prepared as illustrated below in schemes 4 through 7 utilizing moieties such as A through M and a variety of commercial or otherwise known reagents. Moieties A through M are commercially available, known compounds or otherwise prepared as illustrated below in schemes 1, 2 and 3. In the following structures all variables such as $R^1$, $R^2$, $R^4$, $R^5$, $R^6$, and n are as defined above for formula (1) unless otherwise indicated. In the structures "A" represents $C(R^7)(R^8)$ in formula (1) and R', $R^9$, $R^{10}$, $R^{11}$, $R^{12}$, $R^{13}$, $R^{14}$, $R^{17}$, $R^{18}$, $R^{19}$, and $R^{20}$ represent substituents for phenyl or heteroaryl groups as appropriate.

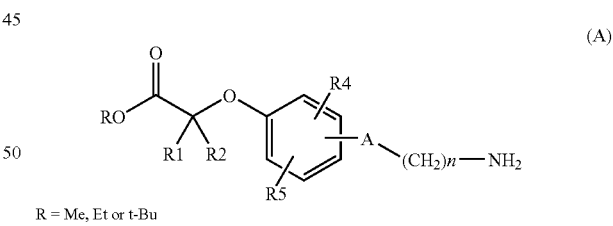

(A)

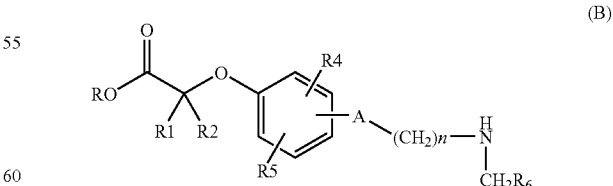

(B)

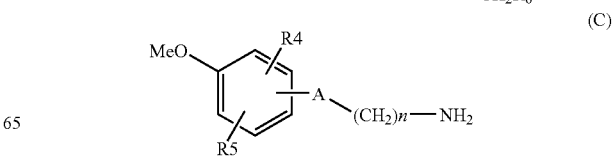

(C)

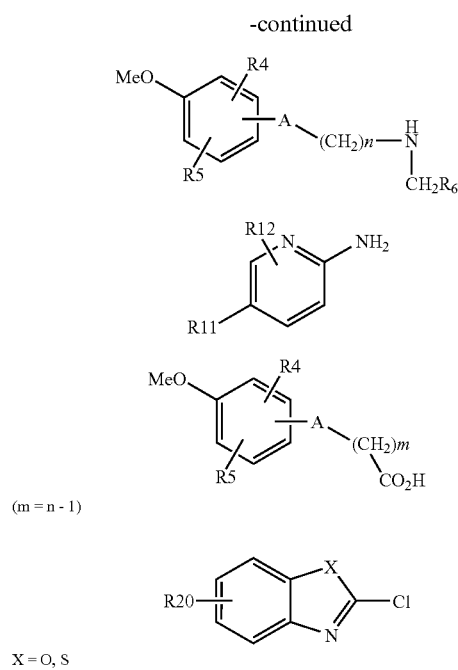
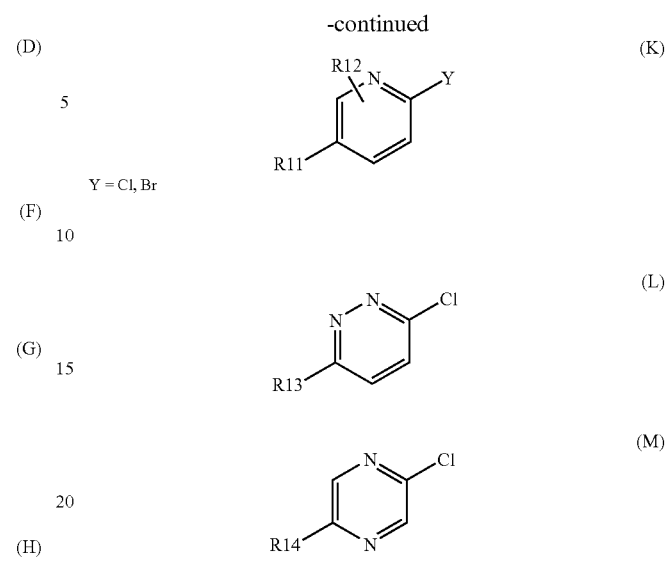

Scheme 1 below illustrates the general preparation of moieties A and B. In such a preparation, alkylation of 3- or 4-bromophenol with an alpha-bromoalkanoic ester in the presence of a suitable base such as $K_2CO_3$, $Cs_2CO_3$ or NaH, followed by Palladium-catalyzed reaction with N-vinyl or allyl-phtalimide affords the olefin intermediates of general formula N. Catalytic hydrogenation of the olefinic compounds N, followed by hydrazinolysis of the phtalimide group provides the primary amine moieties A. These amine moieties A can be condensed with aldehydes under reductive amination conditions, or alkylated with alkyl halides to provide the secondary amine moieties B.

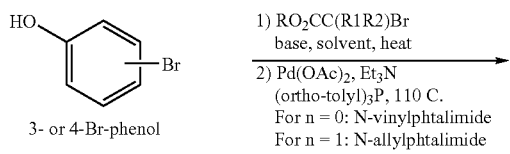
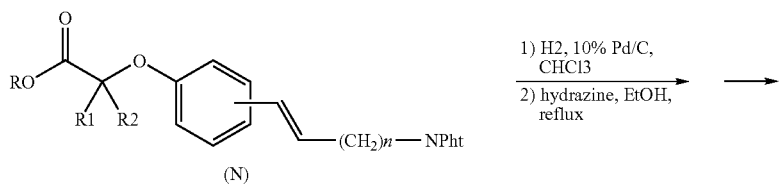
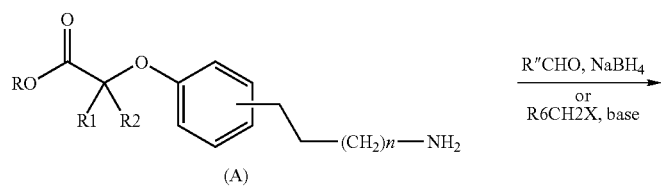

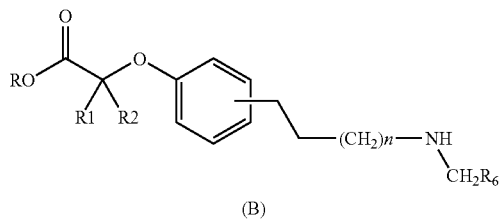

(B)

(R = Me, Et, t-Bu
(n = 0 or 1)

Scheme 2 below illustrates the general preparation of moieties C and D. In such a preparation, condensation of 4-methoxy-benzaldehyde reagents with nitromethane in the presence of NaOH, provides the corresponding nitroolefin derivatives which are subsequently reacted with a reducing agent such as borane to provide the primary amine moieties C. Amine moieties C can be condensed with aldehydes under reductive amination conditions, or alkylated with alkyl halides to provide the secondary amine moieties D.

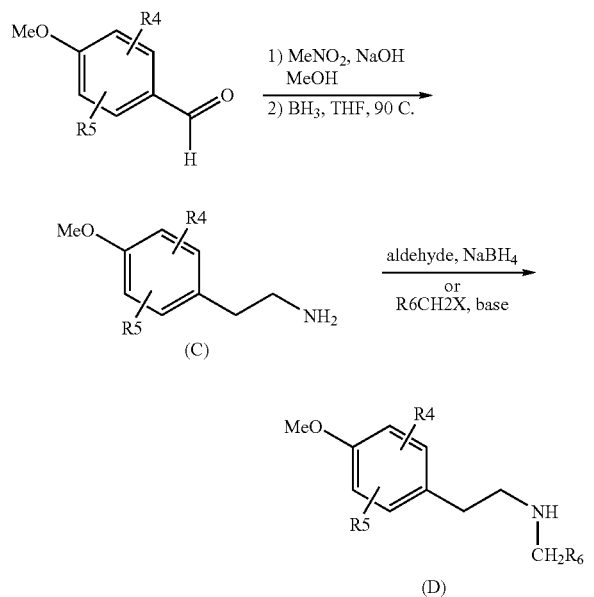

Scheme 3 bellow illustrates an alternative synthetic route for the preparation of moieties B and D. In such a preparation, condensation of 4-hydroxy- or methoxy phenethylamine reagents with aldehydes under reductive amination conditions provides the secondary amine moieties D. Moieties D in which R' is methyl can be O-demethylated with a reagent such as boron tribromide to provide the corresponding unmasked phenol derivatives. These phenol derivatives can be O-alkylated with alpha-bromoalkanoic esters in the presence of a suitable base such as NaH to provide moieties B.

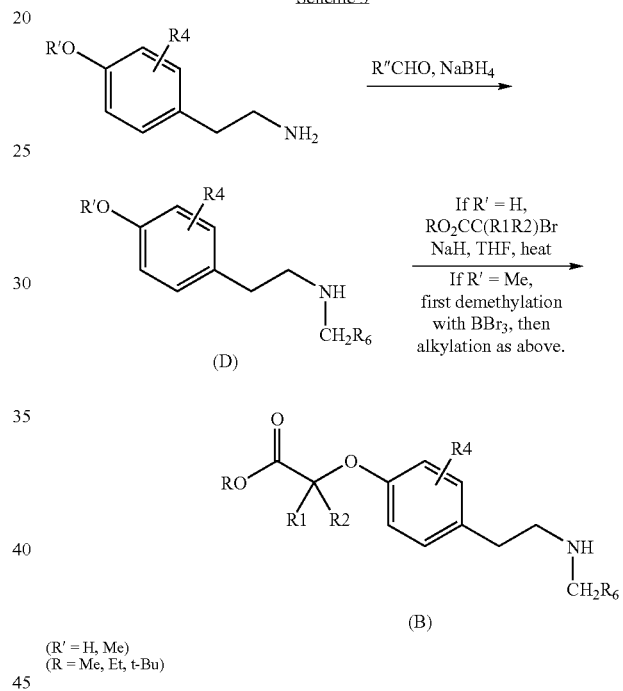

(R' = H, Me)
(R = Me, Et, t-Bu)

Scheme 4 below illustrates a general preparation of compounds of general formula (1) in which $R^3$ is one of the following: benzoxazole, benzothiazole, oxazole, pyrimidine, pyridazine, pyrazine or pyridine. Such a route involves the condensation of a moiety such as A, B, C or D, with a 2-chloro (or bromo)-heterocyclic reagent, such as moieties H through M, at elevated temperatures to provide compounds of general formula O or P. Wherein a primary amine moiety such as A or C is used, the ensuing product O can be further derivatized by alkylation with an alkyl halide using a suitable base, such as NaH, to provide also intermediates of general formula P.

Intermediates of general formula P which are derived from moieties such as A or B have their carboxylic acid functionalities protected as the corresponding methyl, ethyl or tert-butyl esters. Hydrolysis of these esters (with LiOH or NaOH for the methyl and ethyl esters and with TFA for the tert-butyl esters) provides the corresponding carboxylic acids of general formula (1).

Intermediates of general formula P which are derived from moieties such as C or D have their phenol moieties protected as the corresponding methyl ethers. These can be demethylated using a reagent such as boron tribromide and the corresponding unmasked phenol derivatives can be converted to carboxylic acids or tetrazole compounds of formula (1) by one of the three synthetic protocols illustrated in schemes 8 through 10.

In the first protocol, as illustrated in scheme 8, the unmasked phenol can be alkylated directly with 2-trichloromethyl-2-propanol using NaOH in acetone to provide carboxylic acids of formula (1) wherein $R^1=R^2$=methyl.

In the second protocol, as illustrated in scheme 9, the unmasked phenol can be alkylated with an alpha-chloro (or bromo) alkanoic ester to provide the corresponding alpha-phenoxy esters, which are subsequently hydrolyzed to carboxylic acids of formula (1).

In the third protocol, as illustrated in scheme 10, the unmasked phenol is alkylated with chloroacetonitrile using a suitable base such as $Cs_2CO_3$ to provide the corresponding alpha-phenoxy-acetonitrile derivatives. These nitrile intermediates can be reacted at elevated temperatures with trimethylsilyl azide under dibutyltin oxide catalysis to provide tetrazole compounds of formula (1) wherein $R^1=R^2$=hydrogen.

Scheme 5 below illustrates a general preparation of compounds of formula (1) in which $R^3$ is a pyridine ring. Such a route involves the coupling of a carboxylic acid moiety G to a 2-amino-pyridine moiety F, mediated by a suitable coupling agent such as EDCI. The resulting amide intermediate can be reacted with a reducing agent such LAH to provide the corresponding 2-alkylamino-pyridine of general formula Q. Amines Q can be subsequently derivatized by alkylation with an alkyl halide to provide compounds of general formula R. Compounds of general formula R have their phenol moieties protected as the corresponding methyl ether derivatives. Deprotection of these methyl ethers with a reagent such as boron tribromide provides the corresponding phenol derivatives, which can be converted to carboxylic acids or tetrazoles of general formula (1) utilizing one of the three protocols mentioned above and illustrated in schemes 8, 9, and 10.

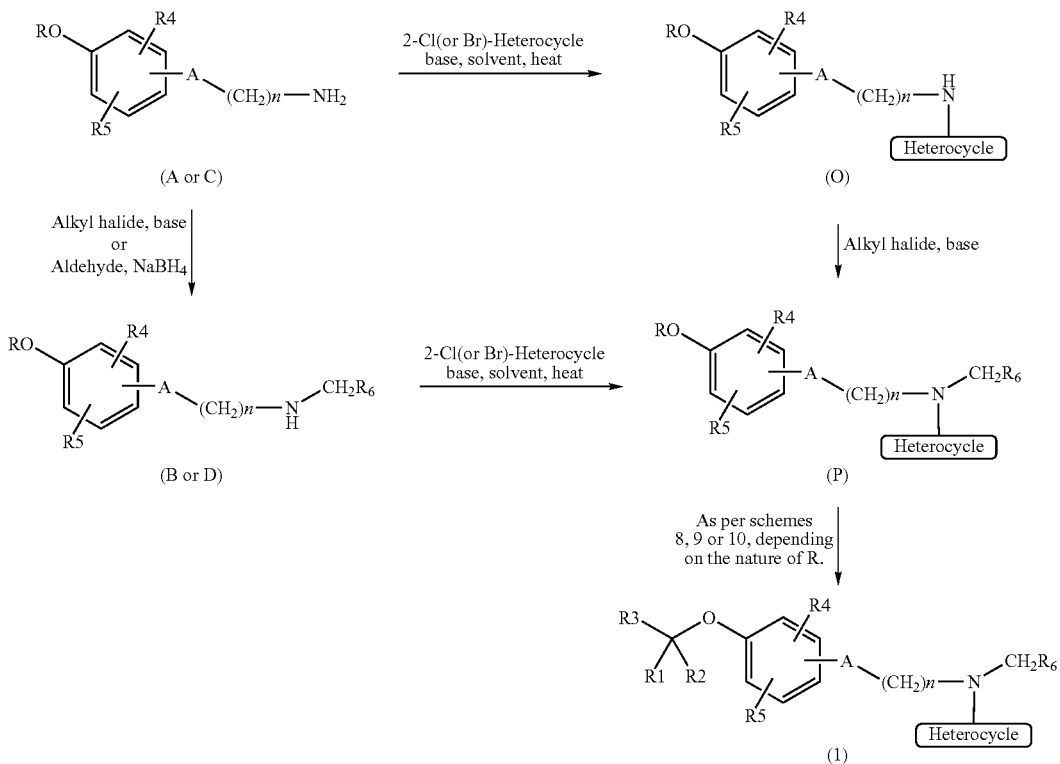

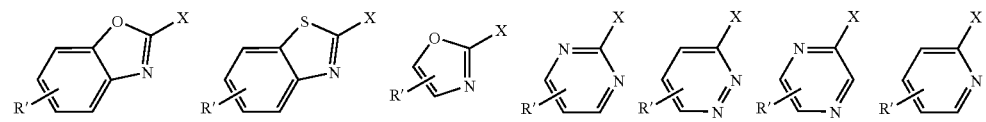

(X = Cl or Br)
(R' denotes the possibility for some substituent other than hydrogen to be present)

Scheme 5

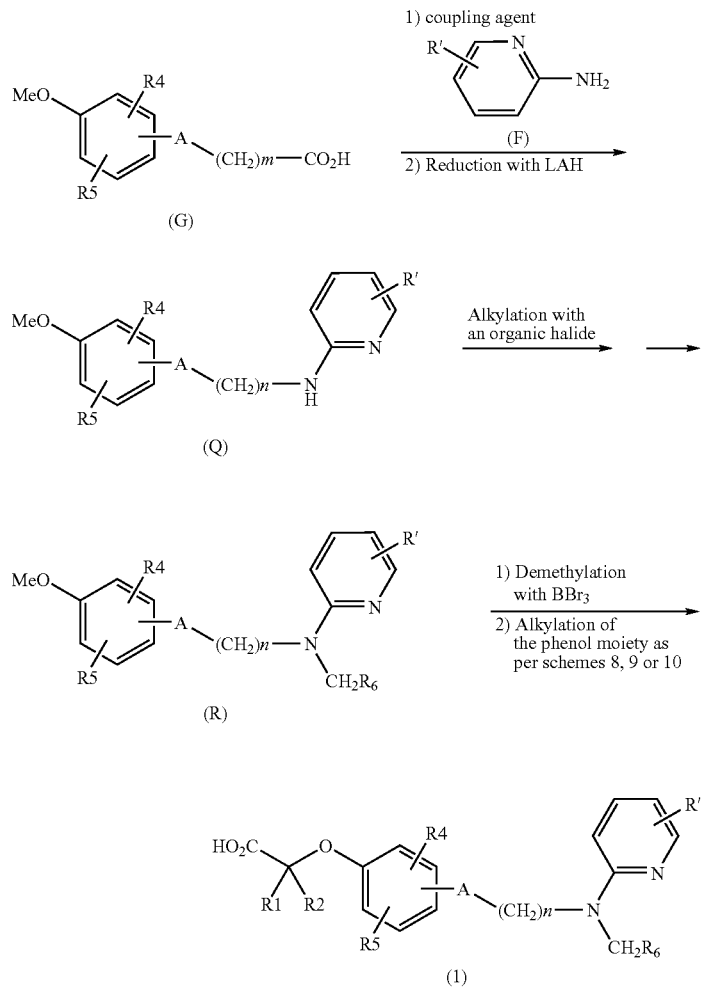

(m = n - 1)
(R' denotes the possibility for substituents other than hydrogen to be present)

Scheme 6 below illustrates the preparation of compounds of formula (1) in which $R^3$ is 1,2,4-oxadiazole. Such a route involves the coupling of a secondary amine moiety B, with cyanogen bromide to provide the corresponding cyanoamine derivative which is subsequently reacted with hydroxylamine to afford N-hydroxy-guanidine compounds of general formula S. These intermediates of formula S can be reacted with an acid chloride in the presence of a suitable base, or with a carboxylic acid mediated by a suitable coupling agent to provide, upon heating, 3-amino-1,2,4-oxadiazole derivatives of general formula T. Intermediates of formula T can be converted to carboxylic acids of general formula (1) by hydrolysis or their ester moieties.

Scheme 6

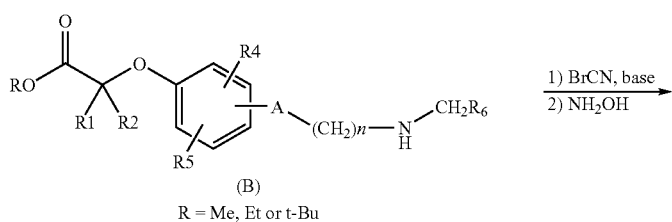

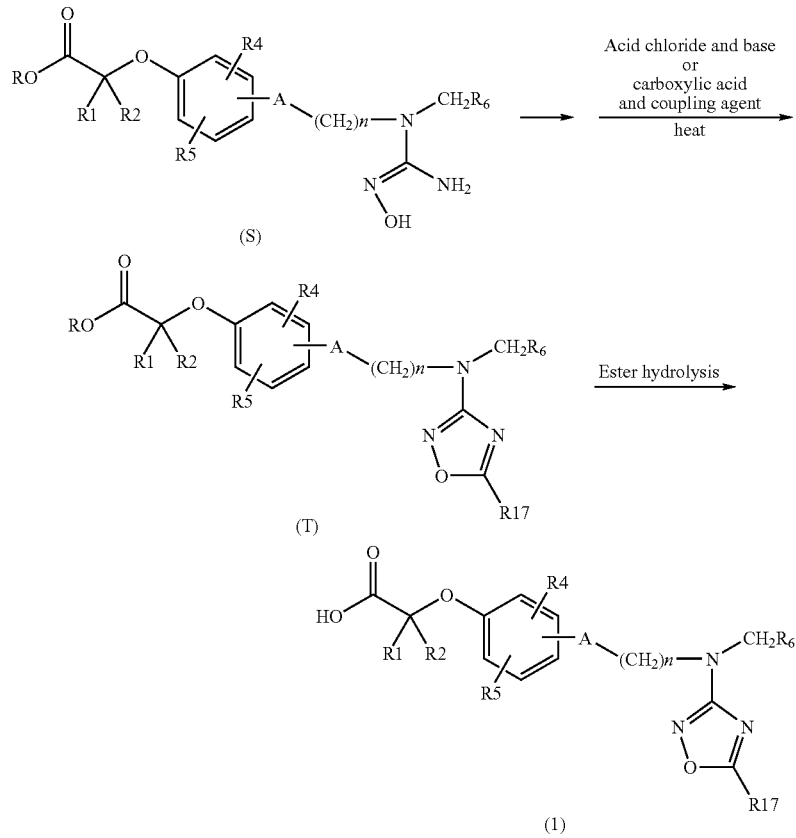

Scheme 7 below illustrates the preparation of compounds of formula (1) in which R³ is 1,3-thiazole. Such a route involves the condensation of a secondary amine moiety B with ammonium thiocyanate at elevated temperatures to provide thiourea derivatives of general formula U. These intermediates are subsequently condensed with phenacyl bromide reagents to afford 2-amino-1,3-thiazole compounds of formula V. The ester functionality present in compounds of formula V can be hydrolyzed with LiOH or NaOH to provide the carboxylic acid compounds of formula (1).

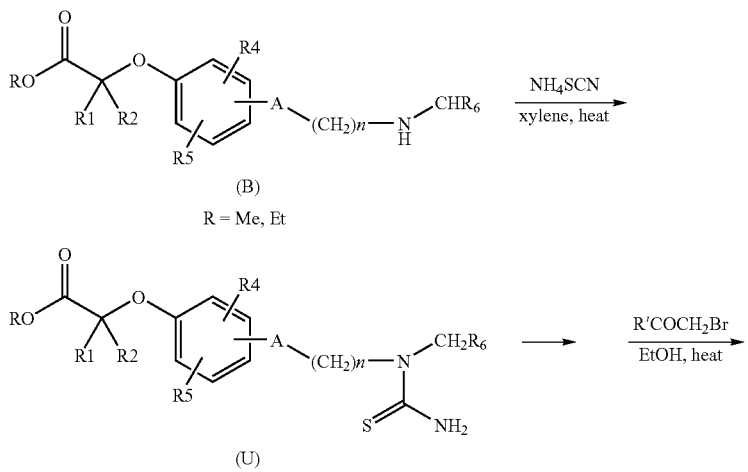

-continued

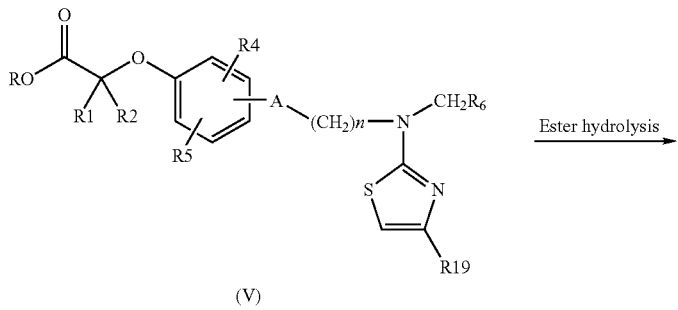

(V)

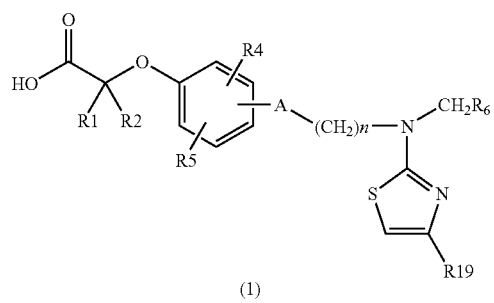

(1)

Scheme 8 below illustrates the one-step preparation of carboxylic acids of general formula (1) by alkylation of intermediate compounds of general formula X with 2-trichloromethyl-2-propanol and NaOH.

Scheme 8

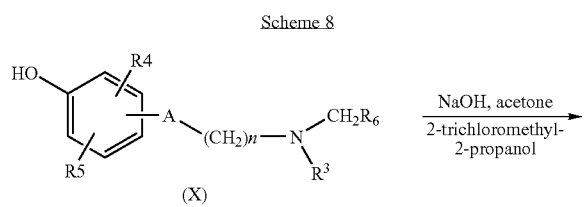

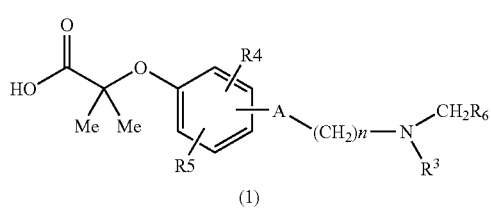

Scheme 9 below illustrates the preparation of carboxylic acids of general formula (1) by a two-step process in which a phenol compound of general formula X is first alkylated with an alpha-bromo alkanoic ester reagent and subsequently the ester moiety is hydrolyzed with lithium or sodium hydroxide (in the case of methyl or ethyl ester derivatives) or with TFA (in the case of tert-butyl ester derivatives).

Scheme 9

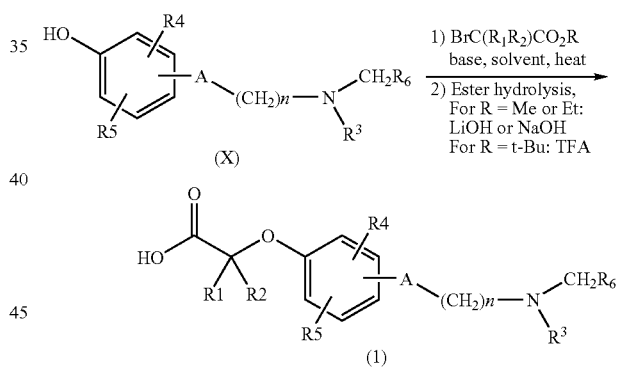

Scheme 10 below illustrates the preparation of tetrazole compounds of formula (1) by a two-step process in which an intermediate phenol moiety X is first alkylated with chloroacetonitrile and subsequently the nitrile moiety converted to a tetrazole moiety by reaction with trimethylsilylazide at elevated temperatures under dibutyltin oxide catalysis.

Scheme 10

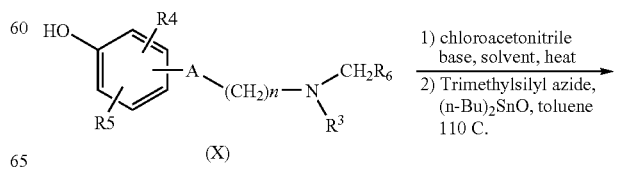

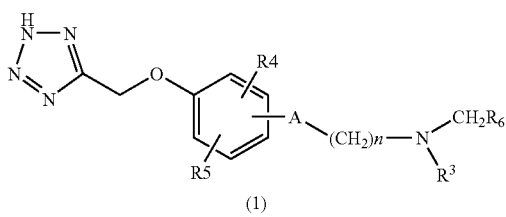

(1)

In addition to the general preparation routes illustrated above, it can be appreciated by those skilled in the art that some intermediates generated during the synthesis of compounds of formula (1) can be further derivatized when an appropriate functional group (such as, for example, bromo, nitro, hydroxyl or carbonyl) is present that would make the molecule amenable to further chemical modification using standard synthetic procedures and reagents.

For example, the intermediate bromo compound X1 below, which was generated during a process such as that exemplified in scheme 4, was reacted with phenylboronic acid under standard Suzuki conditions to provide a novel phenyl derivative, which upon hydrolysis provided a novel compound of formula (1).

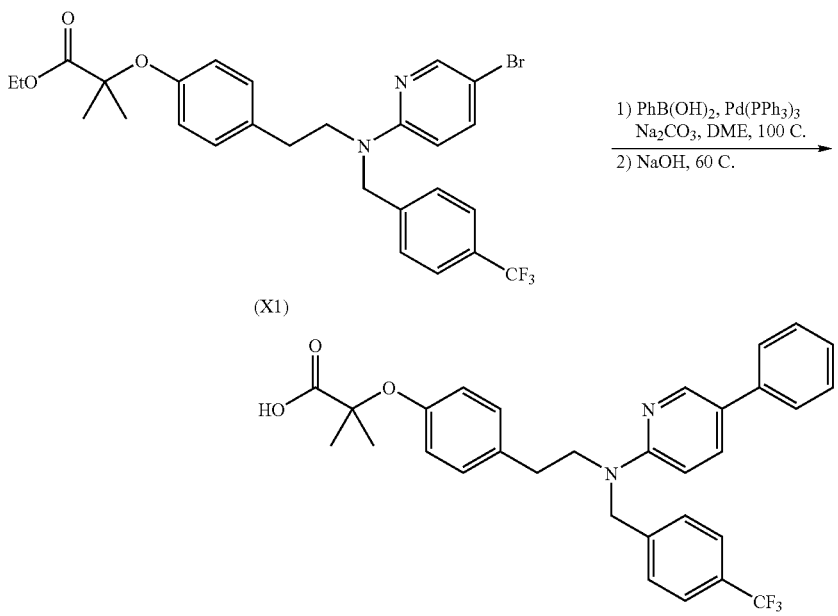

In another example, an aldehyde intermediate, such as compound X2 below, similarly generated during a process such as that illustrated in scheme 4, was reacted with isopropyltriphenylphosphoniumbromide/n-butyl lithium under standard Wittig conditions to provide a novel alkene compound which after catalytic hydrogenation and ester hydrolysis provided a novel compound of formula (1).

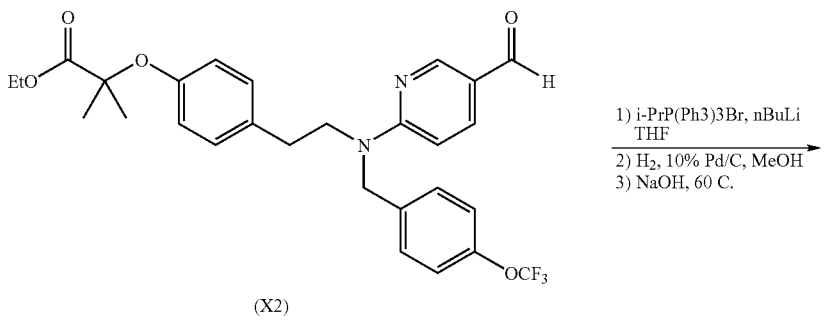

-continued

The invention is further illustrated by the following examples, which should not be construed as constituting a limitation thereto.

EXAMPLES

The structures of the compounds were confirmed by either nuclear magnetic resonance (NMR) or mass spectrometry (MS). Proton NMR ($^1$HNMR) spectra were recorded on a Brucker 300 or 400 MHz spectrometer at ambient temperature. NMR shifts ($\delta$) are given in parts per million (ppm). Coupling constants (J) are given in Hertzs.

Chromatography refers to standard silica gel flash column chromatography or to radial chromatography (using a Chromatotron apparatus).

Compounds used as starting materials are either commercially available or known compounds.

Abbreviations:
TLC: thin layer chromatography
rt: room temperature
h or hr: hour
eq: equivalent
EDCI: 1-ethyl-3-(3-dimethyl-aminopropyl) carbodiimide
LAH: lithium aluminum hydride
BH$_3$: borane
NaHMDS: sodium bis(trimethylsilyl)amide
TFA: trifluoroacetic acid
Na$_2$CO$_3$: sodium carbonate
Cs$_2$CO$_3$: cesium carbonate
NaH: sodium hydride
MeOH: methanol
EtOH: ethanol
DMF: dimethylformamide
THF: tetrahydrofuran
EtOAc: ethyl acetate
CDCl$_3$: deuterated chloroform
CD$_3$OD: deuterated methanol
Acetone-D$_6$: deuterated acetone
NaOMe: sodium methoxide
DIEA: diisopropylethylamine
NaOH: sodium hydroxide
LiOH: lithium hydroxide
HCl: hydrochloric acid
MeCN: acetonitrile
MgSO$_4$: magnesium sulfate What follows are common procedures that were routinely used in the course of preparing the compounds of this invention. In the subsequent experimental section we might refer to these common procedures and note only specific changes or conditions that deviated from these common procedures.

Procedure A: Reductive Amination.

A solution of a primary amine in MeOH (0.1–0.5 M) was treated under nitrogen with 1 eq of the aldehyde and 5 eq of trimethylorthoformate. After stirring at rt for 12 hours, 2.5 eq of sodium borohydride were added in small portions (exothermic). Stirred for one hour and concentrated in a rotary evaporator. The residue was partitioned between equal volumes of ethyl acetate and water. The organic phase was washed with saturated brine, dried over sodium sulfate, filtered and concentrated to provide the secondary amine derivative. The crude amine was carried on to the next step without further purification or, alternatively, it was purified by flash chromatography on silica gel using ethyl acetate-hexane mixtures (5–50% gradient) or methanol-dichloromethane mixtures (1–10% gradient).

Procedure B: Alkylation of Primary Amines with an Alkyl Chloride or Bromide Reagent.

A solution of a primary amine in dichloromethane (0.1–0.5M) was treated with 1 eq of DIEA and 1 eq of the chloride or bromide reagent. After stirring at rt for 12 hours the mixture was concentrated and partitioned between equal volumes of ethyl acetate and saturated Na$_2$CO$_3$. The organic phase was washed with saturated Na$_2$CO$_3$ and brine, dried over sodium sulfate and concentrated to dryness. Purification by chromatography on silica gel using ethyl acetate-hexane mixtures (10–50% gradient) afforded the secondary amines derivatives.

Procedure C: Alkylation of Phenolic Compounds with Bromide or Chloride Reagents.

A solution of a phenolic compound in a solvent such as MeCN, THF or DMF (0.1–0.5 M) was treated under nitrogen with 1.1–2.2 eq of a base such as Cs$_2$CO$_3$, K$_2$CO$_3$. After stirring at rt for 10 minutes, 1.1–2 eq of the bromide or chloride reagent was added and the mixture heated at 75C for 2–14 hours. Upon cooling, the mixture was concentrated and the residue partitioned between equal volumes of ethyl acetate and water. The organic phase was washed with saturated brine, dried over sodium sulfate, filtered and concentrated to dryness. Purification by chromatography on silica gel using ethyl acetate-hexane mixtures (5–50% gradient) provided the alkylated phenol derivative.

Procedure D: Alkylation of Phenolic Compounds with 2-trichloromethyl-2-propanol.

A solution of a phenolic compound in acetone (0.25 M) was treated with 8 eq of NaOH (triturated; slowly, in small portions) and 3 eq of water. After stirring for 10–40 minutes, a solution of 1.5 eq of 2-trichloromethyl-2-propanol in acetone (1M) was added and the mixture stirred at rt for 12 hours. The reaction mixture was concentrated in a rotary evaporator and the residue partitioned between equal volumes of ethyl acetate and water. An aqueous solution of HCl was added to adjust the pH to ~4. The phases were separated and the aqueous phase was extracted with an equal volume of ethyl acetate. The combined organic phases were washed with saturated brine, dried over sodium sulfate and concentrated to provide the crude 2-methyl-2-phenoxy-propanoic acid derivatives.

When needed, as judged by TLC, the crude acid was purified by chromatography on silica gel using methanol-dichloromethane mixtures (1–10% gradient) or methanol-ethyl acetate mixtures (0.5–15% gradient). Alternatively the acid could be crystallized directly or used without any further purification.

Procedure E: Condensation of Amines with 2-chloro(or Bromo)-pyrimidine Reagents.

A pressure tube containing a primary or secondary amine, either neat or in a solvent such as toluene, n-butanol or dioxane (0.5–1M) was treated under nitrogen with 1.1–3 eq of the 2-chloro(or bromo)-pyrimidine reagent and 1.1–3 eq of a base such as DIEA or $K_2CO_3$. The mixture was then heated to 120–230C for 14–72 hours. Upon cooling, the mixture was partitioned between equal volumes of ethyl acetate and water. The aqueous phase was washed with an equal volume of ethyl acetate and the combined organic phases were washed with saturated brine, dried over sodium sulfate, filtered and concentrated to dryness. Purification by chromatography on silica gel using ethyl acetate-hexane mixtures (2–30% gradient) provided the 2-amino-pyrimidine derivatives.

Procedure F: Demethylation of Methyl Aryl Ethers with Boron Tribromide.

A solution of a methyl aryl ether in dichloromethane (0.1–0.5M) was treated under nitrogen, in an ice bath, with 2–4 eq of boron tribromide (commercial 1M solution in dichloromethane). The mixture was stirred for 1–4 hours and then quenched by careful addition of ice in small portions (exothermic). The mixture was diluted with one volume of water, the pH adjusted to ~6 with saturated $K_2CO_3$ solution and the phases separated. The aqueous phase was washed with ethyl acetate and the combined organic phases were washed with saturated brine, dried over sodium sulfate and concentrated to provide the crude phenol.

An alternative workup procedure involved quenching the reaction by careful addition of a few mls of MeOH, concentrating the mixture and azeotroping from MeOH. The residue was then redissolved in MeOH, treated with 1 eq of NaOMe and concentrated. This was followed by a standard aqueous workup.

The crude phenol was used directly or purified by chromatography on silica gel using ethyl acetate-hexane mixtures (10–50% gradient).

Procedure G: Demethylation of Methyl Aryl Ethers with Pyridinium Hydrochloride.

A mixture of a methyl aryl ether and pyridinium hydrochloride (5–20 weight equivalent) was heated at 220C for 20–60 minutes. Upon cooling the mixture was partitioned between equal volumes of ethyl acetate and water. The organic phase was washed with saturated brine, dried over sodium sulfate and concentrated to dryness. Purification by chromatography on silica gel using ethyl acetate-hexane mixtures (10–50% gradient) provided the phenol derivative.

Procedure H: Base-mediated Ester Hydrolysis.

A solution of a methyl or ethyl ester in 1:1 THF:MeOH (0.1–0.5M) was treated with 3–10 eq of 1N NaOH or LiOH and heated to 65C for 2–6 hours. The reaction mixture was concentrated in a rotary evaporator and partitioned between equal volumes of ethyl acetate and water. The pH was adjusted to ~6 with 1N HCl and the phases separated. The aqueous phase was washed with ethyl acetate and the combined organic phases were washed with saturated brine, dried over sodium sulfate and concentrated to dryness. When needed, as judged most commonly by TLC, the material was purified by chromatography on silica gel using methanol-dichloromethane mixtures (1–10% gradient) or methanol-ethyl acetate mixtures (1–15% gradient) to provide the desired carboxylic acid. Alternatively the crude acid was crystallized directly or used without any further purification.

Procedure I: Acid-mediated Ester Hydrolysis.

A solution of a tert-butyl ester in dichloromethane (0.1–0.5M) was treated with triethylsilane (0.2 volumes) and trifluoroacetic acid (0.5 volumes). After stirring for 2–6 hours the mixture was concentrated to dryness and then azeotroped from chloroform four times. Purification by chromatography on silica gel using methanol-dichloromethane mixtures (1–10% gradient) provided the carboxylic acid derivative. Alternatively the acid was crystallized directly or used without any further purification.

PREPARATION OF INTERMEDIATES AND EXAMPLES

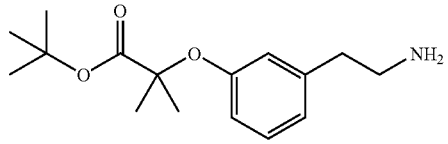

tert-Butyl 2-[3-(2-aminoethyl)phenoxy]-2-methylpropanoate

Step 1. To a solution of 3-bromophenol (55.4 g; 0.32 mol) in acetone (1000 ml) at 0° C. was added chloretone (108.25 g; 0.61 mol) followed by portionwise addition of sodium hydroxide (3 times 33.3 g; total 100 g; 2.39 mole). After the first two portions, the mixture was allowed to warm to 23° C. for 1 h and then cooled to 0C; after the third addition the mixture was stirred at 23° C. for 18 h. The organic solvent was removed by evaporation and the residue was dissolved in water (1500 ml) and acidified to pH 2 with concentrated HCl to afford a red oil. The mixture was extracted with methylene chloride (3×500 ml) and the combined organic layers were dried ($Na_2SO_4$) and evaporated to afford 2-(3-bromophenoxy)-2-methylpropionic acid as a dark oil (82.66 g; 99.6%).

$^1$H NMR (CDCl$_3$) δ 7.14 (m, 3H), 6.86 (d, 1H, J=6), 1.63 (s, 6H).

Step 2. A solution of the above intermediate (82.66 g; 0.32 mole) and concentrated sulfuric acid (5 ml) in methylene chloride (500 ml) was cooled to −78° C. and isobutylene was distilled into the reaction mixture (150 ml). The mixture was allowed to warm to rt and stirred for 18 hr. The acid was then carefully neutralized by the addition of saturated sodium bicarbonate solution. The organic layer was separated, dried ($Na_2SO_4$), and concentrated. The residue was purified by chromatography to afford t-butyl 2-(3-bromophenoxy)-2-methylpropionate as an oil (68 g; 70%).

$^1$H NMR (CDCl$_3$) δ 7.08 (d, 2H, J=5), 7.01 (s, 1H), 6.78 (m, 1H), 1.60 (s, 6H), 1.44 (s, 9H).

Step 3. A mixture of the above intermediate (1 eq), N-vinylphthalimide (1.05 eq), palladium acetate (0.05 eq), tri-o-tolylphosphine (0.10 eq) and triethylamine (2 eq) in a sealed tube was heated at 110° C. for 15 h. The solvent was evaporated and the residue partitioned between 2N HCl and ethyl acetate and filtered through celite. The aqueous phase was washed with ethyl acetate. The combined organic phases were washed with brine, dried (MgSO$_4$) and concentrated. The residue was purified by chromatography using EtOAc-Hexane-CH$_2$Cl$_2$ as eluant to afford t-butyl 2-(3-(2-phthalimidoethenyl)phenoxy)-2-methylpropionate as a yellow solid.

$^1$H NMR (CDCl$_3$) δ 7.88 (m, 2H), 7.75 (m, 2H), 7.58 (d, 2H, J=15), 7.30 (d, 1H, J=15), 7.20 (t, 1H, J=7), 7.08 (d, 1H, J=7), 6.98 (s, 1H), 6.75 (dd, 1H, J=8 and 2), 1.6 (s, 6H), 1.43 (s, 9H).

Step 4. A solution of the above intermediate in chloroform (0.5 M) was treated with 10% Pd/C (0.1 equivalent weight) and hydrogenated in a Parr apparatus under 40 psi of H$_2$ for 6 hr. The mixture was filtered through celite and the filtrate was concentrated to afford t-butyl 2-(3-(2-phthalimidoethyl)phenoxy)-2-methylpropionate as an oil.

$^1$H NMR (CDCl$_3$) δ 7.82 (m, 2H), 7.70 (m, 2H), 7.14 (t, 1H, J=8), 6.87 (d, 1H, J=8), 6.76 (s, 1H), 6.70 (d, 1H, J=8), 3.89 (t, 2H, J=8), 2.92 (t, 2H, J=8), 1.51 (s, 6H), 1.44 (s, 9H).

Step 5. A solution of the above intermediate (1 eq) in ethanol (4M) was treated with hydrazine hydrate (3 eq) and heated at reflux for 5 hours. Upon cooling, the reaction mixture stood at rt for 15 hr. The resultant solids were filtered off and the filtrate was concentrated. The residue was partitioned between 1N NaOH and ethyl ether. The organic phase was washed with 1N NaOH and brine, dried (MgSO$_4$) and concentrated to afford the title compound as an oil in good yield.

$^1$H NMR (CDCl$_3$) δ 7.15 (t, 1H, J=8), 6.80 (d, 1H, J=8), 6.72 (s, 1H), 6.69 (d, 1H, J=8), 2.94 (t, 2H, J=7), 2.68 (t, 2H, J=7), 1.56 (s, 6H), 1.44 (s, 9H), 1.15 (br s, 2H).

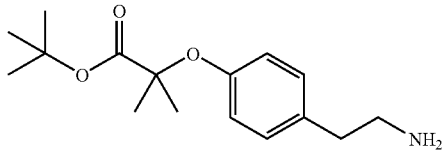

tert-Butyl
2-[4-(2-aminoethyl)phenoxy]-2-methylpropanoate

Similarly prepared from 4-bromo-phenol and vinyl phtalimide.

$^1$H NMR (CDCl$_3$) δ 7.05 (d, 2H, J=8), 6.80 (d, 2H, J=8), 2.92 (t, 2H, J=7), 2.67 (t, 2H, J=7), 1.54 (s, 6H), 1.44 (s, 9H), 1.32 (br s, 2H).

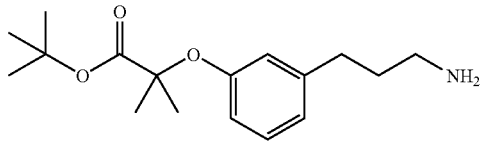

tert-Butyl
2-[3-(3-aminopropyl)phenoxy]-2-methylpropanoate

Similarly prepared from 3-bromo-phenol and allyl phtalimide.

$^1$H NMR (CDCl$_3$) δ 7.12 (t, 1H, J=8), 6.79 (d, 1H, J=8), 6.70 (s, 1H), 6.66 (d, 1H, J=8), 2.70 (t, 2H, J=7), 2.59 (t, 2H, J=7), 1.74 (m, 2H), 1.56 (s, 6H), 1.44 (s, 9H).

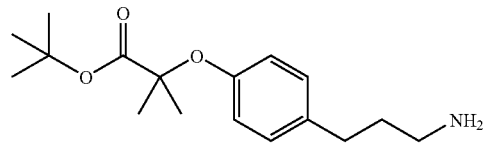

tert-Butyl
2-[4-(3-aminopropyl)phenoxy]-2-methylpropanoate

Similarly prepared from 4-bromo-phenol and allyl phtalimide.

$^1$H NMR (CDCl$_3$) δ 7.03 (d, 2H, J=8), 6.78 (d, 2H, J=8), 2.70 (t, 2H, J=6), 2.57 (t, 2H, J=6), 1.72 (m, 2H), 1.54 (s, 6H), 1.44 (s, 9H), 1.18 (br s, 2H).

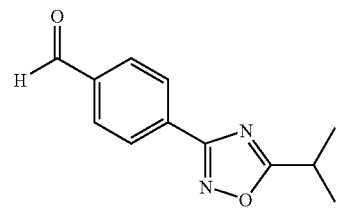

4-(5-Isopropyl-1,2,4-oxadiazol-3-yl)benzaldehyde

Step 1. A suspension of hydroxylamine hydrochloride (31.62 g; 45.5 mmol) in MeOH (350 ml) was treated with sodium methoxide (24.58 g; 45.5 mmol) slowly, in small portions. After stirring for 20 minutes, a solution of 4-(dimethoxymethyl)benzonitrile (67 g; 37.9 mmol) in MeOH (100 ml) was added and the mixture heated to reflux. After 12 hr, it was concentrated and partitioned between ethyl acetate and water. The organic phase was washed with water and brine, dried over sodium sulfate, filtered and concentrated to afford 4-(dimethoxymethyl)-N'-hydroxybenzenecarboximidamide (74.2 g) which was used in the next step without further purification. MS: m/z 211 (M+1).

Step 2. A solution of the previous intermediate (7 g; 33.3 mmol) in pyridine (30 ml) was treated under nitrogen with isobutyryl chloride (3.7 ml; 34.99 mmol) and heated to reflux for 2 hours. Upon cooling, the mixture was partitioned between ethyl acetate and 1N HCl. The organic phase was washed with 1N HCl, water (2×), 1N NaOH and brine, dried over sodium sulfate and concentrated. Purification by flash chromatography using an ethyl acetate-hexane gradient (10–50%) afforded the title compound as a white solid (4.23 g; 59% yield).

$^1$H NMR (CDCl$_3$) δ 10.12 (s, 1H), 8.29 (d, 2H, J=8.2), 8.02 (d, 2H, J=8.2), 3.35 (m, 1H), 1.50 (d, 6H, J=7.0).

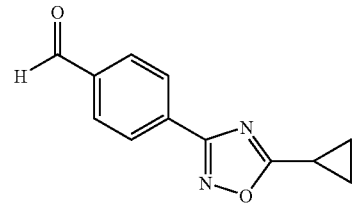

4-(5-cyclopropyl-1,2,4-oxadiazol-3-yl)benzaldehyde

Similarly prepared using cyclopropane carbonyl chloride.
$^1$H NMR (CDCl$_3$) δ 10.1 (s, 1H), 8.27 (d, 2H, J=8.2), 7.98 (d, 2H, J=8.2), 2.28 (m, 1H), 1.30 (m, 4H).

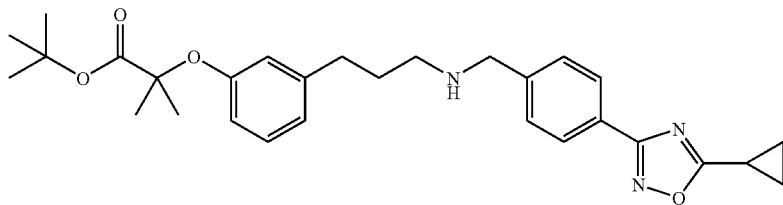

tert-Butyl 2-[3-(3-{[4-(5-cyclopropyl-1,2,4-oxadiazol-3-yl)benzyl]amino}propyl)phenoxy]-2-methylpropanoate Reductive amination of tert-butyl 2-[3-(3-aminopropyl)phenoxy]-2-methylpropanoate with 4-(5-cyclopropyl-1,2,4-oxadiazol-3-yl)benzaldehyde as per general procedure A afforded after column chromatography the title compound in 81% yield.
$^1$H NMR (CDCl$_3$) δ 7.98 (d, 2H, J=8.2), 7.42 (d, 2H, J=8.2), 7.11 (t, 1H, J=7.8), 6.77 (d, 1H, J=7.8), 6.69 (bs, 1H), 6.65 (dd, 1H, J=7.8; 2.2), 3.83 (s, 2H), 2.66 (t, 2H, J=7.2), 2.60 (t, 2H, J=7.6), 2.24 (m, 1H), 1.84 (m, 2H), 1.55 (s, 6H), 1.42 (s, 9H), 1.30 (m, 4H).

Ethyl 2-[4-(2-{[4-(5-cyclopropyl-1,2,4-oxadiazol-3-yl)benzyl]amino}ethyl)phenoxy]-2-methylpropanoate Similarly prepared by reductive amination of ethyl 2-[4-(2-aminoethyl)phenoxy]-2-methylpropanoate with 4-(5-cyclopropyl-1,2,4-oxadiazol-3-yl)benzaldehyde (61% yield).
$^1$H NMR (CDCl$_3$) δ 7.85 (d, 2H, J=8.1), 7.23 (d, 2H, J=8.1), 6.93 (d, 2H, J=8.4), 6.66 (d, 2H, J=8.4), 4.09 (q, 2H, J=7.0), 3.68 (s, 2H), 2.71 (t, 2H, J=6.6), 2.61 (t, 2H, J=6.6), 2.08 (m, 1H), 1.45 (s, 6H), 1.12 (m, 7H).

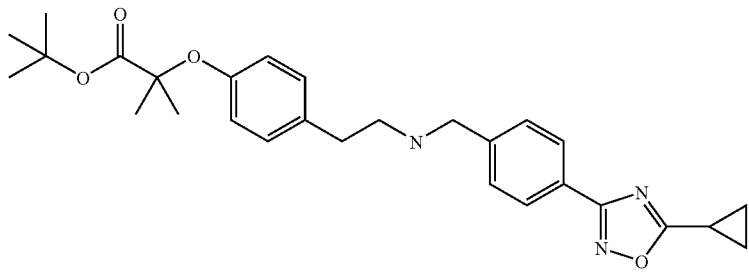

tert-Butyl 2-[4-(2-{[4-(5-cyclopropyl-1,2,4-oxadiazol-3-yl)benzyl]amino}ethyl)phenoxy]-2-methylpropanoate Similarly prepared by reductive amination of tert-butyl 2-[4-(2-aminoethyl)phenoxy]-2-methylpropanoate with 4-(5-cyclopropyl-1,2,4-oxadiazol-3-yl)benzaldehyde (85% yield). $^1$H NMR (CDCl$_3$) δ 8.00 (d, 2H, J=8.2), 7.41 (d, 2H, J=8.2), 7.08 (d, 2H, J=8.5), 6.82 (d, 2H, J=8.5), 3.88 (s, 2H), 2.90 (t, 2H, J=6.6), 2.80 (t, 2H, J=6.6), 2.28 (m, 1H), 1.57 (s, 6H), 1.47 (s, 9H), 1.30 (m, 4H). MS: m/z 478 (M+1).

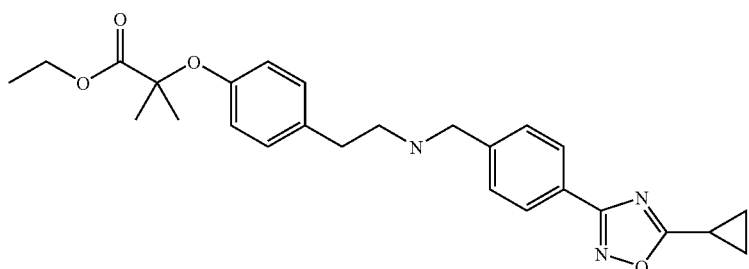

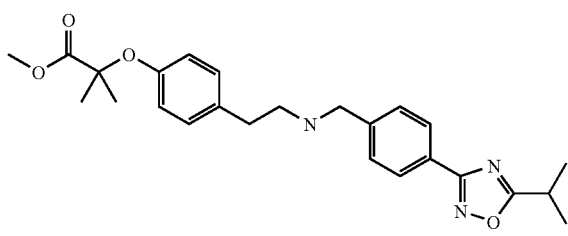

Methyl 2-[4-(2-{[4-(5-isopropyl-1,2,4-oxadiazol-3-yl)benzyl]amino}ethyl)phenoxy]-2-methylpropanoate A solution of methyl 2-[4-(2-aminoethyl)phenoxy]-2-methylpropanoate (1 g; 4.22 mmol) in dichloromethane (30 ml) was treated under nitrogen with 4-(5-isopropyl-1,2,4-oxadiazol-3-yl)benzaldehyde (0.96 g; 4.43 mmol), sodium triacetoxyborohydride (0.94 g; 4.43 mmol) and acetic acid (0.24 ml; 4.23 mmol). After stirring at rt overnight, the mixture was concentrated and partitioned between ethyl acetate and 1N NaOH. The organic phase was washed with brine, dried over sodium sulfate, filtered and concentrated. Purification by flash chromatography using an ethyl acetate-hexane gradient (20–70%) followed by a methanol-dichloromethane gradient (1–10%) afforded the title compound (1.5 g; 81% yield).

$^1$H NMR (CDCl$_3$) δ 7.96 (d, 2H, J=8.1), 7.32 (d, 2H, J=8.1), 7.0 (d, 2H, J=8.5), 6.70 (d, 2H, J=8.5), 3.78 (s, 2H), 3.70 (s, 3H), 3.21 (m, 1H), 2.80 (t, 2H, J=6.9), 2.70 (t, 2H, J=6.9), 1.51 (s, 6H), 1.39 (d, 6H, J=6.9).

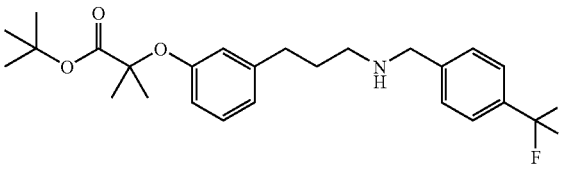

tert-Butyl 2-methyl-2-[3-(3-{[4-(trifluoromethyl)benzyl]amino}propyl)phenoxy]propanoate Reductive amination of tert-butyl 2-[3-(3-aminopropyl)phenoxy]-2-methylpropanoate with 4-trifluoromethyl benzaldehyde as per general procedure A afforded after column chromatography the title compound in 49% yield.

$^1$H NMR (CDCl$_3$) δ 7.58 (d, 2H, J=8.1), 7.44 (d, 2H, J=8.1), 7.13 (t, 1H, J=7.8), 6.79 (d, 1H, J=7.8), 6.72 (bs, 1H), 6.71 (dd, 1H, J=7.8 and 2.4), 3.83 (s, 2H), 2.64 (m, 4H), 1.83 (m, 2H), 1.57 (s, 6H), 1.45 (s, 9H). MS: m/z 452 (M+1).

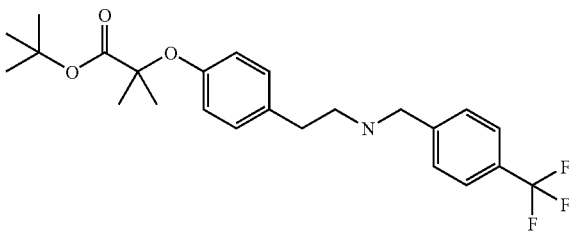

tert-Butyl 2-methyl-2-[4-(2-{[4-(trifluoromethyl)benzyl]amino}ethyl)phenoxy]propanoate Reductive amination of tert-butyl 2-[4-(2-aminoethyl)phenoxy]-2-methylpropanoate with 4-trifluoromethyl benzaldehyde as per general procedure A afforded after column chromatography the title compound in 93% yield.

$^1$H NMR (CDCl$_3$) δ 7.53 (d, 2H, J=8.1), 7.36 (d, 2H, J=8.1), 7.04 (d, 2H, J=8.6), 6.78 (d, 2H, J=8.6), 3.82 (s, 2H), 2.83 (t, 2H, J=6.7), 2.74 (t, 2H, J=6.7), 1.58 (s, 6H), 1.42 (s, 9H).

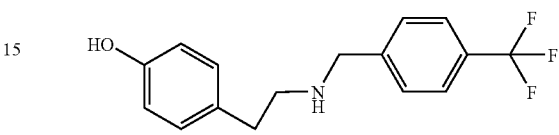

4-(2-{[4-(Trifluoromethyl)benzyl]amino}ethyl)phenol

A suspension of tyramine (1 g; 7.29 mmol) in MeOH (8 ml) was treated with 4-trifluoromethyl benzaldehyde (1.27 g; 7.29 mmol) and trimethylorthoformate (5 ml). The reaction mixture was stirred at rt overnight and then treated with sodium borohydride (0.69 g; 18.23 mmol) in small portions. After stirring for 30 minutes, it was concentrated and partitioned between ethyl acetate and water. The organic phase was washed with brine, dried over sodium sulfate, filtered and concentrated. Crystallization from ethyl ether-hexane provided the title compound as a white crystalline solid (1.67 g; 78% yield). $^1$H NMR (CDCl$_3$) δ 7.54 (d, 2H, J=8.0), 7.37 (d, 2H, J=8.0), 7.00 (d, 2H, J=8.4), 6.68 (d, 2H, J=8.4), 4.50 (bs, 2H), 3.86 (s, 2H), 2.88 (t, 2H, J=6.9), 2.77 (t, 2H, J=6.9).

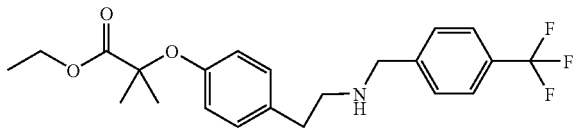

Ethyl 2-methyl-2-[4-(2-{[4-(trifluoromethyl)benzyl]amino}ethyl)phenoxy]propanoate A solution of 4-(2-{[4-(trifluoromethyl)benzyl]amino}ethyl)phenol (1 g; 3.39 mmol) in THF (10 ml) was treated under nitrogen with NaH (0.14 g of a 60% dispersion in oil; 3.56 mmol). After stirring for 10 minutes, ethyl-2-bromo isobutyrate (0.69 g; 3.56 mmol) was added and the mixture heated at 75C for 12 hr. Upon cooling, additional sodium hydride (0.040 g; 1.01 mmol) and bromide (0.21 g; 1.06 mmol) were added. After heating at 75C for 3 hr, the mixture was concentrated and partitioned between ethyl acetate and 1N NaOH. The organic phase was washed with 1N NaOH and brine, dried over sodium sulfate and concentrated. Purification by flash chromatography on silica gel using a methanol-dichloromethane gradient (1–10%) afforded the title compound (1.12 g; 80% yield).

$^1$H NMR (CDCl$_3$) δ 7.50 (d, 2H, J=8.0), 7.35 (d, 2H, J=8.0), 7.03 (d, 2H, J=8.4), 6.76 (d, 2H, J=8.4), 4.18 (q, 2H, J=7.1), 3.79 (s, 2H), 2.81 (t, 2H, J=6.8), 2.72 (t, 2H, J=6.8), 1.55 (s, 6H), 1.20 (t, 3H, J=7.1).

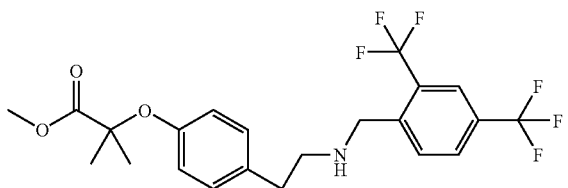

Methyl 2-[4-(2-{[2,4-bis(trifluoromethyl)benzyl]
amino}ethyl)phenoxy]-2-methylpropanoate A solution of methyl 2-[4-(2-aminoethyl)phenoxy]-2-methylpropanoate (Biochim. Biophys. Acta 1997, 1339 (2), 321–330) (2 g; 8.44 mmol) in dichloromethane (20 ml) was treated with DIEA (1.47 ml; 8.44 mmol) and 2,4-bis-trifluoromethyl-benzyl bromide (2.59 g; 8.44 mmol). After stirring at rt overnight, the reaction mixture was concentrated and partitioned between ethyl acetate and saturated Na$_2$CO$_3$ solution. The organic phase was washed with Na$_2$CO$_3$ solution and brine, dried over sodium sulfate and concentrated. Purification by flash chromatography on silica gel using an ethyl acetate-hexane mixture (10–50%) afforded the title compound (2.0 g; 51% yield).

$^1$H NMR (CDCl$_3$) δ 7.83 (s, 1H), 7.79 (d, 1H, J=8.3), 7.73 (d, 1H, J=8.3), 7.04 (d, 2H, J=8.4), 6.74 (d, 2H, J=8.4), 3.99 (s, 2H), 3.74 (s, 3H), 2.86 (t, 2H, J=6.8), 2.75 (t, 2H, J=6.8), 1.55 (s, 6H). MS: m/z 464 (M+1).

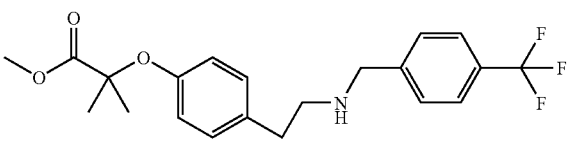

Methyl 2-methyl-2-[4-(2-{[4-(trifluoromethyl)benzyl]amino}ethyl)phenoxy]propanoate Similarly, alkylation of methyl 2-[4-(2-aminoethyl)phenoxy]-2-methylpropanoate with 4-trifluoromethyl benzyl bromide afforded the title compound in 52% yield.

$^1$H NMR (CDCl$_3$) δ 7.52 (d, 2H, J=8.0), 7.36 (d, 2H, J=8.0), 7.05 (d, 2H, J=8.4), 6.76 (d, 2H, J=8.4), 3.81 (s, 2H), 3.74 (s, 3H), 2.82 (t, 2H, J=6.8), 2.73 (t, 2H, J=6.8).

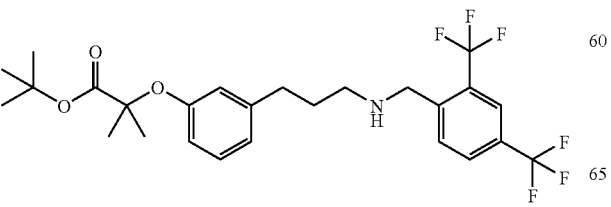

tert-Butyl 2-[3-(3-{[2,4-bis(trifluoromethyl)benzyl]
amino}propyl)phenoxy]-2-methylpropanoate Similarly, alkylation of tert-butyl 2-[3-(3-aminopropyl)phenoxy]-2-methylpropanoate with 2,4-bis-trifluoromethyl-benzyl bromide afforded the title compound in 38% yield.

$^1$H NMR (CDCl$_3$) δ 7.86 (m, 2H), 7.77 (d, 1H, J=8.3), 7.11 (t, 1H, J=7.9), 6.77 (d, 1H, J=7.7), 6.69 (bs, 1H), 6.64 (dd, 1H, J=8.1; 2.4), 3.99 (s, 2H), 2.66 (t, 2H, J=7.0), 2.60 (t, 2H, J=7.7), 1.83 (m, 2H), 1.53 (s, 6H), 1.41 (s, 9H).

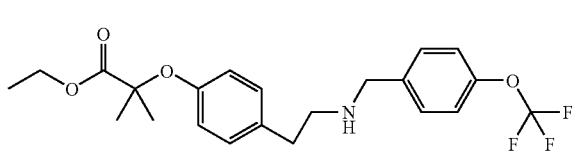

Ethyl 2-methyl-2-[4-(2-{[4-(trifluoromethoxy)benzyl]amino}ethyl)phenoxy]propanoate Step 1. A solution of tyramine (8.56 g; 62.41 mmol) in MeOH (60 ml) was treated with 4-trifluoromethoxy benzaldehyde (11.3 g; 59.4 mmol) and trimethylorthoformate (32 ml) under a nitrogen atmosphere. After stirring at rt overnight, the reaction mixture was cooled in an ice bath and treated with sodium borohydride (5.65 g; 148.6 mmol) in small portions. The mixture was stirred for 1.5 hr and then concentrated. The residue was partitioned between ethyl acetate and water. The organic phase was washed with brine, dried over sodium sulfate, filtered and concentrated to afford 4-(2-{[4-(trifluoromethyl)benzyl]amino}ethyl)phenol, which was used in the next step without further purification.

Step 2. A solution of the previous intermediate (~62.41 mmol) in MeCN (100 ml) was treated under nitrogen with Cs2CO3 (40.66 g; 124.8 mmol) and ethyl-2-bromo-isobutyrate (24.34 g; 124.8 mmol). After heating at 80C for 5 hr, the reaction mixture was concentrated and the residue was partitioned between ethyl acetate and water. The organic phase was washed with brine, dried over sodium sulfate, filtered and concentrated. Purification by flash chromatography on silica gel using an ethyl acetate-hexane gradient (20–80%), followed by a methanol-dichloromethane gradient (1–10%) afforded the title compound (19.4 g; 74% yield).

$^1$H NMR (CDCl$_3$) δ 7.26 (d, 2H, J=8.5), 7.11 (d, 2H, J=8.5), 7.03 (d, 2H, J=8.5), 6.75 (d, 2H, J=8.5), 4.20 (q, 2H, J=7.1), 3.75 (s, 2H), 2.82 (t, 2H, J=6.6), 2.72 (t, 2H, J=6.6), 1.55 (s, 6H), 1.22 (t, 3H, J=7.1).

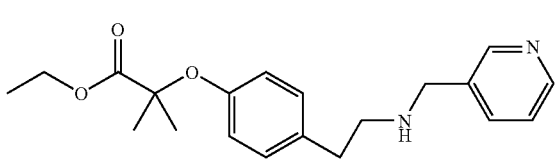

Ethyl 2-methyl-2-(4-{2-[(pyridin-3-ylmethyl)amino]ethyl}phenoxy)propanoate

Similarly prepared from tyramine and 3-pyridine carboxaldehyde.

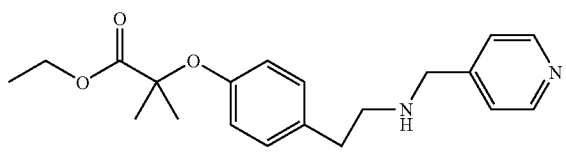

Ethyl 2-methyl-2-(4-{2-[(pyridin-4-ylmethyl)amino]ethyl}phenoxy)propanoate

Similarly prepared from tyramine and 4-pyridine carboxaldehyde.

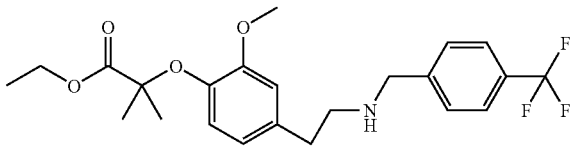

Ethyl 2-[2-methoxy-4-(2-{[4-(trifluoromethyl)benzyl]amino}ethyl)phenoxy]-2-methylpropanoate Similarly prepared from 4-(2-aminoethyl)-2-methoxyphenol and 4-trifluoromethyl benzaldehyde.

Ethyl 2-[2-bromo-4-(2-{[4-(trifluoromethyl)benzyl]amino}ethyl)phenoxy]-2-methylpropanoate Step 1. Reductive amination of 3-bromo-4-methoxyphenethylamine (10 g; 4.35 mmol) with 4-trifluoromethyl benzaldehyde (7.57 g; 4.35 mmol) as per general procedure A provided after workup N-[2-(3-bromo-4-methoxyphenyl)ethyl]-N-[4-(trifluoromethyl)benzyl]amine (15.2 g; 90% yield), which was used in the next step without further purification.

Step 2. Demethylation of the previous intermediate with boron tribromide as per general procedure F afforded after workup 2-bromo-4-(2-{[4-(trifluoromethyl)benzyl]amino}ethyl)phenol, which was used in the next step without further purification.

Step 3. Alkylation of the above intermediate with ethyl-2-bromoisobutyrate as per general procedure C (2.2 eq NaH, THF, reflux, 15 hr) afforded after chromatography the intermediate ethyl ester.

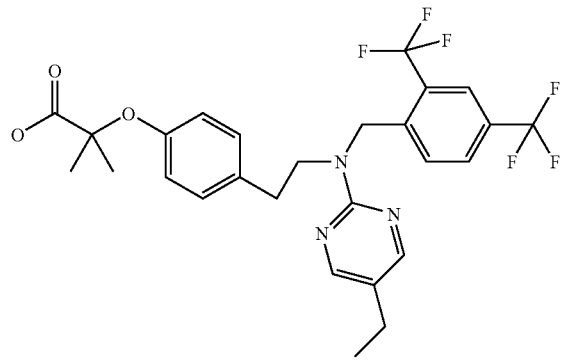

2-(4-{2-[[2,4-Bis(trifluoromethyl)benzyl](5-ethylpyrimidin-2-yl)amino]ethyl}phenoxy)-2-methylpropanoic acid Step 1. Condensation of methyl 2-[4-(2-{[2,4-bis(trifluoromethyl)benzyl]amino}ethyl)phenoxy]-2-methylpropanoate (250 mg; 0.54 mmol) with 2-chloro-5-ethyl-pyrimidine (230 mg; 1.62 mmol) as per general procedure E (conditions: 1 eq DIEA, toluene, 150C, 16 hr) provided after chromatography the intermediate methyl ester (117 mg; 38% yield).

Step 2. Hydrolysis of the ester (117 mg) with NaOH as per general procedure H provided after chromatography the title compound as a glassy solid (55 mg; 48% yield).

$^1$H NMR (CDCl$_3$) δ 8.22 (s, 2H), 7.85 (s, 1H), 7.61 (d, 2H, J=8.3), 7.31 (d, 2H, J=8.3), 7.04 (d, 2H, J=8.5), 6.80 (d, 2H, J=8.5), 4.93 (s, 2H), 3.72 (t, 2H, J=7.5), 2.85 (t, 2H, J=7.5), 2.47 (q, 2H, J=7.6), 1.53 (s, 6H), 1.23 (t, 3H, J=7.6).

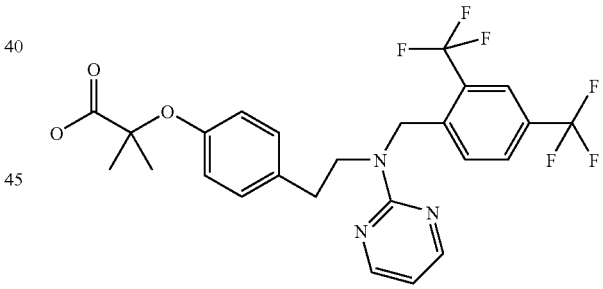

2-(4-{2-[[2,4-Bis(trifluoromethyl)benzyl](pyrimidin-2-yl)amino]ethyl}phenoxy)-2-methylpropanoic acid Step 1. Condensation of methyl 2-[4-(2-{[2,4-bis(trifluoromethyl)benzyl]amino}ethyl)phenoxy]-2-methylpropanoate (200 mg; 0.43 mmol) with 2-chloro-pyrimidine (64 mg; 0.56 mmol) as per general procedure E (conditions: 2 eq. DIEA, THF, 100C, 16 hr) provided after chromatography the intermediate methyl ester (17 mg; 8% yield). MS: m/z 542 (M+1).

Step 2. Hydrolysis of the methyl ester (17 mg) with NaOH as per general procedure H provided after chromatography and crystallization from dichloromethane-hexane, the title compound as a white solid (10 mg; 58% yield).

$^1$H NMR (CDCl$_3$) δ 8.36 (d, 2H, J=4.7), 7.88 (s, 1H), 7.64 (d, 1H, J=8.1), 7.32 (d, 1H, J=8.1), 7.08 (d, 2H, J=8.4), 6.83

(d, 2H, J=8.4), 6.59 (t, 1H, J=4.7), 4.96 (s, 2H), 3.77 (t, 2H, J=7.5), 2.90 (t, 2H, J=7.5), 1.54 (s, 6H).

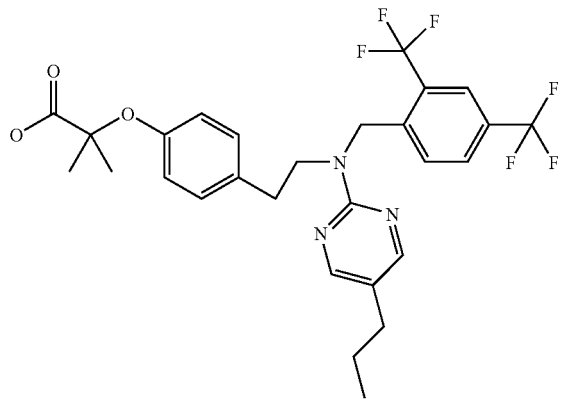

2-(4-{2-[[2,4-Bis(trifluoromethyl)benzyl](5-propylpyrimidin-2-yl)amino]ethyl}phenoxy)-2-methylpropanoic acid Condensation of methyl 2-[4-(2-{[2,4-bis(trifluoromethyl)benzyl]amino}ethyl)phenoxy]-2-methylpropanoate (250 mg; 0.54 mmol) with 2-chloro-5-propyl-pyrimidine (85 mg; 0.54 mmol) as per general procedure E (1.25 eq. K2CO3, dioxane, 220C, 15 hr) was accompanied by partial ester hydrolysis and afforded the title compound in low yield. For ease of purification, the carboxylic acid was converted to its methyl ester derivative (using a standard trimethylsilyldiazomethane/MeOH protocol), chromatographed and subjected to the base-mediated hydrolysis procedure H to afford the title compound in 17% yield (29 mg).

$^1$H NMR (CDCl$_3$) δ 8.20 (s, 2H), 7.85 (s, 1H), 7.62 (d, 1H, J=8.2), 7.32 (d, 1H, J=8.2), 7.04 (d, 1H, J=8.1), 6.80 (d, 1H, J=8.1), 4.93 (s, 2H), 3.72 (t, 2H, J=7.4), 2.86 (t, 2H, J=7.4), 2.40 (t, 2H, J=7.6), 1.58 (m, 2H), 1.53 (s, 6H), 0.93 (t, 3H, J=7.6).

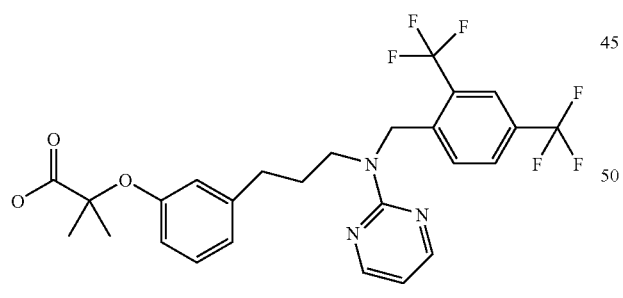

2-(3-{3-[[2,4-Bis(trifluoromethyl)benzyl](pyrimidin-2-yl)amino]propyl}phenoxy)-2-methylpropanoic acid Step 1. Condensation of tert-butyl 2-[3-(3-{[2,4-bis(trifluoromethyl)benzyl]amino}propyl)phenoxy]-2-methylpropanoate (200 mg; 0.39 mmol) with 2-chloro-pyrimidine (133 mg; 1.16 mmol) as per general procedure E (conditions: 3 eq DIEA, dioxane, 120C, 72 hr) provided the intermediate ester (110 mg; 48% yield). MS: m/z 598 (M+1).

Step 2. Hydrolysis of the above tert-butyl ester (110 mg) with TFA as per general procedure I provided after chromatography the title compound as a glassy solid (54 mg; 55% yield).

$^1$H NMR (CDCl$_3$) δ 8.32 (d, 2H, J=4.7), 7.88 (s, 1H), 7.64 (d, 1H, J=8.1), 7.30 (d, 1H, J=8.1), 7.11 (t, 1H, J=7.8), 6.79 (d, 1H, J=7.8), 6.76 (bs, 1H), 6.71 (dd, 1H, J=7.8; 2.2), 6.56 (t, 1H, J=4.7), 5.06 (s, 2H), 3.55 (t, 2H, J=7.6), 2.57 (t, 2H, J=7.6), 1.91 (m, 2H), 1.57 (s, 6H).

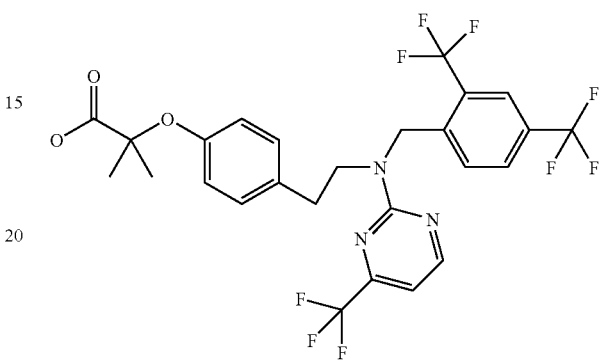

2-[4-(2-{[2,4-bis(trifluoromethyl)benzyl][4-(trifluoromethyl)pyrimidin-2-yl]amino}ethyl)phenoxy]-2-methylpropanoic acid Step 1. Condensation of methyl 2-[4-(2-{[2,4-bis(trifluoromethyl)benzyl]amino}ethyl)phenoxy]-2-methylpropanoate (250 mg; 0.54 mmol) with 2-chloro-4-trifluoromethyl-pyrimidine (108 mg; 0.59 mmol) as per general procedure E (conditions: 1.1 eq. DIEA, toluene, 170C, 16 hr) provided the intermediate ester (300 mg; 83% yield). MS: m/z 610 (M+1).

Step 2. Hydrolysis of the methyl ester (300 mg) with NaOH as per general procedure H provided after chromatography and crystallization from dichloromethane-hexane, the title compound as a white solid (191 mg; 65% yield).

$^1$H NMR (CDCl$_3$) δ 10.2 (bs, 1H), 8.60 (broad d, 1H), 7.90 (s, 1H), 7.65 (d, 1H, J=8.1), 7.33 (d, 1H, J=8.1), 7.08 (d, 2H, J=8.1), 6.84 (m, 3H), 5.02 (s, 2H), 3.79 (t, 2H, J=7.5), 2.90 (t, 2H, J=7.5), 1.55 (s, 6H). MS: m/z 596 (M+1).

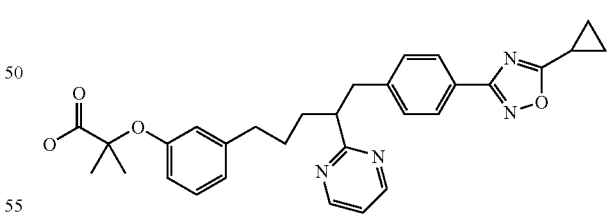

2-(3-{3-[[4-(5-Cyclopropyl-1,2,4-oxadiazol-3-yl)benzyl](pyrimidin-2-yl)amino]propyl}phenoxy)-2-methylpropanoic acid Step 1. Condensation of tert-butyl 2-[3-(3-{[4-(5-cyclopropyl-1,2,4-oxadiazol-3-yl)benzyl]amino}propyl)phenoxy]-2-methylpropanoate (100 mg; 0.20 mmol) with 2-chloro-pyrimidine (26 mg; 0.22 mmol) as per general procedure E (conditions: 1.1 eq DIEA, dioxane, 180C, 16 hr) provided the intermediate ester (76 mg; 66% yield).

Step 2. Hydrolysis of the tert-butyl ester (76 mg) with TFA as per general procedure I provided after radial chromatography and crystallization from hexane, the title compound as a white solid (25 mg; 36% yield).

$^1$H NMR (CDCl$_3$) δ 8.31 (d, 2H, J=4.7), 7.88 (d, 2H, J=8.2), 7.23 (d, 2H, J=8.2), 7.10 (t, 1H, J=7.8), 6.77 (d, 1H, J=7.8), 6.70 (m, 2H), 6.51 (t, 1H, J=4.7), 4.86 (s, 2H), 3.53 (t, 2H, J=7.6), 2.53 (t, 2H, J=7.6), 2.23 (m, 1H), 1.83 (m, 2H), 1.56 (s, 6H), 1.28 (m, 4H). MS: m/z 514 (M+1).

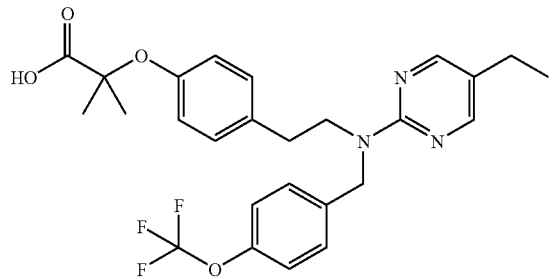

2-[4-(2-{(5-Ethylpyrimidin-2-yl)[4-(trifluoromethoxy)benzyl]amino}ethyl)phenoxy]-2-methylpropanoic acid Step 1. Condensation of ethyl 2-methyl-2-[4-(2-{[4-(trifluoromethyl)benzyl]amino}ethyl)phenoxy]propanoate (1.20 g; 2.82 mmol) with 2-chloro-5-ethyl-pyrimidine (0.38 g; 2.64 mmol) as per general procedure E (conditions: 1.1 eq DIEA, toluene, 210C, 16 hr) provided after chromatography the intermediate ester (900 mg; 64% yield).

Step 2. Hydrolysis of the ethyl ester (900 mg) with NaOH as per general procedure H provided after chromatography the title compound as a glassy solid (680 mg; 79% yield). $^1$H NMR (CDCl$_3$) δ 1.20 (t, 3H, J=7.7); 1.54 (s, 6H); 2.44 (q, 2H, J=7.3); 2.80 (t, 2H, J=7.7); 3.69 (t, 2H, J=7.7); 4.70 (s, 2H); 6.82 (d, 2H, J=8); 7.05 (d, 2H, J=8.9); 7.16 (d, 2H, J=8.6); 7.36 (d, 2H, J=8.3), 8.21 (s, 2H). Anal. Calcd. For C$_{26}$F$_{28}$F$_3$N$_3$O$_4$: C, 62.02; H, 5.61; N, 8.35. Found C, 61.81; H, 5.74; N, 8.06. MS: m/z 504 (M+1).

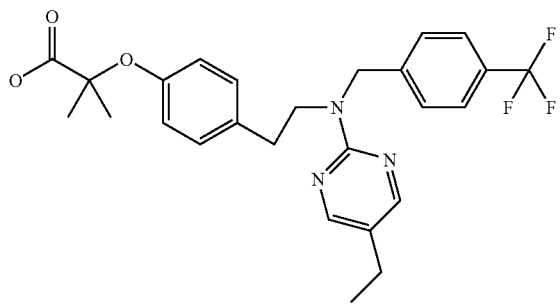

2-[4-(2-{(5-Ethylpyrimidin-2-yl)[4-(trifluoromethyl)benzyl]amino}ethyl)phenoxy]-2-methylpropanoic acid Step 1. Condensation of ethyl 2-methyl-2-[4-(2-{[4-(trifluoromethyl)benzyl]amino}ethyl)phenoxy]propanoate (200 mg; 0.49 mmol) with 2-chloro-5-ethyl-pyrimidine (77 mg; 0.54 mmol) as per general procedure E (conditions: 1.1 eq DIEA, toluene, 205C, 16 hr) provided after chromatography the intermediate ester (110 mg; 43% yield). MS: m/z 516 (M+1).

Step 2. Hydrolysis of the ethyl ester (110 mg) with NaOH as per general procedure H provided after chromatography the title compound as a glassy solid (64 mg; 61% yield). $^1$H NMR (CDCl$_3$) δ 8.23 (s, 2H), 7.47 (d, 2H, J=8.0), 7.22 (d, 2H, J=8.0), 7.02 (d, 2H, J=8.3), 6.79 (d, 2H, J=8.3), 4.71 (s, 2H), 3.72 (t, 2H, J=7.3), 2.80 (t, 2H, J=7.3), 2.46 (q, 2H, J=7.6), 1.53 (s, 6H), 1.18 (t, 3H, J=7.6).

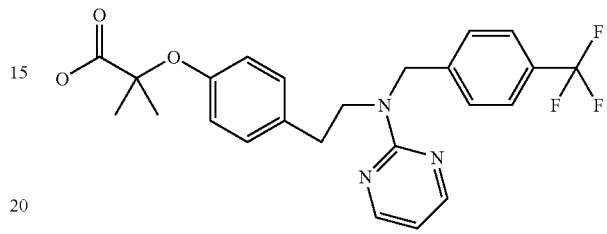

2-Methyl-2-[4-(2-{pyrimidin-2-yl[4-(trifluoromethyl)benzyl]amino}ethyl)phenoxy]propanoic acid Step 1. Condensation of ethyl 2-methyl-2-[4-(2-{[4-(trifluoromethyl)benzyl]amino}ethyl)phenoxy]propanoate (200 mg; 0.49 mmol) with 2-chloro-pyrimidine (62 mg; 0.54 mmol) as per general procedure E (conditions: 1.1 eq DIEA, toluene, 205C, 16 hr) provided after chromatography the intermediate ester (200 mg; 84% yield). MS: m/z 488 (M+1).

Step 2. Hydrolysis of the ethyl ester (200 mg) with NaOH as per general procedure H provided after chromatography the title compound as a glassy solid (112 mg; 58% yield). $^1$H NMR (CDCl$_3$) δ 10.8 (broad s, 1H), 8.36 (d, 2H, J=4.8), 7.48 (d, 2H, J=8.2), 7.24 (d, 2H, J=8.2), 7.03 (d, 2H, J=8.5), 6.81 (d, 2H, J=8.5), 6.54 (t, 1H, J=4.8), 4.74 (s, 2H), 3.74 (t, 2H, J=7.5), 2.81 (t, 2H, J=7.5), 1.54 (s, 6H).

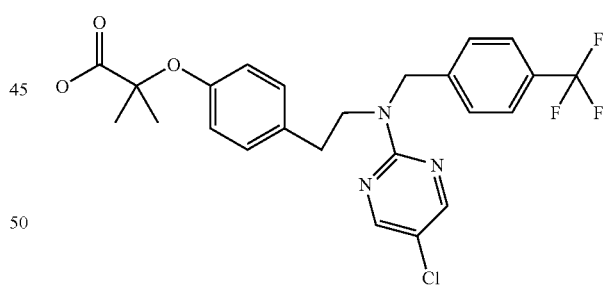

2-[4-(2-{(5-Chloropyrimidin-2-yl)[4-(trifluoromethyl)benzyl]amino}ethyl)phenoxy]-2-methylpropanoic acid Step 1. Condensation of ethyl 2-methyl-2-[4-(2-{[4-(trifluoromethyl)benzyl]amino}ethyl)phenoxy]propanoate (200 mg; 0.49 mmol) with 2,5-dichloro-pyrimidine (70 mg; 0.46 mmol; prepared as in Liebigs Ann. Chem. 1985, p. 316) as per general procedure E (conditions: 2 eq DIEA, dioxane, 205C, 15 hr) provided the intermediate ester (195 mg; 77% yield). MS: m/z 522 (M+1).

Step 2. Hydrolysis of the ethyl ester (200 mg) with NaOH as per general procedure H provided after chromatography the title compound as a glassy solid (90 mg; 65% yield). ¹H NMR (CDCl₃) δ 8.25 (s, 2H), 7.50 (d, 2H, J=8.1), 7.24 (d, 2H, J=8.1), 7.04 (d, 2H, J=8.5), 6.83 (d, 2H, J=8.5), 4.72 (s, 2H), 3.73 (t, 2H, J=7.5), 2.83 (t, 2H, J=7.5), 1.56 (s, 6H). MS: m/z 492 (M−1).

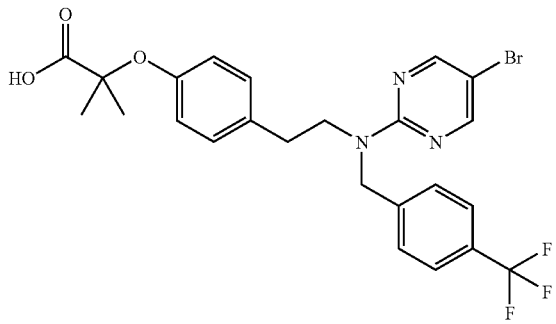

2-[4-(2-{(5-Bromopyrimidin-2-yl)[4-(trifluoromethyl)benzyl]amino}ethyl)phenoxy]-2-methylpropanoic acid Step 1. Condensation of ethyl 2-methyl-2-[4-(2-{[4-(trifluoromethyl)benzyl]amino}ethyl)phenoxy]propanoate (5.16 g; 12.6 mmol) with 2,5-dibromo-pyrimidine (3.0 g; 10.5 mmol) as per general procedure E (conditions: 1.1 eq DIEA, 210C, 2 hr) provided after chromatography the intermediate ethyl 2-[4-(2-{(5-bromopyrimidin-2-yl)[4-(trifluoromethyl)benzyl]amino}ethyl)phenoxy]-2-methylpropanoate (2.2 g; 37% yield).

Step 2. Hydrolysis of the ethyl ester with LiOH as per general procedure provided after workup the title compound in good yield.

¹H NMR (CDCl₃) δ 8.39 (s, 2H), 7.60 (d, 2H, J=8.1), 7.39 (d, 2H, J=8.0), 7.08 (d, 2H, J=8.4), 6.84 (d, 2H, J=8.4), 4.81 (s, 2H), 3.80 (t, 2H, J=7.2), 2.87 (t, 2H, J=7.2), 1.54 (s, 6H).

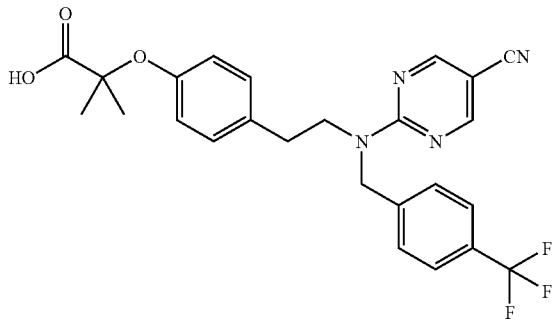

2-[4-(2-{(5-Cyanopyrimidin-2-yl)[4-(trifluoromethyl)benzyl]amino}ethyl)phenoxy]-2-methylpropanoic acid Step 1. Ethyl 2-[4-(2-{(5-bromopyrimidin-2-yl)[4-(trifluoromethyl)benzyl]amino}ethyl)phenoxy]-2-methylpropanoate, (100 mg; 0.18 mmol) was reacted with CuCN (21 mg; 0.23 mmol) in 0.88 ml of DMF at 145C for 14 hours. The reaction mixture was diluted with water and extracted with ethyl acetate. The organic layer was dried over sodium sulfate, filtered and concentrated. Purification by flash chromatography on silica gel using 20% ethyl acetate in hexanes provided the intermediate ester (35 mg; 39% yield).

Step 2. Hydrolysis of the ethyl ester with LiOH as per general procedure H provided after workup the title compound in good yield.

¹H NMR (CD₃OD) δ 8.83 (s, 2H), 7.62 (d, 2H, J=8.1), 7.42 (d, 2H, J=8.0), 7.11 (d, 2H, J=8.4), 6.85 (d, 2H, J=8.5), 4.92 (s, 2H), 3.90 (t, 2H, J=7.0), 2.91 (t, 2H, J=7.1), 1.55 (s, 6H). MS: m/z 503 (M+1).

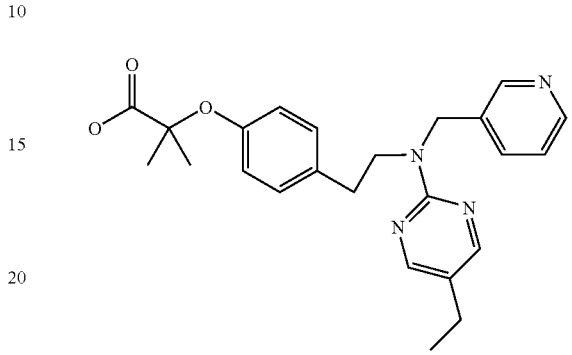

2-(4-{2-[(5-Ethylpyrimidin-2-yl)(pyridin-3-ylmethyl)amino]ethyl}phenoxy)-2-methylpropanoic acid Step 1. Condensation of ethyl 2-methyl-2-(4-{2-[(pyridin-3-ylmethyl)amino]ethyl}phenoxy)propanoate (255 mg; 0.75 mmol) with 2-chloro-5-ethyl-pyrimidine (105 mg; 0.75 mmol) as per general procedure E (conditions: 1 eq DIEA, toluene, 100 C, 16 hr) provided the intermediate ester (31 mg; 9% yield).

Step 2. Hydrolysis of the ethyl ester (31 mg) with LiOH as per general procedure H provided the title compound as a glassy solid (7 mg; 25% yield).

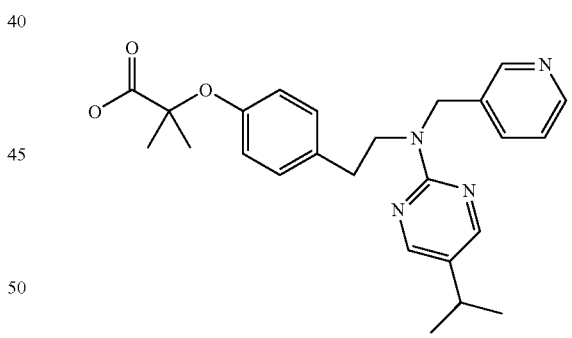

2-(4-{2-[(5-isopropylpyrimidin-2-yl)(pyridin-3-ylmethyl)amino]ethyl}phenoxy)-2-methylpropanoic acid Step 1. Condensation of ethyl 2-methyl-2-(4-{2-[(pyridin-3-ylmethyl)amino]ethyl}phenoxy)propanoate (231 mg; 0.75 mmol) with 2-chloro-5-isopropyl-pyrimidine (106 mg; 0.68 mmol) as per general procedure E (conditions: 2.5 eq DIEA, toluene, 110C, 16 hr) provided the intermediate ester (36 mg; 12% yield).

Step 2. Hydrolysis of the ethyl ester (36 mg) with LiOH as per general procedure H provided the title compound (19 mg; 56% yield).

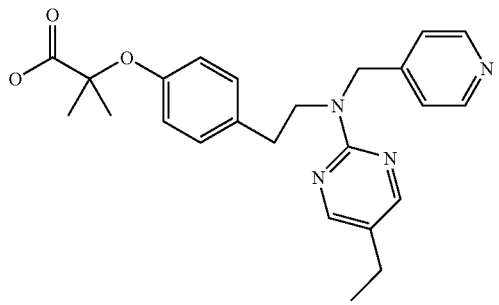

2-(4-{2-[(5-Ethylpyrimidin-2-yl)(pyridin-4-ylmethyl)amino]ethyl}phenoxy)-2-methylpropanoic acid Step 1. Condensation of ethyl 2-methyl-2-(4-{2-[(pyridin-4-ylmethyl)amino]ethyl}phenoxy)propanoate (369 mg; 1.08 mmol) with 2-chloro-5-ethyl-pyrimidine (153 mg; 1.08 mmol) as per general procedure E (conditions: 2.2 eq DIEA, toluene, 110 C, 16 hr) provided the intermediate ester (19 mg; 4% yield)

Step 2. Hydrolysis of the ethyl ester (19 mg) with LiOH as per general procedure H provided the title compound as a light brown oil (10 mg; 54% yield).

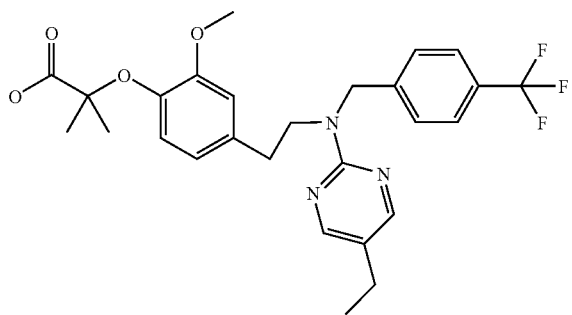

2-[4-(2-{(5-Ethylpyrimidin-2-yl)[4-(trifluoromethyl)benzyl]amino}ethyl)-2-methoxyphenoxy]-2-methylpropanoic acid Step 1. Condensation of ethyl 2-[2-methoxy-4-(2-{[4-(trifluoromethyl)benzyl]amino}ethyl)phenoxy]-2-methylpropanoate (500 mg; 1.14 mmol) with 2-chloro-5-ethyl-pyrimidine (178 mg; 1.25 mmol) as per general procedure E (conditions: 1.2 eq DIEA, toluene, 200C, 16 hr) provided the intermediate ester (142 mg; 26% yield).

Step 2. Hydrolysis of the ethyl ester (142 mg) with LiOH as per general procedure H provided the title compound as a glassy solid (118 mg; 88% yield).

$^1$H NMR (CDCl$_3$) δ 8.18 (s, 2H), 7.49 (d, 2H, J=8.1), 7.25 (d, 2H, J=8.1), 6.86 (d, 1H, J=7.9), 6.64–6.72 (m, 2H), 4.76 (s, 2H), 3.80 (s, 3H), 3.77 (t, 2H, J=7.5), 2.85 (t, 2H, J=7.7), 2.45 (q, 2H, J=7.7), 1.45 (s, 6H), 1.18 (t, 3H, J=7.7).

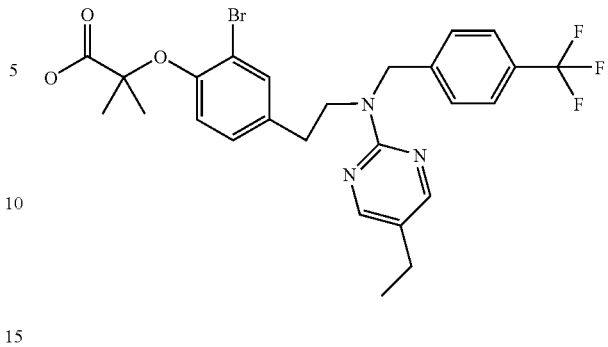

2-[2-Bromo-4-(2-{(5-ethylpyrimidin-2-yl)[4-(trifluoromethyl)benzyl]amino}ethyl)phenoxy]-2-methylpropanoic acid Step 1. Condensation of ethyl 2-[2-bromo-4-(2-{[4-(trifluoromethyl)benzyl]amino}ethyl)phenoxy]-2-methylpropanoate (500 mg; 1.02 mmol) with 2-chloro-5-ethyl-pyrimidine (1 eq) as per general procedure E (conditions: 1.1 eq DIEA, toluene, 200C, 14 hr) provided the intermediate ethyl 2-[2-bromo-4-(2-{(5-ethylpyrimidin-2-yl)[4-(trifluoromethyl)benzyl]amino}ethyl)phenoxy]-2-methylpropanoate (134 mg; 23% yield).

Step 2. Hydrolysis of the ethyl ester with LiOH as per procedure H provided the title compound as a beige solid.

$^1$H NMR (CDCl$_3$) δ 8.20 (s, 2H), 7.49 (d, 2H, J=8.1), 7.36 (d, 1H, J=2.0), 7.24 (d, 2H, J=8.1), 6.97 (dd, 1H, J=8.4, 2.0), 6.88 (d, 1H, J=8.2), 4.77 (s, 2H), 3.72 (t, 2H, J=7.9), 2.79 (t, 2H, J=7.3), 2.46 (q, 2H, J=7.7), 1.57 (s, 6H), 1.18 (t, 3H, J=7.7). MS: m/z 566, 568 (M+1).

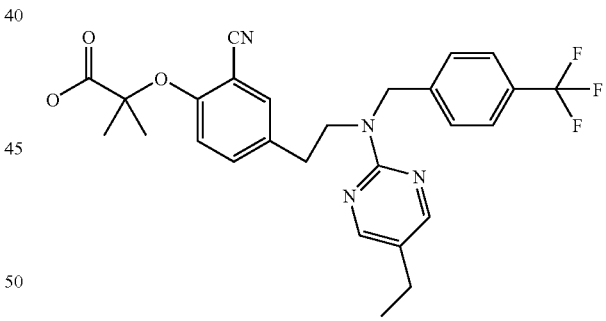

2-[2-Cyano-4-(2-{(5-ethylpyrimidin-2-yl)[4-(trifluoromethyl)benzyl]amino}ethyl)phenoxy]-2-methylpropanoic acid Step 1. A solution of ethyl 2-[2-bromo-4-(2-{(5-ethylpyrimidin-2-yl)[4-(trifluoromethyl)benzyl]amino}ethyl)phenoxy]-2-methylpropanoate (from step 1 in the previous example) (188 mg; 0.32 mmol) in DMF (2 ml) was treated with CuCN (37 mg; 0.41 mmol) and heated to reflux overnight under a nitrogen atmosphere. Upon cooling, the reaction mixture was filtered through a plug of silica gel and eluted with DMF. The filtrate was concentrated and partitioned between dichloromethane and brine. The organic phase was dried over MgSO₄, filtered and concentrated to afford ethyl 2-[2-cyano-4-(2-{(5-ethylpyrimidin-2-yl)[4-(trifluoromethyl)benzyl]amino}ethyl)phenoxy]-2-methylpropanoate (153 mg), which was used in the next step without further purification.

Step 2. Hydrolysis of the ethyl ester with LiOH as per general procedure H provided the title compound.

¹H NMR (CDCl₃) δ 8.21 (s, 2H), 7.48 (d, 2H, J=8.2), 7.33 (s, 1H), 7.23 (d, 2H, J=8.2), 7.17 (d, 1H, J=8.2), 6.77 (d, 1H, J=8.2), 4.78 (s, 2H), 3.78 (t, 2H, J=7.5), 2.77 (t, 2H, J=7.4), 2.46 (q, 2H, J=7.6), 1.60 (s, 6H), 1.18 (t, 3H, J=7.5). MS: m/z 513 (M+1).

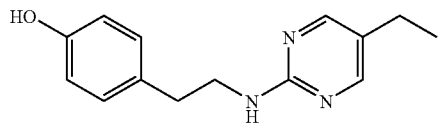

4-{2-[(5-Ethylpyrimidin-2-yl)amino]ethyl}phenol

Tyramine (5.52 g, 0.040 mol) in 40 ml of anhydrous DMF was treated with diisopropylethylamine (6.1 ml, 0.035 mol). After stirring at rt for 15 minutes, 2-chloro-5-ethylpyrimidine (4.25 ml, 0.035 mol) was added and the mixture heated at 80° C. for 14 hours. The solution was allowed to cool to room temperature and was partitioned between equal volumes of water and ethyl acetate. The aqueous phase was washed with ethyl acetate and the combined organic phases were dried over MgSO₄ and concentrated. The residue was purified by flash chromatography eluting with 40% ethyl acetate-hexane to afford the title compound as a colorless solid (4.94 g; 58% yield).

¹H NMR (CDCl₃) δ 1.20 (t, 3H, J=7.6); 2.46 (q, 2H, J=7.6); 2.83 (t, 2H, J=6.3); 3.515 (s, 1H); 3.63 (q, 2H, J=6.3); 5.14 (br s, 1H); 6.70 (d, 2H, J=8.4); 7.02 (d, 2H, J=8.3), 8.19 (s, 2H). MS: m/z 244 (M+1).

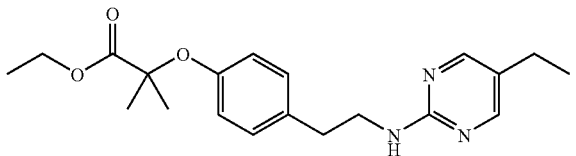

Ethyl 2-(4-{2-[(5-ethylpyrimidin-2-yl)amino]ethyl}phenoxy)-2-methylpropanoate

Alkylation of 4-{2-[(5-ethylpyrimidin-2-yl)amino]ethyl}phenol with 2 eq of ethyl 2-bromoisobutyrate as per general procedure C (conditions: 2 eq Cs₂CO₃, MeCN, 80C, 4 hr) provided the title compound (80% yield).

¹H NMR (CDCl₃) δ 1.19 (t, 3H, J=7.5); 1.26 (t, 3H, J=7.1); 1.60 (s, 6H); 2.45 (q, 2H, J=7.6); 2.84 (t, 2H, J=6.9); 3.62 (q, 2H, J=6.5); 4.23 (q, 2H, J=7.2); 5.00 (s, 2H); 6.80 (d, 2H, J=8.4); 7.11 (d, 2H, J=8.4), and 8.16 (s, 2H). MS: m/z 358 (M+1).

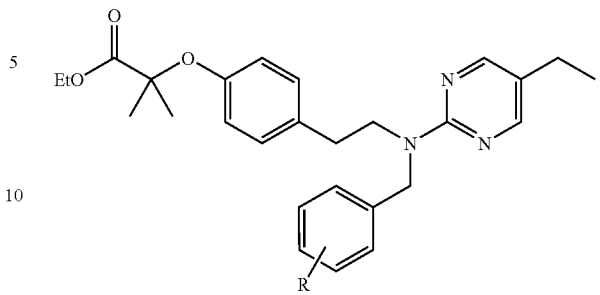

General procedure for N-alkylation of the intermediate ethyl 2-(4-{2-[(5-ethylpyrimidin-2-yl)amino]ethyl}phenoxy)-2-methylpropanoate with chloride or bromide reagents A solution of ethyl 2-(4-{2-[(5-ethylpyrimidin-2-yl)amino]ethyl}phenoxy)-2-methylpropanoate in DMF (0.1–0.5 M) was treated with 1.1–1.5 eq of a base (NaH or NaHMDS). After stirring for 5 minutes, 1–1.5 eq of an appropriate chloride or bromide reagent was added and the mixture heated at 40–80C for 14 hours. Cooled to rt and partitioned between equal volumes of ethyl acetate and water. The organic phase was washed with brine, dried over MgSO₄ and concentrated. Purification by silica gel chromatography eluting with 20% ethyl acetate-hexane afforded the desired N-alkylated product in variable yields.

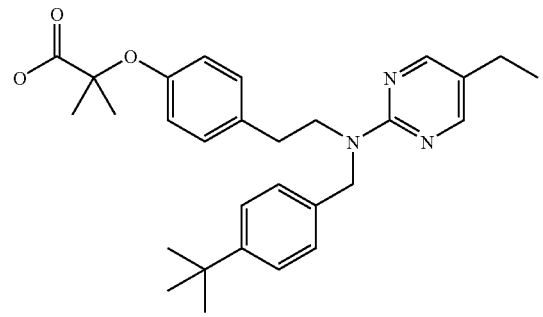

2-(4-{2-[(4-tert-Butylbenzyl)(5-ethylpyrimidin-2-yl)amino]ethyl}phenoxy)-2-methylpropanoic acid Step 1. Alkylation of ethyl 2-(4-{2-[(5-ethylpyrimidin-2-yl)amino]ethyl}phenoxy)-2-methylpropanoate (85 mg; 0.24 mmol) with 4-(tert-butyl)benzyl bromide (1 eq) as per the general N-alkylation procedure above (1.1 eq NaH, 40C) afforded the intermediate ester (46 mg; 38% yield).

Step 2. Hydrolysis of the ethyl ester with LiOH as per general procedure H provided the title compound in low overall yield.

¹H NMR (CDCl₃) δ 1.20 (t, 3H, J=7.7); 1.26 (t, 3H, J=7.7); 1.55 (s, 6H); 2.46 (t, 2H, J=7.5); 2.83 (t, 2H, J=7); 3.73 (t, 2H, J=7.3); 4.21 (q, 2H, J=7); 4.65 (s, 2H); 6.70 (s, 2H); 6.72 (s, 2H); 7.05 (s, 2H), 8.18 (s, 2H).

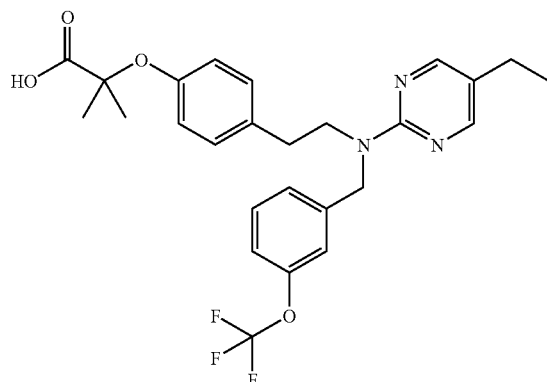

2-[4-(2-{(5-Ethylpyrimidin-2-yl)[3-(trifluoromethoxy)benzyl]amino}ethyl)phenoxy]-2-methylpropanoic acid Similarly prepared by alkylation with 3-trifluoromethoxy-benzyl bromide.

$^1$H NMR (CDCl$_3$) δ 1.28 (t, 3H, J=7); 1.60 (s, 6H); 2.48 (q, 2H, J=7.6); 2.85 (t, 2H, J=7.7); 3.76 (t, 2H, J=7.6); 4.76 (s, 2H); 6.79 (d, 2H, J=8.6); 7.08 (m, 4H); 7.29 (d, 2H, J=7.9), 8.25 (s, 2H). MS: m/z 504 (M+1); anal. Calcd. For C$_{26}$H$_{28}$F$_3$N$_3$O$_4$: C, 62.02; H. 5.61; N, 8.35; Found C, 61.93; H, 5.63; N, 8.17.

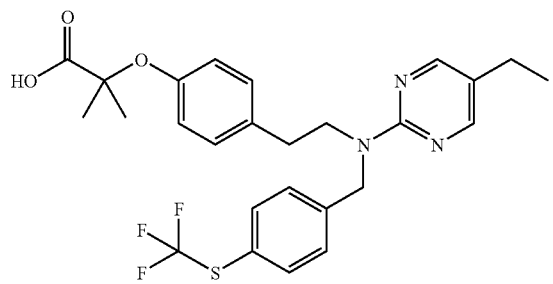

2-{4-[2-((5-Ethylpyrimidin-2-yl){4-[(trifluoromethyl)thio]benzyl}amino)ethyl]phenoxy}-2-methylpropanoic acid Similarly prepared by alkylation with 4-trifluoromethylthio-benzyl bromide.

$^1$H NMR (CDCl$_3$) δ 1.25 (t, 3H, J=7.4); 1.60 (s, 6H); 2.55 (q, 2H, J=7.4); 2.93 (t, 2H, J=7.2); 3.93 (br t, 2H); 4.81 (s, 2H); 6.89 (d, 2H, J=8.3); 7.14 (d, 2H, J=8.2); 7.60 (d, 4H, J=8.0); 8.36 (s, 2H). MS: m/z 520 (M+1).

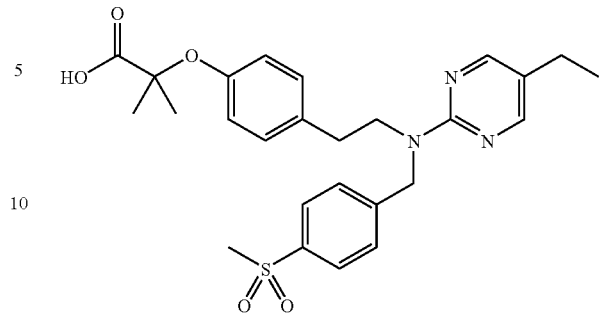

2-[4-(2-{(5-Ethylpyrimidin-2-yl)[4-(methylsulfonyl)benzyl]amino}ethyl)phenoxy]-2-methylpropanoic acid Similarly prepared by alkylation with 4-methylsulfone-benzyl bromide.

$^1$H NMR (CDCl$_3$) δ 1.19 (t, 3H, J=7.6); 1.29 (s, 3H); 1.60 (s, 6H); 2.54 (q, 2H, J=7.6); 2.94 (t, 2H, J=7); 3.91 (br t, 2H); 4.81 (s, 2H); 6.89 (d, 2H, J=8.2); 7.14 (d, 2H, J=8); 7.59 (d, 4H, J=7.9), and 8.34 (s, 2H). MS: m/z 520 (M+Na).

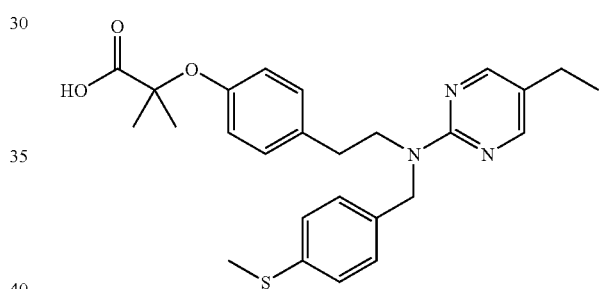

2-[4-(2-{(5-Ethylpyrimidin-2-yl)[4-(methylthio)benzyl]amino}ethyl)phenoxy]-2-methylpropanoic acid Similarly prepared by alkylation with 4-methylthio-benzyl bromide.

$^1$H NMR (CDCl$_3$) δ 1.26 (t, 3H, J=7.6); 1.60 (s, 6H); 2.49 (s, 3H); 2.58 (t, 2H, J=7.5); 2.77 (br t, 2H); 3.96 (br t, 2H); 4.76 (s, 2H); 6.89 (d, 2H, J=8.3); 7.14 (m, 6H), and 8.39 (s, 2H). MS: m/z 466 (M+1).

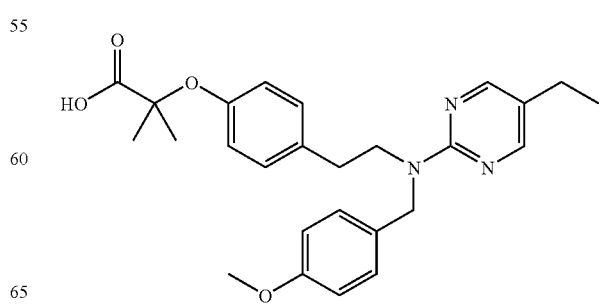

2-(4-{2-[(5-Ethylpyrimidin-2-yl)(4-methoxybenzyl)amino]ethyl}phenoxy)-2-methylpropanoic acid Similarly prepared by alkylation with 4-methoxy-benzyl chloride.

$^1$H NMR (CDCl$_3$) δ 1.16 (t, 3H, J=7.6); 1.54 (s, 6H); 2.43 (q, 2H, J=7.5); 2.73 (t, 2H, J=7.7); 3.65 (t, 2H, J=7.3); 3.73 (s, 3H); 4.64 (s, 2H); 6.78 (dd, 4H, J=8, 5); 7.01 (d, 2H, J=8.2); 7.06 (d, 2H, J=8.5), and 8.22 (s, 2H). MS: m/z 450 (M+1).

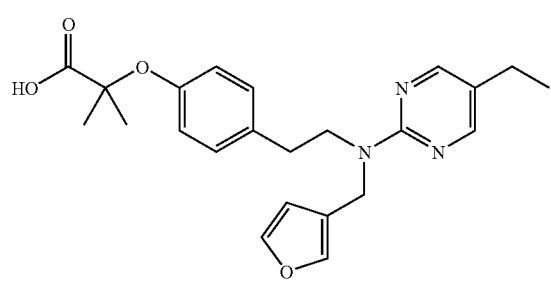

2-(4-{2-[(5-Ethylpyrimidin-2-yl)(3-furylmethyl)amino]ethyl}phenoxy)-2-methylpropanoic acid Similarly prepared by alkylation with chloromethyl-3-furan.

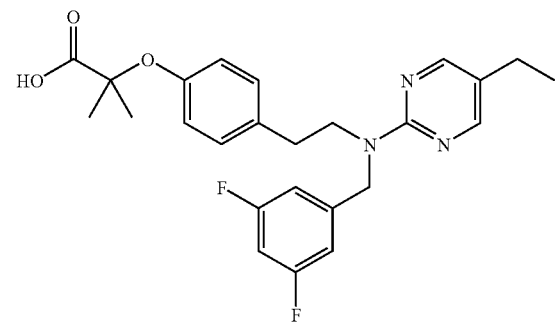

2-(4-{2-[(3,5-Difluorobenzyl)(5-ethylpyrimidin-2-yl)amino]ethyl}phenoxy)-2-methylpropanoic acid Similarly prepared by alkylation with 3,5-difluoro-benzylbromide.

$^1$H NMR (CDCl$_3$) δ 1.26 (t, 3H, J=7.7); 1.61 (s, 6H); 2.56 (q, 2H, J=7.3); 2.96 (br t, 2H); 3.96 (br t, 2H); 4.75 (s, 2H); 6.73 (d, 2H, J=7.1); 6.88 (d, 2H, J=8.1); 7.15 (d, 3H, J=8.1), 8.38 (s, 2H). MS: m/z 456 (M+1).

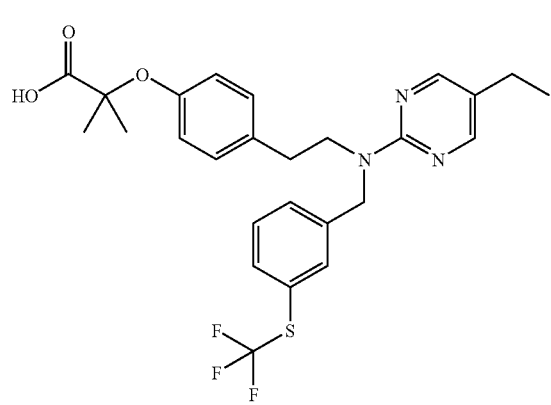

2-{4-[2-((5-Ethylpyrimidin-2-yl){3-[(trifluoromethyl)thio]benzyl}amino)ethyl]phenoxy}-2-methylpropanoic acid Similarly prepared by alkylation with 3-trifluoromethyl benzylbromide.

$^1$H NMR (CDCl$_3$) δ 1.21 (t, 3H, J=7.2); 1.54 (s, 6H); 2.44 (q, 2H, J=7.6); 2.76 (t, 2H, J=7.7); 3.69 (t, 2H, J=7.4); 4.70 (s, 2H); 6.80 (d, 2H, J=8.4); 7.02 (d, 2H, J=8.3); 7.23 (dd, 2H, J=12; 7); 7.42 (s, 1H); 7.45 (t, 1H, J=7), 8.22 (s, 2H).

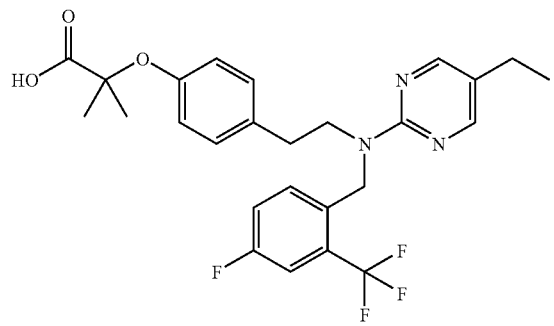

2-[4-(2-{(5-Ethylpyrimidin-2-yl)[4-fluoro-2-(trifluoromethyl)benzyl]amino}ethyl)phenoxy]-2-methylpropanoic acid Similarly prepared by alkylation with 4-fluoro-2-trifluoromethyl-benzylbromide.

$^1$H NMR (CDCl$_3$) δ 1.25 (t, 3H, J=7.2); 1.59 (s, 6H); 2.59 (br q, 2H); 2.99 (br t, 2H); 3.94 (br t, 2H); 4.99 (s, 2H); 6.85 (d, 2H, J=8); 7.17 (d, 2H, J=7.7); 7.29 (s, 1H); 7.39 (d, 2H, J=8.7), 8.40 (s, 2H). MS: m/z 506 (M+1).

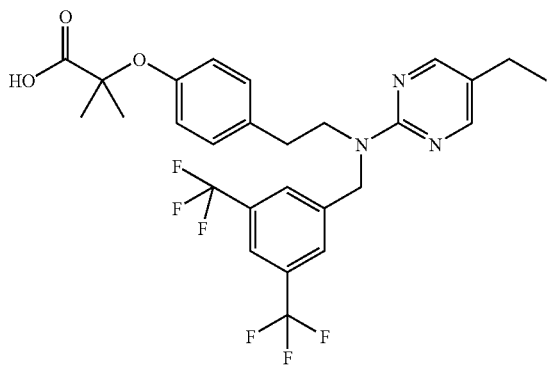

2-(4-{2-[[3,5-Bis(trifluoromethyl)benzyl](5-ethylpyrimidin-2-yl)amino]ethyl}phenoxy)-2-methylpropanoic acid Similarly prepared by alkylation with 3,5-bis-trifluoromethyl benzylbromide.

¹H NMR (CDCl₃) δ 1.24 (t, 3H, J=7.7); 1.60 (s, 6H); 2.51 (q, 2H, J=7.6); 2.88 (t, 2H, J=7.3); 3.82 (t, 2H, J=7); 4.83 (s, 2H); 6.88 (d, 2H, J=8.1); 7.12 (d, 2H, J=8.3); 7.65 (s, 2H); 7.77 (s, 1H); 8.28 (s, 2H). MS: m/z 556 (M+1)

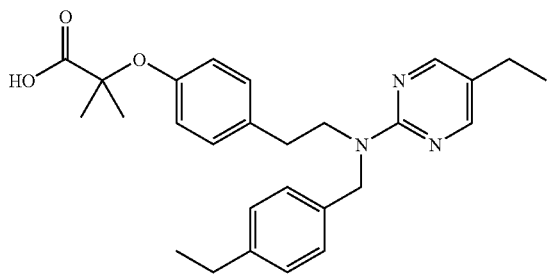

2-(4-{2-[(4-Ethylbenzyl)(5-ethylpyrimidin-2-yl)amino]ethyl}phenoxy)-2-methylpropanoic acid Similarly prepared by alkylation with 4-ethyl-benzylbromide.

¹H NMR (CDCl₃) δ 1.21 (t, 3H, J=7.7); 1.26 (t, 3H, J=7.5); 1.59 (s, 6H); 2.56 (q, 2H, J=7.3); 2.60 (q, 2H, J=7.6); 2.90 (br t, 2H); 3.90 (br t, 2H); 4.78 (s, 2H); 6.85 (d, 2H, J=8); 7.12 (d, 4H, J=7), 8.37 (s, 2H). MS: m/z 448 (M+1).

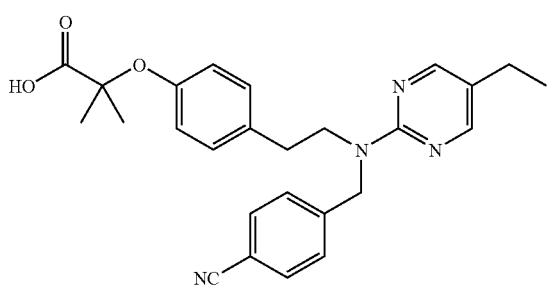

2-(4-{2-[(4-Cyanobenzyl)(5-ethylpyrimidin-2-yl)amino]ethyl}phenoxy)-2-methylpropanoic acid Similarly prepared by alkylation with 4-cyano-benzylbromide.

¹H NMR (CDCl₃) δ 1.21 (t, 3H, J=7.4); 1.60 (s, 6H); 2.55 (q, 2H, J=7.6); 2.92 (t, 2H, J=6.6); 3.98 (br t, 2H); 4.83 (s, 2H); 6.84 (d, 2H, J=8.3); 7.11 (d, 2H, J=8.3); 7.32 (d, 2H, J=8.2); 7.59 (d, 2H, J=8), and 8.38 (s, 2H). MS: m/z 445 (M+1).

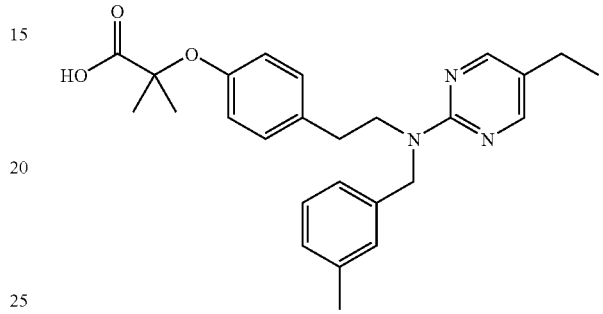

2-(4-{2-[(5-Ethylpyrimidin-2-yl)(3-methylbenzyl)amino]ethyl}phenoxy)-2-methylpropanoic acid Similarly prepared by alkylation with 3-methyl-benzylbromide.

¹H NMR (CDCl₃) δ 1.22 (t, 3H, J=7.5); 1.59 (s, 6H); 2.32 (s, 3H); 2.48 (q, 2H, J=7.6); 2.82 (t, 2H, J=7.8); 3.74 (t, 2H, J=7.9); 4.75 (s, 2H); 6.85 (d, 2H, J=8.5); 6.98 (d, 2H, J=8.2); 7.08 (d, 2H, J=8.4); 7.16 (d, 1H, J=7.5); 7.21 (t, 1H, J=8.3), 8.28 (s, 2H). MS: m/z 434 (M+1).

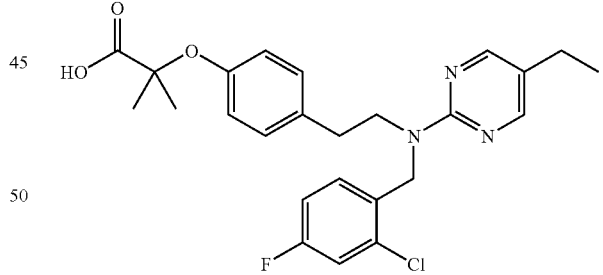

2-(4-{2-[(2-Chloro-4-fluorobenzyl)(5-ethylpyrimidin-2-yl)amino]ethyl}phenoxy)-2-methylpropanoic acid Similarly prepared by alkylation with 2-chloro-4-fluorobenzylbromide.

¹H NMR (CDCl₃) δ 1.17 (t, 3H, J=7.4); 1.60 (s, 6H); 2.42 (q, 2H, J=7.9); 2.80 (t, 2H, J=7.2); 3.70 (t, 2H, J=7.3); 4.77 (s, 2H); 6.70 (d, 2H, J=6.6); 6.82 (d, 2H, J=8.4); 6.92 (d, 1H, J=7.8); 7.05 (d, 1H, J=8.3); 7.06 (s, 1H), 8.18 (s, 2H). MS: m/z 472 (M+1)

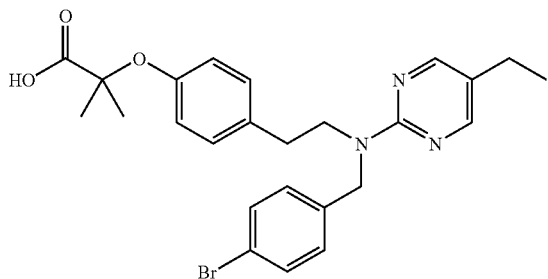

2-(4-{2-[(4-Bromobenzyl)(5-ethylpyrimidin-2-yl)amino]ethyl}phenoxy)-2-methylpropanoic acid Similarly prepared by alkylation with 4-bromo-benzylbromide.

$^1$H NMR (CDCl$_3$) δ 1.23 (t, 3H, J=7.6); 1.60 (s, 6H); 2.50 (q, 2H, J=7.6); 2.85 (t, 2H, J=7.2); 3.77 (t, 2H, J=7.2); 4.71 (s, 2H); 6.86 (d, 2H, J=8.4); 7.07 (dd, 4H, J=11, 8); 7.41 (d, 2H, J=8.3), 8.29 (s, 2H).

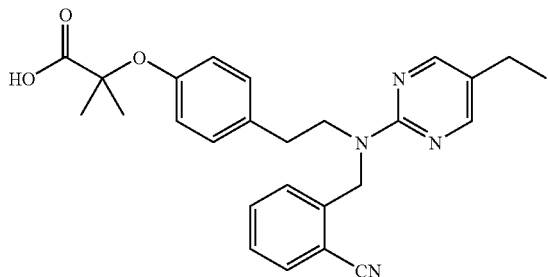

2-(4-{2-[(2-Cyanobenzyl)(5-ethylpyrimidin-2-yl)amino]ethyl}phenoxy)-2-methylpropanoic acid Similarly prepared by alkylation with 2-cyano-benzylbromide.

$^1$H NMR (CDCl$_3$) δ 1.27 (t, 3H, J=7); 1.59 (s, 6H); 2.48 (q, 2H, J=7.6); 2.88 (t, 2H, J=7.4); 3.79 (t, 2H, J=7.8); 5.05 (s, 2H); 6.77 (d, 2H, J=8.4); 7.12 (d, 2H, J=8.6); 7.32 (t, 1H, J=7.6); 7.42 (t, 1H, J=8.4); 7.47 (d, 1H, J=7.8); 7.7 (d, 1H, J=7.5), 8.24 (s, 2H). MS: m/z 445 (M+1).

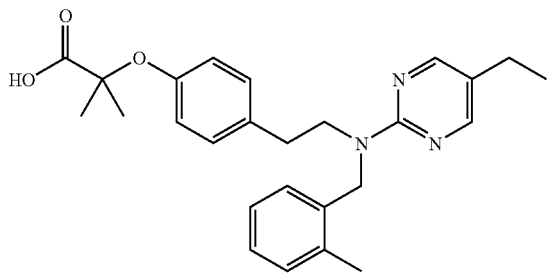

2-(4-{2-[(5-ethylpyrimidin-2-yl)(2-methylbenzyl)amino]ethyl}phenoxy)-2-methylpropanoic acid Similarly prepared by alkylation with 2-methyl-benzylbromide.

$^1$H NMR (CDCl$_3$) δ 1.23 (t, 3H, J=7.6); 1.59 (s, 6H); 2.24 (s, 3H); 2.50 (q, 2H, J=7.6); 2.84 (t, 2H, J=7.5); 3.76 (t, 2H, J=7.6); 4.74 (s, 2H); 6.84 (d, 2H, J=8.4); 7.07 (d, 2H, J=8.4); 7.14 (m, 4H), 8.31 (s, 2H). MS: m/z 434 (M+1).

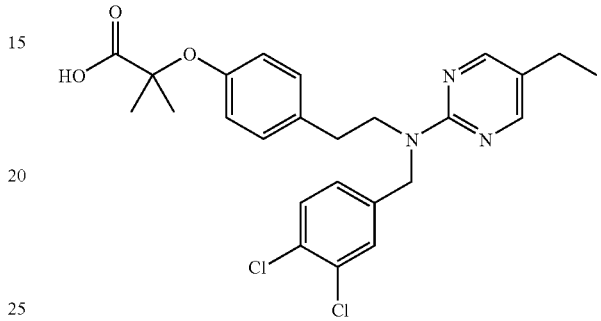

2-(4-{2-[(3,4-Dichlorobenzyl)(5-ethylpyrimidin-2-yl)amino]ethyl}phenoxy)-2-methylpropanoic acid Similarly prepared by alkylation with 3,4-dichloro-benzylbromide.

$^1$H NMR (CDCl$_3$) δ 1.23 (t, 3H, J=7.7); 1.60 (s, 6H); 2.50 (q, 2H, J=7.4); 2.85 (t, 2H, J=7.2); 3.77 (t, 2H, J=7.1); 4.68 (s, 2H); 6.86 (d, 2H, J=8.4); 7.09 (d, 2H, J=8.4); 7.27 (d, 1H, J=7); 7.34 (d, 1H, J=8.2); 7.45 (t, 1H, J=8.5), 8.29 (s, 2H). MS: m/z 488 (M+1).

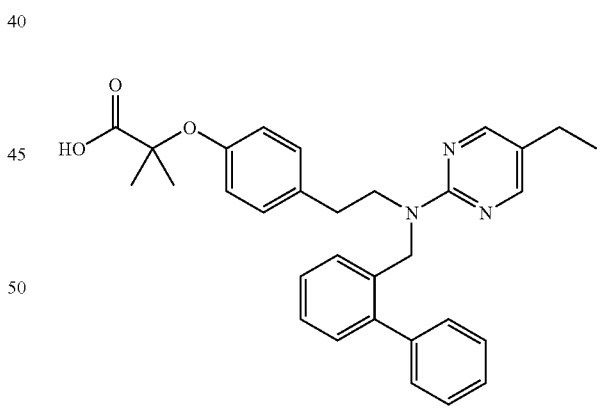

2-(4-{(2-[(1,1'-Biphenyl-2-ylmethyl)(5-ethylpyrimidin-2-yl)amino]ethyl}phenoxy)-2-methylpropanoic acid Similarly prepared by alkylation with 2-phenyl-benzylbromide.

$^1$H NMR (CDCl$_3$) δ 1.17 (t, 3H, J=7.4); 1.51 (s, 6H); 2.44 (q, 2H, J=7.5); 2.61 (t, 2H, J=6.9); 3.56 (br t, 2H); 4.60 (s, 2H); 6.71 (d, 2H, J=8.3); 6.88 (d, 2H, J=7.7); 7.35 (m, 9H), 8.19 (s, 2H). MS: m/z 496 (M+1).

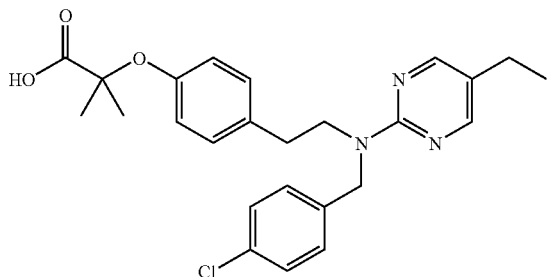

2-(4-{2-[(4-chlorobenzyl)(5-ethylpyrimidin-2-yl)amino]ethyl}phenoxy)-2-methylpropanoic acid Similarly prepared by alkylation with 4-chloro-benzyl-bromide.

$^1$H NMR (CDCl$_3$) δ 1.25 (t, 3H, J=7.7); 1.60 (s, 6H); 2.58 (t, 2H, J=7.6); 2.92 (6.8); 4.00 (t, 2H, J=6.5); 4.79 (s, 2H); 6.84 (d, 2H, J=8.3); 7.14 (d, 4H, J=7.9), 8.45 (s, 2H). MS: m/z 454 (M+1).

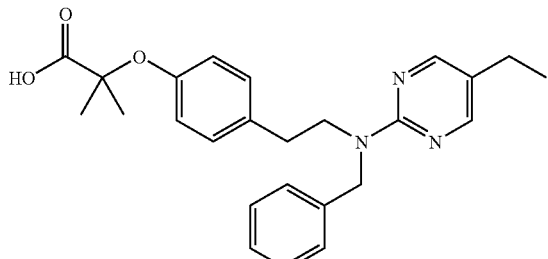

2-(4-{2-[Benzyl(5-ethylpyrimidin-2-yl)amino]ethyl}phenoxy)-2-methylpropanoic acid Similarly prepared by alkylation with benzylbromide.

$^1$H NMR (CDCl$_3$) δ 1.23 (t, 3H, J=7.6); 1.59 (s, 6H); 2.49 (q, 2H, J=7.6); 2.83 (t, 2H, J=7.6); 3.77 (t, 2H, J=7.3); 4.79 (s, 2H); 6.88 (d, 2H, J=8.2); 7.09 (d, 2H, J=8.4); 7.19 (d, 4H, J=7.6); 7.29 (t, 1H, J=7.1), 8.30 (s, 2H). MS: m/z 420 (M+1).

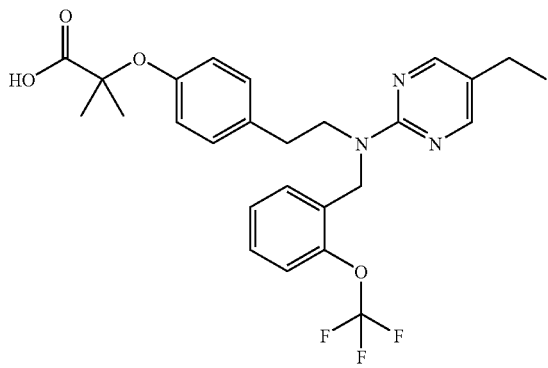

2-[4-(2-{(5-Ethylpyrimidin-2-yl)[2-(trifluoromethoxy)benzyl]amino}ethyl)phenoxy]-2-methylpropanoic acid Similarly prepared by alkylation with 2-trifluoromethoxy-benzyl bromide.

$^1$H NMR (CDCl$_3$) δ 1.22 (t, 3H, J=7.6); 1.59 (s, 6H); 2.45 (q, 2H, J=7.6); 2.85 (t, 2H, J=7.7); 3.73 (t, 2H, J=7.6); 4.88 (s, 2H); 6.78 (d, 2H, J=8.4); 7.09 (d, 2H, J=6.5); 7.21 (dd, 4H, J=14; 6.5), 8.24 (s, 2H). MS: m/z 504 (M+1).

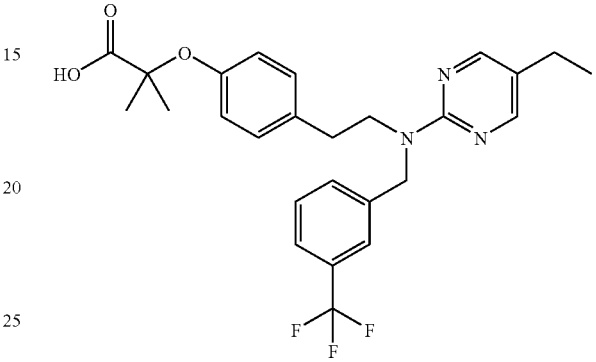

2-[4-(2-{(5-ethylpyrimidin-2-yl)[3-(trifluoromethyl)benzyl]amino}ethyl)phenoxy]-2-methylpropanoic acid Similarly prepared by alkylation with 3-trifluoromethyl-benzylbromide.

$^1$H NMR (CDCl$_3$) δ 1.23 (t, 3H, J=7.7); 1.60 (s, 6H); 2.50 (q, 2H, J=7.6); 2.85 (t, 2H, J=7.6); 3.77 (t, 2H, J=7.1); 4.80 (s, 2H); 6.86 (d, 2H, J=8.4); 7.10 (d, 2H, J=8.4); 7.36 (s, 1H); 7.39 (d, 2H, J=7.4); 7.44 (t, 1H, J=7.3), 8.28 (s, 2H).

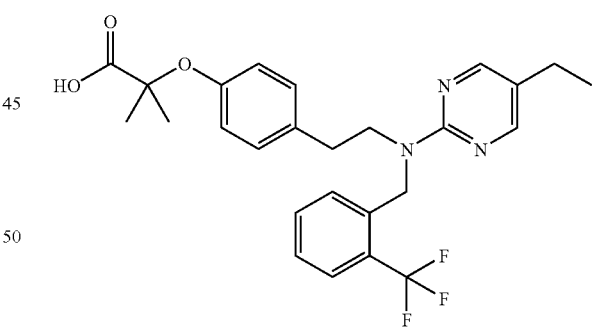

2-[4-(2-{(5-Ethylpyrimidin-2-yl)[2-(trifluoromethyl)benzyl]amino}ethyl)phenoxy]-2-methylpropanoic acid Similarly prepared by alkylation with 2-trifluoromethyl-benzylbromide.

$^1$H NMR (CDCl$_3$) δ 1.22 (t, 3H, J=7.6); 1.58 (s, 6H); 2.49 (q, 2H, J=7.6); 2.88 (t, 2H, J=7.2); 3.73 (t, 2H, J=7.3); 4.99 (s, 2H); 6.85 (d, 2H, J=8.4); 7.10 (d, 2H, J=8.3); 7.23 (qn, 2H); 7.41 (t, 1H, J=7.4); 7.65 (d, 1H, J=7.8), 8.27 (s, 2H). MS: m/z 488 (M+1).

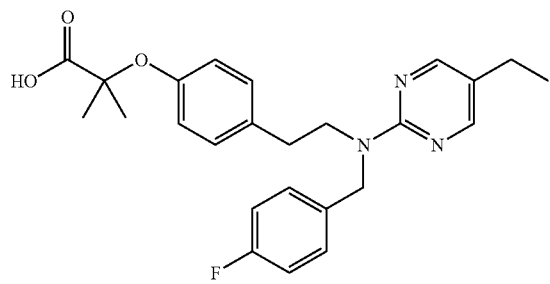

2-(4-{2-[(5-Ethylpyrimidin-2-yl)(4-fluorobenzyl)
amino]ethyl}phenoxy)-2-methylpropanoic acid Similarly prepared by alkylation with 4-fluoro-benzylbromide.

$^1$H NMR (CDCl$_3$) δ 1.22 (t, 3H, J=7.5); 1.59 (s, 6H); 2.48 (q, 2H, J=7.6); 2.80 (t, 2H, J=7.7); 3.70 (t, 2H, J=7.3); 4.71 (s, 2H); 6.84 (d, 2H, J=8.4); 6.97 (dd, 2H, J=8.8); 7.13 (d, 2H, J=6); 7.15 (dd, 2H, J=9; 6), 8.27 (s, 2H). MS: m/z 438 (M+1).

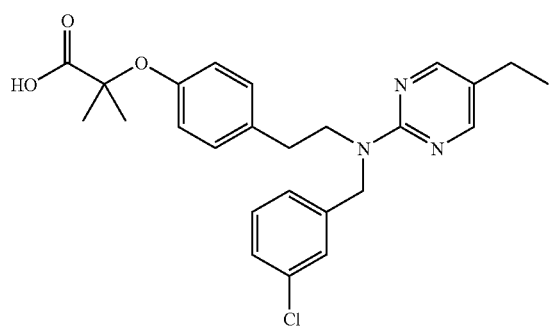

2-(4-{2-[(3-Chlorobenzyl)(5-ethylpyrimidin-2-yl)
amino]ethyl}phenoxy)-2-methylpropanoic acid Similarly prepared by alkylation with 3-chloro-benzyl-bromide.

$^1$H NMR (CDCl$_3$) δ 1.22 (t, 3H, J=7.6); 1.59 (s, 6H); 2.48 (q, 2H, J=7.6); 2.83 (t, 2H, J=7.9); 3.74 (t, 2H, J=7.4); 4.70 (s, 2H); 6.85 (d, 2H, J=8.4); 7.08 (d, 2H, J=8.4); 7.23 (m, 3H); 7.31 (s, 1H), 8.27 (s, 2H).

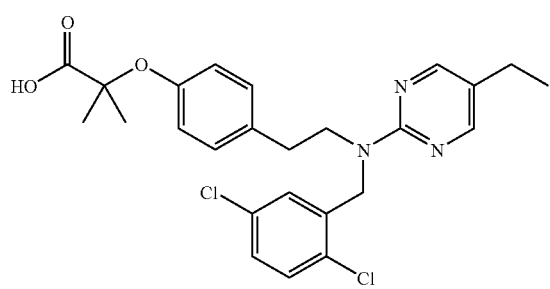

2-(4-{2-[(2,5-Dichlorobenzyl)(5-ethylpyrimidin-2-yl)amino]ethyl}phenoxy)-2-methylpropanoic acid Similarly prepared by alkylation with 2,5-dichloro-benzylbromide.

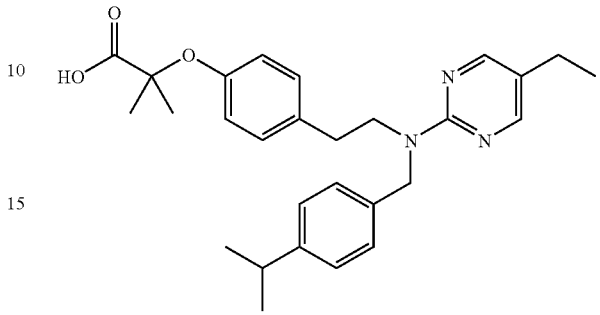

2-(4-{2-[(5-Ethylpyrimidin-2-yl)(4-isopropylbenzyl)
amino]ethyl}phenoxy)-2-methylpropanoic acid Similarly prepared by alkylation with 4-isopropyl-benzyl chloride.

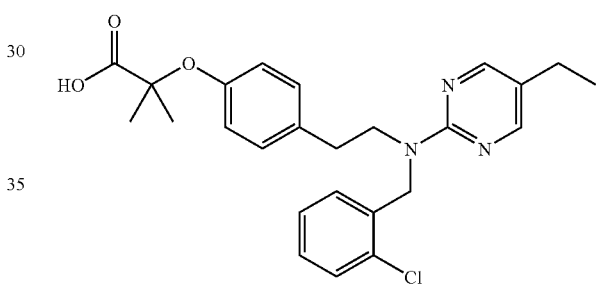

2-(4-{2-[(2-Chlorobenzyl)(5-ethylpyrimidin-2-yl)
amino]ethyl}phenoxy)-2-methylpropanoic acid Similarly prepared by alkylation with 2-chloro-benzyl bromide.

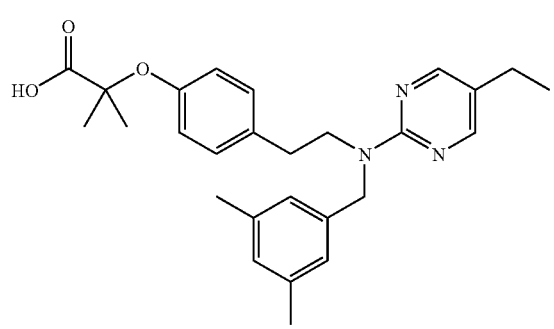

2-(4-{2-[(3,5-Dimethylbenzyl)(5-ethylpyrimidin-2-yl)amino]ethyl}phenoxy)-2-methylpropanoic acid Similarly prepared by alkylation with 3,5-dimethyl-benzyl bromide.

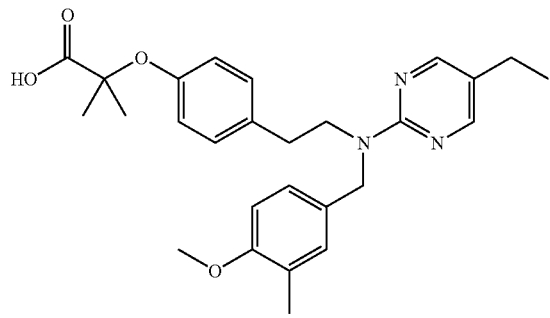

2-(4-{2-[(5-Ethylpyrimidin-2-yl)(4-methoxy-3-methylbenzyl)amino]ethyl}phenoxy)-2-methylpropanoic acid Similarly prepared by alkylation with 3-methyl-4-methoxy-benzyl chloride.

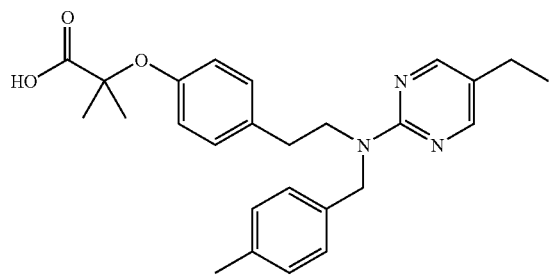

2-(4-{2-[(5-Ethylpyrimidin-2-yl)(4-methylbenzyl)amino]ethyl}phenoxy)-2-methylpropanoic acid Similarly prepared by alkylation with 4-methyl-benzyl bromide.

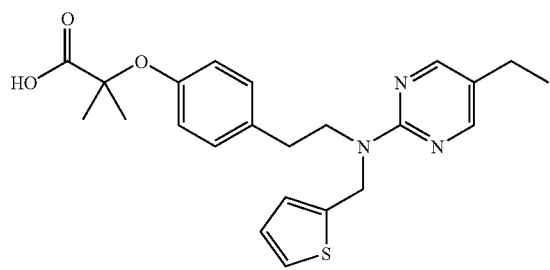

2-(4-{2-[(5-Ethylpyrimidin-2-yl)(thien-2-ylmethyl)amino]ethyl}phenoxy)-2-methylpropanoic acid Similarly prepared by alkylation with 2-chloromethyl-thiophene.

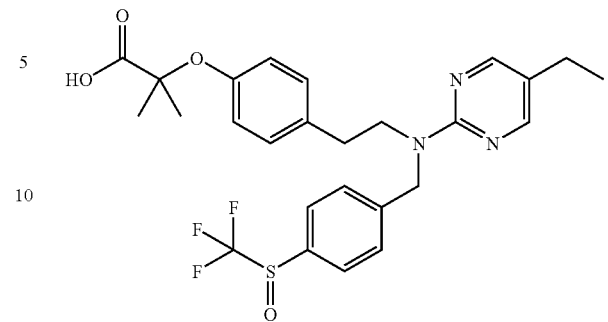

2-{4-[2-((5-Ethylpyrimidin-2-yl){4-[(trifluoromethyl)sulfinyl]benzyl}amino)ethyl]phenoxy}-2-methylpropanoic acid Similarly prepared by alkylation with 1-(bromomethyl)-4-[(trifluoromethyl)sulfinyl]benzene.

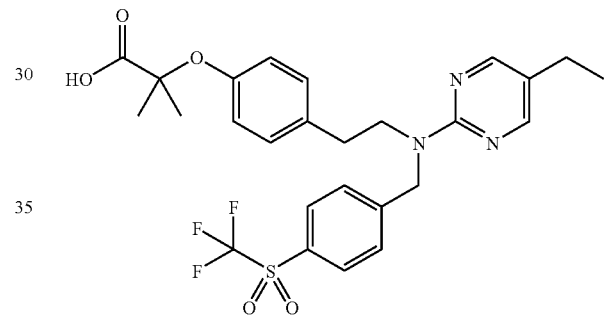

2-{4-[2-((5-Ethylpyrimidin-2-yl){4-[(trifluoromethyl)sulfonyl]benzyl}amino)ethyl]phenoxy}-2-methylpropanoic acid Similarly prepared by alkylation with 1-(bromomethyl)-4-[(trifluoromethyl)sulfonyl]benzene.

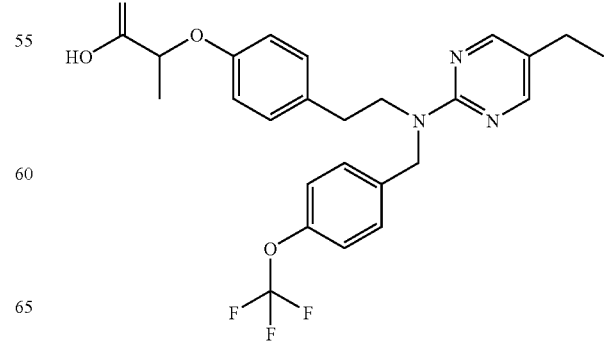

2-[4-(2-{(5-Ethylpyrimidin-2-yl)[4-(trifluoromethoxy)benzyl]amino}ethyl)phenoxy]propanoic acid Step 1. Alkylation of 4-{2-[(5-Ethylpyrimidin-2-yl)amino]ethyl}phenol (135 mg; 0.56 mmol) with ethyl 2-bromopropionate (0.18 ml; 1.39 mmol) as per general procedure C (conditions: 2 eq Cs2CO3, MeCN, 60C, 4 hr). provided ethyl 2-(4-{2-[(5-ethylpyrimidin-2-yl)amino]ethyl}phenoxy)propanoate (143 mg; 75% yield).

Step 2–3. In a two-step sequence similar to the previous example, alkylation of the above intermediate ethyl 2-(4-{2-[(5-ethylpyrimidin-2-yl)amino]ethyl}phenoxy)propanoate with 4-trifluoromethoxy-benzylbromide (1 eq) (1.5 eq NaH; 80C) followed by hydrolysis of the intermediate ester afforded the title compound.

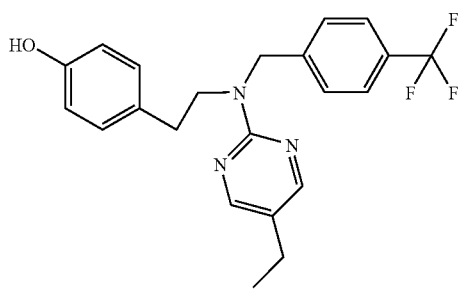

4-(2-{(5-Ethylpyrimidin-2-yl)[4-(trifluoromethyl)benzyl]amino}ethyl)phenol

Condensation of 4-(2-{[4-(trifluoromethyl)benzyl]amino}ethyl)phenol (1.20 g; 4.06 mmol) with 2-chloro-5-ethyl-pyrimidine (0.52 ml; 4.27 mmol) as per general procedure E (conditions: 1.1 eq. DIEA, toluene, 210C, 16 hr) provided the title compound (1.40 g; 85% yield).

$^1$H NMR (CDCl$_3$) δ 8.20 (s, 2H), 7.98 (s, 1H), 7.46 (d, 2H, J=8.2), 7.23 (d, 2H, J=8.5), 6.97 (d, 2H, J=8.5), 6.70 (d, 2H, J=8.5), 4.75 (s, 2H), 3.74 (t, 2H, J=7.3), 2.82 (t, 2H, J=7.3), 2.42 (q, 2H, J=7.5), 1.15 (t, 3H, J=7.5).

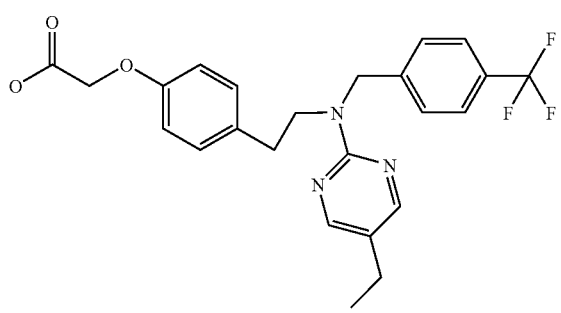

[4-(2-{(5-Ethylpyrimidin-2-yl)[4-(trifluoromethyl)benzyl]amino}ethyl)phenoxy]acetic acid Step 1. Alkylation of 4-(2-{(5-ethylpyrimidin-2-yl)[4-(trifluoromethyl)benzyl]amino}ethyl)phenol (150 mg; 0.37 mmol) with t-butylbromoacetate (81 mg; 0.41 mmol) as per general procedure C (1.1 eq. K$_2$CO$_3$, DMF, 80C, 18 hr) provided the intermediate tert-butyl ester (128 mg; 67% yield).

Step 2. Hydrolysis of the tert-butyl ester (128 mg) with TFA as per general procedure I provided after chromatography and crystallization from dichloromethane-hexane, the title compound as a white solid (103 mg; 90% yield).

$^1$H NMR (CDCl$_3$) δ 8.24 (s, 2H), 7.50 (d, 2H, J=8.0), 7.25 (d, 2H, J=8.0), 7.08 (d, 2H, J=8.6), 6.78 (d, 2H, J=8.6), 4.79 (s, 2H), 4.55 (s, 2H), 3.75 (t, 2H, J=7.6), 2.84 (t, 2H, J=7.6), 2.48 (q, 2H, J=7.6), 1.19 (t, 3H, J=7.6). MS: m/z 460 (M+1).

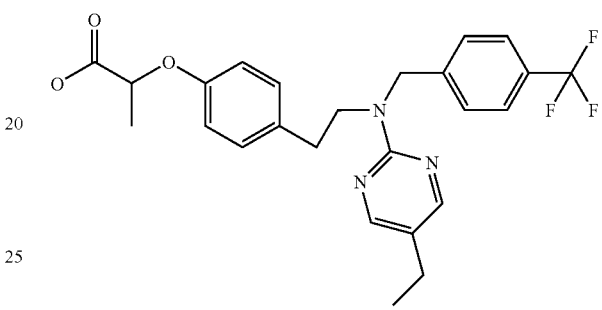

2-[4-(2-{(5-Ethylpyrimidin-2-yl)[4-(trifluoromethyl)benzyl]amino}ethyl)phenoxy]propanoic acid Similarly prepared from 4-(2-{(5-ethylpyrimidin-2-yl)[4-(trifluoromethyl)benzyl]amino}ethyl)phenol and t-butyl 2-bromopropionate.

$^1$H NMR (CDCl$_3$) δ 8.24 (s, 2H), 7.48 (d, 2H, J=8.0), 7.22 (d, 2H, J=8.0), 7.04 (d, 2H, J=8.5), 6.77 (d, 2H, J=8.5), 4.74 (s, 2H), 4.70 (q, 1H, J=6.8), 3.69 (t, 2H, J=7.5), 2.77 (t, 2H, J=7.5), 2.46 (q, 2H, J=7.6), 1.59 (d, 3H, J=6.8), 1.18 (t, 3H, J=7.6). MS: m/z 474 (M+1).

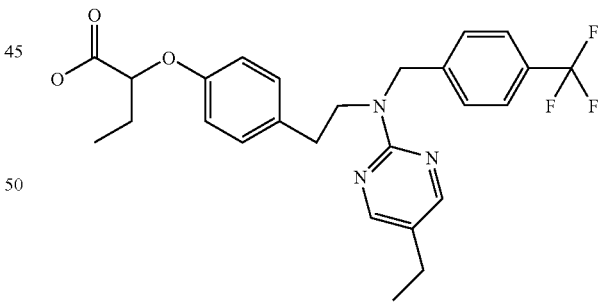

2-[4-(2-{(5-Ethylpyrimidin-2-yl)[4-(trifluoromethyl)benzyl]amino}ethyl)phenoxy]butanoic acid Similarly prepared from 4-(2-{(5-ethylpyrimidin-2-yl)[4-(trifluoromethyl)benzyl]amino}ethyl)phenol and t-butyl 2-bromobutyrate.

$^1$H NMR (CDCl$_3$) δ 8.24 (s, 2H), 7.48 (d, 2H, J=8.0), 7.22 (d, 2H, J=8.0), 7.04 (d, 2H, J=8.5), 6.77 (d, 2H, J=8.5), 4.74 (s, 2H), 4.52 (t, 1H, J=6.1), 3.69 (t, 2H, J=7.5), 2.76 (t, 2H, J=7.5), 2.46 (q, 2H, J=7.6), 1.96 (m, 2H), 1.18 (t, 3H, J=7.6), 1.06 (t, 3H, J=7.4).

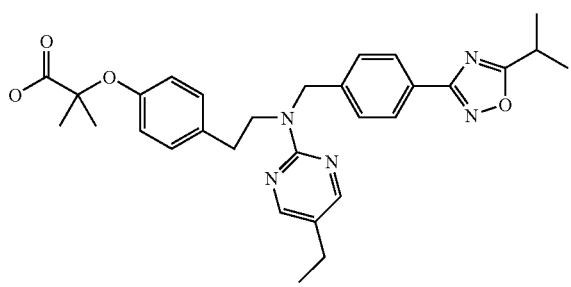

2-[4-(2-{(5-Ethylpyrimidin-2-yl)[4-(5-isopropyl-1,2, 4-oxadiazol-3-yl)benzyl]amino}ethyl)phenoxy]-2-methylpropanoic acid Step 1. Condensation of 4-(2-{[4-(5-isopropyl-1,2,4-oxadiazol-3-yl)benzyl]amino}ethyl)phenol (400 mg; 1.19 mmol) with 2-chloro-5-ethyl-pyrimidine (178 mg; 1.25 mmol) as per general procedure E (conditions: 1.1 eq. DIEA, toluene, 210C, 16 hr) provided the intermediate phenol (200 mg; 38% yield). MS: m/z 444 (M+1).

Step 2. Alkylation of the above intermediate (125 mg; 0.28 mmol) with 2-trichloromethyl-2-propanol (65 mg; 0.37 mmol) as per general procedure D provided after chromatography and crystallization from dichloromethane-hexane, the title compound as a white solid (89 mg; 60% yield).

$^1$H NMR (CDCl$_3$) δ 8.22 (s, 2H), 7.90 (d, 2H, J=8.1), 7.18 (d, 2H, J=8.1), 6.98 (d, 2H, J=8.5), 6.76 (d, 2H, J=8.5), 4.73 (s, 2H), 3.73 (t, 2H, J=7.5), 3.25 (m, 1H), 2.78 (t, 2H, J=7.5), 2.46 (q, 2H, J=7.6), 1.54 (s, 6H), 1.40 (d, 6H, J=7.1), 1.18 (t, 3H, J=7.6).

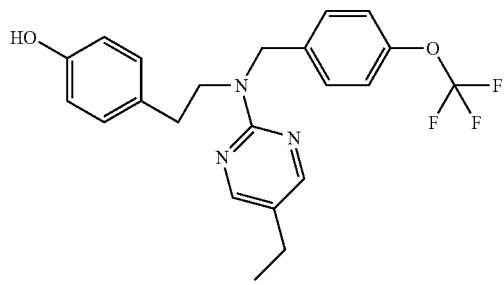

4-(2-{(5-Ethylpyrimidin-2-yl)[4-(trifluoromethoxy)benzyl]amino}ethyl)phenol

Condensation of 4-(2-{[4-(trifluoromethoxy)benzyl]amino}ethyl)phenol (500 mg; 1.61 mmol) with 2-chloro-5-ethyl-pyrimidine (0.19 ml; 1.54 mmol) as per general procedure E (conditions: 5 ml of DIEA, 200C, 16 hr) provided the title compound (490 mg; 76% yield).

$^1$H NMR (CDCl$_3$) δ 8.25 (s, 2H), 7.84 (bs, 1H), 7.19 (d, 2H, J=8.5), 7.10 (d, 2H, J=8.5), 7.01 (d, 2H, J=8.4), 6.71 (d, 2H, J=8.4), 4.73 (s, 2H), 3.77 (t, 2H, J=7.6), 2.85 (t, 2H, J=7.6), 2.48 (q, 2H, J=7.5), 1.21 (t, 3H, J=7.5).

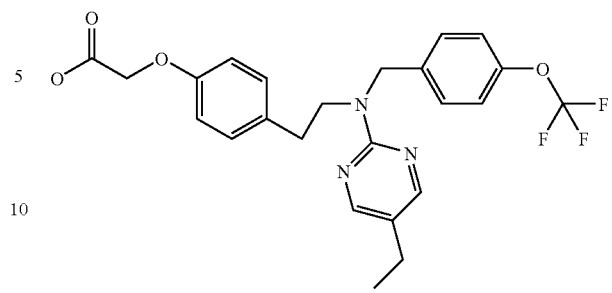

[4-(2-{(5-Ethylpyrimidin-2-yl)[4-(trifluoromethoxy)benzyl]amino}ethyl)phenoxy]acetic acid Step 1. Alkylation of 4-(2-{(5-ethylpyrimidin-2-yl)[4-(trifluoromethoxy)benzyl]amino}ethyl)phenol (125 mg; 0.30 mmol) with t-butyl bromoacetate (79 mg; 0.41 mmol) as per general procedure C (1.35 eq. Cs2CO3, MeCN, 85C, 3 hr) provided the intermediate tert-butyl ester (130 mg; 81% yield).

MS: m/z 532 (M+1).

Step 2. Hydrolysis of the tert-butyl ester (150 mg) with TFA as per general procedure I provided after chromatography and crystallization from dichloromethane-hexane, the title compound as a white solid (107 mg; 90% yield).

$^1$H NMR (CDCl$_3$) δ 8.37 (s, 2H), 7.19 (d, 2H, J=8.5), 7.12 (d, 2H, J=8.5), 7.07 (d, 2H, J=7.9), 6.78 (d, 2H, J=7.9), 4.76 (s, 2H), 4.55 (s, 2H), 3.78 (t, 2H, J=7.4), 2.83 (t, 2H, J=7.4), 2.52 (q, 2H, J=7.6), 1.21 (t, 3H, J=7.6). MS: m/z 477 (M+1).

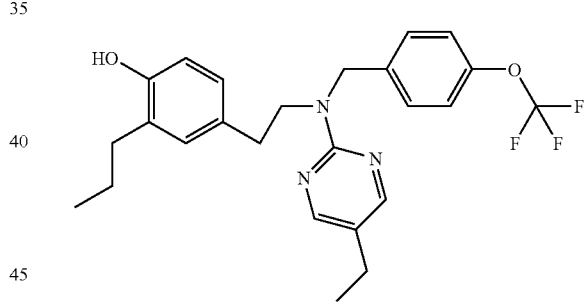

4-(2-{(5-Ethylpyrimidin-2-yl)[4-(trifluoromethoxy)benzyl]amino}ethyl)-2-propylphenol Step 1. Alkylation of 4-(2-{(5-ethylpyrimidin-2-yl)[4-(trifluoromethoxy)benzyl]amino}ethyl)phenol (2.07 g; 4.80 mmol) with allyl bromide (0.45 ml; 5.28 mmol) as per general procedure C (1.1 eq. Cs2CO3, MeCN, 85C, 14 hr) provided N-{2-[4-(allyloxy)phenyl]ethyl}-5-ethyl-N-[4-(trifluoromethoxy)benzyl]pyrmidin-2-amine (2.0 g; 91% yield).

Step 2. A solution of the above intermediate (2.0 g; 4.38 mmol) in dichloromethane (0.4M) is treated under nitrogen, in an ice bath, with boron trichloride (1M solution in hexane; 5.5 ml). After 1 hr. an additional 0.6 eq of boron trichloride was added. Stirred for 30 more minutes and quenched by dropwise addition of methanol (3 ml). Stirred 15 minutes and partitioned between ethyl acetate and saturated sodium bicarbonate solution. The aqueous phase was washed with ethyl acetate. The organic phases were washed with saturated brine, dried over sodium sulfate and concentrated. Purification by flash chromatography on silica gel using an ethyl acetate-hexane gradient (2–30%) afforded 2-allyl-4-(2-{(5-ethylpyrimidin-2-yl)[4-(trifluoromethoxy)benzyl]amino}ethyl)phenol in good yield.

Step 3. A solution of the above intermediate in ethyl acetate (~0.3M) is hydrogenated over 10% Pd on carbon (500 mg) under balloon pressure. After 2 hours, fresh Pd catalyst was added (400 mg) and stirred one extra hour. The catalyst was filtered off and washed with ethyl acetate, chloroform and methanol. The filtrate was concentrated and purified by flash chromatography on silica gel using an ethyl acetate-hexane gradient (5–40%) to afford the title compound in 54% overall yield for the last two steps (1.20 g).

$^1$H NMR (CDCl$_3$) δ 8.25 (s, 2H), 7.21 (d, 2H, J=8.1), 7.12 (d, 2H, J=8.1), 7.11 (s, 1H), 6.94 (d, 1H, J=1.9), 6.83 (dd, 1H, J=8.0; 1.9), 6.63 (d, 1H, J=8.0), 4.75 (s, 2H), 3.78 (t, 2H, J=7.6), 2.84 (t, 2H, J=7.6), 2.55 (q, 2H, J=7.8), 2.49 (q, 2H, J=7.6), 1.60 (m, 2H), 1.22 (t, 3H, J=7.6), 0.95 (t, 3H, J=7.4).

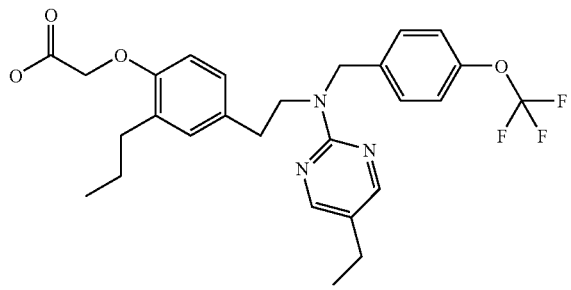

[4-(2-{(5-Ethylpyrimidin-2-yl)[4-(trifluoromethoxy)benzyl]amino}ethyl)-2-propylphenoxy]acetic acid Step 1. Alkylation of the intermediate phenol 4-(2-{(5-ethylpyrimidin-2-yl)[4-(trifluoromethoxy)benzyl]amino}ethyl)-2-propylphenol (550 mg; 1.2 mmol) with tert-butyl bromoacetate (0.25 ml; 1.68 mmol) as per general procedure C (1.4 eq Cs2CO3, MeCN, 85C) afforded the intermediate tert-butyl ester (550 mg; 80% yield).

Step 2. Hydrolysis of the tert-butyl ester (550 mg) with TFA as per general procedure I provided after chromatography and crystallization from ethyl ether-hexane, the title compound as a white solid (456 mg; 90% yield).

$^1$H NMR (CDCl$_3$) δ 8.24 (s, 2H), 7.20 (d, 2H, J=8.4), 7.11 (d, 2H, J=8.4), 6.94 (m, 2H), 6.60 (d, 2H, J=7.9), 4.76 (s, 2H), 4.58 (s, 2H), 3.73 (t, 2H, J=7.4), 2.81 (t, 2H, J=7.4), 2.59 (t, 2H, J=7.6), 2.49 (q, 2H, J=7.6), 1.59 (m, 2H), 1.21 (t, 3H, J=7.6), 0.93 (t, 3H, J=7.4). MS: m/z 518 (M+1).

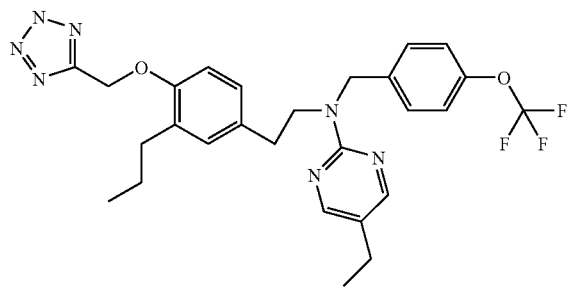

5-Ethyl-N-{2-[3-propyl-4-(2H-tetraazol-5-yl-methoxy)phenyl]ethyl}-N-[4-(trifluoromethoxy)benzyl]pyrimidin-2-amine Step 1. Alkylation of the intermediate phenol 4-(2-{(5-ethylpyrimidin-2-yl)[4-(trifluoromethoxy)benzyl]amino}ethyl)-2-propylphenol (550 mg; 1.2 mmol) with chloroacetonitrile (0.15 ml; 2.40 mmol) as per general procedure C (2 eq Cs2CO3, MeCN, 85C) afforded the intermediate nitrile (530 mg; 88% yield).

Step 2. A solution of the above intermediate (530 mg) in toluene (0.12 M) was treated under nitrogen with azidotrimethylsilane (0.28 ml; 2.09 mmol) and dibutyltin oxide (0.052 mg; 0.21 mmol). Heated to 110C for 14 hr. Cooled down and partitioned between ethyl acetate and 0.1N HCl. The organic phase was washed with saturated brine, dried over sodium sulfate and concentrated. Purification by radial chromatography using a methanol-dichloromethane gradient (1–15%) followed by crystallization from acetone/water afforded the title compound as a white solid in 75% yield (427 mg).

$^1$H NMR (CDCl$_3$) δ 8.20 (s, 2H), 7.19 (d, 2H, J=8.3), 7.10 (d, 2H, J=8.3), 6.91 (m, 2H), 6.72 (d, 1H, J=7.5), 5.39 (bs, 2H), 4.74 (s, 2H), 3.73 (t, 2H, J=7.5), 2.81 (t, 2H, J=7.5), 2.48 (m, 4H), 1.51 (q, 2H, J=7.3), 1.20 (t, 3H, J=7.7), 0.89 (t, 3H, J=7.3).

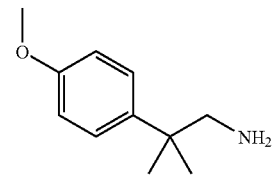

2-(4-Methoxyphenyl)-2-methylpropan-1-amine

Step 1. A solution of lithium diisopropylamide (2M; 61.1 ml; 122.3 mmol;) in heptane/THF/ethylbenzene was cooled in an ice bath and treated dropwise, under nitrogen, with a solution of (4-methoxy-phenyl)acetonitrile (6.0 g; 40.77 mmol) in 30 ml of THF. After stirring for 45 minutes at 0C, iodomethane (12.69 ml; 203.85 mmol) was added and the mixture stirred at rt for 12 hours. The reaction mixture was added to a saturated solution of ammonium chloride (300 ml) and extracted twice with ethyl acetate (200 ml). The organic phase was washed once with saturated brine (100 ml), dried over sodium sulfate and concentrated to dryness. Purification by flash chromatography on silica gel using an ethyl acetate/hexane gradient (5–30%) afforded 2-(4-methoxyphenyl)-2-methylpropanenitrile (6.0 g; 84% yield).

$^1$H NMR (CDCl$_3$) δ 7.36 (d, 2H, J=8.8), 6.88 (d, 2H, J=8.8), 3.78 (s, 3H), 1.67 (s, 6H).

Step 2. A suspension of lithium aluminum hydride (1.63 g; 42.86 mmol) in 20 ml of THF was treated dropwise, under nitrogen, with the previous intermediate (5.0 g; 28.57 mmol) in 30 ml of THF (exothermic). Heated to reflux for 3 hours. Cooled to rt and added additional lithium aluminum hydride (1.01 g; 26.61 mmol). Heated again to reflux for another 7 hours. Cooled to rt and worked up by careful dropwise addition of 2.65 ml of water, 2.65 ml of 15% NaOH and 7.90 ml of water. Stirred for 20 minutes, diluted with ethyl acetate, filtered off the solids and washed them with ethyl acetate (200 ml) and chloroform (100 ml). After concentrating to dryness, the title compound was obtained (5.1 g), which was used without further purification.

¹H NMR (CDCl₃) δ 7.23 (d, 2H, J=8.8), 6.84 (d, 2H, J=8.8), 3.78 (s, 3H), 2.73 (s, 2H), 1.25 (s, 6H).

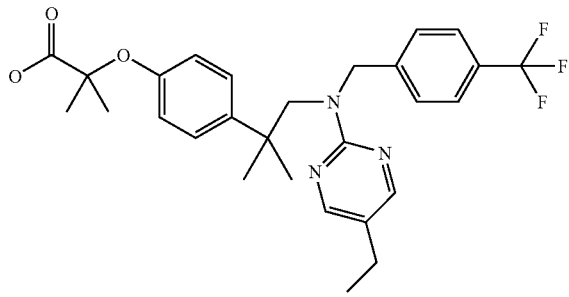

2-[4-(2-{(5-Ethylpyrimidin-2-yl)[4-(trifluoromethyl) benzyl]amino}-1,1-dimethylethyl)phenoxy]-2-methylpropanoic acid Step 1. Reductive amination of 2-(4-methoxyphenyl)-2-methylpropan-1-amine (500 mg; 2.79 mmol) with 4-(trifluoromethyl)benzaldehyde (0.38 ml; 2.79 mmol) as per general procedure A afforded N-[2-(4-methoxyphenyl)-2-methylpropyl]-N-[4-(trifluoromethyl)benzyl]amine (792 mg; 84% yield).

¹H NMR (CDCl₃) δ 7.53 (d, 2H, J=8.1), 7.32 (d, 2H, J=8.1), 7.26 (d, 2H, J=8.8), 6.88 (d, 2H, J=8.8), 3.79 (s, 3H), 3.75 (s, 2H), 2.67 (s, 2H), 1.34 (s, 6H).

Step 2. Demethylation of the above intermediate (792 mg; 2.35 mmol) with boron tribromide (1M in dichloromethane; 9.4 ml; 9.4 mmol), as per general procedure F, afforded 4-(1,1-dimethyl-2-{[4-(trifluoromethyl)benzyl] amino}ethyl)phenol as a white solid (597 mg; 78% yield).

¹H NMR (CDCl₃) δ 7.52 (d, 2H, J=8.1), 7.33 (d, 2H, J=8.1), 7.17 (d, 2H, J=8.7), 6.73 (d, 2H, J=8.7), 3.77 (s, 2H), 2.67 (s, 2H), 1.32 (s, 6H).

Step 3. Alkylation of the above intermediate (500 mg; 0.1.54 mmol) with ethyl-2-bromoisobutyrate (0.45 ml; 3.1 mmol) as per general procedure C (2 eq Cs2CO3, MeCN, 85C, 15 hr) afforded ethyl 2-[4-(1,1-dimethyl-2-{[4-(trifluoromethyl)benzyl]amino}ethyl)phenoxy]-2-methylpropanoate (82 mg; 95% yield).

¹H NMR (CDCl₃) δ 7.51 (d, 2H, J=8.2), 7.30 (d, 2H, J=8.2), 7.18 (d, 2H, J=8.8), 6.78 (d, 2H, J=8.8), 4.22 (q, 2H, J=7.1), 3.72 (s, 2H), 2.63 (s, 2H), 1.57 (s, 6H), 1.30 (s, 6H), 1.22 (t, 3H, J=7.1). MS: m/z 438 (M+1).

Step 4. Condensation of the above intermediate (200 mg; 0.46 mmol) with 2-chloro-5-ethyl-pyrimidine (0.060 ml; 0.49 mmol) as per general procedure E (1.15 eq DIEA, 220C, 50 hr) afforded ethyl 2-[4-(2-{(5-ethylpyrimidin-2-yl)[4-(trifluoromethyl)benzyl]amino}-1,1-dimethylethyl) phenoxy]-2-methylpropanoate (90 mg; 36% yield).

¹H NMR (CDCl₃) δ 8.1 (s, 2H), 7.40 (d, 2H, J=8.1), 7.20 (d, 2H, J=8.7), 6.93 (d, 2H, J=8.1), 6.78 (d, 2H, J=8.7), 4.29 (s, 2H), 4.23 (q, 2H, J=7.2), 3.81 (s, 2H), 2.43 (q, 2H, J=7.6), 1.57 (s, 6H), 1.33 (s, 6H), 1.24 (t, 3H, J=7.2), 1.17 (t, 3H, J=7.6). MS: m/z 544 (M+1).

Step 5. Hydrolysis of the above ester (90 mg) with NaOH as per general procedure H provided after chromatography the title compound as a glassy solid (45 mg; 52% yield). MS: m/z 516 (M+1).

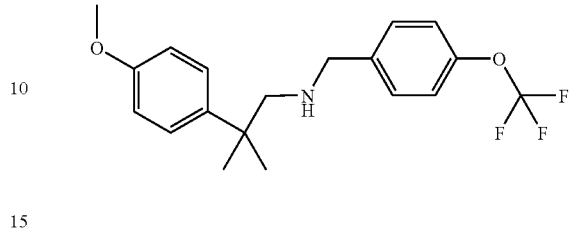

N-[2-(4-Methoxyphenyl)-2-methylpropyl]-N-[4-(trifluoromethoxy)benzyl]amine

Reductive amination of 2-(4-methoxyphenyl)-2-methylpropan-1-amine (3.6 g; 20.11 mmol) with 4-(trifluoromethoxy)benzaldehyde (3.82 g; 20.11 mmol) as per general procedure A provided the title compound (5.0 g; 70% yield).

¹H NMR (CDCl₃) δ 7.26 (d, 2H, J=8.7), 7.24 (d, 2H, J=8.3), 7.13 (d, 2H; J=8.3), 6.86 (d, 2H, J=8.7), 3.80 (s, 3H), 3.70 (s, 2H), 2.68 (s, 2H), 1.34 (s, 6H).

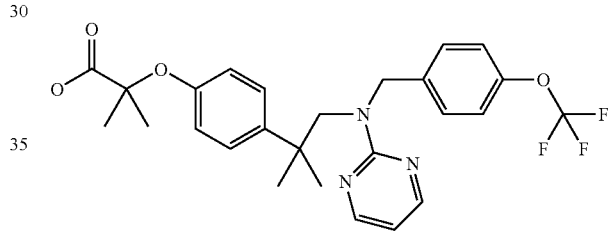

2-[4-(1,1-Dimethyl-2-{pyrimidin-2-yl[4-(trifluoromethoxy)benzyl]amino}ethyl)phenoxy]-2-methylpropanoic acid Step 1. Condensation N-[2-(4-methoxyphenyl)-2-methylpropyl]-N-[4-(trifluoromethoxy)benzyl]amine (250 mg; 0.71 mmol) with 2-chloro-pyrimidine (85 mg; 0.74 mmol) as per general procedure E (2 eq DIEA, 210C, 14 hr) afforded N-[2-(4-methoxyphenyl)-2-methylpropyl]-N-[4-(trifluoromethoxy)benzyl]pyrimidin-2-amine (270 mg; 88% yield). MS: m/z 432 (M+1).

Step 2. Demethylation of the previous intermediate (250 mg; 0.58 mmol) with boron tribromide (1M in dichloromethane; 2.31 ml; 2.31 mmol) as per general procedure F afforded the intermediate phenol (200 mg; 84% yield).

MS: m/z 418 (M+1).

Step 3. Alkylation of the intermediate phenol (100 mg; 0.24 mmol) with 2-trichloromethyl-2-propanol (64 mg; 0.36 mmol) as per general procedure D provided after chromatography and crystallization from dichloromethane-hexane, the title compound as a white solid (85 mg; 23% yield).

¹H NMR (CDCl₃) δ 8.21 (d, 2H, J=4.8), 7.18 (d, 2H, J=8.7), 6.95 (d, 2H, J=8.4), 6.81 (m, 4H), 6.42 (t, 1H, J=4.8), 4.23 (s, 2H), 3.77 (s, 2H), 1.53 (s, 6H), 1.29 (s, 6H).

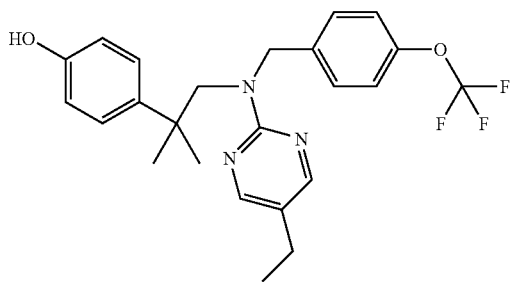

4-(2-{(5-Ethylpyrimidin-2-yl)[4-(trifluoromethoxy)benzyl]amino}-1,1-dimethylethyl)phenol Step 1. Condensation of N-[2-(4-methoxyphenyl)-2-methylpropyl]-N-[4-(trifluoromethoxy)benzyl]amine (3.5 g; 9.92 mmol) with 2-chloro-5-ethyl-pyrimidine (1.51 g; 10.60 mmol) as per general procedure E (1.1 eq DIEA, 220C, 15 hr) afforded the intermediate methyl aryl ether (3.1 g; 68% yield).

$^1$H NMR (CDCl$_3$) δ 8.16 (s, 2H), 7.48 (s, 1H, OH), 7.22 (d, 2H, J=8.6), 7.0 (d, 2H, J=8.2), 6.89 (d, 2H, J=8.6), 6.75 (d, 2H, J=8.2), 4.25 (s, 2H), 3.85 (s, 2H), 2.45 (q, 2H, J=7.6), 1.35 (s, 6H), 1.18 (t, 3H, J=7.6). MS: m/z 460 (M+1).

Step 2. Demethylation of the previous intermediate (2.32 g; 5.05 mmol) with boron tribromide (1M in dichloromethane; 20.2 ml; 20.2 mmol) as per general procedure F provided the title compound (1.56 g; 69% yield).

$^1$H NMR (CDCl$_3$) δ 8.3 (s, 1H), 8.19 (s, 2H), 7.24 (d, 2H, J=8.6), 7.02 (d, 2H, J=8.3), 6.93 (d, 2H, J=8.6), 6.77 (d, 2H, J=8.3), 4.30 (s, 2H), 3.89 (s, 2H), 2.45 (q, 2H, J=7.5), 1.38 (s, 6H), 1.20 (t, 3H, J=7.5).

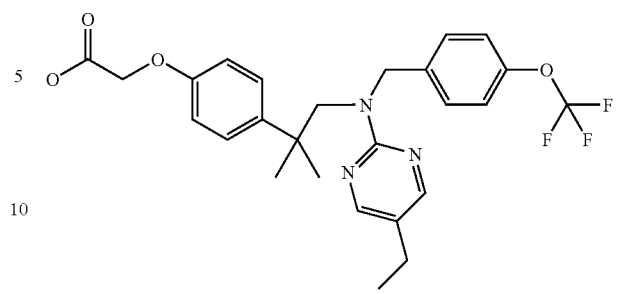

[4-(2-{(5-ethylpyrimidin-2-yl)[4-(trifluoromethoxy)benzyl]amino}-1,1-dimethylethyl)phenoxy]acetic acid Step 1. Alkylation 4-(2-{(5-ethylpyrimidin-2-yl)[4-(trifluoromethoxy)benzyl]amino}-1,1-dimethylethyl)phenol (95 mg; 0.21 mmol) with tert-butyl bromoacetate (50 mg; 0.26 mmol) as per general procedure C (1.2 eq Cs2CO3, MeCN, 80C, 3 hr) afforded the intermediate tert-butyl ester (100 mg; 84% yield).

$^1$H NMR (CDCl$_3$) δ 8.11 (s, 2H), 7.25 (d, 2H, J=8.8), 6.99 (d, 2H, J=8.4), 6.85 (d, 2H, J=8.4), 6.82 (d, 2H, J=8.8), 4.49 (s, 2H), 4.27 (s, 2H), 3.81 (s, 2H), 2.43 (q, 2H, J=7.6), 1.47 (s, 9H), 1.33 (s, 6H), 1.17 (t, 3H, J=7.6). MS: m/z 560 (M+1).

Step 2. Hydrolysis of the tert-butyl ester (100 mg) with TFA as per general procedure I provided after chromatography and crystallization from dichloromethane-hexane, the TFA salt of the title compound as a glassy solid (94 mg; 90% yield).

$^1$H NMR (CDCl$_3$) δ 8.23 (s, 2H), 7.26 (d, 2H, J=8.6), 7.02 (d, 2H, J=8.2), 6.89 (d, 2H, J=8.6), 6.83 (d, 2H, J=8.2), 4.63 (s, 2H), 4.36 (s, 2H), 3.86 (s, 2H), 2.47 (q, 2H, J=7.6), 1.37 (s, 6H), 1.19 (t, 3H, J=7.6). MS: m/z 504 (M+1).

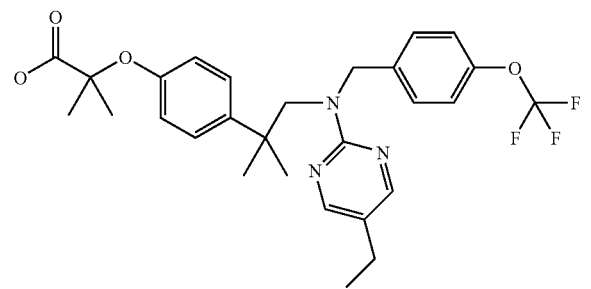

2-[4-(2-{(5-ethylpyrimidin-2-yl)[4-(trifluoromethoxy)benzyl]amino}-1,1-dimethylethyl)phenoxy]-2-methylpropanoic acid Alkylation of 4-(2-{(5-ethylpyrimidin-2-yl)[4-(trifluoromethoxy)benzyl]amino}-1,1-dimethylethyl)phenol (7 g; 15.73 mmol) with 2-trichloromethyl-2-propanol (4.19 g; 23.60 mmol) as per general procedure D provided after flash chromatography the title compound (7.9 g; 94% yield).

$^1$H NMR (CDCl$_3$) δ 8.14 (s, 2H), 7.20 (d, 2H, J=8.7), 6.97 (d, 2H, J=8.3), 6.84 (d, 2H, J=8.7), 6.82 (d, 2H, J=8.3), 4.24 (s, 2H), 3.78 (s, 2H), 2.42 (q, 2H, J=7.5), 1.56 (s, 6H), 1.31 (s, 6H), 1.16 (t, 3H, J=7.5). MS: m/z 531 (M+1).

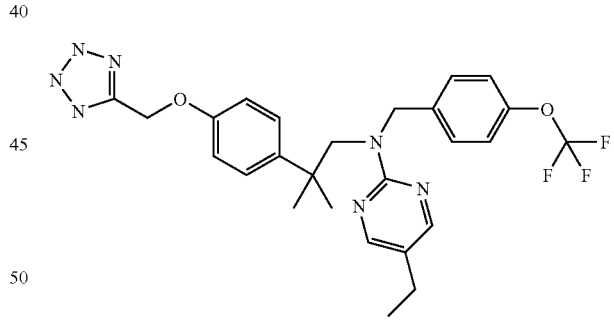

5-ethyl-N-{2-methyl-2-[4-(2H-tetraazol-5-ylmethoxy)phenyl]propyl}-N-[4-(trifluoromethoxy)benzyl]pyrimidin-2-amine Step 1. Alkylation of 4-(2-{(5-ethylpyrimidin-2-yl)[4-(trifluoromethoxy)benzyl]amino}-1,1-dimethylethyl)phenol (150 mg; 0.34 mmol) with chloroacetonitrile (0.043 ml; 0.67 mmol) as per general procedure C (2 eq Cs2CO3, MeCN, 85C, 12 hr) afforded the intermediate nitrile (125 mg; 76% yield).

$^1$H NMR (CDCl$_3$) δ 8.13 (s, 2H), 7.34 (d, 2H, J=8.8), 7.02 (d, 2H, J=8.3), 6.91 (d, 2H, J=8.3), 6.88 (d, 2H, J=8.8), 4.76 (s, 2H), 4.35 (s, 2H), 3.86 (s, 2H), 2.46 (q, 2H, J=7.6), 1.37 (s, 6H), 1.19 (t, 3H, J=7.6).

Step 2. A solution of the previous intermediate (125 mg) in toluene (0.05 M) was treated under nitrogen with azidotrimethylsilane (0.068 ml; 0.52 mmol) and dibutyltin oxide (0.013 mg; 0.05 mmol). Heated to 115C for 14 hr. Cooled down and partitioned between ethyl acetate and 0.1N HCl. The organic phase was washed with saturated brine, dried over sodium sulfate and concentrated. Purification by radial chromatography using a methanol-dichloromethane gradient (1–15%), followed by lyophillization from MeCN-water afforded the title compound as a white powder (124 mg; 91% yield).

$^1$H NMR (CDCl$_3$) δ 8.15 (s, 2H), 7.23 (d, 2H, J=8.8), 6.96 (d, 2H, J=8.3), 6.83 (d, 2H, J=8.3), 6.79 (d, 2H, J=8.8), 5.36 (s, 2H), 4.33 (s, 2H), 3.84 (s, 2H), 2.44 (q, 2H, J=7.6), 1.33 (s, 6H), 1.16 (t, 3H, J=7.6).

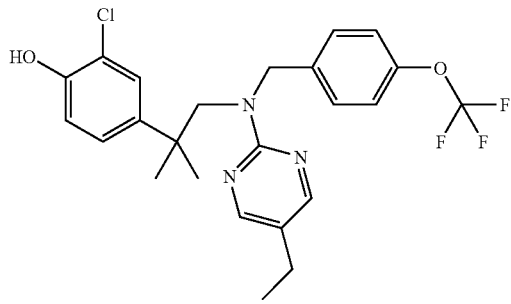

2-Chloro-4-(2-{(5-ethylpyrimidin-2-yl)[4-(trifluoromethoxy)benzyl]amino}-1,1-dimethylethyl)phenol To a solution 4-(2-{(5-ethylpyrimidin-2-yl)[4-(trifluoromethoxy)benzyl]amino}-1,1-dimethylethyl)phenol (300 mg; 0.67 mmol) in ethyl ether (0.1M) was added sulfuryl chloride (0.060 ml; 0.74 mmol). After 10 minutes an additional 0.3 eq of sulfuryl chloride were added. Stirred 20 more minutes. Partitioned between ethyl acetate and dilute sodium bicarbonate solution. Organic phase was washed with saturated brine, dried over sodium sulfate and concentrated. Purification by radial chromatography on silica gel using a dichloromethane-hexane gradient (30–90%) provided the title compound (80 mg; 25% yield).

$^1$H NMR (CDCl$_3$) δ 8.14 (s, 2H), 7.28 (d, 1H, J=2.2), 7.17 (dd, 2H, J=8.5; 2.2), 7.04 (d, 2H, J=8.3), 6.91 (m, 3H), 5.92 (s, 1H, OH), 4.41 (s, 2H), 3.84 (s, 2H), 2.46 (q, 2H, J=7.6), 1.34 (s, 6H), 1.20 (t, 3H, J=7.6). MS: m/z 480 (M+1).

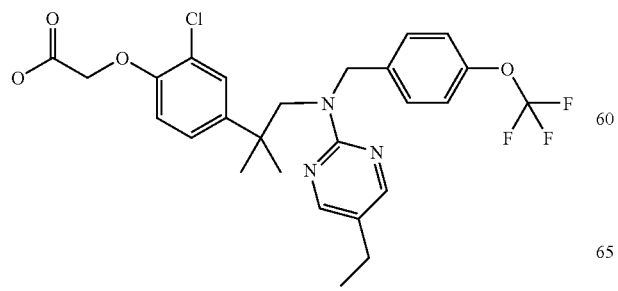

[2-Chloro-4-(2-{(5-ethylpyrimidin-2-yl)[4-(trifluoromethoxy)benzyl]amino}-1,1-dimethylethyl)phenoxy]acetic acid Step 1. Alkylation of 2-chloro-4-(2-{(5-ethylpyrimidin-2-yl)[4-(trifluoromethoxy)benzyl]amino}-1,1-dimethylethyl) phenol (80 mg; 0.16 mmol) with tert-butyl bromoacetate (39 mg; 0.20 mmol) as per general procedure C (1.2 eq Cs2CO3, MeCN, 60C, 1 hr) afforded the intermediate tert-butyl ester (90 mg; 91% yield).

MS: m/z 594 (M+1).

Step 2. Hydrolysis of the tert-butyl ester (90 mg) with TFA as per general procedure I provided after chromatography and lyophillization from MeCN-water, the title compound as a white powder (72 mg; 88% yield).

$^1$H NMR (CDCl$_3$) δ 9.1 (bs, 1H), 8.17 (s, 2H), 7.35 (d, 1H, J=2.2), 7.16 (dd, 2H, J=8.7; 2.2), 7.03 (d, 2H, J=8.4), 6.89 (d, 2H, J=8.4), 6.78 (d, 1H, J=8.7), 4.69 (s, 2H), 4.42 (s, 2H), 3.82 (s, 2H), 2.45 (q, 2H, J=7.6), 1.33 (s, 6H), 1.17 (t, 3H, J=7.6). MS: m/z 538 (M+1).

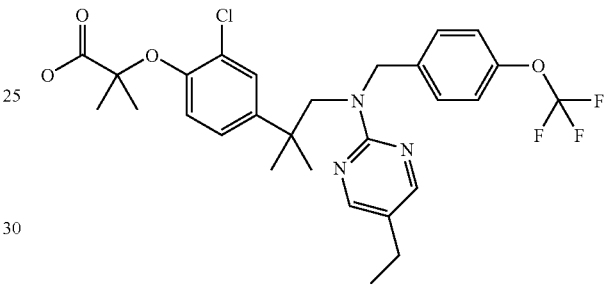

2-[2-Chloro-4-(2-{(5-ethylpyrimidin-2-yl)[4-(trifluoromethoxy)benzyl]amino}-1,1-dimethylethyl)phenoxy]-2-methylpropanoic acid Step 1. Alkylation of the intermediate phenol 2-chloro-4-(2-{(5-ethylpyrimidin-2-yl)[4-(trifluoromethoxy)benzyl] amino}-1,1-dimethylethyl)phenol (70 mg; 0.15 mmol) with ethyl-2-bromoisobutyrate (57 mg; 0.29 mmol) as per general procedure C (2 eq Cs2CO3, MeCN, 85C, 5 hr) provided the intermediate ethyl ester (82 mg; 95% yield).

Step 2. Hydrolysis of the ethyl ester (82 mg) with NaOH as per general procedure H provided after chromatography and lyophillization from MeCN-water, the title compound as a white powder (37 mg; 47% yield).

$^1$H NMR (CDCl$_3$) δ 8.15 (s, 2H), 7.37 (d, 1H, J=2.4), 7.15 (dd, 2H, J=8.6; 2.4), 7.02 (d, 2H, J=8.3), 6.97 (d, 1H, J=8.6), 6.89 (d, 2H, J=8.3), 4.38 (s, 2H), 3.82 (s, 2H), 2.45 (q, 2H, J=7.6), 1.61 (s, 6H), 1.34 (s, 6H), 1.19 (t, 3H, J=7.6).

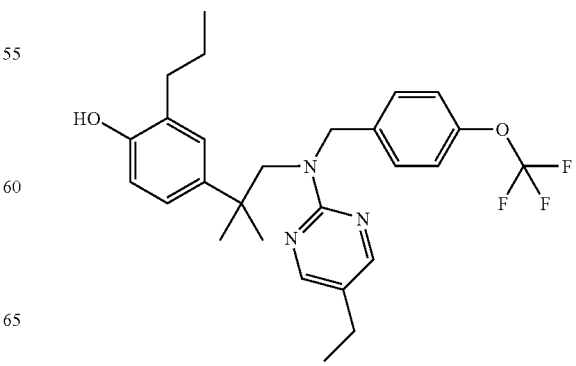

4-(2-{(5-Ethylpyrimidin-2-yl)[4-(trifluoromethoxy)benzyl]amino}-1,1-dimethylethyl)-2-propylphenol Step 1. Alkylation of 4-(2-{(5-ethylpyrimidin-2-yl)[4-(trifluoromethoxy)benzyl]amino}-1,1-dimethylethyl)phenol (5.7 g; 12.96 mmol) with allyl bromide (1.23 ml; 14.26 mmol) as per general procedure C (1.1 eq. Cs2CO3, MeCN, 85C, 14 hr) provided the intermediate allyl ether (5.3 g; 85% yield).

$^1$H NMR (CDCl$_3$) δ 8.16 (s, 2H), 7.29 (d, 2H, J=8.8), 7.03 (d, 2H, J=8.4), 6.91 (d, 2H, J=8.4), 6.88 (d, 2H, J=8.8), 6.09 (m, 1H), 5.44 (dd, 1H, J==17.2; 1.5), 5.30 (dd, 1H, J=10.4; 1.1), 4.55 (d, 2H, J=5.3), 4.35 (s, 2H), 3.86 (s, 2H), 2.46 (q, 2H, J=7.6), 1.38 (s, 6H), 1.21 (t, 3H, J=7.6).

Step 2. A solution of the above intermediate (5.34 g; 11.01 mmol) in dichloromethane (0.12M) is treated under nitrogen, in an ice bath, with boron trichloride (1M solution in hexane; 12.7 ml; 12.7 mmol). After 45 minutes an additional 0.5 eq of boron trichloride was added. Stirred for 15 more minutes and quenched by dropwise addition of methanol (3 ml). Stirred 15 minutes and partitioned between ethyl acetate and sodium bicarbonate solution. The aqueous phase was washed with ethyl acetate. The organic phases were washed with saturated brine, dried over sodium sulfate and concentrated. Purification by flash chromatography on silica gel using an ethyl acetate-hexane gradient (2–30%) afforded 2-allyl-4-(2-(5-ethylpyrimidin-2-yl)[4-(trifluoromethoxy)benzyl]amino-1,1-dimethylethyl)phenol, which crystallized upon standing (3.4 g; 64% yield).

$^1$H NMR (CDCl$_3$) δ 8.15 (s, 2H), 7.10 (m, 2H), 7.01 (d, 2H, J=8.4), 6.89 (d, 2H, J=8.4), 6.71 (d, 1H, J=8.8), 6.01 (bs, 1H, OH), 5.99 (m, 1H), 5.12 (m, 2H), 4.30 (s, 2H), 3.84 (s, 2H), 3.38 (d, 2H, J=6.2), 2.46 (q, 2H, J=7.6), 1.35 (s, 6H), 1.20 (t, 3H, J=7.6). MS: m/z 486 (M+1).

Step 3. A solution of the previous intermediate (125 mg; 0.26 mmol) in ethyl acetate (0.05M) is hydrogenated over 10% Pd on carbon (60 mg) under balloon pressure for 3 hours. The catalyst was filtered off and washed with ethyl acetate, chloroform and methanol. The filtrate was concentrated and purified by flash chromatography on silica gel using an ethyl acetate-hexane gradient (2–25%) to afford the title compound (80 mg; 64% yield).

$^1$H NMR (CDCl$_3$) δ 8.15 (s, 2H), 7.09 (d, 1H, J=2.3), 7.03 (dd, 1H, J=8.2; 2.3), 7.0 (d, 2H, J=8.5), 6.87 (d, 2H, =8.5), 6.67 (d, 1H, J=8.2), 5.73 (s, 1H, OH), 4.28 (s, 2H), 3.84 (s, 2H), 2.55 (t, 2H, J=7.5), 2.45 (q, 2H, J=7.3), 1.61 (m, 2H), 1.35 (s, 6H), 1.19 (t, 3H, J=7.5), 0.94 (t, 3H, J=7.3). MS: m/z 488 (M+1).

2-[4-(2-{(5-Ethylpyrimidin-2-yl)[4-(trifluoromethoxy)benzyl]amino}-1,1-dimethylethyl)-2-propylphenoxy]-2-methylpropanoic acid Step 1. Alkylation of 4-(2-{(5-ethylpyrimidin-2-yl)[4-(trifluoromethoxy)benzyl]amino}-1,1-dimethylethyl)-2-propylphenol (36 mg; 0.075 mmol) with ethyl-2-bromoisobutyrate (22 mg; 0.11 mmol) as per general procedure C (1.5 eq Cs2CO3, MeCN, 85C, 15 hr) afforded the intermediate ethyl ester (40 mg; 88% yield). MS: m/z 602 (M+1).

Step 2. Hydrolysis of the ethyl ester (40 mg) with NaOH as per general procedure H provided after chromatography and lyophillization from MeCN-water, the title compound as a white powder (30 mg; 78% yield).

$^1$H NMR (CDCl$_3$) δ 8.15 (s, 2H), 7.12 (d, 1H, J=2.3), 7.04 (dd, 1H, J=8.6; 2.3), 6.99 (d, 2H, J=8.3), 6.83 (d, 2H, =8.3), 6.71 (d, 1H, J=8.6), 4.27 (s, 2H), 3.81 (s, 2H), 2.55 (t, 2H, J=7.5), 2.45 (q, 2H, J=7.7), 1.60 (s, 6H), 1.56 (m, 2H), 1.34 (s, 6H), 1.19 (t, 3H, J=7.5), 0.93 (t, 3H, J=7.7).

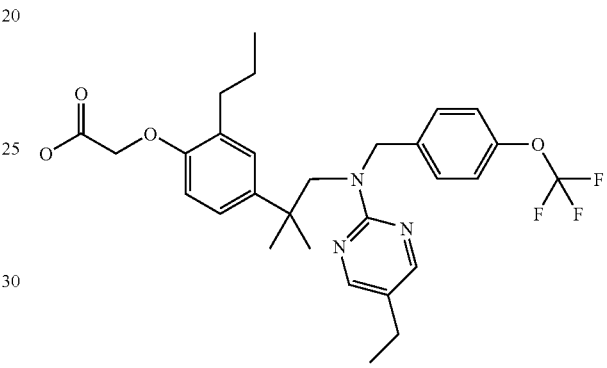

[4-(2-{(5-Ethylpyrimidin-2-yl)[4-(trifluoromethoxy)benzyl]amino}-1,1-dimethylethyl)-2-propylphenoxy]acetic acid Step 1. Alkylation of 4-(2-{(5-ethylpyrimidin-2-yl)[4-(trifluoromethoxy)benzyl]amino}-1,1-dimethylethyl)-2-propylphenol (36 mg; 0.075 mmol) with tert-butyl bromoacetate (18 mg; 0.090 mmol) as per general procedure C (1.2 eq Cs2CO3, MeCN, 85C, 2 hr) afforded the intermediate ester (40 mg; 88% yield). MS: m/z 602 (M+1).

Step 2. Hydrolysis of the tert-butyl ester (40 mg) with TFA as per general procedure I provided after chromatography and lyophillization from MeCN-water, the title compound as a white powder (35 mg; 95% yield).

$^1$H NMR (CDCl$_3$) δ 8.16 (s, 2H), 7.13 (d, 1H, J=2.3), 7.10 (dd, 1H, J=8.5; 2.3), 7.0 (d, 2H, J=8.4), 6.85 (d, 2H, J=8.4), 6.66 (d, 1H, J=8.5), 4.65 (s, 2H), 4.32 (s, 2H), 3.83 (s, 2H), 2.61 (t, 2H, J=7.5), 2.45 (q, 2H, J=7.6), 1.58 (m, 2H), 1.35 (s, 6H), 1.19 (t, 3H, J=7.5), 0.93 (t, 3H, J=7.6).

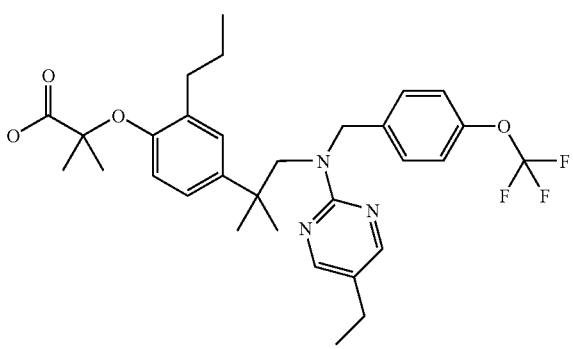

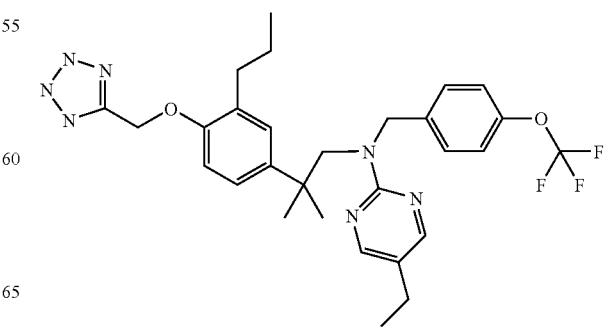

5-Ethyl-N-{2-methyl-2-[3-propyl-4-(2H-tetraazol-5-ylmethoxy)phenyl]propyl}-N-[4-(trifluoromethoxy)benzyl]pyrimidin-2-amine Step 1. Alkylation of 4-(2-{(5-ethylpyrimidin-2-yl)[4-(trifluoromethoxy)benzyl]amino}-1,1-dimethylethyl)-2-propylphenol (210 mg; 0.43 mmol) with chloroacetonitrile (0.055 ml; 0.86 mmol) as per general procedure C (2 eq Cs2CO3, MeCN, 85C, 5 hr) afforded the intermediate nitrile (160 mg; 70% yield).

Step 2. A solution of the previous intermediate (160 mg) in toluene (0.12 M) was treated under nitrogen with azidotrimethylsilane (0.081 ml; 0.61 mmol) and dibutyltin oxide (0.015 mg; 0.06 mmol). Heated to 110C for 14 hr. Cooled down and partitioned between ethyl acetate and 0.1N HCl. The organic phase was washed with saturated brine, dried over sodium sulfate and concentrated. Purification by radial chromatography using a methanol-dichloromethane gradient (1–15%) afforded the title compound as a glassy solid (100 mg; 57% yield).

$^1$H NMR (CDCl$_3$) δ 8.13 (s, 2H), 7.09 (m, 2H), 6.98 (d, 2H, J=8.4), 6.84 (d, 2H, J=8.4), 6.78 (d, 1H, J=9.2), 5.36 (s, 2H), 4.34 (s, 2H), 3.85 (s, 2H), 2.45 (m, 4H), 1.46 (m, 2H), 1.33 (s, 6H), 1.15 (t, 3H, J=7.6), 0.81 (t, 3H, J=7.3). MS: m/z 570 (M+1).

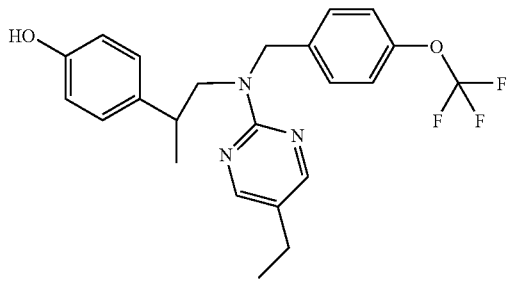

4-(2-{(5-Ethylpyrimidin-2-yl)[4-(trifluoromethoxy)benzyl]amino}-1-methylethyl)phenol Step 1. To a 2M solution of LDA in heptane (commercial grade; 66.2 ml) at 0C, under nitrogen, it was added 4-methoxyphenyl acetic acid (5.5 g; 33.09 mmol). After stirring at 0C for 40 minutes it was added iodomethane (13.18 ml; 211.78 mmol). Allowed to warm to rt and stirred additional 30 minutes. The reaction mixture was then added to 200 ml of saturated ammonium chloride. Extracted 3×150 ml of ethyl ether. The aqueous phase was acidified with 1N HCl and extracted 2×150 ml with ethyl ether. The latter organic phases were dried over sodium sulfate and concentrated to afford 5.8 g of an oil which corresponded to a 2.5:1 mixture of 2-(4-methoxyphenyl)-2-methylpropanoic acid (bis-methylation product) to 2-(4-methoxyphenyl)propanoic acid (monomethylation product) which was used in the next step without any further purification.

Step 2. The previous crude mixture (1.5 g) was dissolved in dichloromethane (~0.6 M) and treated under nitrogen with EDCI (1.36 g; 7.09 mmol). After 10 minutes, 4-trifluoromethoxybenzylamine (1.08 ml; 7.09 mmol) was added and stirred for 1 hr. The reaction mixture is partitioned between ethyl acetate and 0.5N HCl. The organic phase was washed 1×0.5N HCl, 2×0.5N NaOH, 1× saturated brine, dried over sodium sulfate and concentrated. Purification by flash chromatography on silica gel using an ethyl acetate-hexane gradient (5–60%) afforded 2-(4-methoxyphenyl)-N-[4-(trifluoromethoxy)benzyl]propanamide (0.38 g).

Step 3. To a solution of the previous amide (375 mg; 1.06 mmol) in THF (0.2M), under nitrogen, it was added LAH (1M solution in THF; 2.12 ml; 2.12 mmol). After stirring at rt for 1 hr additional LAH was added (2 ml). Stirred at rt for 14 hr and then heated at 80C for 4 hr. Cooled down and added additional LAH (3 ml). Heated at 80C for an extra 6 hr. The reaction was cooled down and worked up using the Fieser procedure: added 0.27 ml of water dropwise (exothermic), followed by 0.27 ml of 15% NaOH solution and 0.81 ml of water. Stirred for 10 minutes, diluted with ethyl acetate and stirred another 10 minutes. The mixture was filtered through a plug of celite and the solids washed with ethyl acetate. The filtrate was concentrated to afford N-[2-(4-methoxyphenyl)propyl]-N-[4-(trifluoromethoxy)benzyl]amine (310 mg) which was used in the next step without further purification. MS: m/z 340 (M+1).

Step 4. Condensation of the previous amine (310 mg; 0.91 mmol) with 2-chloro-5-ethyl pyrimidine (0.136 ml; 1.11 mmol) as per general procedure E (1.1 eq DIEA, toluene, 210C, 48 hr) afforded 5-ethyl-N-[2-(4-methoxyphenyl)propyl]-N-[4-(trifluoromethoxy)benzyl]pyrimidin-2-amine (310 mg; 65% yield). MS: m/z 446 (M+1).

Step 5. Demethylation of the previous intermediate (310 mg; 0.69 mmol) with boron tribromide (1M in dichloromethane; 2.78 ml) as per general procedure F provided the title compound (213 mg; 71% yield).

$^1$H NMR (CDCl$_3$) δ 8.2 (s, 2H), 7.07 (s, 4H), 7.02 (d, 2H, J=8.4), 6.70 (d, 2H, J=8.4), 4.92 (d, 1H, J=16.3), 3.95 (d, 1H, J=16.3), 3.93 (m, 1H), 3.25 (m, 2H), 2.46 (q, 2H, J=7.5), 1.23 (m, 6H). MS: m/z 432 (M+1).

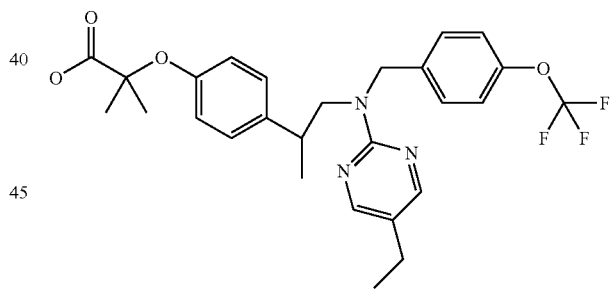

2-[4-(2-{(5-Ethylpyrimidin-2-yl)[4-(trifluoromethoxy)benzyl]amino}-1-methylethyl)phenoxy]-2-methylpropanoic acid Alkylation of 4-(2-{(5-ethylpyrimidin-2-yl)[4-(trifluoromethoxy)benzyl]amino}-1-methylethyl)phenol (106 mg; 0.25 mmol) with 2-trichloromethyl-2-propanol (66 mg; 0.37 mmol) as per general procedure D provided after chromatography the title compound as a glassy solid (90 mg; 75% yield).

$^1$H NMR (CDCl$_3$) δ 8.22 (s, 2H), 7.04 (m, 6H), 6.84 (d, 2H, J=8.6), 4.86 (d, 1H, J=16.3), 4.02 (d, 1H, J=16.3), 3.88 (dd, 1H, J=13.7; 6.4), 3.34 (dd, 1H, J=13.7; 8.5), 3.25 (m, 1H), 2.47 (q, 2H, J=7.7), 1.56 (s, 6H), 1.22 (m, 6H). MS: m/z 518 (M+1).

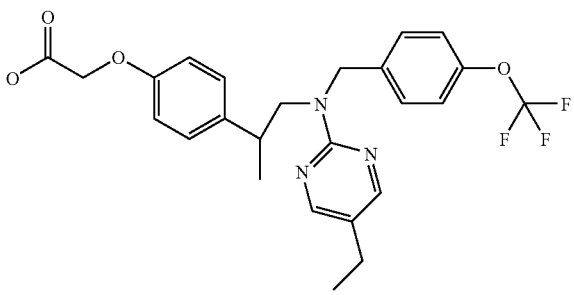

[4-(2-{(5-Ethylpyrimidin-2-yl)[4-(trifluoromethoxy)benzyl]amino}-1-methylethyl)phenoxy]acetic acid Step 1. Alkylation of 4-(2-{(5-ethylpyrimidin-2-yl)[4-(trifluoromethoxy)benzyl]amino}-1-methylethyl)phenol (106 mg; 0.25 mmol) with tert-butyl bromoacetate (0.043 ml; 0.29 mmol) as per general procedure C (1.2 eq Cs2CO3, MeCN, 85C, 3 hr) afforded the intermediate ethyl ester (100 mg; 77% yield).

Step 2. Hydrolysis of the tert-butyl ester (100 mg) with TFA as per general procedure I provided after flash chromatography the title compound as a glassy solid.

$^1$H NMR (CDCl$_3$) δ 9.0 (bs, 1H), 8.23 (s, 2H), 7.09 (d, 2H, J=8.4), 7.06 (bs, 4H), 6.82 (d, 2H, J=8.4), 4.86 (d, 1H, J=16.5), 4.57 (s, 2H), 4.15 (d, 1H, J=16.5), 3.85 (dd, 1H, J=14; 6.9), 3.40 (dd, 1H, J=14; 8.2), 3.26 (m, 1H), 2.47 (q, 2H, J=7.5), 1.23 (m, 6H). MS: m/z 490 (M+1).

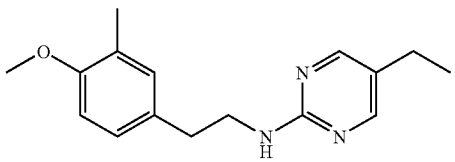

5-Ethyl-N-[2-(4-methoxy-3-methylphenyl)ethyl]pyrimidin-2-amine

Step 1. A solution of 3-methyl-p-anisaldehyde (23.13 g, 154 mmol) and nitromethane (9.40 g, 154 mmol) in MeOH (260 ml) was cooled in an ice bath and treated dropwise with NaOH (162 ml of 1N solution; 162 mmol). The reaction mixture was stirred at rt for 1 hr. Water (50 ml) was then added and the mixture poured into 1N HCl (300 ml). The precipitate was collected and purified by flash chromatography on silica gel eluting with dichloromethane to provide methyl 2-methyl-4-[(E)-2-nitroethenyl]phenyl ether as a yellow solid (14.61 g; 49% yield).

$^1$H NMR (acetone d-6) δ 7.98 (d, 1H, J=13.6), 7.82 (d, 1H, J=13.6), 7.62 (bs, 2H), 7.02 (d, 1H, J=8.9), 3.8 (s, 3H), 2.28 (s, 3H).

Step 2. A solution of methyl 2-methyl-4-[(E)-2-nitroethenyl]phenyl ether (7.89 g; 40.88 mmol) in dry THF (50 ml) was added to borane (245 ml of 1M solution in THF; 245 mmol), under nitrogen, dropwise over 20 minutes. The reaction mixture was then heated to 90C. After 14 hr it was cooled to rt and ice-cold water (100 ml) was added dropwise over 30 minutes. The pH was adjusted to ~2 with 1N HCl and heated to reflux for 5 hr. Upon cooling, the reaction mixture was extracted with ethyl ether (2×300 ml) and the ether phases were discarded. The pH of the aqueous phase was adjusted to 10 with 1N NaOH and extracted with ethyl ether (2×200 ml). The combined organic phases were dried over MgSO$_4$, filtered and concentrated to provide 2-(4-methoxy-3-methylphenyl)ethanamine (5.46 g; 81% yield), which was used without any further purification.

$^1$H NMR (CDCl$_3$) δ 6.95 (d, 1H, J=8.2), 6.94 (s, 1H), 6.72 (d, 1H, J=8.0), 3.8 (s, 3H), 2.88 (t, 2H, 6.8), 2.62 (t, 2H, 6.9), 2.18 (s, 3h).

Step 3. Condensation of 2-(4-methoxy-3-methylphenyl)ethanamine (516 mg; 3.12 mmol) with 2-chloro-5-ethyl pyrimidine (446 mg; 3.12 mmol) as per general procedure E (1.5 eq DIEA, nBuOH, 130C, 20 hr) provided 5-ethyl-N-[2-(4-methoxy-3-methylphenyl)ethyl]pyrimidin-2-amine (435 mg; 51% yield).

$^1$H NMR (CDCl$_3$) δ 8.1 (s, 2H), 7.0 (m, 2H), 6.74 (d, 1H, J=9), 5.0 (bs, 1H), 3.8 (s, 3H), 3.60 (q, 2H, J=6.5), 2.88 (t, 2H, J=6.9), 2.44 (q, 2H, J=7.6), 2.18 (s, 3h), 1.18 (t, 3H, J=7.6).

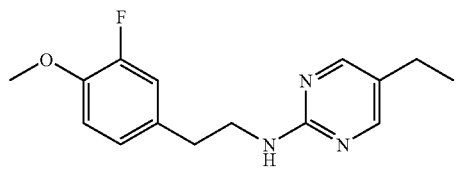

5-Ethyl-N-[2-(3-fluoro-4-methoxyphenyl)ethyl]pyrimidin-2-amine

Similarly prepared from 3-fluoro-4-methoxybenzaldehyde.

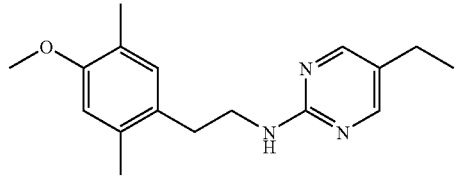

5-Ethyl-N-[2-(4-methoxy-2,5-dimethylphenyl)ethyl]pyrimidin-2-amine

Similarly prepared from 4-methoxy-2,5-dimethylbenzaldehyde.

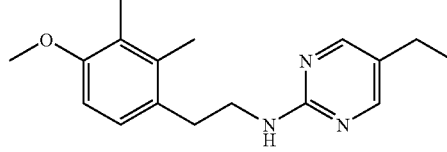

5-Ethyl-N-[2-(4-methoxy-2,3-dimethylphenyl)ethyl]pyrimidin-2-amine

Similarly prepared from 4-methoxy-2,3-dimethylbenzaldehyde.

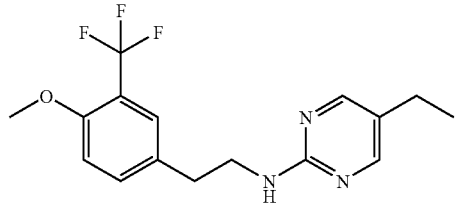

5-Ethyl-N-{2-[4-methoxy-3-(trifluoromethyl)phenyl]ethyl}pyrimidin-2-amine

Similarly prepared from 4-methoxy-3-(trifluoromethyl)benzaldehyde.

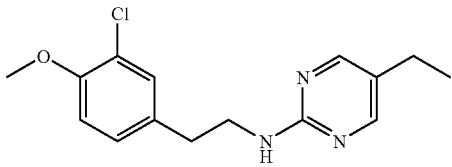

N-[2-(3-chloro-4-methoxyphenyl)ethyl]-5-ethylpyrimidin-2-amine

Similarly prepared from 3-chloro-4-methoxybenzaldehyde.

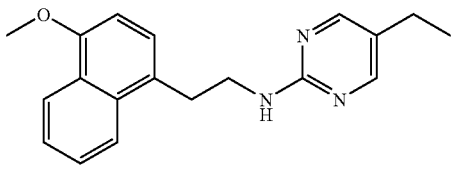

5-Ethyl-N-[2-(4-methoxy-1-naphthyl)ethyl]pyrimidin-2-amine

Similarly prepared from 4-methoxy-1-naphthaldehyde.

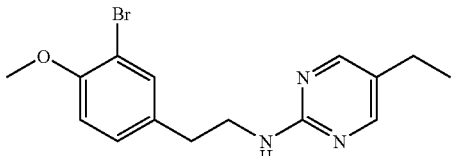

N-[2-(3-Bromo-4-methoxyphenyl)ethyl]-5-ethylpyrimidin-2-amine

A mixture of 2-(3-bromo-4-methoxyphenyl)ethanamine (1 g; 4.35 mmol), 2-chloro-5-ethyl-pyrimidine (0.56 g; 3.92 mmol) and DIEA (0.84 g; 6.53 mmol) in n-butanol was heated to reflux for 14 hr. Upon cooling, the reaction mixture was concentrated and partitioned between 1N HCl and ether. The aqueous phase was basified with 6N NaOH and extracted with ether. The combined organic phases were washed with a saturated solution of NaHCO₃, dried over MgSO₄, filtered and concentrated to provide a colorless solid, which was triturated with hexane, filtered and dried to provide the title compound as a white crystalline solid (0.89 g; 67% yield).

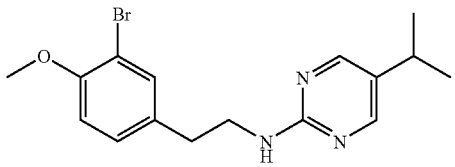

N-[2-(3-Bromo-4-methoxyphenyl)ethyl]-5-isopropylpyrimidin-2-amine

Similarly prepared from 2-(3-bromo-4-methoxyphenyl)ethanamine and 2-chloro-5-isopropyl-pyrimidine (see below).

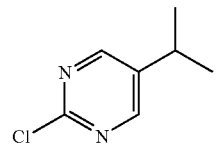

Synthesis of 2-chloro-5-isopropylpyrimidine

Step 1. A mixture of 3-ethoxy-2-isopropylprop-2-enal (ref. Menicagli, R. et al. Tetrahedron 1987, 43, 171–177) (250 mg, 1.76 mmol) and urea (250 mg, 4.16 mmol) in ethanol (2.5 ml) was treated with concentrated HCl (0.5 ml) and heated to reflux for 1 hour. Upon cooling, the reaction mixture was neutralized with 1N NaOH (0.6 ml) and extracted with chloroform. The organic layer was dried over MgSO₄ and concentrated to provide 5-isopropylpyrimidin-2(1H)-one as an off-white solid (0.20 g; 82% yield).

¹H NMR (CDCl₃) δ 8.15 (s, 2H), 2.72 (sept, 1H, J=6.9), 1.14 (d, 6H, J=6.9).

Step 2. A mixture of 5-isopropylpyrimidin-2(1H)-one (2.1 g, 15.2 mmol), POCl₃ (15 ml), and N,N-dimethylaniline (5 drops) was heated at reflux under a nitrogen atmosphere for 2 h. Upon cooling, the majority of the POCl₃ was removed under reduced pressure. The residue was poured into ice water and extracted with chloroform (3×20 ml). The combined organic extracts were washed with brine, dried over MgSO₄ and concentrated to provide 2-chloro-5-isopropylpyrimidine as a light brown oil, which was used without further purification.

¹H NMR (CDCl₃) δ 8.53 (s, 2H), 2.99 (sept, 1H, J=6.9), 1.34 (d, 6H, J=6.9).

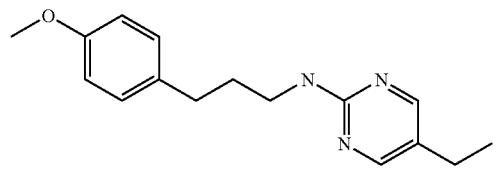

5-Ethyl-N-[3-(4-methoxyphenyl)propyl]pyrimidin-2-amine

Similarly prepared from 2-(3-bromo-4-methoxyphenyl)ethanamine and 2-chloro-5-ethyl-pyrimidine.

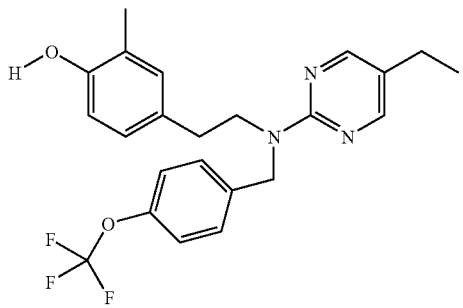

4-(2-{(5-Ethylpyrimidin-2-yl)[4-(trfluoromethoxy)benzyl]amino}ethyl)-2-methylphenol Step 1. A solution of 5-ethyl-N-[2-(4-methoxy-3-methylphenyl)ethyl]pyrimidin-2-amine (0.83 g; 3.07 mmol) and 4-trifluoromethoxy benzyl bromide (1.18 g; 4.61 mmol) in dry DMF (6 ml) was treated under nitrogen with NaH (95% dispersion in oil; 0.12 g; 4.61 mmol) and the mixture heated at 60C for 1 hr. Cooled to rt and quenched with a saturated solution of ammonium chloride. Diluted with water and extracted with ethyl acetate. The organic phase was dried over MgSO4, filtered and concentrated. Purification by flash chromatography on silica gel using dichloromethane-hexane mixture (4:1) afforded 5-ethyl-N-[2-(4-methoxy-3-methylphenyl)ethyl]-N-[4-(trifluoromethoxy)benzyl]pyrimidin-2-amine (1.26 g; 82% yield).

$^1$H NMR (CDCl$_3$) δ 8.18 (s, 2H), 7.2 (d, 2H, J=8.4), 7.1 (d, 2H, J=8.4), 6.96 (bs, 2H), 6.74 (m, 1H), 4.72 (s, 2H), 3.8 (s, 3H), 3.7 (t, 2H, J=7.6), 2.78 (t, 2H, J=7.6), 2.45 (q, 2H, J=7.6), 2.16 (s, 3H), 1.18 (t, 3H, J=7.6).

Step 2. A solution of 5-ethyl-N-[2-(4-methoxy-3-methylphenyl)ethyl]-N-[4-(trifluoromethoxy)benzyl]pyrimidin-2-amine (1.12 g; 2.53 mmol) in dichloromethane (70 ml) was cooled in an ice bath and treated under nitrogen with boron tribromide (1M solution in dichloromethane; 2.78 ml). Allowed to warm to rt and additional boron tribromide (2.53 ml) was added. Stirred for 2 hr and concentrated. Azeotroped 3× with MeOH, redissolved in MeOH and treated with sodium methoxide (0.14 g; 2.53 mmol). Stirred for 30 minutes and concentrated. The residue was partitioned between ethyl acetate and water. The organic phase was dried over MgSO$_4$, filtered and concentrated to afford 4-(2-{(5-ethylpyrimidin-2-yl)[4-(trifluoromethoxy)benzyl]amino}ethyl)-2-methylphenol as a dark brown oil (0.98 g; 90% crude yield) which was used in subsequent steps without further purification.

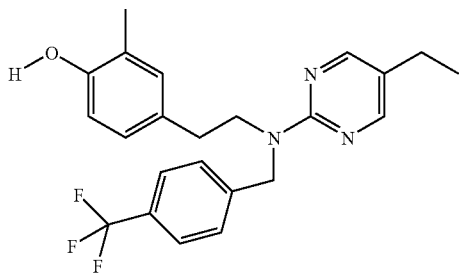

4-(2-{(5-Ethylpyrimidin-2-yl)[4-(trifluoromethyl)benzyl]amino}ethyl)-2-methylphenol Similarly prepared from 5-ethyl-N-[2-(4-methoxy-3-methylphenyl)ethyl]pyrimidin-2-amine and 4-trifluoromethylbenzyl bromide.

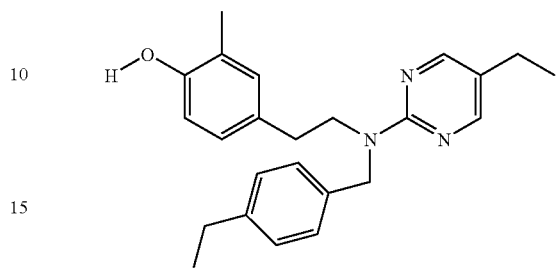

4-{2-[(4-Ethylbenzyl)(5-ethylpyrimidin-2-yl)amino]ethyl}-2-methylphenol

Similarly prepared from 5-ethyl-N-[2-(4-methoxy-3-methylphenyl)ethyl]pyrimidin-2-amine and 4-ethyl-benzyl bromide.

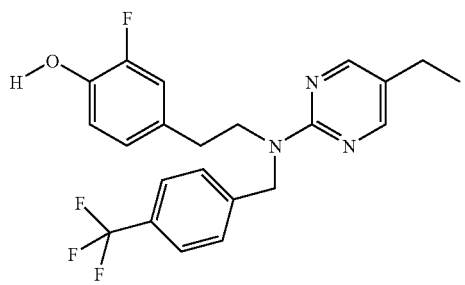

4-(2-{(5-Ethylpyrimidin-2-yl)[4-(trifluoromethyl)benzyl]amino}ethyl)-2-fluorophenol Similarly prepared from 5-ethyl-N-[2-(3-fluoro-4-methoxyphenyl)ethyl]pyrimidin-2-amine and 4-trifluoromethyl benzyl bromide.

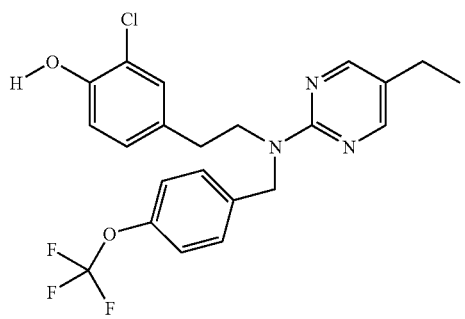

2-Chloro-4-(2-{(5-ethylpyrimidin-2-yl)[4-(trifluoromethoxy)benzyl]amino}ethyl)phenol Similarly prepared from N-[2-(3-chloro-4-methoxyphenyl)ethyl]-5-ethylpyrimidin-2-amine and 4-trifluoromethoxy benzyl bromide.

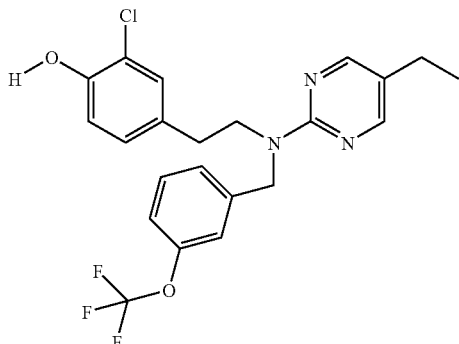

2-Chloro-4-(2-{(5-ethylpyrimidin-2-yl)[3-(trifluoromethoxy)benzyl]amino}ethyl)phenol Similarly prepared from N-[2-(3-chloro-4-methoxyphenyl)ethyl]-5-ethylpyrimidin-2-amine and 3-trifluoromethoxy benzyl bromide.

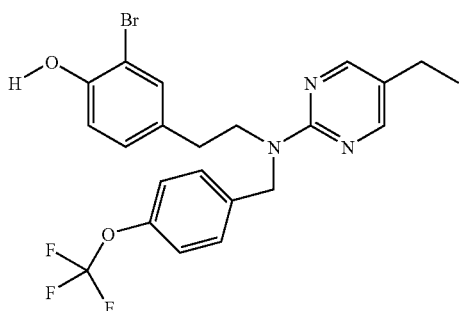

2-Bromo-4-(2-{(5-ethylpyrimidin-2-yl)[4-(trifluoromethoxy)benzyl]amino}ethyl)phenol Similarly prepared from N-[2-(3-bromo-4-methoxyphenyl)ethyl]-5-ethylpyrimidin-2-amine and 4-trifluoromethoxy benzyl bromide.

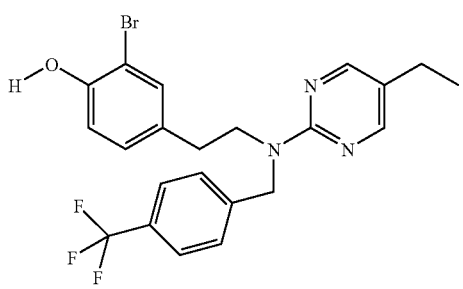

2-Bromo-4-(2-{(5-ethylpyrimidin-2-yl)[4-(trifluoromethyl)benzyl]amino}ethyl)phenol Similarly prepared from N-[2-(3-bromo-4-methoxyphenyl)ethyl]-5-ethylpyrimidin-2-amine and 4-trifluoromethyl benzyl bromide.

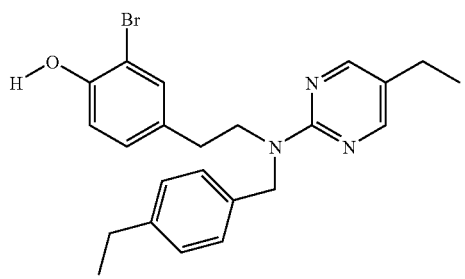

2-Bromo-4-{2-[(4-ethylbenzyl)(5-ethylpyrimidin-2-yl)amino]ethyl}phenol

Similarly prepared from N-[2-(3-bromo-4-methoxyphenyl)ethyl]-5-ethylpyrimidin-2-amine and 4-ethyl benzyl bromide.

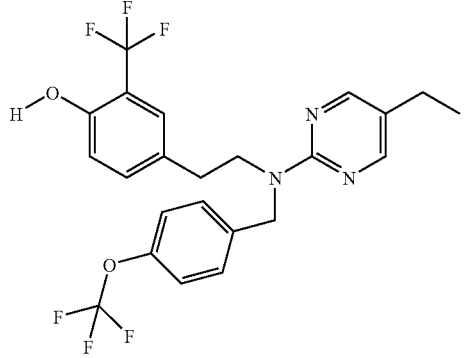

4-(2-{(5-Ethylpyrimidin-2-yl)[4-(trifluoromethoxy)benzyl]amino}ethyl)-2-(trifluoromethyl)phenol Similarly prepared from 5-ethyl-N-{2-[4-methoxy-3-(trifluoromethyl)phenyl]ethyl}pyrimidin-2-amine and 4-trifluoromethoxy benzyl bromide.

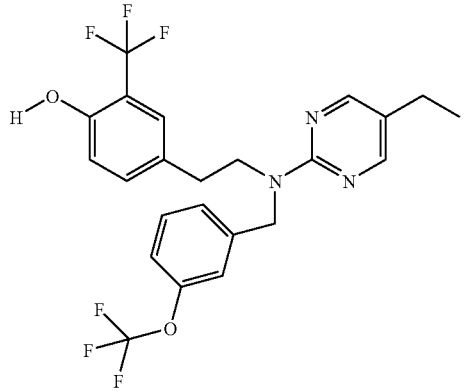

4-(2-{(5-Ethylpyrimidin-2-yl)[3-(trifluoromethoxy) benzyl]amino}ethyl)-2-(trifluoromethyl)phenol Similarly prepared from 5-ethyl-N-{2-[4-methoxy-3-(trifluoromethyl)phenyl]ethyl}pyrimidin-2-amine and 3-trifluoromethoxy benzyl bromide.

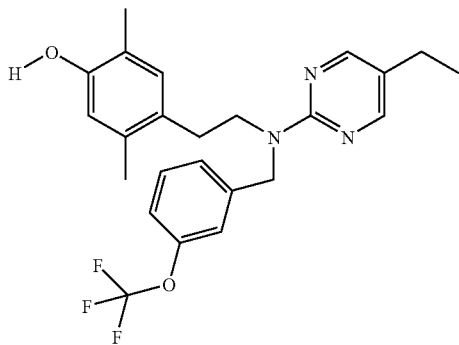

4-(2-{(5-Ethylpyrimidin-2-yl)[3-(trifluoromethoxy) benzyl]amino}ethyl)-2,5-dimethylphenol Similarly prepared from 5-ethyl-N-[2-(4-methoxy-2,5-dimethylphenyl)ethyl]pyrimidin-2-amine and 3-trifluoromethoxy benzyl bromide.

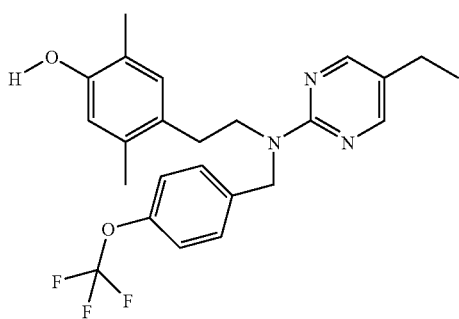

4-(2-{(5-Ethylpyrimidin-2-yl)[4-(trifluoromethoxy) benzyl]amino}ethyl)-2,5-dimethylphenol Similarly prepared from 5-ethyl-N-[2-(4-methoxy-2,5-dimethylphenyl)ethyl]pyrimidin-2-amine and 4-trifluoromethoxy benzyl bromide.

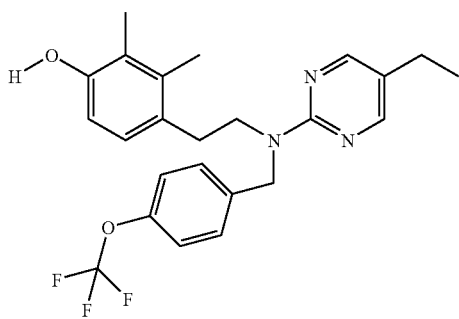

4-(2-{(5-Ethylpyrimidin-2-yl)[4-(trifluoromethoxy) benzyl]amino}ethyl)-2,3-dimethylphenol Similarly prepared from 5-ethyl-N-[2-(4-methoxy-2,3-dimethylphenyl)ethyl]pyrimidin-2-amine and 4-trifluoromethoxy benzyl bromide.

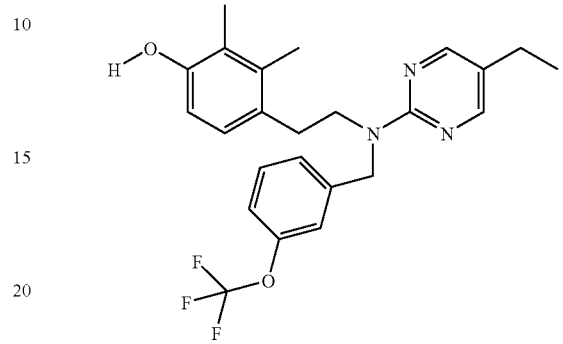

4-(2-{(5-Ethylpyrimidin-2-yl)[3-(trifluoromethoxy) benzyl]amino}ethyl)-2,3-dimethylphenol Similarly prepared from 5-ethyl-N-[2-(4-methoxy-2,3-dimethylphenyl)ethyl]pyrimidin-2-amine and 3-trifluoromethoxy benzyl bromide.

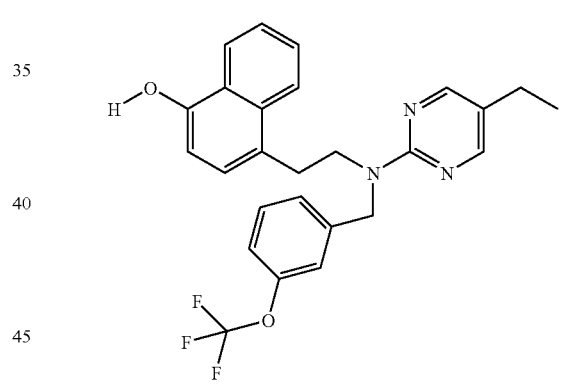

4-(2-{(5-ethylpyrimidin-2-yl)[3-(trifluoromethoxy) benzyl]amino}ethyl)-2,3-dimethylphenol Similarly prepared from 5-ethyl-N-[2-(4-methoxy-1-naphthyl)ethyl]pyrimidin-2-amine.

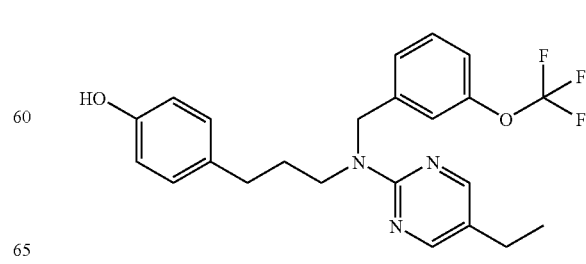

4-(3-{(5-Ethylpyrimidin-2-yl)[3-(trifluoromethoxy)benzyl]amino}propyl)phenol Similarly prepared from 5-ethyl-N-[3-(4-methoxyphenyl)propyl]pyrimidin-2-amine and 3-trifluoromethoxy benzyl bromide.

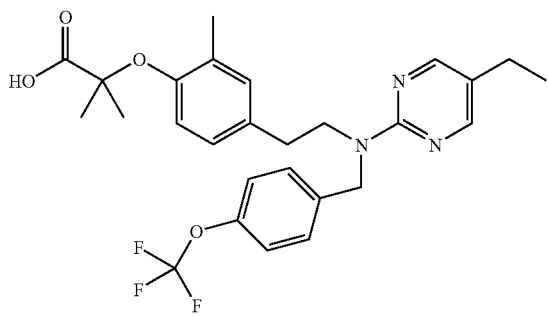

2-[4-(2-{(5-Ethylpyrimidin-2-yl)[4-(trifluoromethoxy)benzyl]amino}ethyl)-2-methylphenoxy]-2-methylpropanoic acid Step 1. Alkylation of 4-(2-{(5-ethylpyrimidin-2-yl)[4-(trfluoromethoxy)benzyl]amino}ethyl)-2-methylphenol (208 mg; 0.48 mmol) with ethyl-2-bromoisobutyrate (141 mg; 0.72 mmol) as per general procedure C (1.5 eq Cs2CO3, DMF, 80C, 72 hr) afforded the intermediate ethyl ester (104 mg; 40% yield).

$^1$H NMR (CDCl$_3$) δ 8.18 (s, 2H), 7.17 (d, 2H, J=8.4), 7.08 (d, 2H, J=8.4), 6.96 (bs, 1H), 6.83 (d, 1H, J=8.1), 6.56 (d, 1H, J=8.3), 4.70 (s, 2H), 4.2 (q, 2H, J=7.2), 3.7 (t, 2H, J=7.6), 2.78 (t, 2H, J=7.6), 2.45 (q, 2H, J=7.6), 2.16 (s, 3H), 1.52 (s, 6H), 1.24 (t, 3H, J=7.0), 1.18 (t, 3H, J=7.6).

Step 2. Hydrolysis of the ethyl ester (104 mg) with LiOH as per general procedure H provided after workup the title compound as a light yellow solid (94 mg; 97% yield).

$^1$H NMR (CDCl$_3$) δ 8.18 (s, 2H), 7.17 (d, 2H, J=8.4), 7.08 (d, 2H, J=8.4), 6.96 (bs, 1H), 6.87 (d, 1H, J=8.1), 6.70 (d, 1H, J=8.1), 4.88 (s, 2H), 3.9 (bs, 2H), 2.80 (t, 2H, J=7.4), 2.49 (q, 2H, J=7.6), 2.16 (s, 3H), 1.52 (s, 6H), 1.20 (t, 3H, J=7.8).

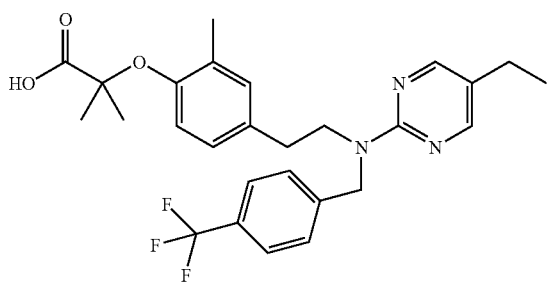

2-[4-(2-{(5-Ethylpyrimidin-2-yl)[4-(trifluoromethyl)benzyl]amino}ethyl)-2-methylphenoxy]-2-methylpropanoic acid Similarly prepared from 4-(2-{(5-ethylpyrimidin-2-yl)[4-(trifluoromethyl)benzyl]amino}ethyl)-2-methylphenol.

$^1$H NMR (CDCl$_3$) δ 8.26 (s, 2H), 7.5 (d, 2H, J=8.5), 7.25 (d, 2H, J=8.3), 6.97 (s, 1H), 6.96 (d, 1H, J=8.4), 6.70 (d, 1H, J=8.1), 4.72 (s, 2H), 3.78 (t, 2H, J=7.4), 2.80 (t, 2H, J=7.4), 2.49 (q, 2H, J=7.6), 2.17 (s, 3H), 1.55 (s, 6H), 1.20 (t, 3H, J=7.6).

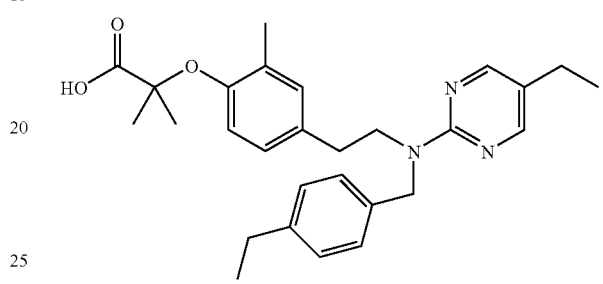

2-(4-{2-[(4-Ethylbenzyl)(5-ethylpyrimidin-2-yl)amino]ethyl}-2-methylphenoxy)-2-methylpropanoic acid Similarly prepared from 4-{2-[(4-ethylbenzyl)(5-ethylpyrimidin-2-yl)amino]ethyl}-2-methylphenol.

$^1$H NMR (CDCl$_3$) δ 8.19 (s, 2H), 7.07 (s, 4H), 6.94 (d, 1H, J=8.8), 6.96 (s, 1H), 6.86 (d, 1H, J=8.3), 6.70 (d, 1H, J=8.2), 4.71 (s, 2H), 3.69 (t, 2H, J=7.5), 2.76 (t, 2H, J=7.4), 2.57 (q, 2H, J=7.6), 2.45 (q, 2H, J=7.8), 2.17 (s, 3H), 1.52 (s, 6H), 1.18 (m, 6H).

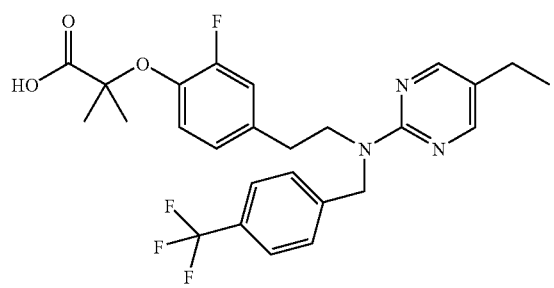

2-[4-(2-{(5-Ethylpyrimidin-2-yl)[4-(trifluoromethyl)benzyl]amino}ethyl)-2-fluorophenoxy]-2-methylpropanoic acid Similarly prepared from 4-(2-{(5-ethylpyrimidin-2-yl)[4-(trifluoromethyl)benzyl]amino}ethyl)-2-fluorophenol.

$^1$H NMR (CDCl$_3$) δ 8.18 (s, 2H), 7.49 (d, 2H, J=8.0), 7.25 (d, 2H, J=7.8), 6.94 (d, 1H, J=8.8), 6.91 (s, 1H), 6.84 (d, 1H, J=8.1), 4.78 (s, 2H), 3.73 (t, 2H, J=7.5), 2.83 (t, 2H, J=7.4), 2.45 (q, 2H, J=7.8), 1.52 (s, 6H), 1.18 (t, 3H, J=7.7).

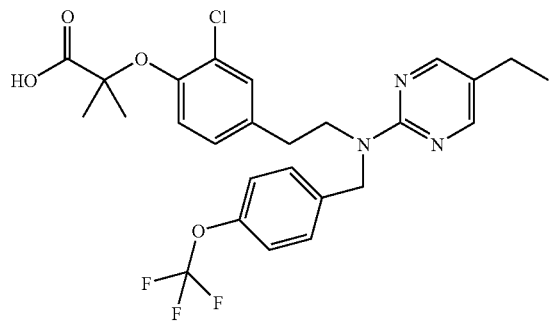

2-[2-Chloro-4-(2-{(5-ethylpyrimidin-2-yl)[4-(trifluoromethoxy)benzyl]amino}ethyl)phenoxy]-2-methylpropanoic acid Similarly prepared from 2-chloro-4-(2-{(5-ethylpyrimidin-2-yl)[4-(trifluoromethoxy)benzyl]amino}ethyl)phenol.

$^1$H NMR (CDCl$_3$) δ 8.20 (s, 2H), 7.21 (d, 1H, J=1.7), 7.18 (d, 2H, J=8.6), 7.09 (d, 2H, J=8.5), 6.96–6.92 (m, 2H), 4.74 (s, 2H), 3.71 (t, 2H, J=7.5), 2.80 (t, 2H, J=7.4), 2.46 (q, 2H, J=7.6), 1.56 (s, 6H), 1.19 (t, 3H, J=7.6).

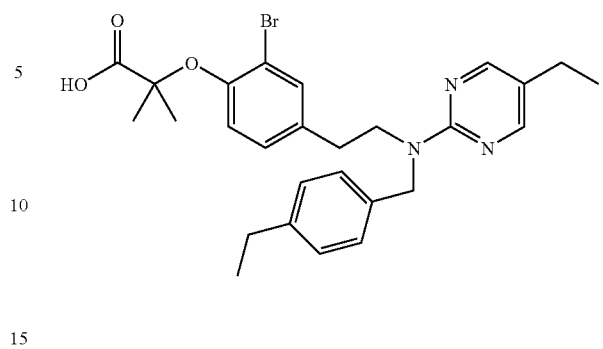

2-(2-Bromo-4-{2-[(4-ethylbenzyl)(5-ethylpyrimidin-2-yl)amino]ethyl}phenoxy)-2-methylpropanoic acid Similarly prepared from 2-bromo-4-{(2-[(4-ethylbenzyl)(5-ethylpyrimidin-2-yl)amino]ethyl}phenol.

$^1$H NMR (CDCl$_3$) δ 8.20 (s, 2H), 7.35 (s, 1H), 7.06–7.14 (m, 4H), 6.99 (d, 1H, J=8.2), 6.89 (d, 1H, J=8.2), 4.55 (s, 2H), 3.70 (t, 2H, J=7.5), 2.78 (t, 2H, J=7.6), 2.59 (q, 2H, J=7.5), 2.46 (q, 2H, J=7.7), 1.19 (t, 3H, J=7.5), 1.18 (t, 3H, J=7.7). MS: m/z 526, 528 (M+1).

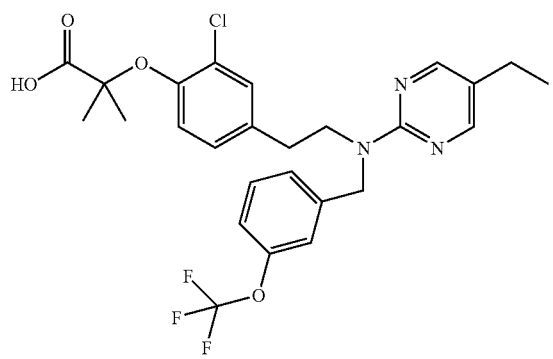

2-[2-Chloro-4-(2-{(5-ethylpyrimidin-2-yl)[3-(trifluoromethoxy)benzyl]amino}ethyl)phenoxy]-2-methylpropanoic acid Similarly prepared from 2-chloro-4-(2-{(5-ethylpyrimidin-2-yl)[3-(trifluoromethoxy)benzyl]amino}ethyl)phenol.

$^1$H NMR (CDCl$_3$) δ 8.19 (s, 2H), 7.38 (s, 1H), 7.18 (m, 2H), 7.11 (m, 3H), 6.84 (d, 1H J=8.6), 4.74 (s, 2H), 3.72 (t, 2H, J=7.1), 2.84 (t, 2H, J=7.4), 2.46 (q, 2H, J=7.6), 1.60 (s, 6H), 1.19 (t, 3H, J=7.6).

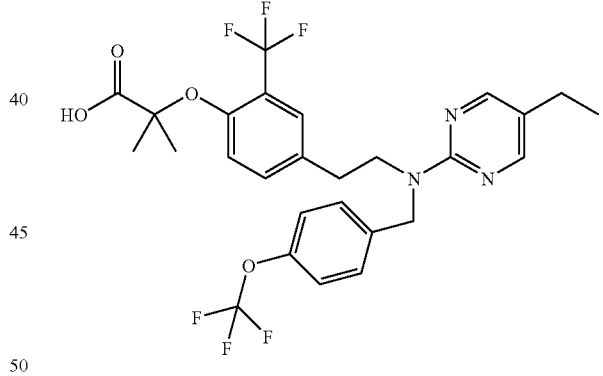

2-[4-(2-{(5-Ethylpyrimidin-2-yl)[4-(trifluoromethoxy)benzyl]amino}ethyl)-2-(trifluoromethyl)phenoxy]-2-methylpropanoic acid Similarly prepared from 4-(2-{(5-ethylpyrimidin-2-yl)[4-(trifluoromethoxy)benzyl]amino}ethyl)-2-(trifluoromethyl)phenol.

$^1$H NMR (CDCl$_3$) δ 8.18 (s, 2H), 7.6–7.3 (m, 4H), 7.08 (d, 2H, J=8.4), 6.85 (d, 1H, J=7.7), 4.73 (s, 2H), 3.72 (t, 2H, J=7.5), 2.83 (t, 2H, J=7.5), 2.46 (q, 2H, 7.6), 1.52 (bs, 6H), 1.19 (t, 3H, J=7.6).

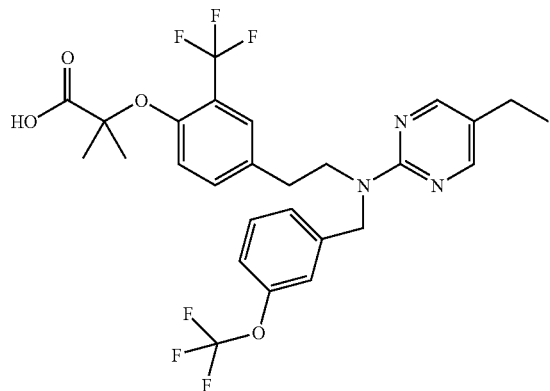

2-[4-(2-{(5-Ethylpyrimidin-2-yl)[3-(trifluoromethoxy)benzyl]amino}ethyl)-2-(trifluoromethyl)phenoxy]-2-methylpropanoic acid Similarly prepared from 4-(2-{(5-ethylpyrimidin-2-yl)[3-(trifluoromethoxy)benzyl]amino}ethyl)-2-(trifluoromethyl)phenol.
$^1$H NMR (CDCl$_3$) δ 8.19 (s, 2H), 7.38 (s, 1H), 7.27–7.20 (m, 2H), 7.10–7.03 (m, 3H), 6.84 (d, 1H J=8.4), 4.77 (s, 2H), 3.73 (t, 2H, J=7.1), 2.84 (t, 2H, J=7.4), 2.46 (q, 2H, J=7.6), 1.60 (s, 6H), 1.19 (t, 3H, J=7.6).

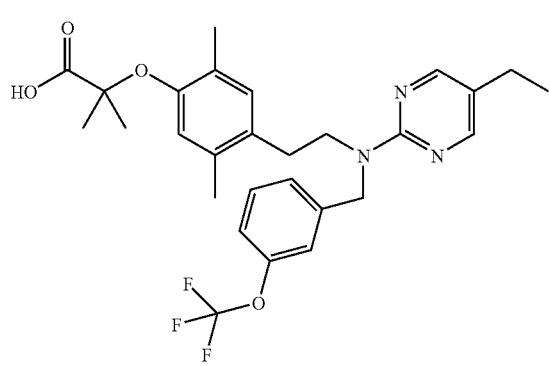

2-[4-(2-{(5-Ethylpyrimidin-2-yl)[3-(trifluoromethoxy)benzyl]amino}ethyl)-2,5-dimethylphenoxy]-2-methylpropanoic acid Similarly prepared from 4-(2-{(5-ethylpyrimidin-2-yl)[3-(trifluoromethoxy)benzyl]amino}ethyl)-2,5-dimethylphenol.
$^1$H NMR (CDCl$_3$) δ 8.19 (s, 2H), 7.29–7.25 (m, 1H), 7.12–7.04 (m, 3H), 6.88 (s, 1H), 6.61 (s, 1H), 4.77 (s, 2H), 3.64 (t, 2H, J=7.6), 2.77 (t, 2H, J=7.6), 2.46 (q, 2H, J=7.6), 2.20 (s, 3H), 2.13 (s, 3H), 1.52 (s, 6H), 1.19 (t, 3H, J=7.6).

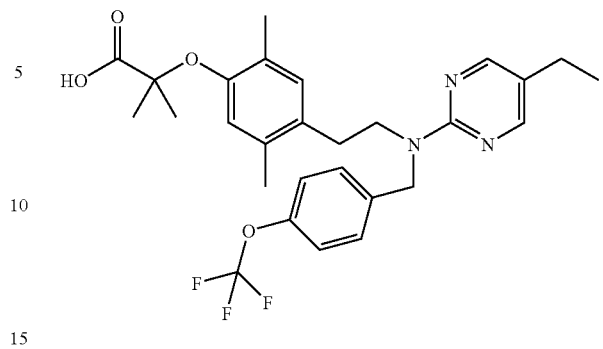

2-[4-(2-{(5-Ethylpyrimidin-2-yl)[4-(trifluoromethoxy)benzyl]amino}ethyl)-2,5-dimethylphenoxy]-2-methylpropanoic acid Similarly prepared from 4-(2-{(5-ethylpyrimidin-2-yl)[4-(trifluoromethoxy)benzyl]amino}ethyl)-2,5-dimethylphenol.
$^1$H NMR (Acetone-D$_6$) δ 8.2 (s, 2H), 7.4 (bs, 2H), 7.2 (bs, 2H), 6.9 (s, 1H), 6.691 (s, 1H), 4.77 (s, 2H), 3.7 (bs, 2H), 2.8 (bs, 2H), 2.46 (bs, 2H), 2.20 (s, 3H), 2.13 (s, 3H), 1.52 (s, 6H), 1.19 (bs, 3H).

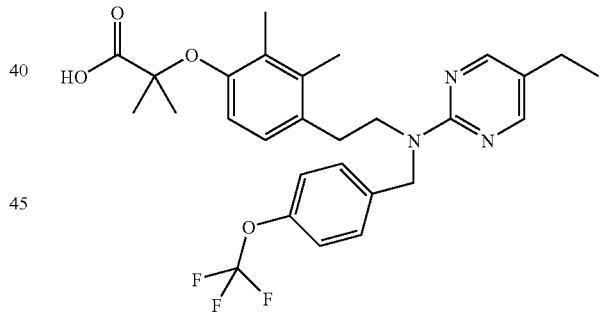

2-[4-(2-{(5-Ethylpyrimidin-2-yl)[4-(trifluoromethoxy)benzyl]amino}ethyl)-2,3-dimethylphenoxy]-2-methylpropanoic acid Similarly prepared from 4-(2-{(5-ethylpyrimidin-2-yl)[4-(trifluoromethoxy)benzyl]amino}ethyl)-2,3-dimethylphenol.
$^1$H NMR (CDCl$_3$) δ 8.19 (s, 2H), 7.18 (d, 2H, J=8.4), 7.08 (d, 2H, J=8.3), 6.83 (d, 1H, J=8.1), 6.62 (d, 1H, J=8.2), 4.73 (s, 2H), 3.614 (t, 2H, J=7.4), 2.847 (t, 2H, J=7.6), 2.46 (q, 2H, J=7.6), 2.19 (s, 3H), 2.13 (s, 3H), 1.52 (s, 6H), 1.19 (t, 3H, J=7.6)

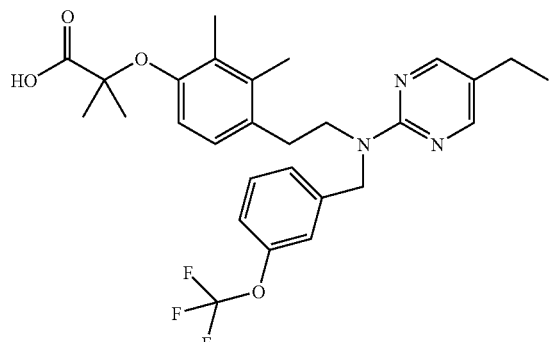

2-[4-(2-{(5-Ethylpyrimidin-2-yl)[3-(trifluoromethoxy)benzyl]amino}ethyl)-2,3-dimethylphenoxy]-2-methylpropanoic acid Similarly prepared from 4-(2-{(5-ethylpyrimidin-2-yl)[3-(trifluoromethoxy)benzyl]amino}ethyl)-2,3-dimethylphenol.

$^1$H NMR (CDCl$_3$) δ 8.19 (s, 2H), 7.25 (m, 1H), 7.09–7.02 (m, 3H), 6.83 (bd, 1H), 6.62 (d, 1H, J=8.1), 4.79 (s, 2H), 3.614 (bt, 2H), 2.847 (bt, 2H), 2.46 (q, 2H, J=7.6), 2.19 (s, 3H), 2.13 (s, 3H), 1.52 (s, 6H), 1.19 (t, 3H, J=7.6).

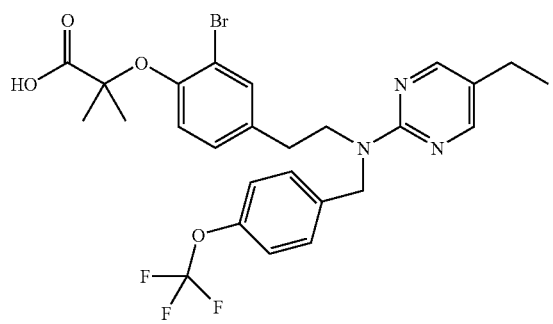

2-[2-Bromo-4-(2-{(5-ethylpyrimidin-2-yl)[4-(trifluoromethoxy)benzyl]amino}ethyl)phenoxy]-2-methylpropanoic acid Alkylation of 2-bromo-4-(2-{(5-ethylpyrimidin-2-yl)[4-(trifluoromethyl)benzyl]amino}ethyl)phenol with 2-trichloromethyl-2-propanol as per procedure D, followed by a standard aqueous workup, provided the title compound as a light red oil.

$^1$H NMR (CDCl$_3$) δ 8.23 (s, 2H), 7.36 (d, 1H, J=8.0), 7.18 (d, 2H, J=8.4), 7.10 (d, 2H, J=8.2), 6.99 (dd, 1H, J=8.2, 1.5), 6.89 (d, 1H, J=8.3), 4.75 (s, 2H), 3.72 (t, 2H, J=7.3), 2.79 (t, 2H, J=7.7), 2.48 (q, 2H, J=7.5), 1.58 (s, 6H), 1.20 (t, 3H, J=7.5). MS: m/z 582, 584 (M+1).

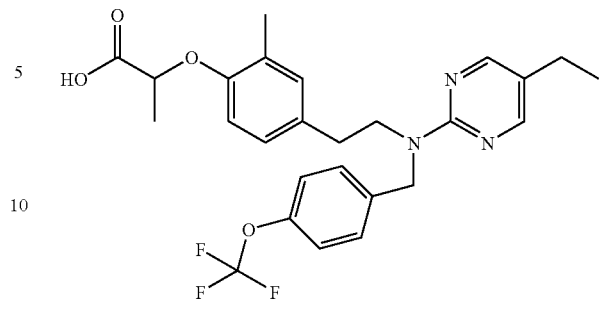

2-[4-(2-{(5-Ethylpyrimidin-2-yl)[4-(trifluoromethoxy)benzyl]amino}ethyl)-2-methylphenoxy]propanoic acid Step 1. Alkylation of 4-(2-{(5-ethylpyrimidin-2-yl)[4-(trifluoromethoxy)benzyl]amino}ethyl)-2-methylphenol (284 mg; 0.66 mmol) with methyl 2-chloropropionate (89 mg; 0.73 mmol) as per general procedure C (1.5 eq Cs2CO3, DMF, 80C, 2 hr) afforded the intermediate methyl ester (152 mg; 44% yield).

$^1$H NMR (CDCl$_3$) δ 8.18 (s, 2H), 7.18 (d, 2H, J=8.4), 7.08 (d, 2H, J=8.4), 6.96 (bs, 1H), 6.88 (d, 1H, J=8.3), 6.56 (d, 1H, J=8.3), 4.72 (s, 2H), 4.70 (q, 1H, J=6.8), 3.7 (m, 5H), 2.78 (t, 2H, J=7.6), 2.45 (q, 2H, J=7.6), 2.21 (s, 3H), 1.59 (d, 3H, J=6.8), 1.18 (t, 3H, J=7.6).

Step 2. Hydrolysis of the methyl ester (152 mg) with LiOH as per general procedure H provided after workup the title compound (140 mg; 95% yield).

$^1$H NMR (CDCl$_3$) δ 8.21 (s, 2H), 7.18 (d, 2H, J=8.6), 7.08 (d, 2H, J=8.611, 6.96 (bs, 1H), 6.88 (d, 1H, J=8.3), 6.62 (d, 1H, J=8.3), 4.69 (m, 3H), 3.7 (t, 2H, J=7.6), 2.76 (t, 2H, J=7.6), 2.45 (q, 2H, J=7.6), 2.21 (s, 3H), 1.59 (d, 3H, J=6.8), 1.18 (t, 3H, J=7.6).

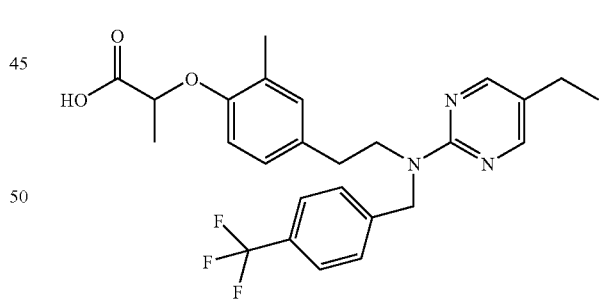

2-[4-(2-{(5-Ethylpyrimidin-2-yl)[4-(trifluoromethyl)benzyl]amino}ethyl)-2-methylphenoxy]propanoic acid Similarly prepared from 4-(2-{(5-ethylpyrimidin-2-yl)[4-(trifluoromethyl)benzyl]amino}ethyl)-2-methylphenol.

$^1$H NMR (CDCl$_3$) δ 8.21 (s, 2H), 7.49 (d, 2H, J=8.1), 7.25 (d, 2H, J=8.0), 6.95 (s, 1H), 6.88 (d, 1H, J=8.3), 6.60 (d, 1H, J=7.8), 4.78 (s, 2H), 4.70 (q, 1H, J=7.1), 3.69 (t, 2H, J=7.5), 2.77 (t, 2H, J=7.6), 2.45 (q, 2H, J=7.6), 2.21 (s, 3H), 1.61 (d, 3H, J=7.8), 1.18 (t, 3H, J=7.6).

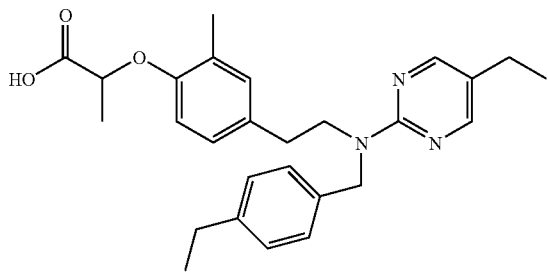

2-(4-{2-[(4-Ethylbenzyl)(5-ethylpyrimidin-2-yl)amino]ethyl}-2-methylphenoxy)propanoic acid Similarly prepared from 4-{2-[(4-ethylbenzyl)(5-ethylpyrimidin-2-yl)amino]ethyl}-2-methylphenol.

$^1$H NMR (CDCl$_3$) δ 8.29 (s, 2H), 7.09 (s, 4H), 6.95 (s, 1H), 6.91 (bs, 1H), 6.62 (d, 1H, J=8.5), 4.73 (m, 3H), 3.72 (t, 2H, J=6.5), 2.8 (t, 2H, J=7.1), 2.58 (q, 2H, J=7.6), 2.50 (q, 2H, J=7.3), 1.67 (d, 3H, J=6.6), 1.20 (t, 3H, J=7.6), 1.17 (t, 3H, J=7.6).

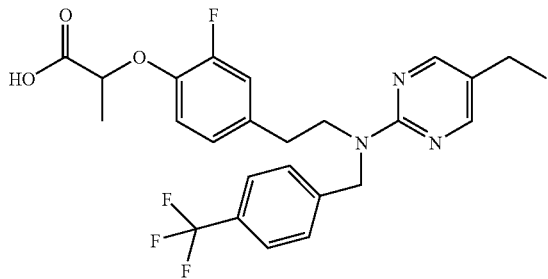

2-[4-(2-{(5-Ethylpyrimidin-2-yl)[4-(trifluoromethyl)benzyl]amino}ethyl)-2-fluorophenoxy]propanoic acid Similarly prepared from 4-(2-{(5-ethylpyrimidin-2-yl)[4-(trifluoromethyl)benzyl]amino}ethyl)-2-fluorophenol.

$^1$H NMR (Acetone D$_6$) δ 8.24 (s, 2H), 7.60 (d, 2H, J=8.1), 7.44 (d, 2H, J=8.1), 7.03 (d, 1H, J=11.8), 6.93 (m, 2H), 4.908 (s, 2H), 4.84 (q, 1H, J=6.81), 3.81 (t, 2H, J=7.5), 2.87 (t, 2H, J=7.7), 2.48 (q, 2H, J=7.6), 1.57 (d, 3H, J=67.8), 1.17 (t, 3H, J=7.5).

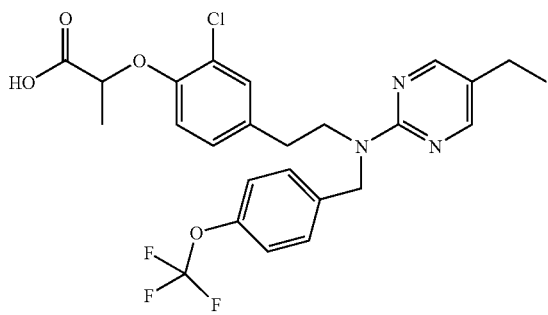

2-[2-Chloro-4-(2-{(5-ethylpyrimidin-2-yl)[4-(trifluoromethoxy)benzyl]amino}ethyl)phenoxy]propanoic acid Similarly prepared from 2-chloro-4-(2-{(5-ethylpyrimidin-2-yl)[4-(trifluoromethoxy)benzyl]amino}ethyl)phenol.

$^1$H NMR (CDCl$_3$) δ 8.23 (s, 2H), 7.18 (m, 3H), 7.09 (d, 2H, J=8.2), 6.93 (d, 2H, J=6.8)), 6.75 (d, 1H, J=8.2), 4.74 (m, 3H), 3.67 (t, 2H, J=7.5), 2.75 (t, 2H, J=7.4), 2.46 (q, 2H, J=7.6), 1.67 (d, 3H, J=6.7), 1.19 (t, 3H, J=7.6).

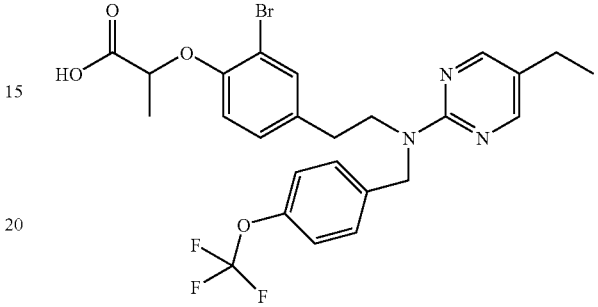

2-[2-bromo-4-(2-{(5-ethylpyrimidin-2-yl)[4-(trifluoromethoxy)benzyl]amino}ethyl)phenoxy]propanoic acid Step 1. Alkylation of 2-bromo-4-(2-{(5-ethylpyrimidin-2-yl)[4-(trifluoromethyl)benzyl]amino}ethyl)phenol (500 mg; 1.0 mmol) with t-butyl 2-bromopropionate (230 mg; 1.1 mmol) as per general procedure C (2 eq. K2CO3, acetone, reflux, 14 hr) provided the intermediate tert-butyl ester (520 mg; 83% yield).

Step 2. Hydrolysis of the tert-butyl ester (260 mg) with TFA as per general procedure I provided the title compound.

$^1$H NMR (CDCl$_3$) δ 8.23 (s, 2H), 7.36 (d, 1H, J=1.9), 7.19 (d, 2H, J=8.6), 7.10 (d, 2H, J=8.3), 7.00 (d, 1H, J=7.2), 6.73 (d, 1H, J=8.5), 4.77 (s, 2H), 4.75 (q, 1H, J=7.1), 3.70 (t, 2H, J=7.6), 2.77 (t, 2H, J=7.4), 2.48 (q, 2H, J=7.6), 1.67 (d, 3H, J=6.9), 1.20 (t, 3H, J=7.6).

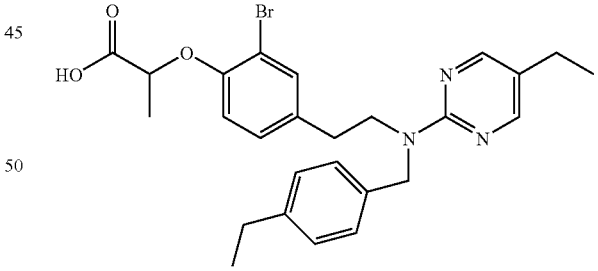

2-(2-Bromo-4-{2-[(4-ethylbenzyl)(5-ethylpyrimidin-2-yl)amino]ethyl}phenoxy)propanoic acid Similarly prepared from 2-bromo-4-(2-{(5-ethylpyrimidin-2-yl)[4-(trifluoromethyl)benzyl]amino}ethyl)phenol.

$^1$H NMR (CDCl$_3$) δ 8.32 (s, 2H), 7.26 (d, 1H, J=1.7), 7.12 (d, 2H, J=8.4), 7.10 (d, 2H, J=8.4), 6.99 (dd, 1H, J=8.4, 1.7), 6.71 (d, 1H, J=8.4), 4.65–4.85 (m, 3H), 3.67–3.83 (m, 2H), 2.73 (t, 2H, J=7.3), 2.58 (q, 2H, J=7.5), 2.51 (q, 2H, J=7.5), 1.64 (d, 3H, J=6.98), 1.21 (t, 3H, J=7.3), 1.19 (t, 3H, J=7.3). MS: m/z 512, 514 (M+1).

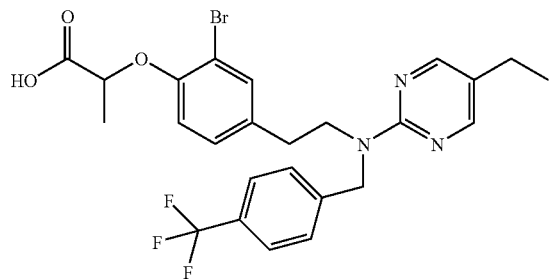

2-[2-Bromo-4-(2-{(5-ethylpyrimidin-2-yl)[4-(trifluoromethyl)benzyl]amino}ethyl)phenoxy]propanoic acid Similarly prepared from 2-bromo-4-(2-{(5-ethylpyrimidin-2-yl)[4-(trifluoromethyl)benzyl]amino}ethyl)phenol.

$^1$H NMR (CDCl$_3$) δ 8.24 (s, 2H), 7.50 (d, 2H, J=8.1), 7.36 (s, 1H), 7.25 (d, 2H, J=8.1), 6.95 (d, 1H, J=8.1), 6.70 (d, 1H, J=8.3), 4.79 (s, 2H), 4.71 (q, 1H, J=6.8), 3.69 (t, 2H, J=7.9), 2.76 (t, 2H, J=7.5), 2.48 (q, 2H, J=7.5), 1.66 (d, 3H, J=6.8), 1.19 (t, 3H, J=7.5). MS: m/z 552, 554 (M+1).

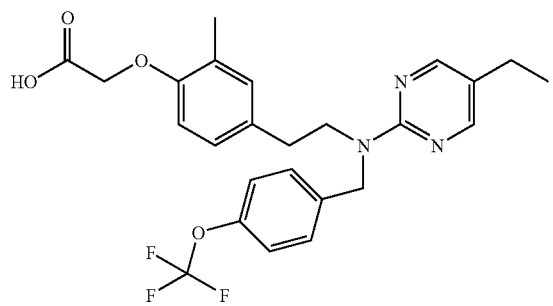

[4-(2-{(5-Ethylpyrimidin-2-yl)[4-(trifluoromethoxy)benzyl]amino}ethyl)-2-methylphenoxy]acetic acid Step 1. Alkylation of 4-(2-{(5-ethylpyrimidin-2-yl)[4-(trifluoromethoxy)benzyl]amino}ethyl)-2-methylphenol (376 mg; 0.87 mmol) with tert-butyl chloroacetate (197 mg; 1.31 mmol) as per general procedure C (1.5 eq Cs2CO3, DMF, 80C, 2 hr) afforded the intermediate tert-butyl ester (224 mg; 47% yield).

$^1$H NMR (CDCl$_3$) δ 8.18 (s, 2H), 7.18 (d, 2H, J=8.4), 7.08 (d, 2H, J=8.4), 6.96 (bs, 1H), 6.88 (d, 1H, J=8.3), 6.56 (d, 1H, J=8.3), 4.8 (s, 2H), 4.48 (s, 2H), 3.7 (t, 2H, J=7.6), 2.78 (t, 2H, J=7.6), 2.45 (q, 2H, J=7.6), 2.23 (s, 3H), 1.48 (s, 9H), 1.18 (t, 3H, J=7.6).

Step 2. Hydrolysis of the tert-butyl ester (224 mg) with TFA as per general procedure I provided after chromatography the title compound (83 mg; 41% yield).

$^1$H NMR (CDCl$_3$) δ 8.18 (s, 2H), 7.18 (d, 2H, J=8.4), 7.08 (d, 2H, J=8.4), 6.96 (bs, 1H), 6.88 (d, 1H, J=8.3), 6.56 (d, 1H, J=8.3), 4.8 (s, 2H), 4.48 (s, 2H), 3.7 (t, 2H, J=7.6), 2.78 (t, 2H, J=7.6), 2.45 (q, 2H, J=7.6), 2.23 (s, 3H), 1.18 (t, 3H, J=7.6).

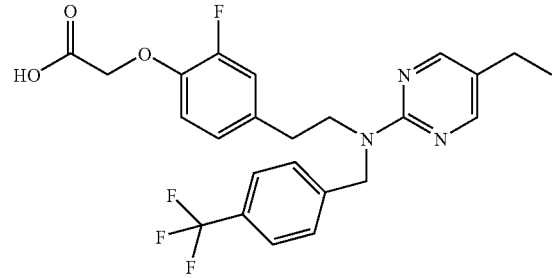

[4-(2-{(5-Ethylpyrimidin-2-yl)[4-(trifluoromethyl)benzyl]amino}ethyl)-2-fluorophenoxy]acetic acid Similarly prepared from 4-(2-{(5-ethylpyrimidin-2-yl)[4-(trifluoromethyl)benzyl]amino}ethyl)-2-fluorophenol.

$^1$H NMR (CDCl$_3$) δ 8.27 (s, 2H), 7.51 (d, 2H, J=8.3), 7.26 (d, 2H, J=6.1), 6.90 (d, 1H, J=10.7), 6.85–6.75 (m, 2H), 4.80 (s, 2H), 4.65 (s, 2H), 3.75 (t, 2H, J=7.5), 2.82 (t, 2H, J=7.6), 2.49 (q, 2H, J=7.6), 1.18 (t, 3H, J=7.6).

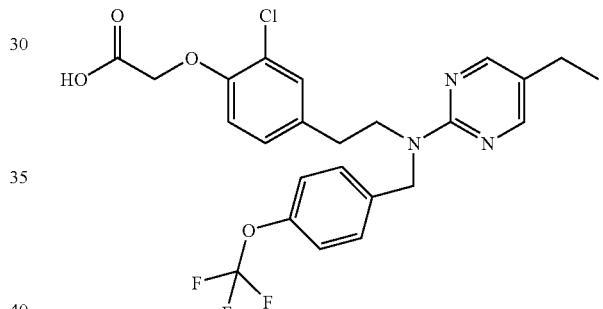

[2-Chloro-4-(2-{(5-ethylpyrimidin-2-yl)[4-(trifluoromethoxy)benzyl]amino}ethyl)phenoxy]acetic acid Similarly prepared from 2-chloro-4-(2-{(5-ethylpyrimidin-2-yl)[4-(trifluoromethoxy)benzyl]amino}ethyl)phenol.

$^1$H NMR (CDCl$_3$) δ 8.27 (s, 2H), 7.18 (m, 3H), 7.09 (d, 2H, J=8.4), 6.97 (d, 2H, J=6.5)), 6.71 (d, 1H, J=8.3), 4.76 (s, 2H), 4.65 (s, 2H), 3.71 (t, 2H, J=7.3), 2.78 (t, 2H, J=7.5), 2.49 (q, 2H, J=7.6), 1.20 (t, 3H, J=7.6).

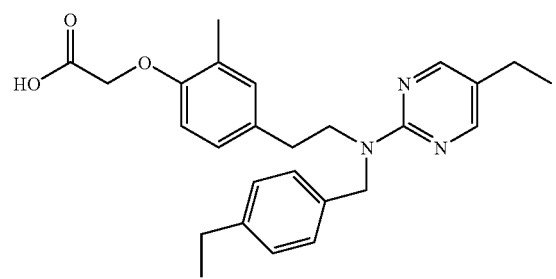

(4-{2-[(4-Ethylbenzyl)(5-ethylpyrimidin-2-yl)amino]ethyl}-2-methylphenoxy)acetic acid Similarly prepared from 4-{2-[(4-ethylbenzyl)(5-ethylpyrimidin-2-yl)amino]ethyl}-2-methylphenol.

$^1$H NMR (CDCl$_3$) δ 8.20 (s, 2H), 7.26–6.95 (bs, 4H), 6.92 (bs, 2H), 6.50 (bs, 1H), 4.79 (s, 2H), 3.7 (bs, 2H), 2.79–2.25 (bm, 6H), 2.1 (s, 3H), 1.18 (bs, 6H).

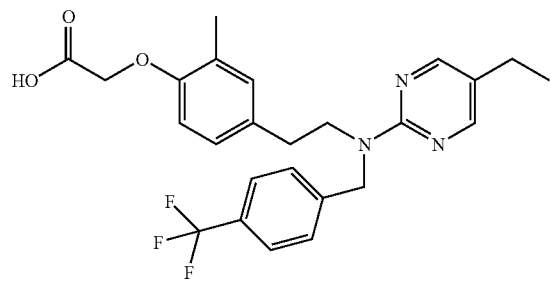

[4-(2-{(5-Ethylpyrimidin-2-yl)[4-(trifluoromethyl)benzyl]amino}ethyl)-2-methylphenoxy]acetic acid Similarly prepared from 4-(2-{(5-ethylpyrimidin-2-yl)[4-(trifluoromethyl)benzyl]amino}ethyl)-2-methylphenol.

$^1$H NMR (CDCl$_3$) δ 8.21 (s, 2H), 7.49 (d, 2H, J=7.9), 7.26 (d, 2H, J=8.1), 6.96 (s, 1H), 6.92 (d, 1H, J=8.1), 6.60 (d, 1H, J=8.3), 4.79 (s, 2H), 5.59 (s, 2H), 3.71 (t, 2H, J=7.5), 2.79 (t, 2H, J=7.5), 2.46 (q, 2H, J=7.6), 2.22 (s, 3H), 1.19 (t, 3H, J=7.6).

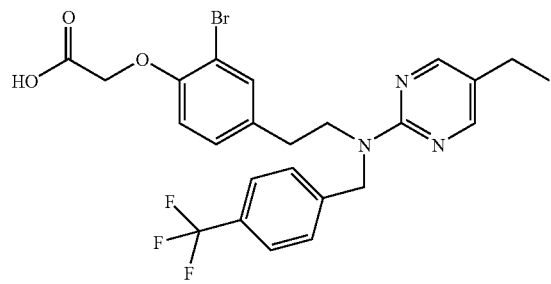

[2-Bromo-4-(2-{(5-ethylpyrimidin-2-yl)[4-(trifluoromethyl)benzyl]amino}ethyl)phenoxy]acetic acid Similarly prepared from 2-bromo-4-(2-{(5-ethylpyrimidin-2-yl)[4-(trifluoromethyl)benzyl]amino}ethyl)phenol.

$^1$H NMR (CDCl$_3$) δ 8.23 (s, 2H), 7.58–7.64 (d, 2H, J=8.6), 7.30–7.43 (m, 3H), 7.08 (d, 1H, J=7.4), 6.81 (dd, 1H, J=8.5, 3.45), 4.82 (s, 2H), 4.60 (s, 2H), 3.65–3.75 (m, 2H), 2.50–2.60 (m, 2H), 2.35–2.45 (m, 2H), 1.05–1.15 (m, 3H). MS: m/z 538, 540 (M+1).

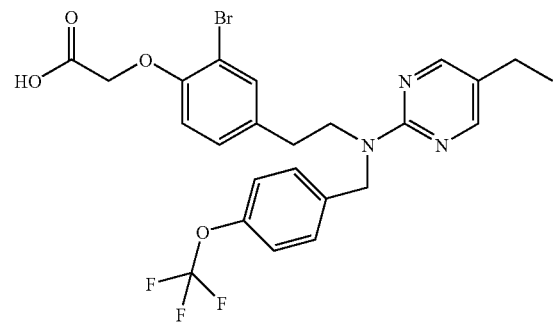

[2-Bromo-4-(2-{(5-ethylpyrimidin-2-yl)[4-(trifluoromethoxy)benzyl]amino}ethyl)phenoxy]acetic acid Similarly prepared from 2-bromo-4-(2-{(5-ethylpyrimidin-2-yl)[4-(trifluoromethyl)benzyl]amino}ethyl)phenol.

$^1$H NMR (CDCl$_3$) δ 8.26 (s, 2H), 7.34 (d, 1H, J=1.4), 7.19 (d, 2H, J=8.5), 7.11 (d, 2H, J=8.3), 7.02 (d, 1H, J=8.3), 6.66 (d, 1H, J=8.3), 4.77 (s, 2H), 4.63 (s, 2H), 3.71 (t, 2H, J=7.6), 2.77 (t, 2H, J=7.6), 2.49 (q, 2H, J=7.6), 1.20 (q, 3H, J=7.6). MS: m/z 554, 556 (M+1).

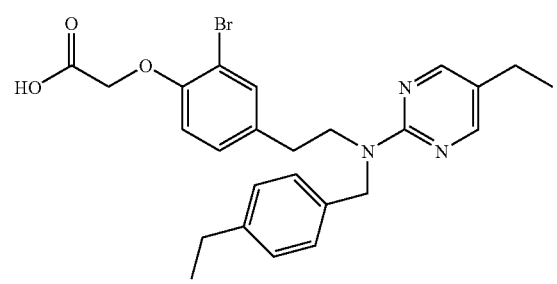

(2-Bromo-4-{2-[(4-ethylbenzyl)(5-ethylpyrimidin-2-yl)amino]ethyl}phenoxy)acetic acid Similarly prepared from 2-bromo-4-(2-{(5-ethylpyrimidin-2-yl)[4-(trifluoromethyl)benzyl]amino}ethyl)phenol.

$^1$H NMR (CDCl$_3$) δ 8.18 (s, 2H), 7.36 (d, 1H, J=1.9), 7.06–7.12 (m, 4H), 7.01 (dd, 1H, J=8.5, 1.9), 6.66 (d, 1H, J=8.5), 4.73 (s, 2H), 4.52 (s, 2H), 3.69 (t, 2H, J=7.7), 2.77 (t, 2H, J=7.6), 2.57 (q, 2H), 2.45 (q, 2H), 1.19 (t, 3H, J=7.6), 1.18 (t, 3H, J=7.6). MS: m/z 498, 500 (M+1).

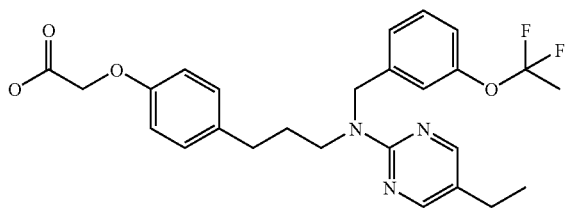

[4-(3-{(5-Ethylpyrimidin-2-yl)[3-(trifluoromethoxy)benzyl]amino}propyl)phenoxy]acetic acid Similarly prepared from 4-(3-{(5-ethylpyrimidin-2-yl)[3-(trifluoromethoxy)benzyl]amino}propyl)phenol.

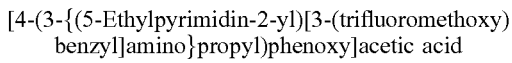

¹H NMR (CDCl₃) δ 8.24 (s, 2H), 7.27 (t, 1H, J=8), 7.1–7.02 (m, 4H), 6.77 (d, 2H, 8.4), 4.83 (s, 2H), 4.60 (s, 2H), 3.60 (bs, 2H), 2.55 (bs, 2H), 2.47 (q, 2H, J=7.4), 1.87 (bs, 2H), 1.18 (t, 3H, J=7.6).

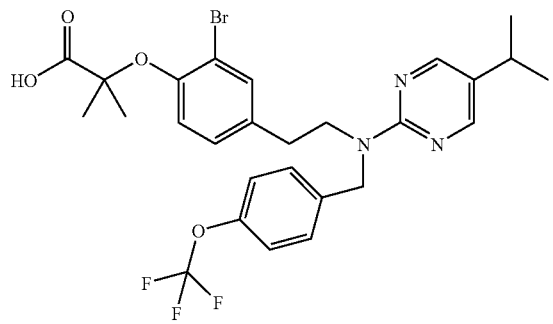

2-[2-Bromo-4-(2-{(5-isopropylpyrimidin-2-yl)[4-(trifluoromethoxy)benzyl]amino}ethyl)phenoxy]-2-methylpropanoic acid Step 1. A solution of N-[2-(3-bromo-4-methoxyphenyl)ethyl]-5-isopropylpyrimidin-2-amine (157 mg; 0.45 mmol) in dry THF was treated under nitrogen with KtBuO (75 mg; 0.67 mmol). After stirring for 15 minutes, 4-trifluoromethoxybenzyl bromide (171 mg; 0.67 mmol) was added and stirred for 30 minutes. The reaction was quenched by addition of an aqueous solution of NaHSO4 and extracted with dichloromethane. The organic phase was washed with brine, dried over MgSO4, filtered and concentrated to afford N-[2-(3-bromo-4-methoxyphenyl)ethyl]-5-isopropyl-N-[4-(trifluoromethoxy)benzyl]pyrimidin-2-amine as an oil in moderate yield, which was used in the next step without further purification Step 2. Demethylation of the previous intermediate with boron tribromide as per general procedure F, afforded after chromatography the intermediate phenol as an oil in moderate yield.

Step 3. Alkylation of the above phenol with 2-trichloromethyl-2-propanol as per general procedure D afforded after chromatography the title compound.

¹H NMR (CDCl₃) δ 8.31 (d, 2H), 7.43 (d, 1H, J=1.5), 7.05–7.33 (m, 5H), 6.97 (d, 1H, J=8.4), 4.82 (s, 2H), 3.83 (t, 2H, J=7.2), 2.78–2.96 (m, 3H), 1.64 (s, 6H), 1.29 (d, 6H, J=5.1). MS: m/z 596, 598 (M+1).

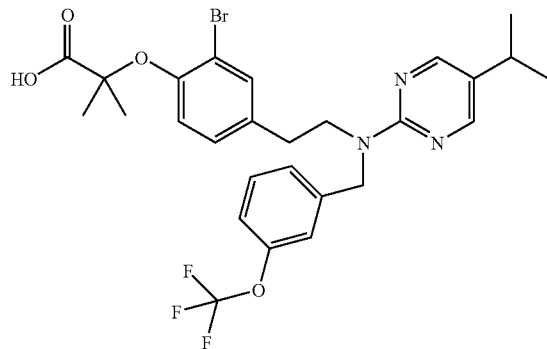

2-[2-Bromo-4-(2-{(5-isopropylpyrimidin-2-yl)[3-(trifluoromethoxy)benzyl]amino}ethyl)phenoxy]-2-methylpropanoic acid Similarly prepared by alkylation with 3-trifluoromethoxybenzyl bromide.

¹H NMR (CDCl₃) δ 8.28 (s, 2H), 6.86–7.50 (m, 7H), 4.83 (s, 2H), 3.70–3.88 (m, 2H), 2.75–2.97 (m, 3H), 1.64 (s, 6H), 1.29 (d, 6H, J=6.9). MS: m/z 596, 598 (M+1).

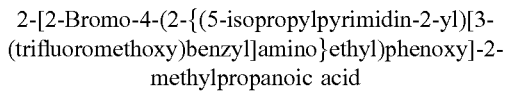

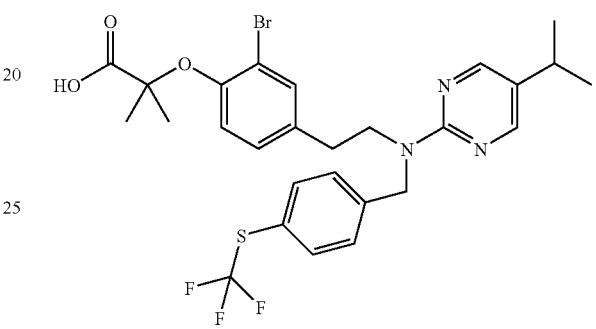

2-{2-Bromo-4-[2-((5-isopropylpyrimidin-2-yl){4-[(trifluoromethyl)thio]benzyl}amino)ethyl]phenoxy}-2-methylpropanoic acid Similarly prepared by alkylation with 4-trifluoromethylthiobenzyl bromide.

¹H NMR (CDCl₃) δ 8.32 (s, 2H), 7.62 (d, 2H, J=8.0), 7.42 (d, 1H, J=1.7), 7.28, (d, 2H, J=8.0), 7.10 (d, 1H, J=8.0), 6.96 (d, 1H, J=8.4), 4.86 (s, 2H), 3.85 (t, 2H, J=6.9), 2.80–2.94 (m, 3H), 1.64 (s, 6H), 1.30 (d, 6H, J=5.4). MS: m/z 612, 614 (M+1).

The following 6 compounds were prepared using procedures similar to those described above.

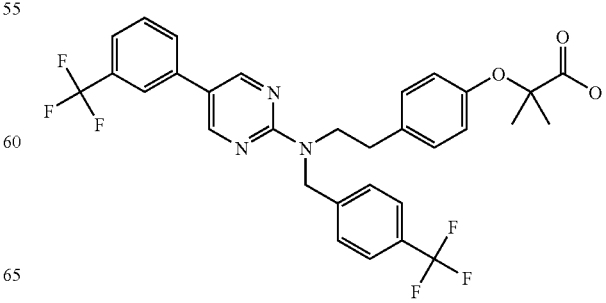

103

2-methyl-2-{4-[2-([4-(trifluoromethyl)benzyl]{5-[3-(trifluoromethyl)phenyl]pyrimidin-2-yl}amino)ethyl]phenoxy}propanoic acid

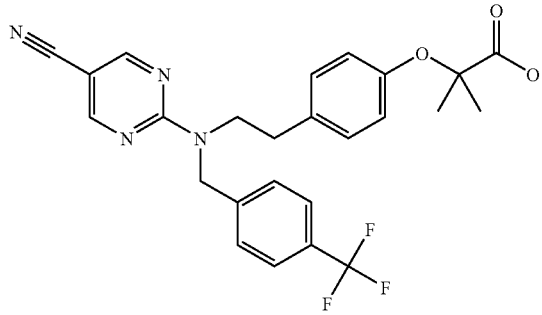

2-[4-(2-{(5-cyanopyrimidin-2-yl)[4-(trifluoromethyl)benzyl]amino}ethyl)phenoxy]-2-methylpropanoic acid

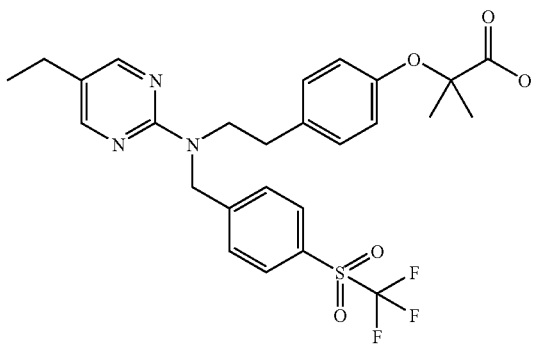

2-{4-[2-((5-ethylpyrimidin-2-yl){4-[(trifluoromethyl)sulfonyl]benzyl}amino)ethyl]phenoxy}-2-methylpropanoic acid

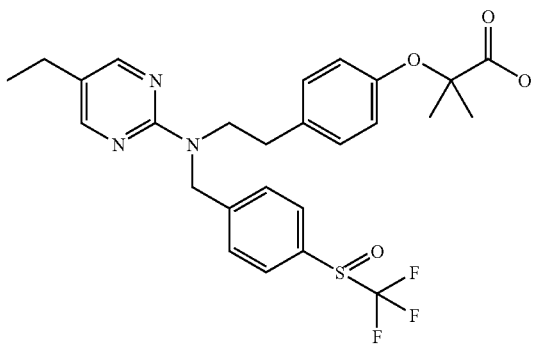

104

2-{4-[2-((5-ethylpyrimidin-2-yl){4-[(trifluoromethyl)sulfinyl]benzyl}amino)ethyl]phenoxy}-2-methylpropanoic acid

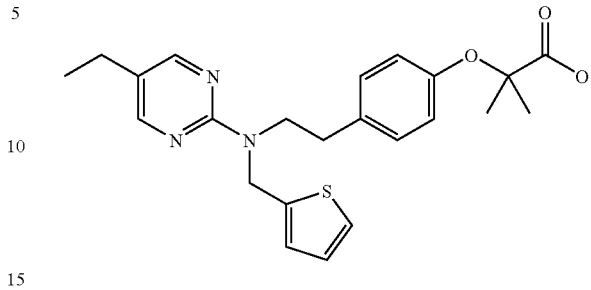

2-(4-{2-[(5-ethylpyrimidin-2-yl)(thien-2-ylmethyl)amino]ethyl}phenoxy)-2-methylpropanoic acid

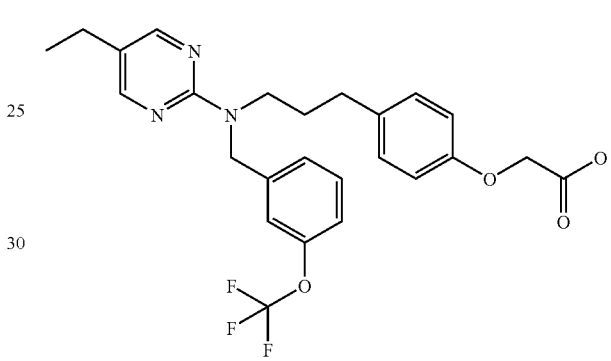

[4-(3-{(5-ethylpyrimidin-2-yl)[3-(trifluoromethoxy)benzyl]amino}propyl)phenoxy]acetic acid

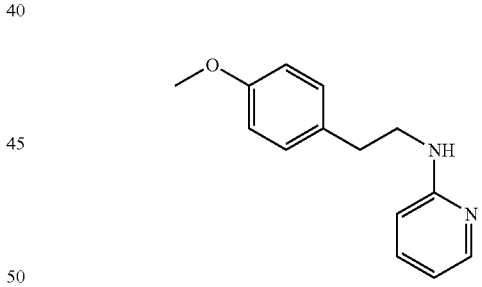

N-[2-(4-methoxyphenyl)ethyl]pyridin-2-amine

Step 1. To a solution of 4-methoxyphenyl acetic acid (5 g; 30.08 mmol) in 30 ml of dichloromethane, under nitrogen, it was added 1-ethyl-3-(3-dimethylaminopropyl)carbodiimide (6.34 g; 33.09 mmol) in small portions. After 10 minutes 2-aminopyridine (2.83 g; 30.08 mmol) was added and stirred for 4 hours at rt. The reaction mixture was concentrated and partitioned between ethyl acetate and 0.5N HCl. The organic phase was washed with 0.5N HCl (2×) and 0.5N NaOH (2×). The pH of the acidic/aqueous phase was adjusted to ~7 with 0.5N NaOH and extracted twice with ethyl acetate. The basic/aqueous phase was also extracted twice with ethyl acetate. The combined organic phases were washed with brine, dried over sodium sulfate and concentrated to afford 2-(4-methoxyphenyl)-N-pyridin-2-ylacetamide (7 g; 92% yield), which was used in the next step without further purification. MS: m/z 243 (M+1).

Step 2. To a solution of the above intermediate (4.5 g; 18.60 mmol) in 40 ml of dry THF, under nitrogen, it was added lithium aluminum hydride (1.7 g; 44.74 mmol) slowly, in small portions (exothermic). After stirring at rt for 4 hours, the reaction was worked up via the Fieser procedure: 1) added 1.7 ml of water, slowly, dropwise (exothermic); 2) added 1.7 ml of 15% NaOH and 3) added 5.1 ml of water. After stirring for 10 minutes, it was diluted with ethyl acetate and stirred an additional 30 minutes. The solids were filtered through a plug of celite and washed with ethyl acetate. The filtrate was concentrated to dryness to afford the title compound (3.6 g; 84% crude yield) which was used without further purification.

$^1$H NMR (CDCl$_3$) δ 8.02 (d, 1H, J=4.8), 7.35 (m, 1H), 7.09 (d, 2H, J=7.7), 6.80 (d, 2H, J=7.7), 6.51 (m, 1H), 6.31 (d, 1H, J=8.3), 4.70 (bs, 1H), 3.72 (s, 3H), 3.46 (broad q, 2H), 2.80 (broad t, 2H). MS: m/z 229 (M+1).

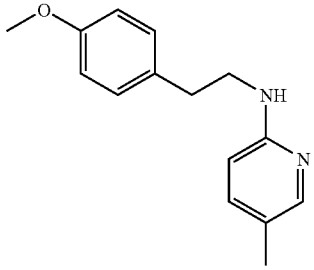

N-[2-(4-Methoxyphenyl)ethyl]-5-methylpyridin-2-amine

Similarly prepared from 4-methoxyphenyl acetic acid and 2-amino-5-picoline.
MS: m/z 243 (M+1).

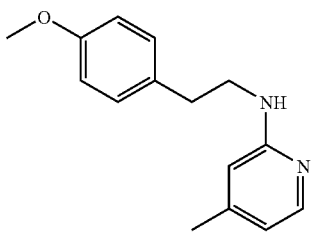

N-[2-(4-Methoxyphenyl)ethyl]-4-methylpyridin-2-amine

Similarly prepared from 4-methoxyphenyl acetic acid and 2-amino-4-picoline.
MS: m/z 243 (M+1).

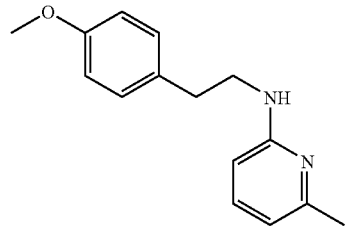

N-[2-(4-Methoxyphenyl)ethyl]-6-methylpyridin-2-amine

Similarly prepared from 4-methoxyphenyl acetic acid and 2-amino-6-picoline.
MS: m/z 243 (M+1).

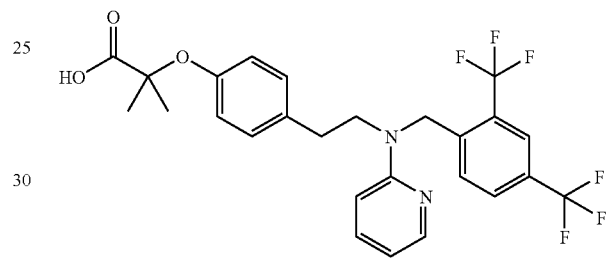

2-(4-{2-[[2,4-Bis(trifluoromethyl)benzyl](pyridin-2-yl)amino]ethyl}phenoxy)-2-methylpropanoic acid Step 1. A solution of N-[2-(4-methoxyphenyl)ethyl]pyridin-2-amine (150 mg; 0.66 mmol) in 3 ml of dioxane, under nitrogen, was treated with K$_2$CO3 (113 mg; 0.82 mmol) and 2,4-bis-trifluoromethyl-benzyl bromide (0.13 ml; 0.69 mmol) and heated in a pressure tube at 190–220C for 16 hours. Upon cooling, the reaction mixture was partitioned between ethyl acetate and saturated sodium bicarbonate. The organic phase was washed with saturated brine, dried over sodium sulfate and concentrated. Purification by radial chromatography on silica gel using an ethyl acetate-hexane gradient (5–50%) afforded N-[2,4-bis(trifluoromethyl)benzyl]-N-[2-(4-methoxyphenyl)ethyl]pyridin-2-amine (130 mg; 44% yield).

$^1$H NMR (CDCl$_3$) δ 8.17 (d, 1H, J=3.8), 7.89 (s, 1H), 7.62 (d, 1H, J=8.2), 7.46 (m, 1H), 7.37 (d, 1H, J=8.2), 7.09 (d, 2H, J=8.5), 6.81 (d, 2H, J=8.5), 6.61 (dd, 1H, J=7.1; 5.0), 6.47 (d, 1H, J=8.6), 4.89 (s, 2H), 3.77 (s, 3H), 3.67 (t, 2H, J=7.7), 2.90 (t, 2H, J=7.7). MS: m/z 455 (M+1).

Step 2. The above intermediate (500 mg; 1.1 mmol) was mixed with pyridine hydrochloride (1500 mg) and set in an oil bath preheated to 220C. The melted mixture was stirred at 220C for 1 hr. Upon cooling, the mixture was partitioned between ethyl acetate and water. The organic phase was washed with water and brine, dried over sodium sulfate and concentrated. Purification by radial chromatography on silica gel using an ethyl acetate-hexane gradient (5–40%) afforded 4-{2-[[2,4-bis(trifluoromethyl)benzyl](pyridin-2-yl)amino]ethyl}phenol (345 mg; 71% yield).

¹H NMR (CDCl₃) δ 8.17 (dd, 1H, J=5.1; 1.7), 7.86 (s, 1H), 7.60 (d, 1H, J=8.1), 7.50 (m, 1H), 7.36 (d, 1H, J=8.1), 6.98 (d, 2H, J=8.4), 6.68 (d, 2H, J=8.4), 6.65 (dd, 1H, J=7.0; 5.1), 6.51 (d, 1H, J=8.6), 4.87 (s, 2H), 3.68 (t, 2H, J=7.6), 2.88 (t, 2H, J=7.6). MS: m/z 441 (M+1).

Step 3. A solution of the above phenol (150 mg; 0.34 mol) in 3 ml of acetone was treated with 2-trichloromethyl-2-propanol (79 mg; 0.44 mmol) followed by slow addition of NaOH (triturated, 102 mg; 2.55 mmol) in small portions. After stirring at rt for 12 hr, the mixture was concentrated and the residue partitioned between ethyl acetate and phosphate buffer (pH 7). The organic phase was washed with brine, dried over sodium sulfate and concentrated. Purification by radial chromatography using a methanol-dichloromethane gradient (1–6%), followed by crystallization from dichloromethane-hexane afforded the title compound as a white solid (103 mg; 57% yield).

¹H NMR (CDCl₃) δ 8.17 (dd, 1H, J=5.0; 1.6), 7.86 (s, 1H), 7.62 (d, 1H, J=8.1), 7.44 (m, 1H), 7.35 (d, 1H, J=8.1), 7.04 (d, 2H, J=8.5), 6.82 (d, 2H, J=8.5), 6.61 (dd, 1H, J=7.0; 5.0), 6.41 (d, 1H, J=8.6), 4.80 (s, 2H), 3.68 (t, 2H, J=7.4), 2.87 (t, 2H, J=7.4), 1.53 (s, 6H). MS: m/z 527 (M+1).

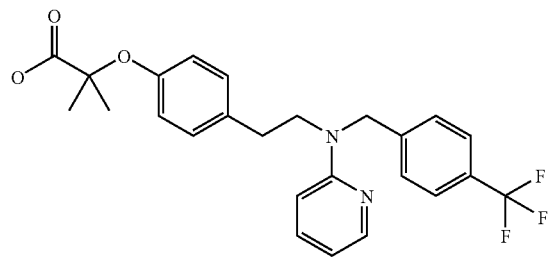

2-Methyl-2-[4-(2-{pyridin-2-yl[4-(trifluoromethyl)benzyl]amino}ethyl)phenoxy]propanoic acid Similarly prepared from N-[2-(4-methoxyphenyl)ethyl]pyridin-2-amine and 4-trifluoromethyl benzyl bromide.

¹H NMR (CDCl₃) δ 8.16 (d, 1H, J=3.8), 7.47 (d, 2H, J=8.1), 7.40 (m, 1H), 7.20 (d, 2H, J=8.1), 7.01 (d, 2H, J=8.2), 6.81 (d, 2H, J=8.2), 6.58 (dd, 1H, J=6.7; 5.3), 6.43 (d, 1H, J=8.6), 4.59 (s, 2H), 3.66 (t, 2H, J=7.4), 2.81 (t, 2H, J=7.4), 1.53 (s, 6H). MS: m/z 459 (M+1).

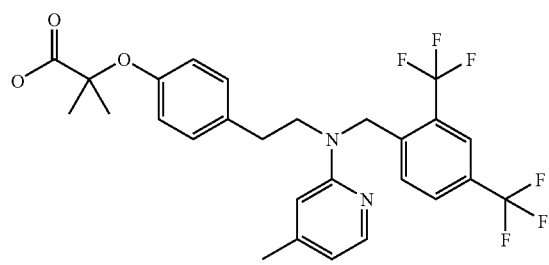

2-(4-{2-[[2,4-Bis(trifluoromethyl)benzyl](4-methylpyridin-2-yl)amino]ethyl}phenoxy)-2-methylpropanoic acid Similarly prepared from N-[2-(4-methoxyphenyl)ethyl]-4-methylpyridin-2-amine and 2,4-bis-trifluoromethyl-benzyl bromide.

¹H NMR (CDCl₃) δ 8.05 (d, 1H, J=5.2), 7.86 (s, 1H), 7.62 (d, 1H, J=8.0), 7.35 (d, 1H, J=8.0), 7.0 (d, 2H, J=8.4), 6.80 (d, 2H, J=8.4), 6.47 (d, 1H, J=5.2), 6.23 (s, 1H), 4.77 (s, 2H), 3.66 (t, 2H, J=7.3), 2.84 (t, 2H, J=7.3), 2.22 (s, 3H), 1.52 (s, 6H). MS: m/z 541 (M+1).

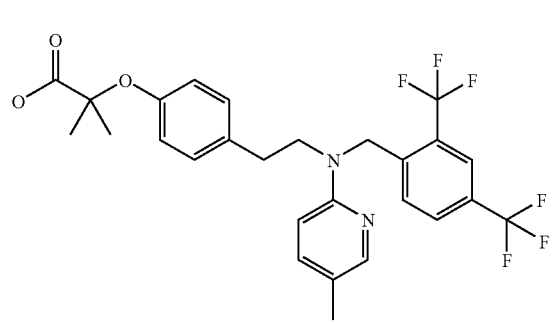

2-(4-{2-[[2,4-Bis(trifluoromethyl)benzyl](5-methylpyridin-2-yl)amino]ethyl}phenoxy)-2-methylpropanoic acid Similarly prepared from N-[2-(4-methoxyphenyl)ethyl]-5-methylpyridin-2-amine and 2,4-bis-trifluoromethyl-benzyl bromide.

¹H NMR (CDCl₃) δ 8.0 (d, 1H, J=2), 7.86 (s, 1H), 7.61 (d, 1H, J=8.2), 7.35 (d, 1H, J=8.2), 7.27 (dd, 1H, J=8.6; 2.0), 7.02 (d, 2H, J=8.5), 6.81 (d, 2H, J=8.5), 6.34 (d, 1H, J=8.6), 4.76 (s, 2H), 3.66 (t, 2H, J=7.4), 2.84 (t, 2H, J=7.4), 2.16 (s, 3H), 1.53 (s, 6H). MS: m/z 541 (M+1).

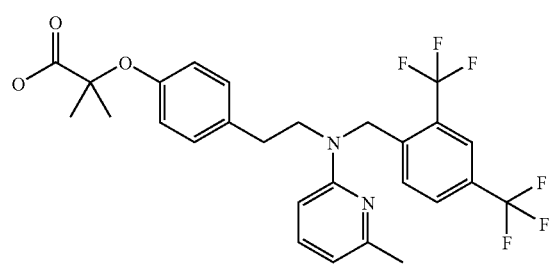

2-(4-{2-[[2,4-Bis(trifluoromethyl)benzyl](6-methylpyridin-2-yl)amino]ethyl}phenoxy)-2-methylpropanoic acid Similarly prepared from N-[2-(4-methoxyphenyl)ethyl]-6-methylpyridin-2-amine and 2,4-bis-trifluoromethyl-benzyl bromide.

¹H NMR (CDCl₃) δ 7.89 (s, 1H), 7.63 (d, 2H, J=8.1), 7.43 (d, 1H, J=8.1), 7.34 (t, 1H, J=7.8), 7.08 (d, 2H, J=8.1), 6.85 (d, 2H, J=8.1), 6.46 (d, 1H, J=7.8), 6.23 (d, 1H, J=7.8), 4.87 (s, 2H), 3.70 (t, 2H, J=7.2), 2.89 (t, 2H, J=7.2), 2.37 (s, 3H), 1.57 (s, 6H).

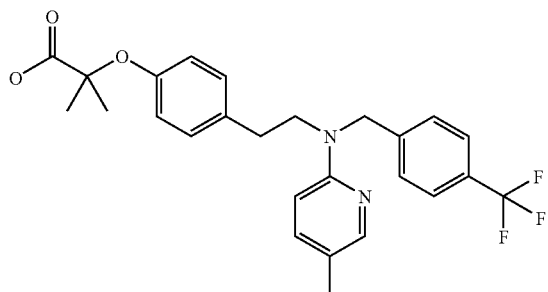

2-Methyl-2-[4-(2-{(5-methylpyridin-2-yl)[4-(trifluoromethyl)benzyl]amino}ethyl)phenoxy]propanoic acid Similarly prepared from N-[2-(4-methoxyphenyl)ethyl]-5-methylpyridin-2-amine and 4-trifluoromethyl-benzyl bromide.

¹H NMR (CDCl₃) δ 8.0 (bs, 1H), 7.45 (d, 2H, J=8.1), 7.28 (dd, 1H, J=8.8; 1.9), 7.18 (d, 2H, J=8.1), 6.96 (d, 2H, J=8.4), 6.80 (d, 2H, J=8.4), 6.38 (d, 1H, J=8.8), 4.53 (s, 2H), 3.65 (t, 2H, J=7.3), 2.77 (t, 2H, J=7.3), 2.14 (s, 3H), 1.53 (s, 6H). MS: m/z 473 (M+1).

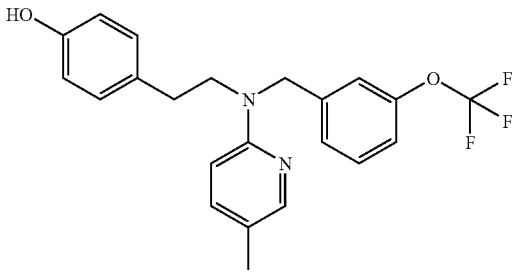

4-(2-{(5-Methylpyridin-2-yl)[3-(trifluoromethoxy)benzyl]amino}ethyl)phenol

Step 1. Alkylation of N-[2-(4-methoxyphenyl)ethyl]-5-methylpyridin-2-amine with 3-trifluoromethoxy-benzyl bromide as in the first step of the previous examples afforded N-[2-(4-methoxyphenyl)ethyl]-5-methyl-N-[3-(trifluoromethoxy)benzyl]pyridin-2-amine. MS: m/z 417 (M+1).

Step 2. Demethylation of the above intermediate with boron tribromide as per general procedure F provided the title compound.

¹H NMR (CDCl₃) δ 8.5 (bs, 1H), 8.0 (d, 1H, J=2.0), 7.32 (dd, 1H, J=8.6; 2.0), 7.23 (t, 1H, J=8.1), 7.0 (m, 3H), 6.98 (d, 2H, J=8.5), 6.73 (d, 2H, J=8.5), 6.49 (d, 1H, J=8.6), 4.60 (s, 2H), 3.67 (t, 2H, J=7.5), 2.82 (t, 2H, J=7.5), 2.17 (s, 3H).

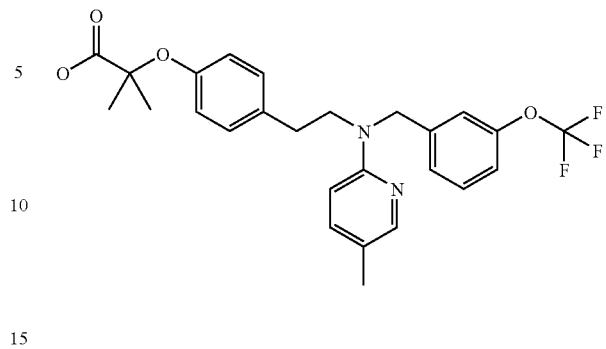

2-Methyl-2-[4-(2-{(5-methylpyridin-2-yl)[3-(trifluoromethoxy)benzyl]amino}ethyl)phenoxy]propanoic acid Step 1. Alkylation of 4-(2-{(5-methylpyridin-2-yl)[3-(trifluoromethoxy)benzyl]amino}ethyl)phenol with ethyl-2-bromo-isobutyrate (2 eq) as per general procedure C (2 eq Cs2CO3, MeCN, 90C) afforded the intermediate ethyl ester. MS: m/z 517 (M+1).

Step 2. Hydrolysis of the intermediate ester with NaOH as per general procedure H afforded after chromatography the title compound as a glassy solid.

¹H NMR (CDCl₃) δ 11.9 (bs, 1H), 8.02 (d, 1H, J=2.0), 7.29 (dd, 1H, J=8.8; 2.0), 7.25 (t, 1H, J=7.9), 7.03 (broad d, 2H, J=7.9), 6.98 (broad d, 3H, J=8.4), 6.83 (d, 2H, J=8.4), 6.41 (d, 1H, J=8.8), 4.53 (s, 2H), 3.67 (t, 2H, J=7.3), 2.78 (t, 2H, J=7.3), 2.16 (s, 3H), 1.55 (s, 6H).

MS: m/z 489 (M+1).

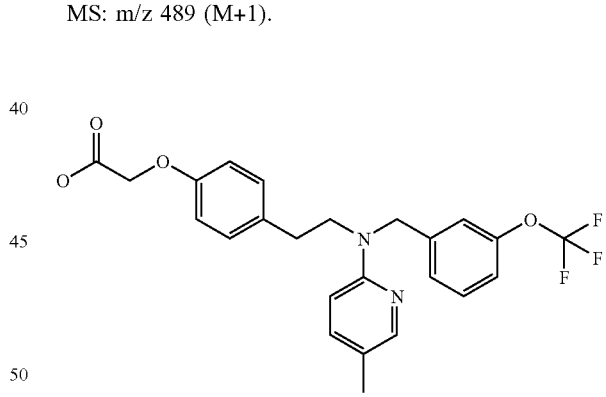

[4-(2-{(5-Methylpyridin-2-yl)[3-(trifluoromethoxy)benzyl]amino}ethyl)phenoxy]acetic acid Similarly prepared by alkylation of 4-(2-{(5-methylpyridin-2-yl)[3-(trifluoromethoxy)benzyl]amino}ethyl)phenol with tert-butyl-bromo-acetate, followed by standard TFA hydrolysis (general procedure I).

¹H NMR (CDCl₃) δ 14.0 (bs, 1H), 8.0 (bs, 1H), 7.35 (dd, 1H, J=8.9; 2.0), 7.27 (d, 1H, J=8.1), 7.03 (m, 5H), 6.77 (d, 2H, J=8.4), 6.45 (d, 1H, J=8.9), 4.56 (s, 2H), 4.49 (s, 2H), 3.71 (t, 2H, J=7.3), 2.80 (t, 2H, J=7.3), 2.16 (s, 3H). MS: m/z 461 (M+1).

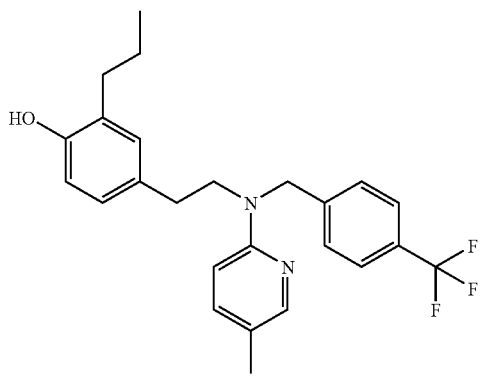

4-(2-{(5-Methylpyridin-2-yl)[4-(trifluoromethyl)benzyl]amino}ethyl)-2-propylphenol Step 1. Alkylation of 4-(2-{(5-methylpyridin-2-yl)[4-(trifluoromethyl)benzyl]amino}ethyl)phenol (110 mg; 0.30 mmol; an intermediate in the previously described synthesis of 2-methyl-2-[4-(2-{(5-methylpyridin-2-yl)[4-(trifluoromethyl)benzyl]amino}ethyl)phenoxy]propanoic acid) with allyl bromide (0.027 ml; 0.31 mmol) as per general procedure C (1.1 eq $Cs_2CO_3$, MeCN, 70 C) afforded the allyl ether intermediate (105 mg; 86% yield).

Step 2. A solution of the previous intermediate (105 mg; 0.25 mmol) in 5 ml of dichloromethane was cooled in an ice bath, under nitrogen, and treated with boron trichloride (1M in hexane; 0.51 ml). After 20 minutes, the reaction was quenched by addition of 0.4 ml of methanol. After stirring 5 minutes, the mixture was partitioned between ethyl acetate and saturated $K_2CO_3$. The organic phase was washed with brine, dried over sodium sulfate and concentrated. Purification by radial chromatography using an ethyl acetate-hexane gradient (5–30%) afforded 2-allyl-4-(2-{(5-methylpyridin-2-yl)[4-(trifluoromethyl)benzyl]amino}ethyl)phenol.

Step 3. A solution of the previous intermediate in ethyl acetate was treated with 10% Pd/C (0.5 weight equivalent) and hydrogenated under balloon pressure for 2 hr. The catalyst was filtered off and washed with chloroform, ethyl acetate and methanol. The filtrate was concentrated and purified by radial chromatography using an ethyl acetate-hexane gradient (5–30%) to afford the title compound (95 mg; 90% combined yield for the last two steps).

$^1$H NMR ($CDCl_3$) δ 8.0 (bs, 1H), 7.50 (d, 2H, J=8.1), 7.30 (dd, 1H, J=8.6; 2.0), 7.27 (m, 2H), 6.88 (d, 1H, J=1.7), 6.83 (dd, 1H, J=8.1; 1.7), 6.66 (d, 1H, J=8.1), 6.44 (d, 1H, J=8.6), 5.83 (bs, 1H, OH), 4.66 (s, 2H), 3.65 (t, 2H, J=7.5), 2.81 (t, 2H, J=7.5), 2.52 (t, 2H, J=7.7), 2.18 (s, 3H), 1.59 (m, 2H), 0.96 (t, 3H, J=7.3).

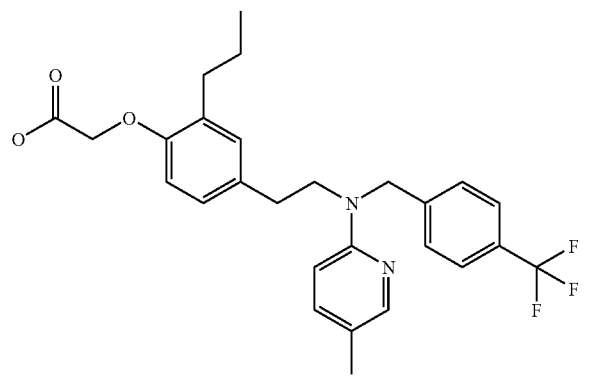

[4-(2-{(5-Methylpyridin-2-yl)[4-(trifluoromethyl)benzyl]amino}ethyl)-2-propylphenoxy]acetic acid Alkylation of 4-(2-{(5-methylpyridin-2-yl)[4-(trifluoromethyl)benzyl]amino}ethyl)-2-propylphenol with tert-butyl-bromo-acetate, followed by standard TFA hydrolysis (as described in previous examples) provided after chromatography the title compound as a white foam.

$^1$H NMR ($CDCl_3$) δ 8.01 (bs, 1H), 7.50 (d, 2H, J=8.1), 7.31 (dd, 1H, J=8.8; 2.2), 7.24 (d, 2H, J=8.1), 6.89 (bs, 1H), 6.86 (dd, 1H, J=8.2; 1.8), 6.60 (d, 1H, J=8.2), 6.41 (d, 1H, J=8.8), 4.59 (s, 2H), 4.53 (s, 2H), 3.72 (t, 2H, J=7.5), 2.80 (t, 2H, J=7.5), 2.57 (t, 2H, J=7.7), 2.17 (s, 3H), 1.57 (m, 2H), 0.90 (t, 3H, J=7.3).

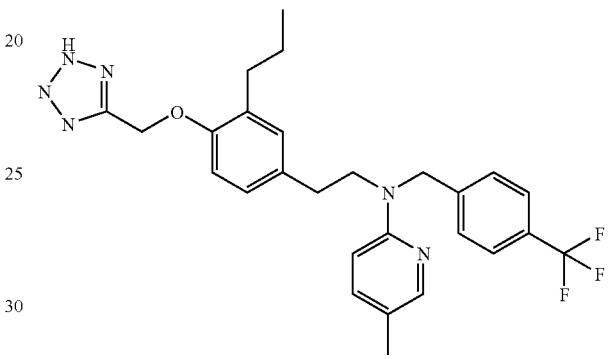

5-Methyl-N-{2-[3-propyl-4-(2H-tetraazol-5-ylmethoxy)phenyl]ethyl}-N-[4-(trifluoromethyl)benzyl]pyridin-2-amine The title compound was prepared from 4-(2-{(5-methylpyridin-2-yl)[4-(trifluoromethyl)benzyl]amino}ethyl)-2-propylphenol via a two-step sequence similar to that described for 5-ethyl-N-{2-methyl-2-[3-propyl-4-(2H-tetraazol-5-ylmethoxy)phenyl]propyl}-N-[4-(trifluoromethoxy)benzyl]pyrimidin-2-amine.

$^1$H NMR ($CDCl_3$) δ 7.94 (s, 1H), 7.49 (d, 2H, J=8.2), 7.36 (dd, 1H, J=8.8; 2.2), 7.21 (d, 2H, J=8.2), 6.75 (m, 3H), 6.48 (d, 1H, J=8.8), 5.34 (s, 2H), 4.61 (s, 2H), 3.74 (t, 2H, J=7.2), 2.78 (t, 2H, J=7.2), 2.35 (t, 2H, J=7.6), 2.17 (s, 3H), 1.38 (m, 2H), 0.75 (t, 3H, J=7.3).

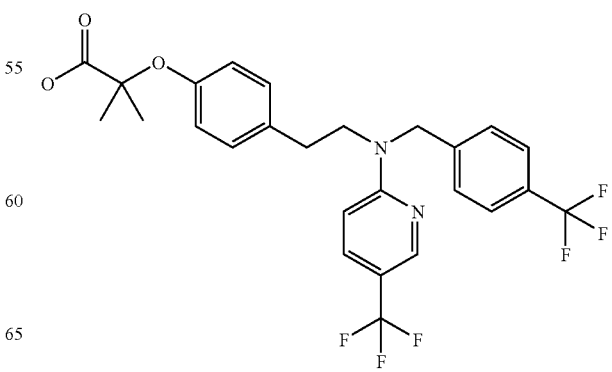

2-Methyl-2-[4-(2-{[4-(trifluoromethyl)benzyl][5-(trifluoromethyl)pyridin-2-yl]amino}ethyl)phenoxy]propanoic acid A solution of ethyl 2-methyl-2-[4-(2-{[4-(trifluoromethyl)benzyl]amino}ethyl)phenoxy]propanoate (250 mg; 0.61 mmol) in 3 ml of dioxane was treated with 2-chloro-5-trifluoromethyl-pyridine (111 mg; 0.61 mmol) and K2CO3 (106 mg; 0.76 mmol) and heated in a pressure tube at 220C overnight. Accidental loss of the solvent during heating produced a dark brown residue, which was partitioned into ethyl acetate, water and methanol. The aqueous phase was washed with ethyl acetate. The combined organic phases were washed with brine, dried over sodium sulfate and concentrated.

Under the reaction conditions described above, substantial ethyl ester hydrolysis occurred to produce the title compound directly, but it proved difficult to isolate from the crude mixture. For ease of purification, the crude acid was converted to the intermediate methyl ester using standard trimethylsilyldiazomethane/methanol conditions. The ester was subsequently purified by chromatography and hydrolyzed with NaOH using the standard protocol to provide the title compound (27 mg; 9% yield).

$^1$H NMR (CDCl$_3$) δ 8.40 (s, 1H), 7.56 (d, 1H, J=9.0), 7.51 (d, 2H, J=7.9), 7.22 (m, 2H), 7.06 (d, 2H, J=8.3), 6.85 (d, 2H, J=8.3), 6.42 (d, 1H, J=9.0), 4.67 (s, 2H), 3.73 (t, 2H, J=7.5), 2.87 (t, 2H, J=7.5), 1.55 (s, 6H).

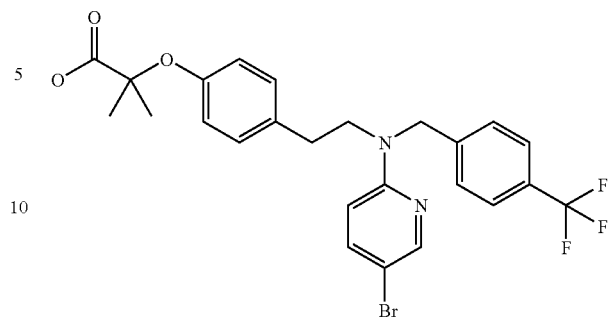

2-[4-(2-{(5-bromopyridin-2-yl)[4-(trifluoromethyl)benzyl]amino}ethyl)phenoxy]-2-methylpropanoic acid Hydrolysis of ethyl 2-[4-(2-{(5-bromopyridin-2-yl)[4-(trifluoromethyl)benzyl]amino}ethyl)phenoxy]-2-methylpropanoate with NaOH as per general procedure H provided after chromatography and crystallization from dichloromethane-hexane, the title compound as a white solid (56 mg; 52% yield).

$^1$H NMR (CDCl$_3$) δ 8.16 (d, 1H, J=2.4), 7.50 (d, 2H, J=8.2), 7.44 (dd, 1H, J=9.0; 2.4), 7.21 (d, 2H, J=8.2), 7.03 (d, 2H, J=8.5), 6.84 (d, 2H, J=8.5), 6.31 (d, 1H, J=9.0), 4.58 (s, 2H), 3.66 (t, 2H, J=7.5), 2.83 (t, 2H, J=7.5), 1.56 (s, 6H). MS: m/z 538 (M+1).

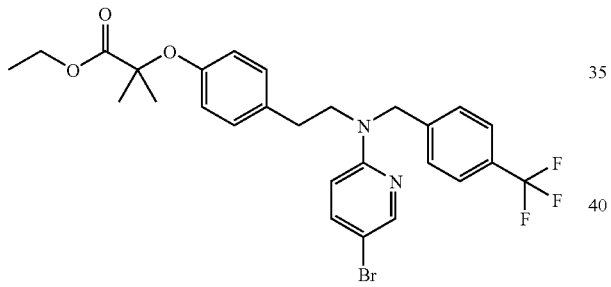

Ethyl 2-[4-(2-{(5-bromopyridin-2-yl)[4-(trifluoromethyl)benzyl]amino}ethyl)phenoxy]-2-methylpropanoate A solution of ethyl 2-methyl-2-[4-(2-{[4-(trifluoromethyl)benzyl]amino}ethyl)phenoxy]propanoate (3 g; 7.3 mmol) in 7 ml of dioxane was treated under nitrogen with 2,5-dibromopyridine (1.9 g; 8.1 mmol) and DIEA (1.4 ml; 8.1 mmol) and heated in a pressure tube for 2 days at 210C. Upon cooling, additional DIEA (1.4 ml) was added and heated 2 more days. Upon cooling, the reaction mixture was partitioned between ethyl acetate and 0.5N HCl. The organic phase was washed with 0.5N HCl and saturated brine, dried over sodium sulfate and concentrated. Purification by silica gel chromatography using an ethyl acetate-hexane gradient (5–60%) afforded the title compound (0.75 g; 18% yield).

$^1$H NMR (CDCl$_3$) δ 8.14 (d, 1H, J=2.6), 7.48 (d, 2H, J=8.1), 7.41 (dd, 1H, J=9.0; 2.6), 7.22 (d, 2H, J=8.1), 7.0 (d, 2H, J=8.5), 6.76 (d, 2H, J=8.5), 6.30 (d, 1H, J=9.0), 4.59 (s, 2H), 4.20 (q, 2H, J=7.1), 3.63 (t, 2H, J=7.5), 2.81 (t, 2H, J=7.5), 1.54 (s, 6H), 1.20 (t, 3H, J=7.1).

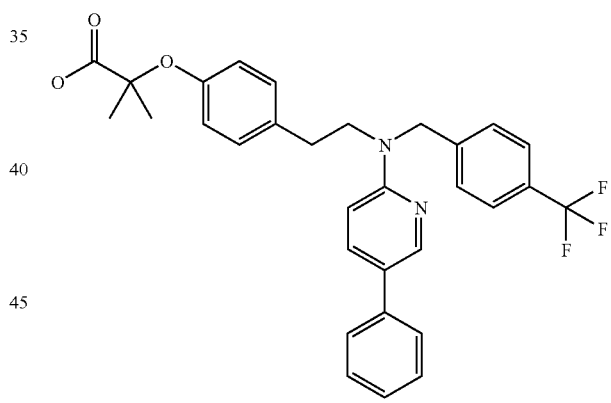

2-Methyl-2-[4-(2-{(5-phenylpyridin-2-yl)[4-(trifluoromethyl)benzyl]amino}ethyl)phenoxy]propanoic acid Step 1. A solution of ethyl 2-[4-(2-{(5-bromopyridin-2-yl)[4-(trifluoromethyl)benzyl]amino}ethyl)phenoxy]-2-methylpropanoate (150 mg; 0.27 mmol) in 2 ml of DMF is treated under nitrogen with tetrakis(triphenylphosphine)palladium (0) (31 mg; 0.027 mmol), phenyl boronic acid (49 mg; 0.40 mmol) and sodium carbonate (0.27 ml of a 2M aqueous solution). The mixture was heated to 100C for 4 hours. Upon cooling, additional phenyl boronic acid (49 mg), Pd catalyst (31 mg) and Na2CO3 solution (0.27 ml) were added and heated again at 100C for 4 hr. Upon cooling, the mixture was partitioned between ethyl acetate and saturated sodium carbonate. The organic phase was washed with saturated sodium carbonate and brine, dried over sodium sulfate and concentrated. Purification by radial chromatography using an ethyl acetate-hexane gradient (5–50%) afforded the ethyl ester intermediate (67 mg; 45% yield). MS: m/z 563 (M+1).

Step 2. Hydrolysis of the previous intermediate (67 mg) with NaOH as per general procedure H provided after chromatography and crystallization from dichloromethane-hexane the title compound as a white solid (42 mg; 65% yield).

$^{1}$H NMR (CDCl$_3$) δ 8.45 (d, 1H, J=2.4), 7.68 (dd, 1H, J=8.8; 2.4), 7.50 (t, 4H, J=7.3), 7.39 (t, 2H, J=7.6), 7.28 (m, 3H), 7.05 (d, 2H, J=8.4), 6.85 (d, 2H, J=8.4), 6.52 (d, 1H, J=8.8), 4.64 (s, 2H), 3.72 (t, 2H, J=7.3), 2.87 (t, 2H, J=7.3), 1.55 (s, 6H). MS: m/z 535 (M+1).

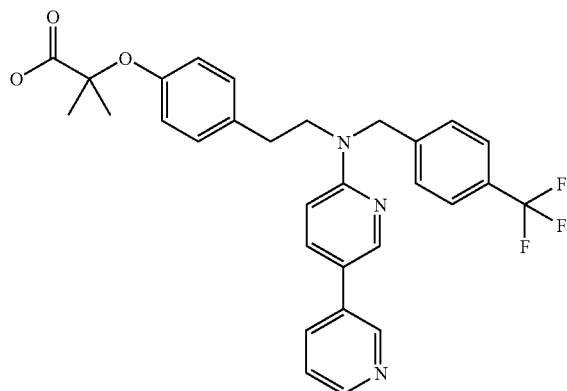

2-[4-(2-{3,3'-Bipyridin-6-yl[4-(trifluoromethyl)benzyl]amino}ethyl)phenoxy]-2-methylpropanoic acid Similarly prepared using pyridine-3-boronic acid.
$^{1}$H NMR (CDCl$_3$) δ 8.81 (s, 1H), 8.50 (d, 1H, J=4.8), 8.39 (d, 1H, J=2.4), 7.87 (d, 1H, J=8.0), 7.62 (dd, 1H, J=9.0; 2.4), 7.48 (d, 2H, J=8.3), 7.40 (dd, 1H, J=8.0; 4.8), 7.24 (d, 2H, J=8.3), 7.03 (d, 2H, J=8.5), 6.88 (d, 2H, J=8.5), 6.49 (d, 1H, J=9.0), 4.65 (s, 2H), 3.71 (t, 2H, J=7.3), 2.85 (t, 2H, J=7.3), 1.59 (s, 6H). MS: m/z 536 (M+1).

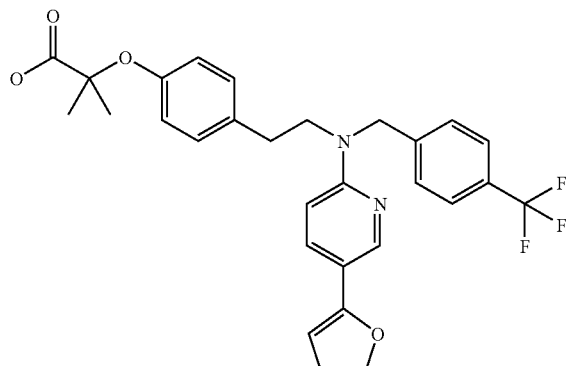

2-[4-(2-{[5-(2-Furyl)pyridin-2-yl][4-(trifluoromethyl)benzyl]amino}ethyl)phenoxy]-2-methylpropanoic acid Similarly prepared using 2-furan-boronic acid.
$^{1}$H NMR (CDCl$_3$) δ 10.4 (bs, 1H), 8.50 (d, 1H, J=2.2), 7.68 (dd, 1H, J=9.0; 2.2), 7.49 (d, 2H, J=8.1), 7.39 (d, 1H, J=1.6), 7.23 (d, 2H, J=8.1), 7.05 (d, 2H, J=8.5), 6.84 (d, 2H, J=8.5), 6.41 (m, 3H), 4.64 (s, 2H), 3.71 (t, 2H, J=7.4), 2.85 (t, 2H, J=7.4), 1.55 (s, 6H). MS: m/z 525 (M+1).

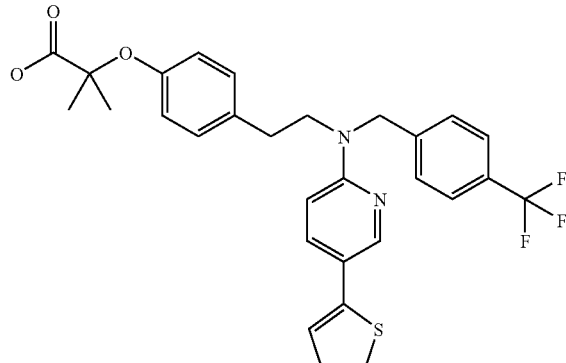

2-Methyl-2-[4-(2-{(5-thien-2-ylpyridin-2-yl)[4-(trifluoromethyl)benzyl]amino}ethyl)phenoxy]propanoic acid Similarly prepared using 2-thiophene-boronic acid.
$^{1}$H NMR (CDCl$_3$) δ 8.45 (d, 1H, J=2.6), 7.62 (dd, 1H, J=8.8; 2.6), 7.50 (d, 2H, J=8.3), 7.24 (d, 2H, J=8.3), 7.17 (d, 1H, J=5.0), 7.12 (d, 1H, J=3.5), 7.05 (d, 2H, J=8.5), 7.01 (dd, 1H, J=5.0; 3.5), 6.84 (d, 2H, J=8.5), 6.44 (d, 1H, J=8.8), 4.64 (s, 2H), 3.71 (t, 2H, J=7.4), 2.86 (t, 2H, J=7.4), 1.55 (s, 6H). MS: m/z 541 (M+1).

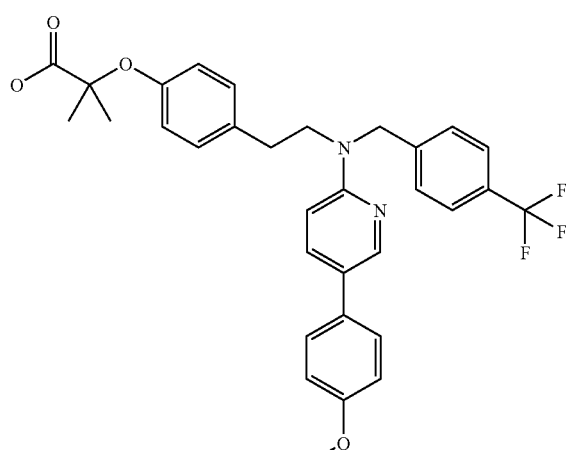

2-[4-(2-{[5-(4-Methoxyphenyl)pyridin-2-yl][4-(trifluoromethyl)benzyl]amino}ethyl)phenoxy]-2-methylpropanoic acid Similarly prepared using 4-methoxyphenyl-boronic acid.
$^{1}$H NMR (CDCl$_3$) δ 8.39 (d, 1H, J=2.4), 7.62 (dd, 1H, J=8.8; 2.4), 7.50 (d, 2H, J=8.1), 7.41 (d, 2H, J=8.8), 7.24 (d, 2H, J=8.1), 7.04 (d, 2H, J=8.5), 6.93 (d, 2H, J=8.8), 6.83 (d, 2H, J=8.5), 6.49 (d, 1H, J=8.8), 4.62 (s, 2H), 3.80 (s, 3H), 3.72 (t, 2H, J=7.4), 2.85 (t, 2H, 7.4), 1.54 (s, 6H).

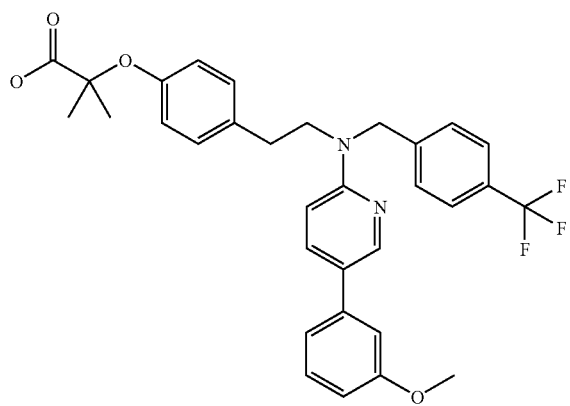

2-[4-(2-{[5-(3-Methoxyphenyl)pyridin-2-yl][4-(trifluoromethyl)benzyl]amino}ethyl)phenoxy]-2-methylpropanoic acid Similarly prepared using 3-methoxyphenyl-boronic acid.

$^1$H NMR (CDCl$_3$) δ 8.44 (d, 1H, J=2.4), 7.66 (dd, 1H, J=8.8; 2.4), 7.50 (d, 2H, J=8.3), 7.30 (t, 1H, J=7.9), 7.24 (d, 2H, J=8.3), 7.07 (m, 4H), 6.83 (m, 3H), 6.50 (d, 1H, J=8.8), 4.64 (s, 2H), 3.82 (s, 3H), 3.73 (t, 2H, J=7.4), 2.87 (t, 2H, 7.4), 1.55 (s, 6H).

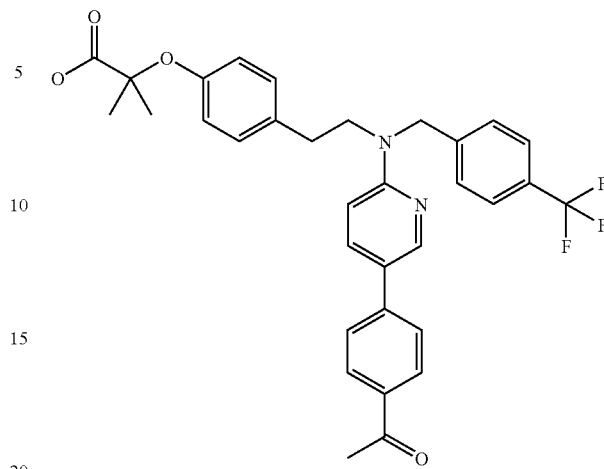

2-[4-(2-{[5-(4-Acetylphenyl)pyridin-2-yl][4-(trifluoromethyl)benzyl]amino}ethyl)phenoxy]-2-methylpropanoic acid Similarly prepared using 4-acetyl-phenyl-boronic acid.

$^1$H NMR (CDCl$_3$) δ 8.5 (d, 1H, J=2.4), 7.97 (d, 2H, J=8.5), 7.71 (dd, 1H, J=9.0; 2.4), 7.57 (d, 2H, J=8.5), 7.50 (d, 2H, J=8.1), 7.24 (d, 2H, J=8.1), 7.06 (d, 2H, J=8.5), 6.85 (d, 2H, J=8.5), 6.53 (d, 1H, J=9.0), 4.66 (s, 2H), 3.74 (t, 2H, J=7.4), 2.88 (t, 2H, 7.4), 2.59 (s, 3H), 1.54 (s, 6H).

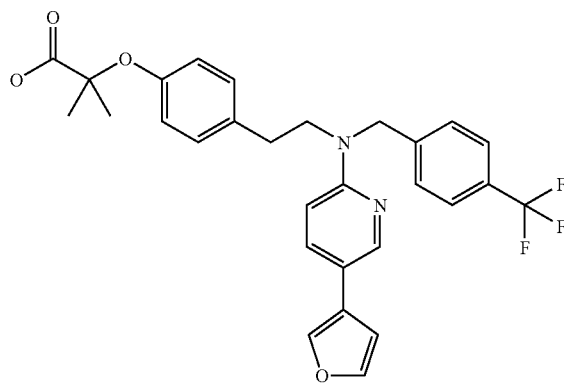

2-[4-(2-{[5-(3-Furyl)pyridin-2-yl][4-(trifluoromethyl)benzyl]amino}ethyl)phenoxy]-2-methylpropanoic acid Similarly prepared using 3-furan-boronic acid.

$^1$H NMR (CDCl$_3$) δ 8.33 (d, 1H, J=2.3), 7.60 (s, 1H), 7.53 (dd, 1H, J=8.8; 2.3), 7.50 (d, 2H, J=8.3), 7.42 (t, 1H, J=1.6), 7.24 (d, 2H, J=8.3), 7.04 (d, 2H, J=8.5), 6.84 (d, 2H, J=8.5), 6.59 (bs, 1H), 6.46 (d, 1H, J=8.8), 4.62 (s, 2H), 3.72 (t, 2H, J=7.4), 2.85 (t, 2H, 7.4), 1.54 (s, 6H).

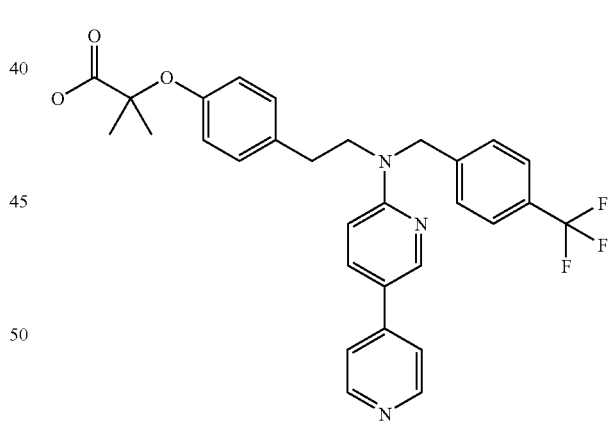

2-[4-(2-{3,4'-bipyridin-6-yl[4-(trifluoromethyl)benzyl]amino}ethyl)phenoxy]-2-methylpropanoic acid Similarly prepared using 4-pyridyl-boronic acid.

$^1$H NMR (CDCl$_3$) δ 8.6 (d, 2H, J=5.3), 8.54 (s, 1H), 7.72 (d, 1H, J=9.0), 7.58 (d, 2H, J=5.3), 7.51 (d, 2H, J=8.1), 7.24 (d, 2H, J=8.1), 7.04 (d, 2H, J=8.2), 6.87 (d, 2H, J=8.2), 6.51 (d, 1H, J=9.0), 4.68 (s, 2H), 3.73 (t, 2H, J=7.4), 2.86 (t, 2H, 7.4), 1.58 (s, 6H).

MS: m/z 536 (M+1).

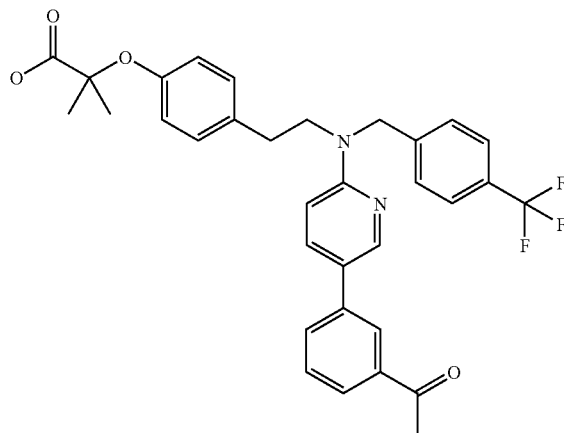

2-[4-(2-{[5-(3-Acetylphenyl)pyridin-2-yl][4-(trifluoromethyl)benzyl]amino}ethyl)phenoxy]-2-methylpropanoic acid Similarly prepared using 3-acetyl-phenyl-boronic acid.

$^1$H NMR (CDCl$_3$) δ 8.46 (s, 1H), 8.08 (s, 1H), 7.85 (d, 1H, J=7.7), 7.7 (m, 2H), 7.50 (m, 3H), 7.26 (d, 2H, J=7.9), 7.07 (d, 2H, J=8.3), 6.85 (d, 2H, J=8.3), 6.53 (d, 1H, J=9.0), 4.68 (s, 2H), 3.76 (t, 2H, J=7.4), 2.89 (t, 2H, J=7.4), 2.62 (s, 3H), 1.55 (s, 6H).
MS: m/z 577 (M+1).

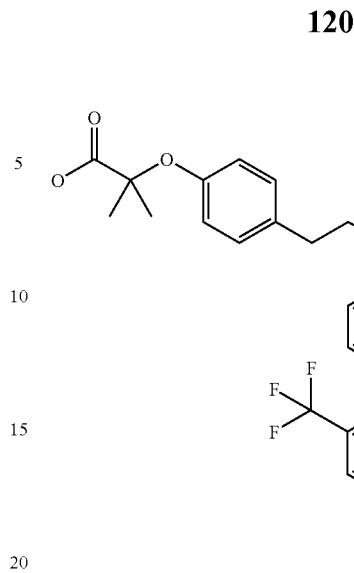

2-Methyl-2-{4-[2-([4-(trifluoromethyl)benzyl]{5-[2-(trifluoromethyl)phenyl]pyridin-2-yl}amino)ethyl]phenoxy}propanoic acid Similarly prepared using 2-trifluoromethyl-phenyl-boronic acid.

$^1$H NMR (CDCl$_3$) δ 8.15 (d, 1H, J=2.0), 7.73 (d, 1H, J=7.9), 7.52 (m, 3H), 7.43 (m, 2H), 7.31 (m, 3H), 7.05 (d, 2H, J=8.4), 6.85 (d, 2H, J=8.4), 6.48 (d, 1H, J=8.8), 4.69 (s, 2H), 3.72 (t, 2H, J=7.4), 2.88 (t, 2H, J=7.4), 1.55 (s, 6H).
MS: m/z 603 (M+1).

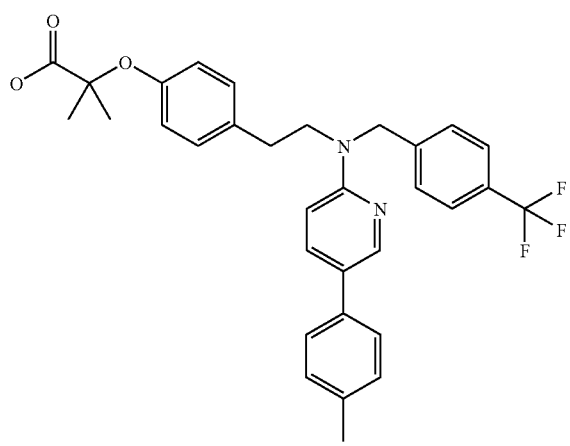

2-Methyl-2-[4-(2-{[5-(4-methylphenyl)pyridin-2-yl][4-(trifluoromethyl)benzyl]amino}ethyl)phenoxy]propanoic acid Similarly prepared using 4-methyl-phenyl-boronic acid.

$^1$H NMR (CDCl$_3$) δ 8.42 (d, 1H, J=2.2), 7.65 (dd, 1H, J=8.9; 2.2), 7.50 (d, 2H, J=8.1), 7.38 (d, 2H, J=8.1), 7.25 (d, 2H, J=8.1), 7.20 (d, 2H, J=8.1), 7.06 (d, 2H, J=8.5), 6.84 (d, 2H, J=8.5), 6.51 (d, 1H, J=8.9), 4.64 (s, 2H), 3.74 (t, 2H, J=7.4), 2.87 (t, 2H, 7.4), 2.35 (s, 3H), 1.55 (s, 6H). MS: m/z 549 (M+1).

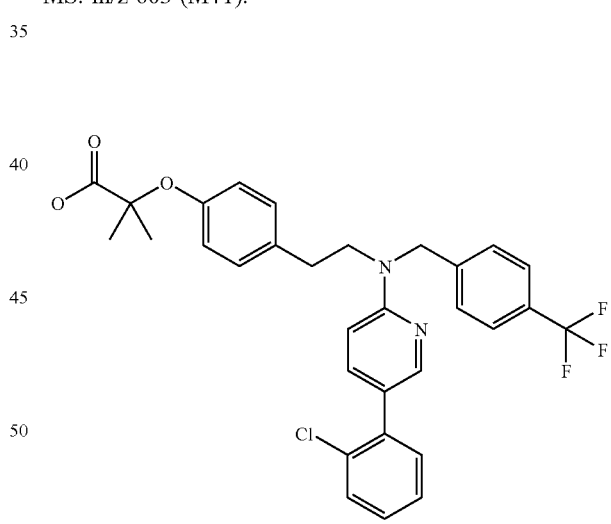

2-[4-(2-{[5-(2-Chlorophenyl)pyridin-2-yl][4-(trifluoromethyl)benzyl]amino}ethyl)phenoxy]-2-methylpropanoic acid Similarly prepared using 2-chloro-phenyl-boronic acid.

$^1$H NMR (CDCl$_3$) δ 8.27 (d, 1H, J=2.4), 7.61 (dd, 1H, J=8.8; 2.4), 7.52 (d, 2H; J=8.1), 7.43 (d, 1H, J=7.9), 7.29 (m, 5H), 7.06 (d, 2H, J=8.4), 6.85 (d, 2H, J=8.4), 6.51 (d, 1H, J=8.8), 4.68 (s, 2H), 3.73 (t, 2H, J=7.3), 2.88 (t, 2H, J=7.3), 1.55 (s, 6H). MS: m/z 569 (M+1).

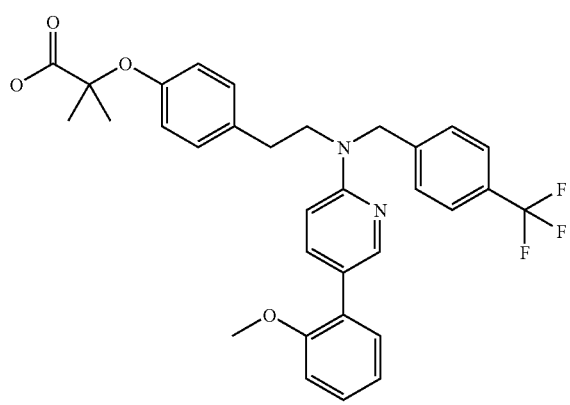

2-[4-(2-{[5-(2-Methoxyphenyl)pyridin-2-yl][4-(trifluoromethyl)benzyl]amino}ethyl)phenoxy]-2-methylpropanoic acid Similarly prepared using 2-methoxy-phenyl-boronic acid.
$^1$H NMR (CDCl$_3$) δ 8.38 (d, 1H, J=2.2), 7.70 (dd, 1H, J=8.8; 2.2), 7.50 (d, 2H; J=8.2), 7.28 (m, 4H), 7.05 (d, 2H, J=8.4), 7.0 (t, 1H, J=7.5), 6.95 (d, 1H, J=8.4), 6.84 (d, 2H, J=8.4), 6.5 (d, 1H, J=8.8), 4.65 (s, 2H), 3.81 (s, 3H), 3.72 (t, 2H, J=7.4), 2.87 (t, 2H, J=7.4), 1.55 (s, 6H). MS: m/z 565 (M+1).

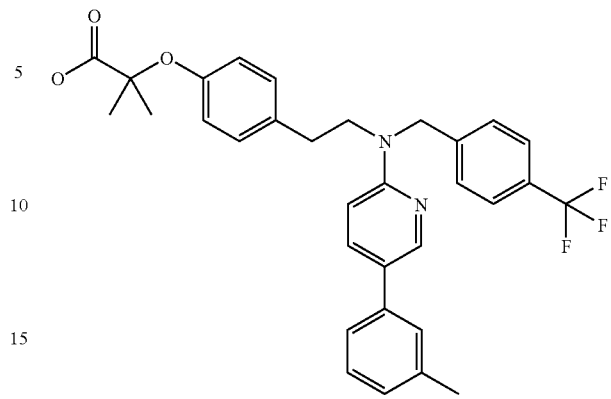

2-Methyl-2-[4-(2-{[5-(3-methylphenyl)pyridin-2-yl][4-(trifluoromethyl)benzyl]amino}ethyl)phenoxy]propanoic acid Similarly prepared using 3-methyl-phenyl-boronic acid.
$^1$H NMR (CDCl$_3$) δ 8.43 (d, 1H, J=2.2), 7.66 (dd, 1H, J=8.8; 2.2), 7.50 (d, 2H; J=8.1), 7.28 (m, 5H), 7.09 (m, 1H), 7.06 (d, 2H, J=8.4), 6.84 (d, 2H, J=8.4), 6.50 (d, 1H, J=8.8), 4.65 (s, 2H), 3.73 (t, 2H, J=7.4), 2.88 (t, 2H, J=7.4), 2.37 (s, 3H), 1.55 (s, 6H). MS: m/z 549 (M+1).

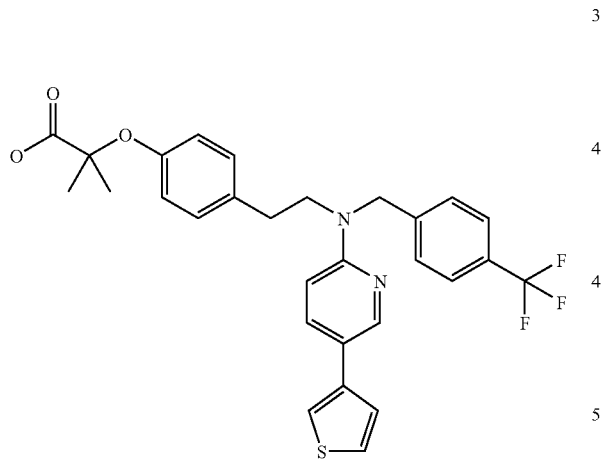

2-Methyl-2-[4-(2-{(5-thien-3-ylpyridin-2-yl)[4-(trifluoromethyl)benzyl]amino}ethyl)phenoxy]propanoic acid Similarly prepared using 3-thiophene-boronic acid.
$^1$H NMR (CDCl$_3$) δ 8.46 (d, 1H, J=2.4), 7.65 (dd, 1H, J=8.8; 2.4), 7.50 (d, 2H, J=8.1), 7.36 (m, 1H), 7.28 (m, 1H), 7.25 (d, 2H, J=8.1), 7.04 (d, 2H, J=8.4), 6.85 (d, 2H, J=8.4), 6.48 (d, 1H, J=8.8), 4.64 (s, 2H), 3.72 (t, 2H, J=7.4), 2.86 (t, 2H, J=7.4), 1.55 (s, 6H). MS: m/z 541 (M+1).

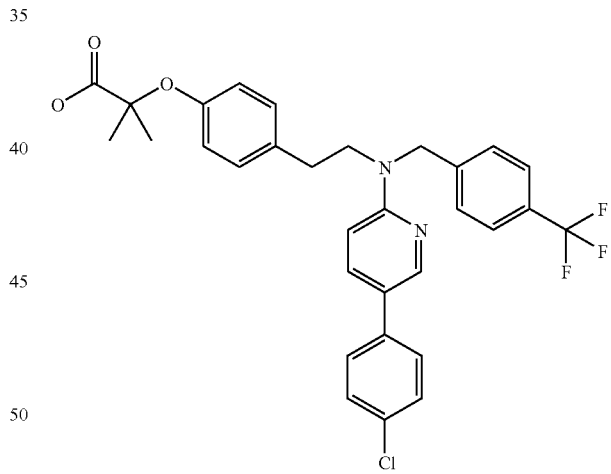

2-[4-(2-{[5-(4-Chlorophenyl)pyridin-2-yl][4-(trifluoromethyl)benzyl]amino}ethyl)phenoxy]-2-methylpropanoic acid Similarly prepared using 4-chloro-phenyl-boronic acid.
$^1$H NMR (CDCl$_3$) δ 8.41 (d, 1H, J=2.4), 7.62 (dd, 1H, J=9.0; 2.4), 7.50 (d, 2H; J=8.3), 7.40 (d, 2H, J=8.6), 7.34 (d, 2H, J=8.6), 7.24 (d, 2H, J=8.3), 7.05 (d, 2H, J=8.4), 6.84 (d, 2H, J=8.4), 6.50 (d, 1H, J=9.0), 4.64 (s, 2H), 3.73 (t, 2H, J=7.4), 2.86 (t, 2H, J=7.4), 1.55 (s, 6H). MS: m/z 569 (M+1).

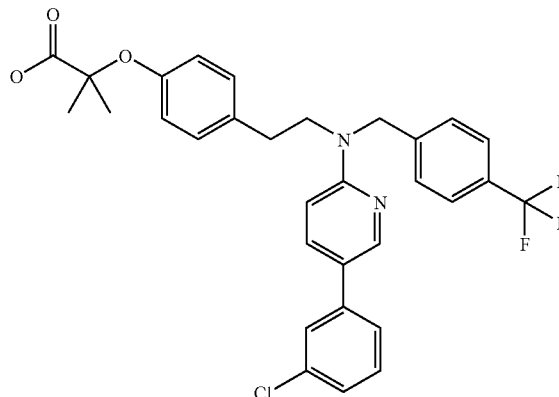

2-[4-(2-{[5-(3-Chlorophenyl)pyridin-2-yl][4-(trifluoromethyl)benzyl]amino}ethyl)phenoxy]-2-methyl-propanoic acid Similarly prepared using 3-chloro-phenyl-boronic acid.

$^1$H NMR (CDCl$_3$) δ 8.40 (d, 1H, J=2.4), 7.62 (dd, 1H, J=9.0; 2.4), 7.50 (d, 2H; J=8.1), 7.45 (bs, 1H), 7.35 (d, 1H, J=7.8), 7.30 (t, 1H, J=7.8), 7.24 (m, 3H), 7.06 (d, 2H, J=8.4), 6.85 (d, 2H, J=8.4), 6.50 (d, 1H, J=9.0), 4.65 (s, 2H), 3.73 (t, 2H, J=7.4), 2.87 (t, 2H, J=7.4), 1.55 (s, 6H). MS: m/z 569 (M+1).

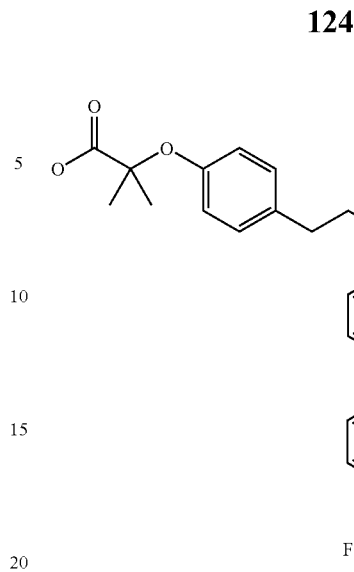

2-Methyl-2-{4-[2-([4-(trifluoromethyl)benzyl]{5-[4-(trifluoromethyl)phenyl]pyridin-2-yl}amino)ethyl]phenoxy}propanoic acid Similarly prepared using 4-trifluoromethyl-phenyl-boronic acid.

$^1$H NMR (CDCl$_3$) δ 8.45 (d, 1H, J=2.4), 7.67 (dd, 1H; J=8.9; 2.4), 7.63 (d, 2H, J=8.5), 7.58 (d, 2H, J=8.5), 7.51 (d, 2H, J=8.2), 7.26 (d, 2H, J=8.2), 7.07 (d, 2H, J=8.6), 6.85 (d, 2H, J=8.6), 6.53 (d, 1H, J=8.9), 4.68 (s, 2H), 3.75 (t, 2H, J=7.4), 2.89 (t, 2H, J=7.4), 1.55 (s, 6H). MS: m/z 603 (M+1).

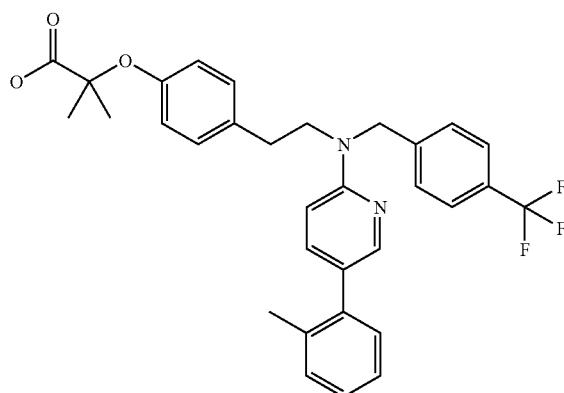

2-Methyl-2-[4-(2-{[5-(2-methylphenyl)pyridin-2-yl][4-(trifluoromethyl)benzyl]amino}ethyl)phenoxy]propanoic acid Similarly prepared using 2-methyl-phenyl-boronic acid.

$^1$H NMR (CDCl$_3$) δ 8.17 (d, 1H, J=2.4), 7.51 (d, 2H, J=8.1), 7.45 (dd, 1H; J=8.8; 2.4), 7.27 (d, 2H, J=8.1), 7.22 (m, 4H), 7.05 (d, 2H, J=8.4), 6.84 (d, 2H, J=8.4), 6.50 (d, 1H, J=8.8), 4.66 (s, 2H), 3.72 (t, 2H, J=7.4), 2.87 (t, 2H, J=7.4), 2.29 (s, 3H), 1.54 (s, 6H). MS: m/z 549 (M+1).

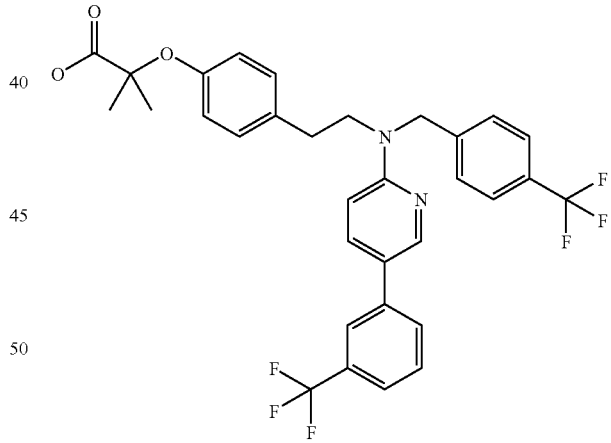

2-Methyl-2-{4-[2-([4-(trifluoromethyl)benzyl]{5-[3-(trifluoromethyl)phenyl]pyridin-2-yl}amino)ethyl]phenoxy}propanoic acid Similarly prepared using 3-trifluoromethyl-phenyl-boronic acid.

$^1$H NMR (CDCl$_3$) δ 8.43 (d, 1H, J=2.4), 7.71 (s, 1H), 7.67 (m, 2H), 7.51 (m, 4H), 7.25 (d, 2H, J=8.9), 7.07 (d, 2H, J=8.5), 6.85 (d, 2H, J=8.5), 6.52 (d, 1H, J=9.0), 4.67 (s, 2H), 3.75 (t, 2H, J=7.4), 2.89 (t, 2H, J=7.4), 1.55 (s, 6H). MS: m/z 603 (M+1).

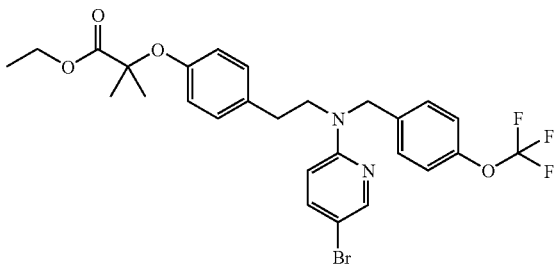

Ethyl 2-[4-(2-{(5-bromopyridin-2-yl)[4-(trifluoromethoxy)benzyl]amino}ethyl)phenoxy]-2-methylpropanoate Step 1. A mixture of 2,5-dibromo-pyridine (5 g; 21.10 mmol) and tyramine (5.79 g; 42.21 mmol) was heated at 200C for 1 hour. Upon cooling the residue was taken up into ethyl acetate, water and 1N HCl. The phases were separated and the organic phase was washed twice with 1N HCl. The combined aqueous phases were basified to pH-9 with 2N NaOH and extracted twice with ethyl acetate. The combined organic phases were washed with brine, dried over sodium sulfate and concentrated to afford 4-{2-[(5-bromopyridin-2-yl)amino]ethyl}phenol as a beige solid (5 g; 80% yield), which was used in the next step without further purification.

Step 2. The previous intermediate (5 g; 17.06 mmol) was alkylated with ethyl-2-bromo-isobutyrate (6.65 g; 34.12 mmol) as per general procedure C (2 eq Cs2CO3, MeCN, 80C, 15 hr). Purification by flash chromatography (5–20% ethyl acetate-hexane gradient) afforded ethyl 2-(4-{2-[(5-bromopyridin-2-yl)amino]ethyl}phenoxy)-2-methylpropanoate (6.3 g; 91% yield).

Step 3. A solution of the previous intermediate (1 g; 2.45 mmol) in 8 ml of dry DMF was treated under nitrogen with NaH (60% dispersion in oil; 123 mg; 3.07 mmol). After stirring for 5 minutes, 4-trifluoromethoxy-benzyl bromide (0.49 ml; 3.07 mmol) was added and the mixture heated at 90C for 4 hours. Upon cooling the reaction mixture was partitioned between ethyl acetate and 0.05N HCl. The organic phase was washed with 0.05N HCl and brine, dried over sodium sulfate and concentrated. Purification by flash chromatography afforded the title compound (0.65 g; 45% yield).

$^1$H NMR (CDCl$_3$) δ 8.17 (d, 1H, J=2.4), 7.44 (dd, 1H, J=9.0; 2.1), 7.15 (d, 2H, J=8.6), 7.10 (d, 2H, J=8.6), 7.01 (d, 2H, J=8.6), 6.77 (d, 2H, J=8.6), 6.31 (d, 2H, J=9.0), 4.55 (s, 2H), 4.22 (q, 2H, J=7.1), 3.64 (t, 2H, J=7.4), 2.81 (t, 2H, J=7.4), 1.55 (s, 6H), 1.25 (t, 3H, J=7.1).

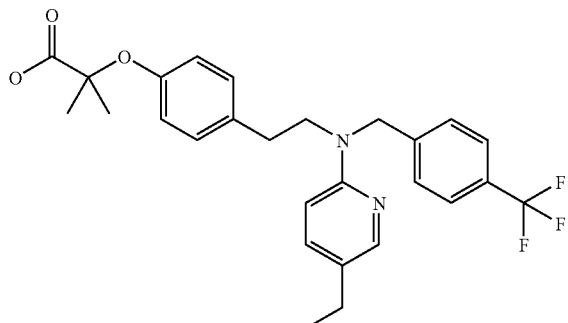

2-[4-(2-{(5-Ethylpyridin-2-yl)[4-(trifluoromethyl)benzyl]amino}ethyl)phenoxy]-2-methylpropanoic acid Step 1. A solution of ethyl 2-[4-(2-{(5-bromopyridin-2-yl)[4-(trifluoromethyl)benzyl]amino}ethyl)phenoxy]-2-methylpropanoate (150 mg; 0.27 mmol) in 2 ml of toluene was treated under nitrogen with tetrakis(triphenylphosphine)palladium (0) (61 mg; 0.053 mmol), vinyltributyltin (252 mg; 0.80 mmol), lithium chloride (34 mg; 0.80 mmol) and 2,6-di-tert-butyl-4-methyl-phenol (3 mg). The mixture was heated at 110C overnight. Upon cooling, the mixture was diluted with 10 ml each of ethyl acetate and water. A saturated solution of KF (10 ml) was added and the phases were separated. The organic phase was washed with brine, dried over sodium sulfate and concentrated. Purification by radial chromatography using an ethyl acetate-hexane gradient (5–50%) afforded ethyl 2-methyl-2-(4-{2-[[4-(trifluoromethyl)benzyl](5-vinylpyridin-2-yl)amino]ethyl}phenoxy)propanoate (71 mg; 52% yield).

MS: m/z 513 (M+1).

Step 2. A solution of the previous intermediate (71 mg) in 3 ml of ethyl acetate was treated with 10% Pd/C (25 mg) and hydrogenated under balloon pressure. After 3 hours additional catalyst (20 mg) was added and hydrogenated for another hour. The catalyst was filtered off and washed with ethyl acetate and chloroform/methanol. The filtrate was concentrated and purified by radial chromatography to afford the intermediate ethyl ester (70 mg; 98% yield).

Step 3. The previous intermediate (70 mg) was hydrolyzed with NaOH as per general procedure H. Purification by radial chromatography (1–5% methanol-dichloromethane gradient) afforded the title compound as a glassy solid (22 mg; 35% yield).

$^1$H NMR (CDCl$_3$) δ 9.3 (bs, 1H), 8.01 (d, 1H, J=2.4), 7.46 (d, 2H, J=8.3), 7.31 (dd, 1H, J=8.8; 2.4), 7.18 (d, 2H, J=8.3), 6.99 (d, 2H, J=8.5), 6.81 (d, 2H, J=8.5), 6.40 (d, 1H, J=8.8), 4.54 (s, 2H), 3.65 (t, 2H, J=7.4), 2.78 (t, 2H, J=7.4), 2.48 (q, 2H, J=7.6), 1.54 (s, 6H), 1.15 (t, 3H, J=7.6). MS: m/z 487 (M+1).

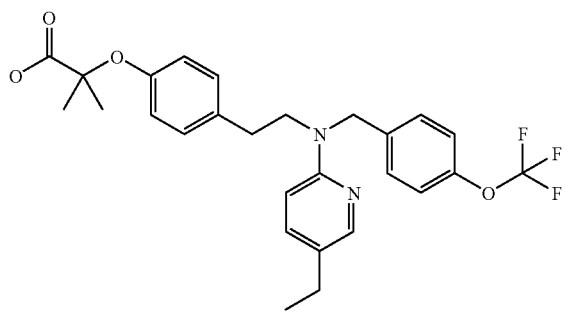

2-[4-(2-{(5-Ethylpyridin-2-yl)[4-(trifluoromethoxy)benzyl]amino}ethyl)phenoxy]-2-methylpropanoic acid Similarly prepared from ethyl 2-[4-(2-{(5-bromopyridin-2-yl)[4-(trifluoromethoxy)benzyl]amino}ethyl)phenoxy]-2-methylpropanoate and vinyltributyltin. $^1$H NMR (CDCl$_3$) δ 8.02 (d, 1H, J=2.0), 7.32 (dd, 1H, J=8.8; 2.0), 7.12 (d, 2H, J=8.6), 7.07 (d, 2H, J=8.5), 7.0 (d, 2H, J=8.4), 6.82 (d, 2H, J=8.4), 6.42 (d, 1H, J=8.8), 4.50 (s, 2H), 3.67 (t, 2H, J=7.4), 2.80 (t, 2H, J=7.4), 2.49 (q, 2H, J=7.6), 1.55 (s, 6H), 1.19 (t, 3H, J=7.6). MS: m/z 503 (M+1).

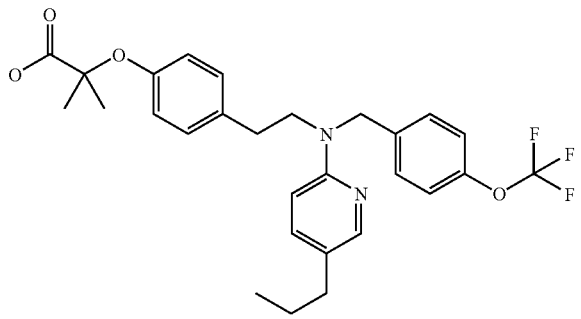

2-Methyl-2-[4-(2-{(5-propylpyridin-2-yl)[4-(trifluoromethoxy)benzyl]amino}ethyl)phenoxy]propanoic acid Similarly prepared from ethyl 2-[4-(2-{(5-bromopyridin-2-yl)[4-(trifluoromethoxy)benzyl]amino}ethyl)phenoxy]-2-methylpropanoate and allyltributyltin.

$^1$H NMR (CDCl$_3$) δ 8.0 (d, 1H, J=2.0), 7.33 (dd, 1H, J=9.0; 2.0), 7.08 (d, 2H, J=8.6), 7.06 (d, 2H, J=8.6), 6.96 (d, 2H, J=8.5), 6.78 (d, 2H, J=8.5), 6.45 (d, 1H, J=9.0), 4.49 (s, 2H), 3.69 (t, 2H, J=7.4), 2.79 (t, 2H, J=7.4), 2.41 (t, 2H, J=7.4), 1.54 (m, 2H), 1.50 (s, 6H), 0.90 (t, 3H, J=7.4). MS: m/z 517 (M+1).

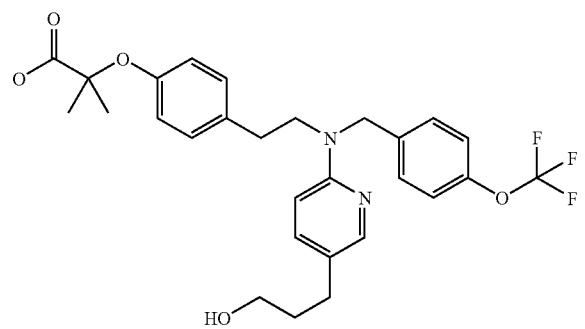

2-[4-(2-{[5-(3-Hydroxypropyl)pyridin-2-yl][4-(trifluoromethoxy)benzyl]amino}ethyl)phenoxy]-2-methylpropanoic acid Step 1. A solution of ethyl 2-[4-(2-{(5-bromopyridin-2-yl)[4-(trifluoromethoxy)benzyl]amino}ethyl)phenoxy]-2-methylpropanoate (500 mg; 0.86 mmol) in 3 ml of Et$_3$N was treated under nitrogen with tetrakis(triphenylphosphine)palladium (0) (99 mg; 0.086 mmol) and copper (I) iodide (16 mg; 0.086 mmol). After stirring at rt for 5 minutes, propargyl alcohol (72 mg; 1.29 mmol) was added and the mixture heated at 65C for 7 hr. Upon cooling the reaction mixture was concentrated and the residue was partitioned between ethyl acetate and 0.1N HCl. The organic phase was washed with 0.1N HCl and brine, dried over sodium sulfate and concentrated. Purification by radial chromatography using ethyl acetate-hexane mixtures (5–50% gradient) afforded ethyl 2-[4-(2-{[5-(3-hydroxyprop-1-ynyl)pyridin-2-yl][4-(trifluoromethoxy)benzyl]amino}ethyl)phenoxy]-2-methylpropanoate.

Step 2. A solution of the previous intermediate in ethyl acetate was treated with 10% Pd/C and hydrogenated under balloon pressure for 2 hr. The catalyst was filtered off and washed with ethyl acetate and chloroform/methanol. The filtrate was concentrated and purified by radial chromatography (5–40% ethyl acetate-hexane gradient) to afford ethyl 2-[4-(2-{[5-(3-hydroxypropyl)pyridin-2-yl][4-(trifluoromethoxy)benzyl]amino}ethyl)phenoxy]-2-methylpropanoate.

MS: m/z 561 (M+1). CD$_3$OD

Step 3. The above ester was hydrolyzed with NaOH as per general procedure H. Purification by radial chromatography afforded the title compound as a light yellow foam (30 mg; 7% combined yield).

$^1$H NMR (CDCl$_3$+CD$_3$OD) δ 7.89 (d, 1H, J=2.0), 7.27 (dd, 1H, J=9.0; 2.0), 7.12 (d, 2H, J=8.6), 7.06 (d, 2H, J=8.6), 7.0 (d, 2H, J=8.5), 6.77 (d, 2H, J=8.5), 6.38 (d, 1H, J=9.0), 4.52 (s, 2H), 3.63 (t, 2H, J=7.4), 3.55 (t, 2H, J=6.4), 2.79 (t, 2H, J=7.4), 2.50 (t, 2H, J=7.5), 1.75 (m, 2H), 1.50 (s, 6H). MS: m/z 533 (M+1).

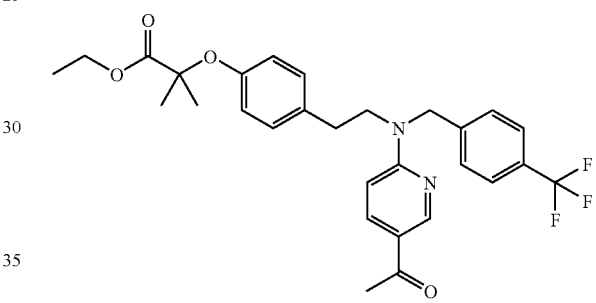

Ethyl 2-[4-(2-{(5-acetylpyridin-2-yl)[4-(trifluoromethyl)benzyl]amino}ethyl)phenoxy]-2-methylpropanoate A mixture of ethyl 2-methyl-2-[4-(2-{[4-(trifluoromethyl)benzyl]amino}ethyl)phenoxy]propanoate (1.05 g; 2.57 mmol), 2-chloro-5-acetyl-pyridine (0.40 g; 2.57 mmol) and DIEA (0.36 g; 2.83 mmol) was heated in a pressure tube at 180C for 5 hr. Upon cooling, the residue was chromatographed using 20% ethyl acetate-hexane mixtures to afford ethyl 2-[4-(2-{(5-acetylpyridin-2-yl)[4-(trifluoromethyl)benzyl]amino}ethyl)phenoxy]-2-methylpropanoate (0.48 g; 35% yield).

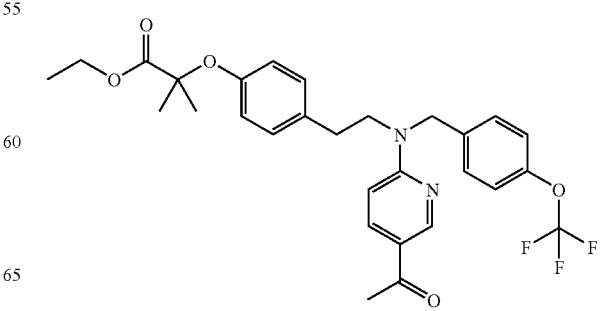

Ethyl 2-[4-(2-{(5-acetylpyridin-2-yl)[4-(trifluoromethoxy)benzyl]amino}ethyl)phenoxy]-2-methylpropanoate Similarly prepared from ethyl 2-methyl-2-[4-(2-{[4-(trifluoromethoxy)benzyl]amino}ethyl)phenoxy]propanoate and 2-chloro-5-acetyl-pyridine.

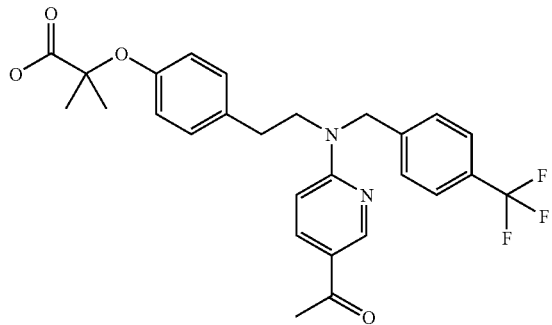

2-[4-(2-{(5-Acetylpyridin-2-yl)[4-(trifluoromethyl)benzyl]amino}ethyl)phenoxy]-2-methylpropanoic acid Hydrolysis of ethyl 2-[4-(2-{(5-acetylpyridin-2-yl)[4-(trifluoromethyl)benzyl]amino}ethyl)phenoxy]-2-methylpropanoate with LiOH as per general procedure H afforded after a standard aqueous workup the title compound.

$^1$H NMR (CD$_3$OD) δ 8.79 (d, 1H, J=2.2), 8.01 (dd, 1H, J=9.1 and 2.4), 7.62 (d, 2H, J=8.1), 7.39 (d, 2H, J=8.0), 7.13 (d, 2H, J=8.4), 6.85 (d, 2H, J=8.5), 6.65 (d, 1H, J=9.3), 4.85 (s, 2H), 3.85 (t, 2H, J=7.1), 2.94 (t, 2H, J=7.3), 2.56 (s, 3H), 1.49 (s, 6H). MS: m/z 501 (M+1).

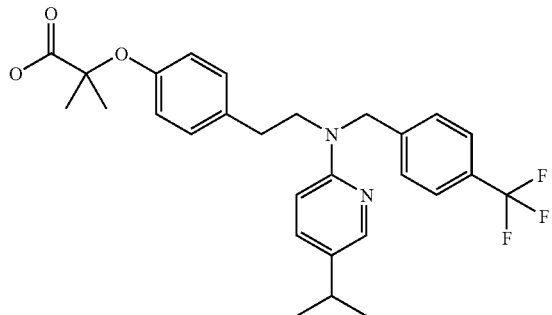

2-[4-(2-{(5-Isopropylpyridin-2-yl)[4-(trifluoromethyl)benzyl]amino}ethyl)phenoxy]-2-methylpropanoic acid Step 1. A solution of methyltriphenylphosphonium bromide (101 mg; 0.28 mmol) in 0.76 ml of THF was treated under nitrogen with potassium tert-butoxide (0.28 ml of a 1M solution in tert-butanol). After 10 minutes, ethyl 2-[4-(2-{(5-acetylpyridin-2-yl)[4-(trifluoromethyl)benzyl]amino}ethyl)phenoxy]-2-methylpropanoate (100 mg; 0.19 mmol) was added. After 2 hours the reaction mixture was concentrated and the residue was partitioned between ethyl acetate and water. The organic phase was dried over sodium sulfate and concentrated. Purification by flash chromatography using 10% ethyl acetate-hexane mixtures afforded ethyl 2-[4-(2-{(5-isopropenylpyridin-2-yl)[4-(trifluoromethyl)benzyl]amino}ethyl)phenoxy]-2-methylpropanoate (30 mg; 30% yield).

$^1$H NMR (CDCl$_3$) δ 8.30 (s, 1H), 7.57 (d, 1H, J=8.8), 7.51 (d, 2H, J=7.9), 7.25 (d, 2H, J=7.7), 7.03 (d, 2H, J=8.0), 6.77 (d, 2H, J=8.3), 6.42 (d, 1H, J=8.9), 5.23 (s, 1H), 4.92 (s, 1H), 4.66 (s, 2H), 4.21 (q, 2H, J=7.1), 3.69 (t, 2H, J=6.9), 2.85 (t, 2H, J=6.8), 2.09 (s, 3H), 1.55 (s, 6H), 1.24 (t, 3H, J=7.2).

Step 2. A solution of the previous intermediate in EtOH was treated with 10% Pd/C and hydrogenated under 1 atm of H2 for 4 hr. The catalyst was filtered off and washed with ethyl acetate. The filtrate was concentrated to afford ethyl 2-[4-(2-{(5-isopropylpyridin-2-yl)[4-(trifluoromethyl)benzyl]amino}ethyl)phenoxy]-2-methylpropanoate.

$^1$H NMR (CD$_3$OD) δ 7.96 (s, 1H), 7.60 (d, 2H, J=8.1), 7.45 (d, 1H, J=8.8), 7.36 (d, 2H, J=7.8), 7.13 (d, 2H, J=8.6), 6.80 (d, 2H, J=8.5), 6.58 (d, 1H, J=8.9), 4.71 (s, 2H), 4.22 (q, 2H, J=7.1), 3.74 (t, 2H, J=7.4), 2.92–2.84 (m, 3H), 1.56 (s, 6H), 1.36–1.21 (m, 9H).

Step 3. Hydrolysis of the above ester with LiOH as per general procedure H provided after standard aqueous workup the title compound.

$^1$H NMR (CDCl$_3$) δ 8.04 (s, 1H), 7.48 (d, 2H, J=7.7), 7.36 (d, 1H, J=8.6) 7.21 (d, 2H, J=7.7), 7.00 (d, 2H, J=8.0), 6.82 (d, 2H, J=8.1), 6.43 (d, 1H, J=9.0), 4.56 (s, 2H), 3.67 (t, 2H, J=7.1), 2.83–2.76 (m, 3H), 1.54 (s, 6H), 1.19 (d, 6H, J=6.8). MS: m/z 501 (M+1).

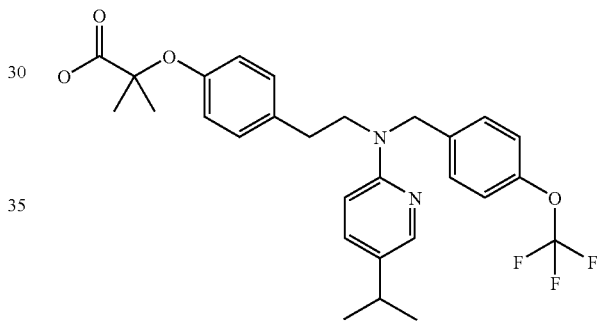

2-[4-(2-{5-Isopropylpyridin-2-yl)[4-(trifluoromethoxy)benzyl]amino}ethyl)phenoxy]-2-methylpropanoic acid Similarly prepared from ethyl 2-[4-(2-{(5-acetylpyridin-2-yl)[4-(trifluoromethoxy)benzyl]amino}ethyl)phenoxy]-2-methylpropanoate.

$^1$H NMR (CD$_3$OD) δ 7.80 (d, 1H, J=1.6), 7.56 (dd, 1H, J=9.1 and 2.1), 7.24 (d, 2H, J=8.4), 7.18 (d, 2H, J=8.4), 7.07 (d, 2H, J=8.2), 6.80 (d, 2H, J=8.4), 6.72 (d, 2H, J=9.2), 4.64 (s, 2H), 3.73 (t, 2H, J=7.4), 3.28–2.79 (m, 3H), 1.50 (s, 6H), 1.19 (d, 6H, J=6.8). MS: m/z 517 (M+1).

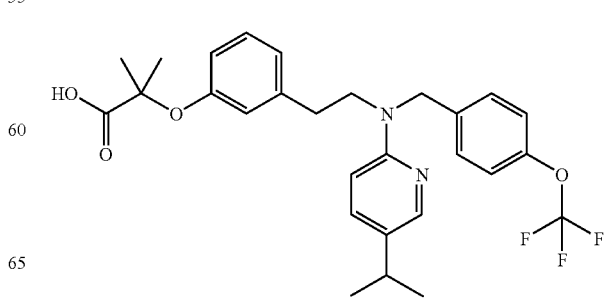

2-[3-(2-{(5-Isopropylpyridin-2-yl)[4-(trifluoromethoxy)benzyl]amino}ethyl)phenoxy]-2-methylpropanoic acid Similarly prepared starting with 3-methoxyphenethylamine.

¹H NMR (CD₃OD) δ 7.87 (d, 1H, J=2.2), 7.43 (dd, 1H, J=8.8 and 2.4), 7.23–7.07 (m, 5H), 6.81–6.70 (m, 3H), 6.57 (d, 1H, J=8.8), 4.60 (s, 2H), 3.68 (t, 2H, J=7.3), 2.83–2.74 (m, 3H), 1.48 (s, 6H), 1.18 (d, 6H, J=6.9). MS: m/z 517 (M+1).

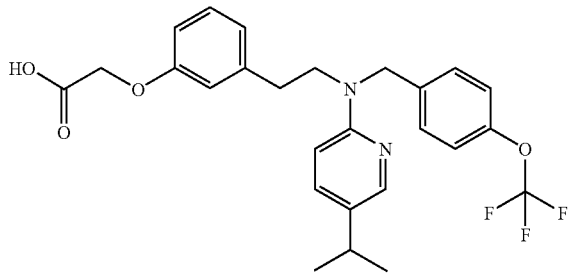

[3-(2-{(5-Isopropylpyridin-2-yl)[4-(trifluoromethoxy)benzyl]amino}ethyl)phenoxy]acetic acid Similarly prepared starting with 3-methoxyphenethylamine.

¹H NMR (CD₃OD) δ 7.92 (d, 1H, J=9.5), 7.62 (s, 1H), 7.31–7.09 (m, 7H), 6.82 (d, 1H, J=4.5), 6.77 (d, 1H, J=8.4), 4.71 (s, 2H), 4.62 (s, 2H), 3.91 (t, 2H, J=6.7), 2.98 (t, 2H, J=6.7), 2.90–2.89 (m, 1H), 1.21 (d, 6H, J=6.8). MS: m/z 489 (M+1).

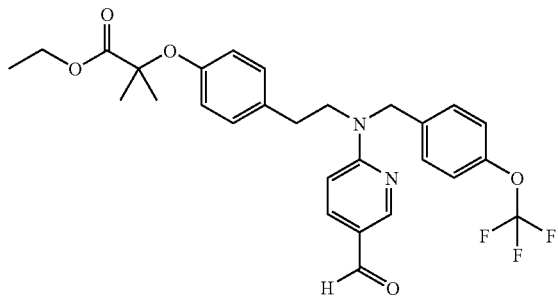

Ethyl 2-[4-(2-{(5-formylpyridin-2-yl)[4-(trifluoromethoxy)benzyl]amino}ethyl)phenoxy]-2-methylpropanoate A solution of ethyl 2-methyl-2-[4-(2-{[4-(trifluoromethoxy)benzyl]amino}ethyl)phenoxy]propanoate (3.0 g; 7.05 mmol) in 8 ml of DMF was treated with 6-chloronicotinaldehyde (0.91 g; 6.42 mmol) and K₂CO₃ (0.97 g; 7.05 mmol). The reaction mixture was heated at 150C for 4 hr. Upon cooling, the mixture was partitioned between ethyl acetate and 0.05N HCl. The organic phase was washed with 0.05N HCl and brine, dried over sodium sulfate, filtered and concentrated. Purification by flash chromatography using ethyl acetate-hexane mixtures (5–50%) afforded the title compound (2.3 g; 68% yield).

¹H NMR (CDCl₃) δ 9.77 (s, 1H), 8.57 (d, 1H, J=2.1), 7.87 (dd, 1H, J=9.0; 2.1), 7.15 (d, 2H, J=8.8), 7.11 (d, 2H, J=8.8), 7.02 (d, 2H, J=8.5), 6.76 (d, 2H, J=8.5), 6.49 (d, 1H, J=9.0), 4.67 (s, 2H), 4.21 (q, 2H, J=7.2), 3.72 (t, 2H, J=7.5), 2.85 (t, 2H, J=7.5), 1.54 (s, 6H), 1.23 (t, 3H, J=7.2).

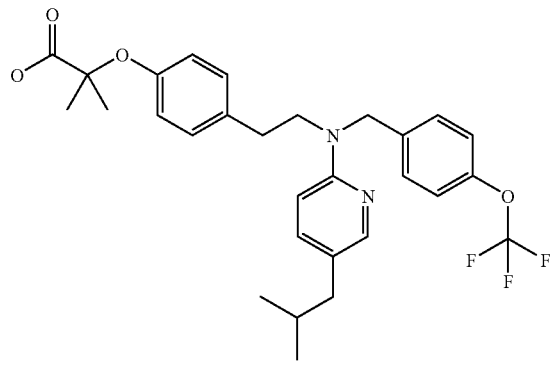

2-[4-(2-{(5-isobutylpyridin-2-yl)[4-(trifluoromethoxy)benzyl]amino}ethyl)phenoxy]-2-methylpropanoic acid Step 1. A solution of isopropyltriphenylphosphonium bromide (326 mg; 0.75 mmol) in 1.5 ml of dry THF was treated in an ice bath, under nitrogen, with n-butyl lithium (0.425 ml of a 1.6M solution in hexane; 0.68 mmol), dropwise. After stirring for 15 minutes, this mixture was added, via syringe, into an ice-cold solution of ethyl 2-[4-(2-{(5-formylpyridin-2-yl)[4-(trifluoromethoxy)benzyl]amino}ethyl)phenoxy]-2-methylpropanoate (200 mg; 0.38 mmol) in 2 ml of dry THF. After stirring at rt overnight, the reaction mixture was partitioned between ethyl acetate and water. The organic phase was washed with water and brine, dried over sodium sulfate, filtered and concentrated. Purification by radial chromatography using ethyl acetate-hexane mixtures (5–20% gradient) afforded ethyl 2-methyl-2-[4-(2-{[5-(2-methylprop-1-enyl)pyridin-2-yl][4-(trifluoromethoxy)benzyl]amino}ethyl)phenoxy]propanoate (70 mg; 33% yield).

Step 2. A solution of the above intermediate (65 mg) in 3 ml of ethyl acetate was treated with 10% Pd/C (60 mg) and hydrogenated under balloon pressure for 3 hr. The catalyst was filtered off and washed with ethyl acetate and chloroform/methanol. The filtrate was concentrated and purified by radial chromatography to afford ethyl 2-[4-(2-{(5-isobutylpyridin-2-yl)[4-(trifluoromethoxy)benzyl]amino}ethyl)phenoxy]-2-methylpropanoate (44 mg; 68% yield). MS: m/z 559 (M+1).

Step 3. The above ester (44 mg) was hydrolyzed with NaOH as per general procedure H. Purification by radial chromatography afforded the title compound as a glassy solid (30 mg; 73% yield).

¹H NMR (CDCl₃) δ 7.81 (d, 1H, J=2.2), 7.24 (dd, 1H, J=8.8; 2.2), 7.14 (d, 2H, J=8.5), 7.06 (d, 2H, J=8.5), 6.99 (d, 2H, J=8.3), 6.80 (d, 2H, J=8.3), 6.43 (d, 1H, J=8.8), 4.54 (s, 2H), 3.58 (t, 2H, J=7.4), 2.77 (t, 2H, J=7.4), 2.27 (d, 2H, J=7.1), 1.71 (m, 1H), 1.45 (s, 6H), 0.84 (d, 6H, J=6.7).

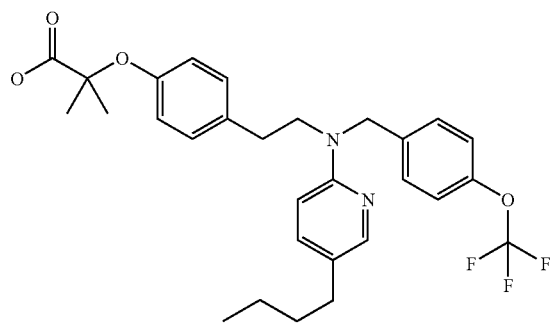

2-[4-(2-{(5-Butylpyridin-2-yl)[4-(trifluoromethoxy)benzyl]amino}ethyl)phenoxy]-2-methylpropanoic acid Similarly prepared using propyltriphenylphosphonium bromide/nbutyl litium.

$^1$H NMR (CDCl$_3$) δ 7.97 (d, 1H, J=2.2), 7.24 (dd, 1H, J=8.8; 2.2), 7.11 (d, 2H, J=8.5), 7.05 (d, 2H, J=8.5), 6.95 (d, 2H, J=8.5), 6.72 (d, 2H, J=8.5), 6.37 (d, 1H, J=8.8), 4.53 (s, 2H), 3.60 (t, 2H, J=7.4), 2.77 (t, 2H, J=7.4), 2.42 (d, 2H, J=7.6), 1.49 (m, 2H), 1.43 (s, 6H), 1.31 (m, 2H), 0.89 (t, 3H, J=7.4).

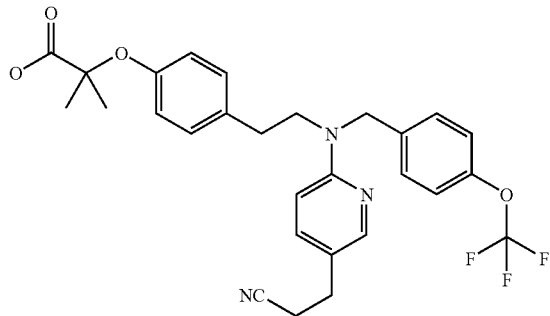

2-[4-(2-{[5-(2-Cyanoethyl)pyridin-2-yl][4-(trifluoromethoxy)benzyl]amino}ethyl)phenoxy]-2-methylpropanoic acid Similarly prepared using diethyl (cyanomethyl) phosphonate/NaHMDS.

$^1$H NMR (CDCl$_3$) δ 8.4 (bs, 1H), 8.07 (d, 1H, J=2.2), 7.35 (dd, 1H, J=8.8; 2.2), 7.14 (d, 2H, J=8.6), 7.09 (d, 2H, J=8.6), 7.02 (d, 2H, J=8.5), 6.83 (d, 2H, J=8.5), 6.43 (d, 1H, J=8.8), 4.56 (s, 2H), 3.66 (t, 2H, J=7.4), 2.80 (m, 4H), 2.55 (t, 2H, J=7.2), 1.56 (s, 6H). MS: m/z 528 (M+1)

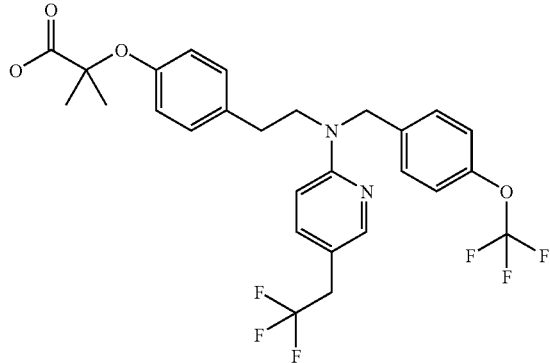

2-Methyl-2-[4-(2-{[5-(2,2,2-trifluoroethyl)pyridin-2-yl][4-(trifluoromethoxy)benzyl]amino}ethyl)phenoxy]propanoic acid Step 1. A solution of ethyl 2-[4-(2-{(5-formylpyridin-2-yl)[4-(trifluoromethoxy)benzyl]amino}ethyl)phenoxy]-2-methylpropanoate (400 mg; 0.75 mmol) in 5 ml of dry THF was treated in an ice bath, under nitrogen, with trifluoromethyltrimethylsilane (128 mg; 0.90 mmol), followed by tetrabutylammonium fluoride (0.075 ml of a 1M solution in THF; 0.075 mmol). The reaction mixture was allowed to warm to rt and stirred overnight. Additional trifluoromethyltrimethylsilane (128 mg; 0.90 mmol) and tetrabutylammonium fluoride (0.075 ml) were added. After 6 hours the previous reagents were added again in the same amounts. After stirring at rt overnight, the reaction mixture was partitioned between ethyl acetate and water. The organic phase was washed with water and brine, dried over sodium sulfate and concentrated. Purification by radial chromatography using ethyl acetate-hexane mixtures (5–40% gradient) afforded ethyl 2-methyl-2-[4-(2-{[5-(2,2,2-trifluoro-1-hydroxyethyl)pyridin-2-yl][4-(trifluoromethoxy)benzyl]amino}ethyl)phenoxy]propanoate (247 mg; 55% yield).

Step 2. A solution of the above intermediate (210 mg; 0.35 mmol) in 6 ml of dichloromethane was treated with phenyl chlorothionoformate (0.053 ml; 0.39 mmol) and DMAP (94 mg; 0.77 mmol). After stirring at rt for 2 hr, the mixture was concentrated and the residue was partitioned between ethyl acetate and 0.5N HCl. The organic phase was washed with 0.5N HCl and brine, dried over sodium sulfate and concentrated. Purification by radial chromatography using a dichloromethane-hexane gradient (20–80%) followed by a methanol-dichloromethane gradient (1–3%) afforded ethyl 2-methyl-2-(4-{2-[[4-(trifluoromethoxy)benzyl](5-{2,2,2-trifluoro-1-[(phenoxycarbonothioyl)oxy]ethyl}pyridin-2-yl)amino]ethyl}phenoxy)propanoate (145 mg; 57% yield). MS: m/z 737 (M+1).

Step 3. A solution of the above intermediate (145 mg; 0.20 mmol) in 5 ml of toluene was treated under nitrogen with azoisobutyronitrile (AIBN) (7 mg; 0.039 mmol) and tributyltin hydride (0.080 ml; 0.296 mmol) and the mixture heated at 80C for 1 hour. Upon cooling, additional AIBN (7 mg) and tributyltin hydride (0.080 ml) were added and the mixture heated again at 80C for 2 hours. The reaction mixture was concentrated and the residue partitioned between ethyl acetate and a saturated solution of KF. The organic phase was washed with saturated KF three times. The combined aqueous phases were washed twice with ethyl acetate. The combined organic phases were washed with 0.5N NaOH and brine, dried over sodium sulfate and concentrated. Purification by radial chromatography using dichloromethane-hexane mixtures (20–90%) afforded ethyl 2-methyl-2-[4-(2-{[5-(2,2,2-trifluoroethyl)pyridin-2-yl][4-(trifluoromethoxy)benzyl]amino}ethyl)phenoxy]propanoate (85 mg; 73% yield).

Step 4. The above ester was hydrolyzed with NaOH as per general procedure H. Purification by radial chromatography using ethyl acetate-hexane mixtures (20–80%) followed by methanol-dichloromethane mixtures (2–10%) afforded the title compound as a glassy solid (57 mg; 70% yield).

$^1$H NMR (CDCl$_3$) δ 8.06 (d, 1H, J=2.1), 7.34 (dd, 1H, J=8.6; 2.1), 7.15 (d, 2H, J=8.6), 7.09 (d, 2H, J=8.6), 7.04 (d, 2H, J=8.1), 6.83 (d, 2H, J=8.1), 6.41 (d, 1H, J=8.6), 4.58 (s, 2H), 3.66 (t, 2H, J=7.6), 3.20 (q, 2H, J=10.7), 2.83 (t, 2H, J=7.6), 1.54 (s, 6H). MS: m/z 557 (M+1).

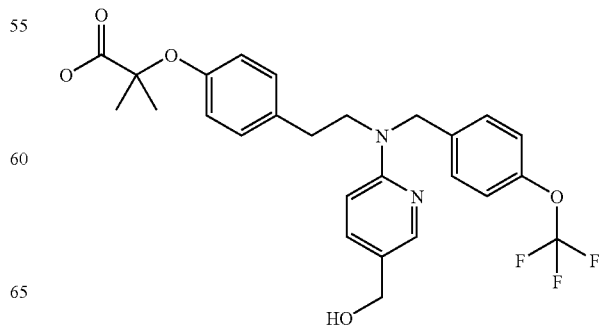

2-[4-(2-{[5-(Hydroxymethyl)pyridin-2-yl][4-(trifluoromethoxy)benzyl]amino}ethyl)phenoxy]2-methylpropanoic acid Step 1. A solution of ethyl 2-[4-(2-{(5-formylpyridin-2-yl)[4-(trifluoromethoxy)benzyl]amino}ethyl)phenoxy]-2-methylpropanoate (500 mg; 0.94 mmol) in 7 ml of methanol was cooled in an ice bath and treated with sodium borohydride (65 mg; 1.7 mmol) in small portions. After 30 minutes, the reaction mixture was concentrated and the residue partitioned between ethyl acetate and saturated brine. The organic phase was washed with water and the combined aqueous phases reextracted with ethyl acetate. The combined organic phases were washed with brine, dried over sodium sulfate and concentrated. Purification by radial chromatography using ethyl acetate-hexane mixtures (5–50% gradient) afforded ethyl 2-[4-(2-{[5-(hydroxymethyl)pyridin-2-yl][4-(trifluoromethoxy)benzyl]amino}ethyl)phenoxy]-2-methylpropanoate (450 mg; 85% yield).

MS: m/z 533 (M+1).

Step 2. The ester intermediate was hydrolyzed with NaOH as per general procedure H. Purification by radial chromatography (1–12% methanol-dichloromethane gradient), followed by crystallization from dichloromethane-hexane afforded the title compound as a white solid.

$^1$H NMR (CDCl$_3$+CD$_3$OD) δ 7.96 (d, 1H, J=2.2), 7.42 (dd, 1H, J=9.0; 2.2), 7.09 (d, 2H, J=8.6), 7.04 (d, 2H, J=8.6), 6.94 (d, 2H, J=8.5), 6.73 (d, 2H, J=8.5), 6.38 (d, 1H, J=9.0), 4.53 (s, 2H), 4.41 (s, 2H), 3.63 (t, 2H, J=7.4), 2.76 (t, 2H, J=7.4), 1.47 (s, 6H). MS: m/z 505 (M+1).

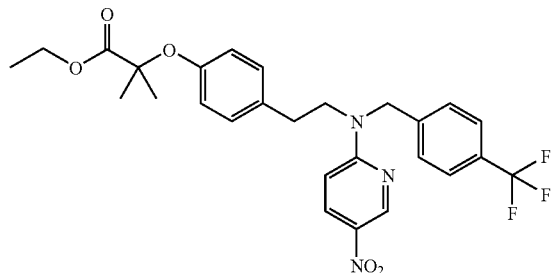

Ethyl 2-methyl-2-[4-(2-{(5-nitropyridin-2-yl)[4-(trifluoromethyl)benzyl]amino}ethyl)phenoxy]propanoate A mixture of ethyl 2-methyl-2-[4-(2-{[4-(trifluoromethyl)benzyl]amino}ethyl)phenoxy]propanoate (250 mg; 0.61 mmol), 2-chloro-5-nitro-pyridine (116 mg; 0.73 mmol) and K$_2$CO$_3$ (126 mg; 0.92 mmol) in 2 ml of dioxane was heated at 220C in a pressure tube under nitrogen for 16 hr. Upon cooling, the mixture was partitioned between ethyl acetate and water. The aqueous phase was washed with ethyl acetate and the combined organic phases were washed with brine, dried over sodium sulfate and concentrated. Purification by radial chromatography using ethyl acetate-hexane mixtures (2–30% gradient) afforded the title compound (254 mg; 78% yield).

$^1$H NMR (CDCl$_3$) δ 9.03 (d, 1H, J=2.6), 8.13 (dd, 1H, J=9.3; 2.6), 7.52 (d, 2H, J=8.1), 7.22 (d, 2H, J=8.1), 7.01 (d, 2H, J=8.5), 6.76 (d, 2H, J=8.5), 6.39 (d, 1H, J=9.3), 4.73 (s, 2H), 4.20 (q, 2H, J=7.1), 3.76 (bs, 2H), 2.87 (t, 2H, J=7.4), 1.54 (s, 6H), 122 (t, 3H, J=7.1). MS: m/z 532 (M+1).

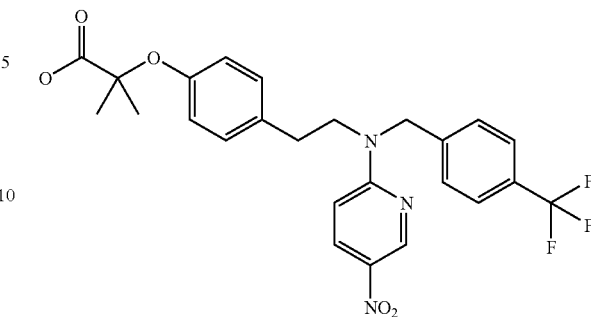

2-Methyl-2-[4-(2-{(5-nitropyridin-2-yl)[4-(trifluoromethyl)benzyl]amino}ethyl)phenoxy]propanoic acid Ethyl 2-methyl-2-[4-(2-{(5-nitropyridin-2-yl)[4-(trifluoromethyl)benzyl]amino}ethyl)phenoxy]propanoate (80 mg) was hydrolyzed with NaOH as per general procedure H. Purification by radial chromatography (1–5% methanol-dichloromethane gradient) followed by crystallization from dichloromethane-hexane afforded the title compound as a white solid (37 mg; 49% yield).

$^1$H NMR (CDCl$_3$) δ 9.05 (bs, 1H), 8.15 (d, 1H, J=9.3), 7.53 (d, 2H, J=8.1), 7.24 (d, 2H, J=8.1), 7.06 (d, 2H, J=8.2), 6.86 (d, 2H, J=8.2), 6.39 (d, 1H, J=9.3), 4.74 (s, 2H), 3.79 (broad t, 2H), 2.90 (t, 2H, J=7.4), 1.57 (s, 6H). MS: m/z 504 (M+1).

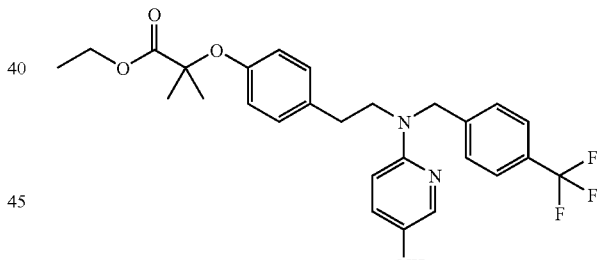

Ethyl 2-[4-(2-{(5-aminopyridin-2-yl)[4-(trifluoromethyl)benzyl]amino}ethyl)phenoxy]-2-methylpropanoate A solution of ethyl 2-methyl-2-[4-(2-{(5-nitropyridin-2-yl)[4-(trifluoromethyl)benzyl]amino}ethyl)phenoxy]propanoate (149 mg; 1.73 mmol) in 10 ml of MeOH was treated with 10% Pd/C (60 mg) and hydrogenated under balloon pressure for 2 hr. The catalyst was filtered off and washed with chloroform/methanol. The filtrate was concentrated and the residue purified by radial chromatography using a methanol-dichloromethane gradient (1–10%) to afford the title compound as a dark-colored oil (125 mg; 89% yield).

$^1$H NMR (CDCl$_3$) δ 7.75 (d, 1H, J=2.8), 7.47 (d, 2H, J=8.1), 7.24 (d, 2H, J=8.1), 7.00 (d, 2H, J=8.5), 6.91 (d, 1H,

J=9.0; 2.8), 6.74 (d, 2H, J=8.5), 6.32 (d, 1H, J=9.0), 4.58 (s, 2H), 4.20 (q, 2H, J=7.2), 3.61 (t, 2H, J=7.4), 3.18 (bs, 2H), 2.80 (t, 2H, J=7.4), 1.54 (s, 6H), 1.22 (t, 3H, J=7.2). MS: m/z 502 (M+1).

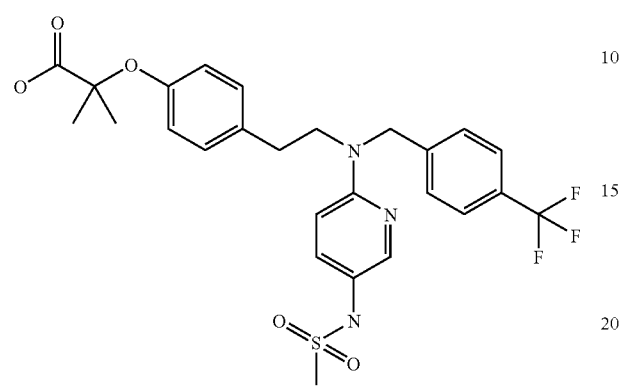

2-Methyl-2-[4-(2-{{5-[(methylsulfonyl)amino]pyridin-2-yl}[4-(trifluoromethyl)benzyl]amino}ethyl) phenoxy]propanoic acid Step 1. A solution of ethyl 2-[4-(2-{(5-aminopyridin-2-yl)[4-(trifluoromethyl)benzyl]amino}ethyl)phenoxy]-2-methylpropanoate (65 mg; 0.13 mmol) in 3 ml of dichloromethane was treated with Et$_3$N (0.019 ml; 0.14 mmol) and methanesulfonyl chloride (0.011 ml; 0.14 mmol). After 30 minutes, additional amounts of Et$_3$N (0.019 ml) and methanesulfonyl chloride (0.011 ml) were added and stirred for another 30 minutes. The reaction mixture was concentrated and the residue partitioned between ethyl acetate and 0.5N HCl. The organic phase was washed with 0.5N HCl and brine, dried over sodium sulfate and concentrated. Purification by radial chromatography using an ethyl acetate-hexane gradient (10–70%) provided two main products: ethyl 2-methyl-2-[4-(2-{{5-[(methylsulfonyl)amino]pyridin-2-yl}[4-(trifluoromethyl)benzyl]amino}ethyl)phenoxy]propanoate (10 mg; 13% yield; MS: m/z 580 (M+1)) and ethyl 2-[4-(2-{{5-[bis(methylsulfonyl)amino]pyridin-2-yl}[4-(trifluoromethyl)benzyl]amino}ethyl)phenoxy]-2-methylpropanoate (39 mg; 46% yield; MS: m/z 658 (M+1)). (Both of these products can be hydrolyzed to the title compound).

Step 2. Ethyl 2-[4-(2-{{5-[bis(methylsulfonyl)amino]pyridin-2-yl}[4-(trifluoromethyl)benzyl]amino}ethyl)phenoxy]-2-methylpropanoate (39 mg) was reacted with NaOH (17 eq) as per general procedure H. Purification by radial chromatography (1–10% methanol-dichloromethane gradient), followed by crystallization from dichloromethane-hexane afforded the title compound as a white solid (21 mg; 66% yield).

$^1$H NMR (CDCl$_3$) δ 8.04 (d, 1H, J=2.6), 7.50 (d, 2H, J=8.3), 7.42 (dd, 1H, J=9.1; 2.6), 7.23 (d, 2H, J=8.3), 7.03 (d, 2H, J=8.5), 6.80 (d, 2H, J=8.5), 6.35 (d, 1H, J=9.1), 4.64 (s, 2H), 3.69 (t, 2H, J=7.4), 2.94 (s, 3H), 2.83 (t, 2H, J=7.4), 1.54 (s, 6H). MS: m/z 552 (M+1).

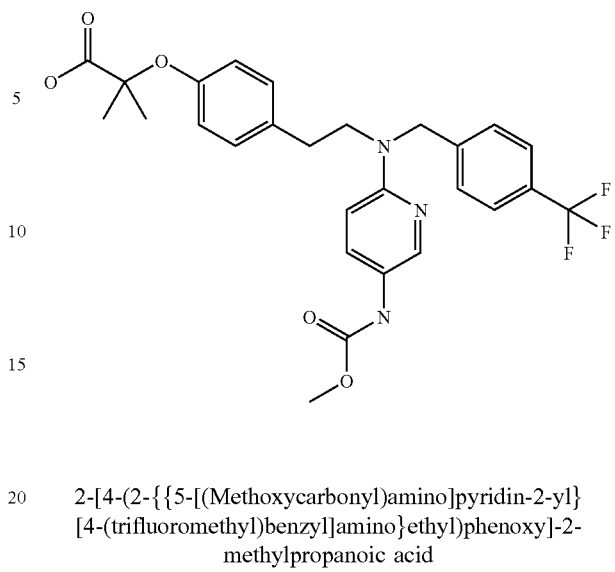

2-[4-(2-{{5-[(Methoxycarbonyl)amino]pyridin-2-yl}[4-(trifluoromethyl)benzyl]amino}ethyl)phenoxy]-2-methylpropanoic acid Similarly prepared from ethyl 2-[4-(2-{(5-aminopyridin-2-yl)[4-(trifluoromethyl)benzyl]amino}ethyl)phenoxy]-2-methylpropanoate and methylchloroformate.

$^1$H NMR (CDCl$_3$) δ 8.0 (d, 1H, J=2.8), 7.59 (bs, 1H), 7.48 (d, 2H, J=8.0), 7.22 (d, 2H, J=8.0), 7.02 (d, 2H, J=8.4), 6.79 (d, 2H, J=8.4), 6.66 (bs, 1H), 6.30 (d, 1H, J=9.2), 4.63 (s, 2H), 3.72 (s, 3H), 3.68 (t, 2H, J=7.4), 2.81 (t, 2H, J=7.4), 1.55 (s, 6H).

MS: m/z 532 (M+1).

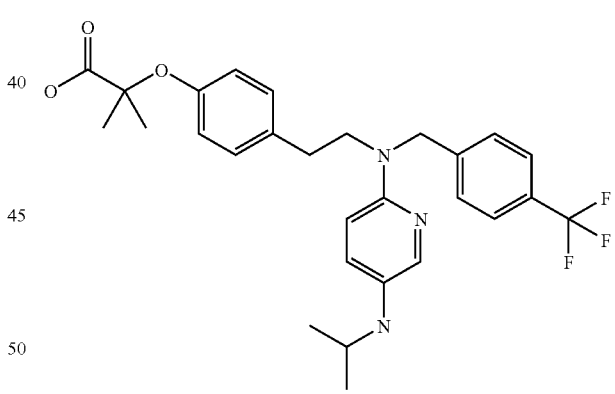

2-[4-(2-{[5-(isopropylamino)pyridin-2-yl][4-(trifluoromethyl)benzyl]amino}ethyl)phenoxy]-2-methylpropanoic acid Step 1. A solution of ethyl 2-[4-(2-{(5-aminopyridin-2-yl)[4-(trifluoromethyl)benzyl]amino}ethyl)phenoxy]-2-methylpropanoate (135 mg; 0.27 mmol) in 2 ml of dichloromethane was treated with acetone (0.021 ml; 0.28 mmol), sodium triacetoxyborohydride (60 mg; 0.28 mmol) and acetic acid (0.016 ml; 0.28 mmol). After 2 hr, the reaction mixture was partitioned between ethyl acetate and saturated NaHCO3. The organic phase was washed with brine, dried over sodium sulfate and concentrated. Purification by radial chromatography using ethyl acetate-hexane mixtures (5–50% gradient) afforded the intermediate ethyl ester (125 mg; 85% yield). MS: m/z 544 (M+1).

Step 2. A solution of the above intermediate (125 mg) in 4 ml of THF:MeOH (1:1) was treated with 1N NaOH (1 ml) and heated to 65C for 2 hr. Upon cooling, it was diluted with ethyl acetate and treated with 1N HCl (1 ml). The mixture was partitioned between ethyl acetate and phosphate buffer (pH 7). The aqueous phase was washed with ethyl acetate. The combined organic phases were washed with brine, dried over sodium sulfate and concentrated to give a purple residue. Methanol was added, heated with a heat gun and the undissolved solids were removed by filtration. The filtrate was concentrated and purified by radial chromatography using a methanol-dichloromethane gradient (1–8%). The partially purified product was repurified by chromatography using an ethyl acetate-hexane gradient (30–100%) and subsequently crystallized from dichloromethane to afford the title compound as a light grey solid (21 mg; 18% yield).

$^1$H NMR (CDCl$_3$+CD$_3$OD) δ 7.64 (d, 1H, J=2.8), 7.44 (d, 2H, J=8.1), 7.22 (d, 2H, J=8.1), 6.92 (dd, 1H, J=9.1; 2.8), 6.87 (d, 2H, J=8.5), 6.67 (d, 2H, J=8.5), 6.20 (d, 1H, J=9.1), 4.58 (s, 2H), 3.58 (t, 2H, J=7.4), 3.36 (m, 1H), 2.72 (t, 2H, J=7.4), 1.48 (s, 6H), 1.12 (d, 6H, J=6.4).

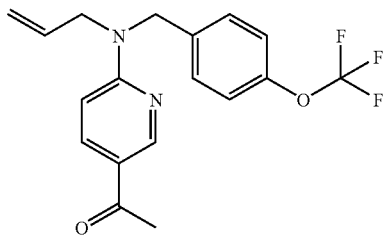

1-(6-{Allyl[4-(trifluoromethoxy)benzyl]amino}pyridin-3-yl)ethanone

Step 1. To a solution of allylamine (17.8 g; 312 mmol) in 200 ml of dichloromethane was added 4-trifluoromethoxy-benzyl bromide (16 g; 62.4 mmol) and DIEA 8.88 g; 68.4 mmol). After stirring at rt overnight the reaction mixture was extracted with one volume of water. The organic phase was dried over sodium sulfate and concentrated to afford N-[4-(trifluoromethoxy)benzyl]prop-2-en-1-amine (14 g; 97% crude yield), which was used in the next step without further purification.

$^1$H NMR (CDCl$_3$) δ 7.40 (d, 2H, J=8.4), 7.21 (d, 2H, J=8.1), 6.02–5.89 (m, 1H), 5.33–5.12 (m, 2H), 3.83 (s, 2H), 3.31 (d, 2H, J=6.0).

Step 2. A mixture of the above intermediate (7.4 g; 32.1 mmol), 5-acetyl-2-chloro-pyridine (5.0 g; 32.1 mmol) and DIEA (4.56 g; 35.3 mmol) was heated in a pressure tube at 200C for 3 hr. The crude reaction mixture was purified by flash chromatography using ethyl acetate-hexane mixtures (10–70% gradient) to afford the title compound (9.5 g; 84% yield).

$^1$H NMR (CDCl$_3$) δ 8.76 (d, 1H, J=2.4), 8.00 (dd, 1H, J=9.0 and 2.2), 7.23 (d, 2H, J=8.3), 7.14 (d, 2H, J=8.3), 6.48 (d, 1H, J=9.1), 5.85–5.76 (m, 1H), 5.27–5.15 (m, 2H), 4.84 (s, 2H), 4.12 (d, 2H, J=4.3), 2.48 (s, 3H).

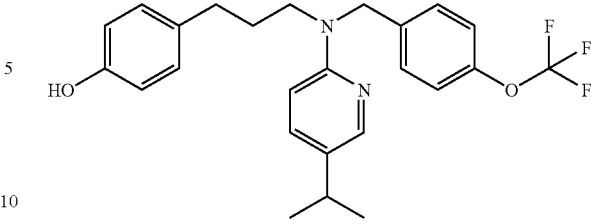

4-(3-{(5-Isopropylpyridin-2-yl)[4-(trifluoromethoxy)benzyl]amino}propyl)phenol

Step 1. A mixture of 1-(6-{allyl[4-(trifluoromethoxy)benzyl]amino}pyridin-3-yl)ethanone (10 g; 28.5 mmol), 4-bromo-anisole (5.6 g; 29.9 mmol), palladium (II) acetate (0.14 g; 0.63 mmol) and tri-o-tolylphosphine (0.57 g; 1.88 mol) in 11 ml of MeCN and 8 ml of DIEA was heated to reflux overnight. Upon cooling, the mixture was concentrated and the residue partitioned between ethyl acetate and 1N NaOH. The organic phase was dried over sodium sulfate and concentrated. Purification by flash chromatography eluting with dichloromethane afforded 1-(6-{[(2E)-3-(4-methoxyphenyl)prop-2-enyl][4-(trifluoromethoxy)benzyl]amino}pyridin-3-yl)ethanone (7.4 g; 54% yield).

Step 2. To a solution of methyltriphenylphosphonium bromide (11.6 g; 32.4 mmol) in dry THF was added potassium tert-butoxide (32.4 mmol of a 1M solution in tert-butanol). After stirring at rt for 30 minutes, a solution of the above intermediate (7.4 g) in THF was added and stirred for 2 hr. The mixture was concentrated and the residue purified by flash chromatography using 20% ethyl acetate-hexane mixtures to afford 5-isopropenyl-N-[(2E)-3-(4-methoxyphenyl)prop-2-enyl]-N-[4-(trifluoromethoxy)benzyl]pyridin-2-amine. $^1$H NMR (CD$_3$OD) δ 8.18 (d, 1H, J=2.4), 7.54 (dd, 1H, J=9.0 and 2.4), 7.22 (d, 2H, J=8.4), 7.15 (d, 2H, J=8.7), 7.10 (d, 2H, J=8.2), 6.71 (d, 2H, J=8.8), 6.50 (d, 1H, J=8.9), 6.33 (d, 1H, J=15.9), 6.01–5.96 (m, 1H), 5.18 (s, 1H), 4.85 (s, 1H), 4.71 (s, 2H), 4.14 (d, 2H, J=5.5), 3.66 (s, 3H), 1.95 (s, 3H).

Step 3. A solution of the above intermediate (700 mg; 1.82 mmol) in ethyl acetate was hydrogenated with 10% Pd/C (60 mg) under 1 atm of hydrogen for 2 hr The catalyst was filtered off and the filtrate concentrated to afford 5-isopropyl-N-[3-(4-methoxyphenyl)propyl]-N-[4-(trifluoromethoxy)benzyl]pyridin-2-amine, which was used in the next step without further purification.

Step 4. The above intermediate was demethylated with boron tribromide as per general procedure F. After standard aqueous workup the tittle compound was obtained, which was used in the next step without further purification.

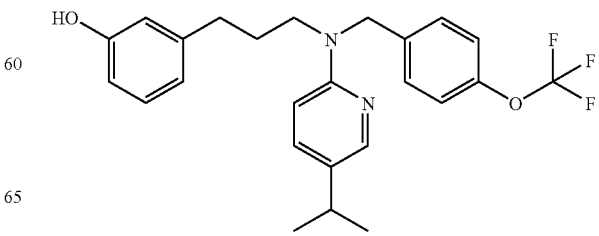

3-(3-{(5-Isopropylpyridin-2-yl)[4-(trifluoromethoxy)benzyl]amino}propyl)phenol Similarly prepared from 1-(6-{allyl[4-(trifluoromethoxy)benzyl]amino}pyridin-3-yl)ethanone and 3-bromo-anisole.

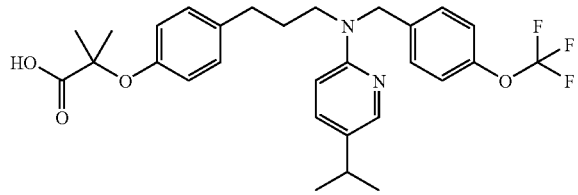

2-[4-(3-{(5-Isopropylpyridin-2-yl)[4-(trifluoromethoxy)benzyl]amino}propyl)phenoxy]-2-methylpropanoic acid Step 1. Alkylation of 4-(3-{(5-isopropylpyridin-2-yl)[4-(trifluoromethoxy)benzyl]amino}propyl)phenol (410 mg; 0.78 mmol) with ethyl-2-bromo-isobutyrate (300 mg; 1.56 mmol) as per general procedure C (2 eq $Cs_2CO_3$, MeCN, 80C) provided the intermediate ethyl ester.

Step 2. Hydrolysis of the above intermediate with LiOH as per general procedure H afforded after chromatography the title compound (92 mg; 35% yield).

$^1$H NMR (CD$_3$O D) δ 7.84 (d, 1H, J=2.2), 7.45 (dd, 1H, J=8.9 and 2.3), 7.24 (d, 2H, J=8.4), 7.17 (d, 2H, J=8.4), 7.02 (d, 2H, J=8.4), 6.80 (d, 2H, J=8.6), 6.53 (d, 1H, J=8.8), 4.71 (s, 2H), 3.46 (t, 2H, J=7.5), 2.81–2.75 (m, 1H), 2.56 (t, 2H, J=7.5), 1.89–1.83 (m, 2H), 1.51 (s, 6H), 1.19 (d, 6H, J=6.9). MS: m/z 531 (M+1).

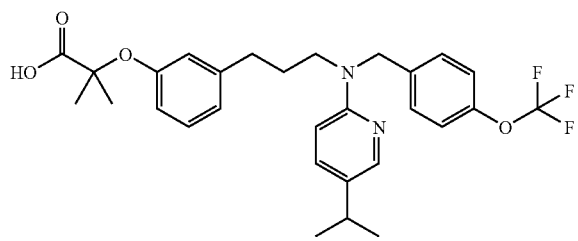

2-[3-(3-{(5-Isopropylpyridin-2-yl)[4-(trifluoromethoxy)benzyl]amino}propyl)phenoxy]-2-methylpropanoic acid Similarly prepared by alkylation of 3-(3-{(5-isopropylpyridin-2-yl)[4-(trifluoromethoxy)benzyl]amino}propyl)phenol with ethyl-2-bromo-isobutyrate followed by standard base-mediated hydrolysis.

$^1$H NMR (CD$_3$OD) δ 7.84 (d, 1H, J=2.2), 7.51–7.45 (m, 1H), 7.25–7.08 (m, 5H), 6.80–6.69 (m, 3H), 6.56 (d, 1H, J=9.0), 4.72 (s, 2H), 3.47 (t, 2H, J=7.6), 2.80–2.75 (m, 1H), 2.58 (t, 2H, J=7.3), 1.91–1.85 (m, 2H), 1.52 (s, 6H), 1.21 (d, 6H, J=6.9). MS: m/z 531 (M+1).

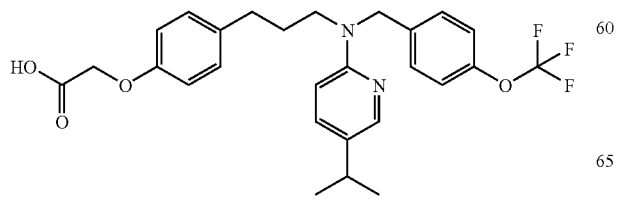

[4-(3-{(5-Isopropylpyridin-2-yl)[4-(trifluoromethoxy)benzyl]amino}propyl)phenoxy]acetic acid Similarly prepared by alkylation of 4-(3-{(5-isopropylpyridin-2-yl)[4-(trifluoromethoxy)benzyl]amino}propyl)phenol with tert-butyl-bromo-acetate followed by standard TFA hydrolysis.

$^1$H NMR (CD$_3$OD) δ 7.98 (dd, 1H, J=9.5 and 2.2), 7.65 (d, 1H, J=2.0), 7.34–7.22 (m, 4H), 7.11–7.09 (m, 3H), 6.83 (d, 2H, J=8.6), 4.82 (s, 2H), 4.62 (s, 2H), 3.61 (t, 2H, J=7.6), 2.92–2.88 (m, 1H), 2.63 (t, 2H, J=7.5), 1.99–1.95 (m, 2H), 1.23 (d, 6H, J=6.9). MS: m/z 503 (M+1).

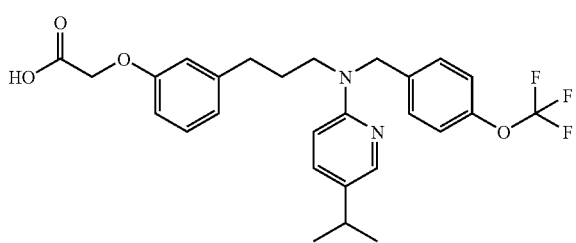

[3-(3-{(5-Isopropylpyridin-2-yl)[4-(trifluoromethoxy)benzyl]amino}propyl)phenoxy]acetic acid Similarly prepared by alkylation of 3-(3-{(5-isopropylpyridin-2-yl)[4-(trifluoromethoxy)benzyl]amino}propyl)phenol with tert-butyl-bromo-acetate followed by standard TFA hydrolysis.

$^1$H NMR (CD$_3$OD) δ 7.98 (dd, 1H, J=9.0 and 2.2), 7.68 (d, 1H, J=1.8), 7.32–7.10 (m, 7H), 6.80–6.74 (m, 2H), 4.83 (s, 2H), 4.63 (s, 2H), 3.64 (t, 2H, J=7.7), 2.93–2.90 (m, 1H), 2.68 (t, 2H, J=7.4), 2.06–1.99 (m, 2H), 1.24 (d, 6H, J=6.8). MS: m/z 503 (M+1).

The following 14 compounds were prepared by procedures similar to those described above.

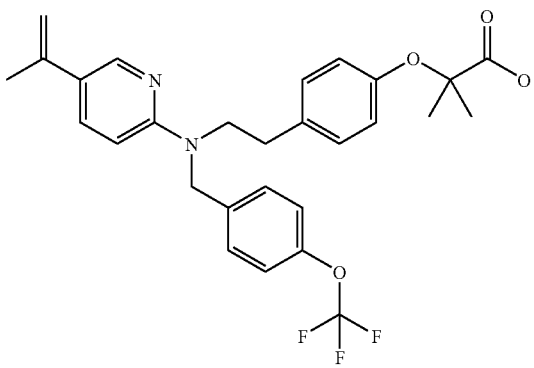

143

2-[4-(2-{(5-isopropenylpyridin-2-yl)[4-(trifluoromethoxy)benzyl]amino}ethyl)phenoxy]-2-methylpropanoic acid

144

2-[4-(2-{(3-methoxypyridin-2-yl)[4-(trifluoromethoxy)benzyl]amino}ethyl)phenoxy]-2-methylpropanoic acid

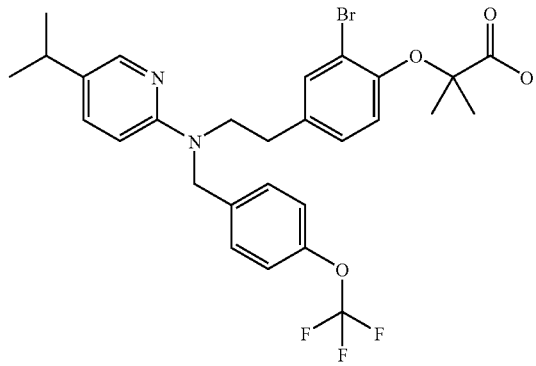

2-[2-bromo-4-(2-{(5-isopropylpyridin-2-yl)[4-(trifluoromethoxy)benzyl]amino}ethyl)phenoxy]-2-methylpropanoic acid

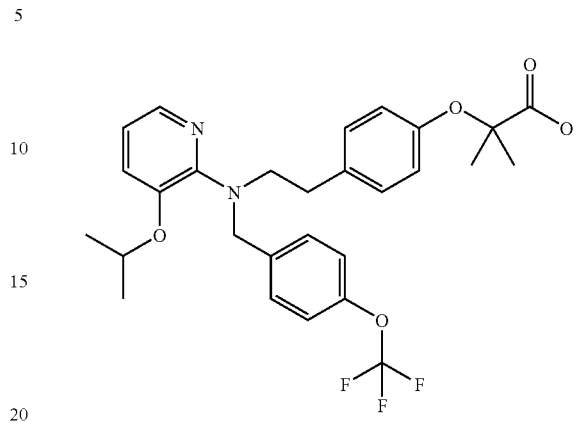

2-[4-(2-{(3-isopropoxypyridin-2-yl)[4-(trifluoromethoxy)benzyl]amino}ethyl)phenoxy]-2-methylpropanoic acid

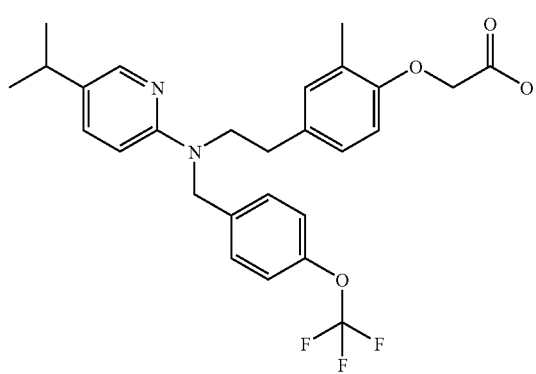

[4-(2-{(5-isopropylpyridin-2-yl)[4-(trifluoromethoxy)benzyl]amino}ethyl)-2-methylphenoxy]acetic acid

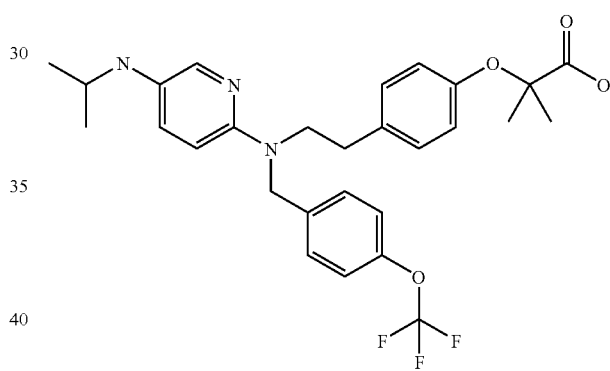

2-[4-(2-{[5-(isopropylamino)pyridin-2-yl][4-(trifluoromethoxy)benzyl]amino}ethyl)phenoxy]-2-methylpropanoic acid

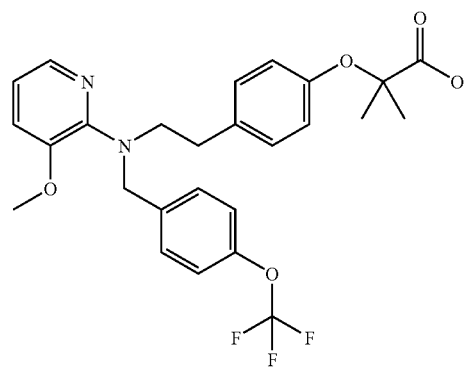

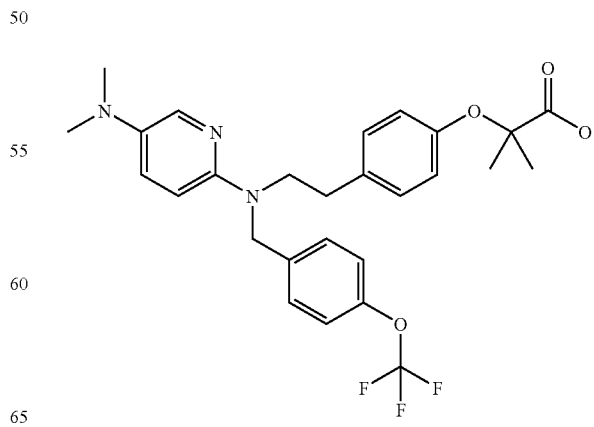

145

2-[4-(2-{[5-(dimethylamino)pyridin-2-yl][4-(trifluoromethoxy)benzyl]amino}ethyl)phenoxy]-2-methylpropanoic acid

146

2-[4-(1,1-dimethyl-2-{pyridin-2-yl[4-(trifluoromethoxy)benzyl]amino}ethyl)-2-propylphenoxy]-2-methylpropanoic acid

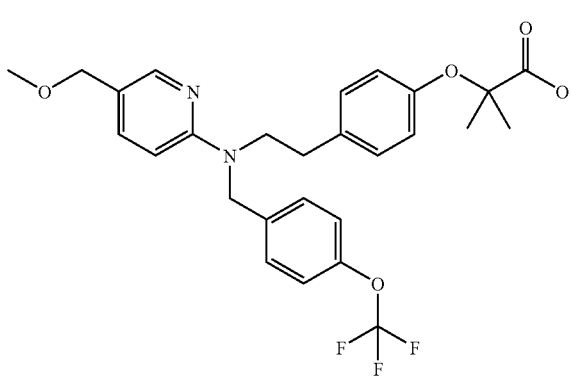

2-[4-(2-{[5-(methoxymethyl)pyridin-2-yl][4-(trifluoromethoxy)benzyl]amino}ethyl)phenoxy]-2-methylpropanoic acid MS: m/z 519.5 (M+1)

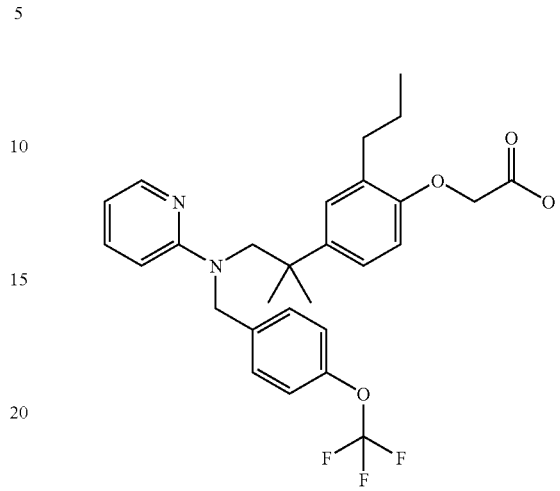

[4-(1,1-dimethyl-2-{pyridin-2-yl[4-(trifluoromethoxy)benzyl]amino}ethyl)-2-propylphenoxy] acetic acid

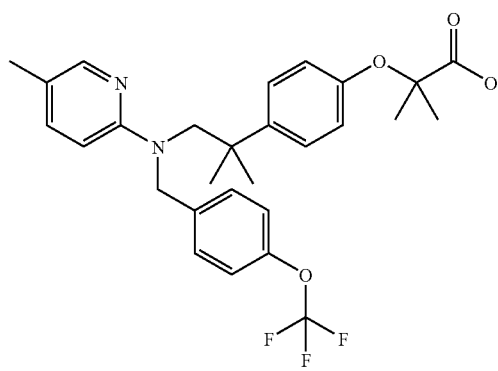

2-[4-(1,1-dimethyl-2-{(5-methylpyridin-2-yl)[4-(trifluoromethoxy)benzyl]amino}ethyl)phenoxy]-2-methylpropanoic acid MS: m/z 517.5 (M+1)

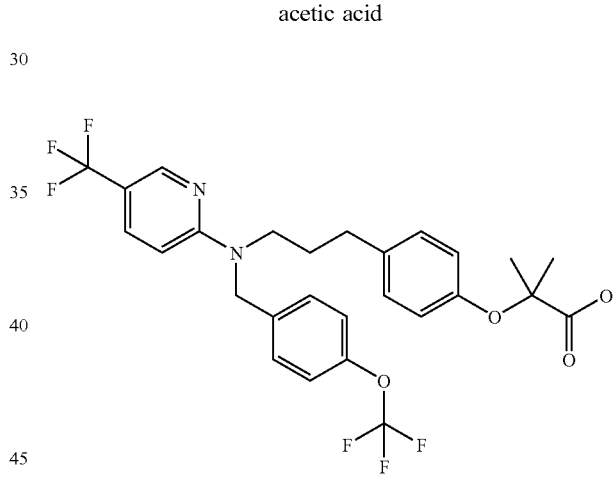

2-methyl-2-[4-(3-{[4-(trifluoromethoxy)benzyl][5-(trifluoromethyl)pyridin-2-yl]amino}propyl)phenoxy]propanoic acid

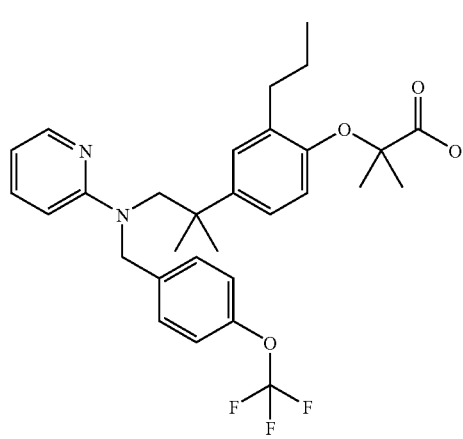

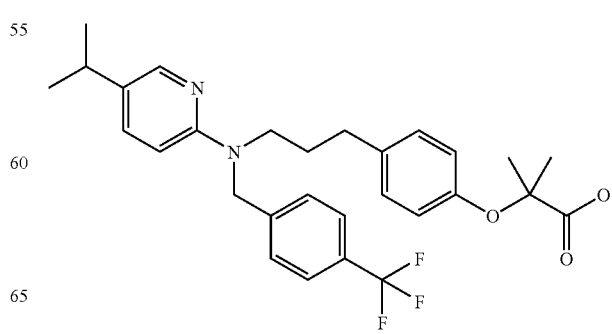

2-[4-(3-{(5-isopropylpyridin-2-yl)[4-(trifluoromethyl)benzyl]amino}propyl)phenoxy]-2-methylpropanoic acid

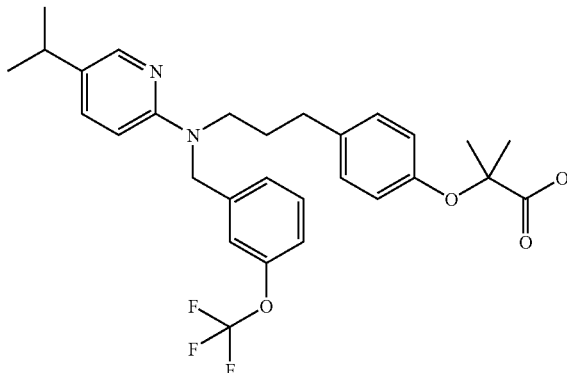

2-[4-(3-{(5-isopropylpyridin-2-yl)[3-(trifluoromethoxy)benzyl]amino}propyl)phenoxy]-2-methylpropanoic acid

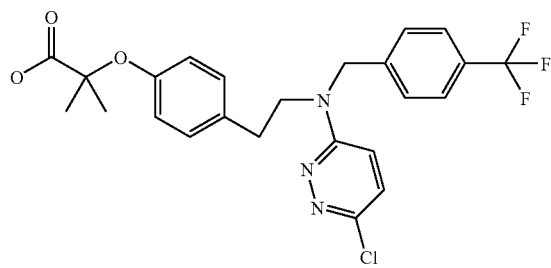

2-[4-(2-{(6-Chloropyridazin-3-yl)[4-(trifluoromethyl)benzyl]amino}ethyl)phenoxy]-2-methylpropanoic acid Step 1. Ethyl 2-methyl-2-[4-(2-{[4-(trifluoromethyl)benzyl]amino}ethyl)phenoxy]propanoate (200 mg; 0.49 mmol) was condensed with 3,6-dichloropyridazine (87 mg; 0.61 mmol) as per general procedure E (conditions: 1.25 eq DIEA, dioxane, 220C, 6 hr). Purification by radial chromatography (5–40% ethyl acetate-hexane gradient) afforded the intermediate ethyl ester (60 mg; 24% yield). MS: m/z 522 (M+1).

Step 2. The above ester (60 mg) was hydrolyzed with NaOH as per general procedure H. Standard aqueous workup followed by crystallization from dichloromethane-hexane afforded the title compound as a white solid (39 mg; 68% yield).

$^1$H NMR (CDCl$_3$) δ 7.50 (d, 2H, J=8.1), 7.24 (d, 2H, J=8.1), 7.09 (d, 1H, J=9.4), 7.02 (d, 2H, J=8.3), 6.82 (d, 2H, J=8.3), 6.58 (d, 1H, J=9.4), 4.65 (s, 2H), 3.76 (t, 2H, J=7.1), 2.86 (t, 2H, J=7.1), 1.54 (s, 6H). MS: m/z 494 (M+1).

2-(4-{2-[[2,4-Bis(trifluoromethyl)benzyl](6-chloropyridazin-3-yl)amino]ethyl}phenoxy)-2-methylpropanoic acid

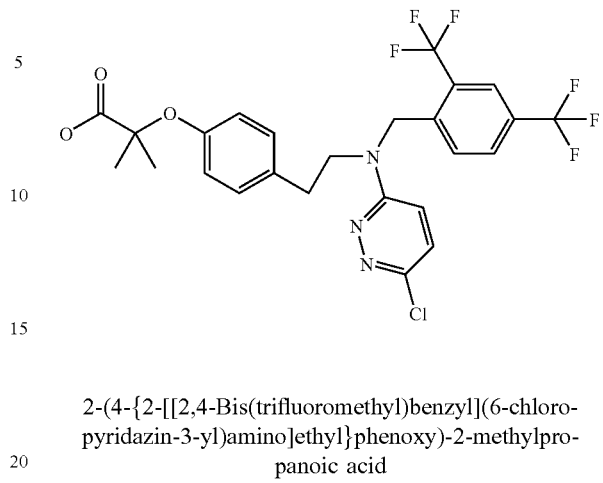

Similarly prepared from methyl 2-[4-(2-{[2,4-bis(trifluoromethyl)benzyl]amino}ethyl)phenoxy]-2-methylpropanoate and 3,6-dichloropyridazine.

$^1$H NMR (CDCl$_3$) δ 7.90 (s, 1H), 7.65 (d, 1H, J=8.1), 7.31 (d, 1H, J=8.1), 7.14 (d, 1H, J=9.5), 7.08 (d, 2H, J=8.5), 6.85 (d, 2H, J=8.5), 6.56 (d, 1H, J=9.5), 4.84 (s, 2H), 3.79 (t, 2H, J=7.1), 2.94 (t, 2H, J=7.1), 1.55 (s, 6H). MS: m/z 562 (M+1).

2-Methyl-2-[4-(2-{pyrazin-2-yl[4-(trifluoromethyl)benzyl]amino}ethyl)phenoxy]propanoic acid

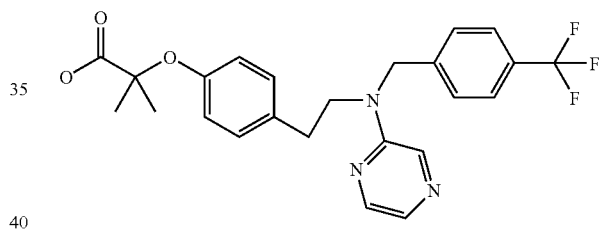

Similarly prepared from ethyl 2-methyl-2-[4-(2-{[4-(trifluoromethyl)benzyl]amino}ethyl)phenoxy]propanoate and chloropyrazine.

$^1$H NMR (CDCl$_3$) δ 8.08 (bs, 1H), 7.91 (bs, 1H), 7.77 (bs, 1H), 7.51 (d, 2H, J=8.1), 7.24 (d, 2H, J=8.1), 7.02 (d, 2H, J=8.4), 6.83 (d, 2H, J=8.4), 4.67 (s, 2H), 3.68 (t, 2H, J=7.2), 2.83 (t, 2H, J=7.2), 1.56 (s, 6H). MS: m/z 488 (M+1).

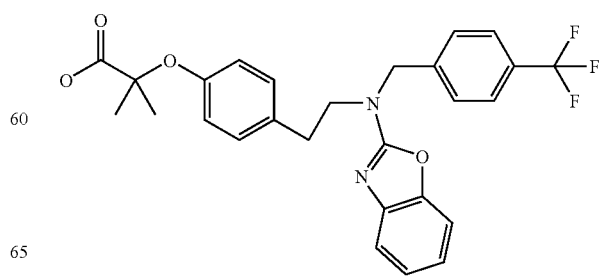

2-[4-(2-{1,3-Benzoxazol-2-yl[4-(trifluoromethyl)benzyl]amino}ethyl)phenoxy]-2-methylpropanoic acid Step 1. Ethyl 2-methyl-2-[4-(2-{[4-(trifluoromethyl)benzyl]amino}ethyl)phenoxy]propanoate (150 mg; 0.37 mmol) was condensed with 2-chloro-benzoxazole (0.046 ml; 0.40 mmol) as per procedure E (conditions: 1.1 eq DIEA; dioxane, 200C, 16 hr). Purification by radial chromatography (5–50% ethyl acetate-hexane gradient) afforded the intermediate ester (170 mg; 88% yield). MS: m/z 527 (M+1).

Step 2. The above ester (170 mg) was hydrolyzed with NaOH as per procedure H. Purification by radial chromatography (1–10% methanol-dichloromethane gradient), followed by crystallization from dichloromethane-hexane afforded the title compound as a white solid (132 mg; 83% yield).

$^1$H NMR (CDCl$_3$) δ 7.51 (d, 2H, J=8.1), 7.42 (d, 1H, J=7.8), 7.27 (m, 3H), 7.16 (t, 1H, J=7.8), 7.02 (m, 3H), 6.82 (d, 2H, J=8.5), 4.60 (s, 2H), 3.65 (t, 2H, J=7.2), 2.85 (t, 2H, J=7.2), 1.54 (s, 6H). MS: m/z 499 (M+1).

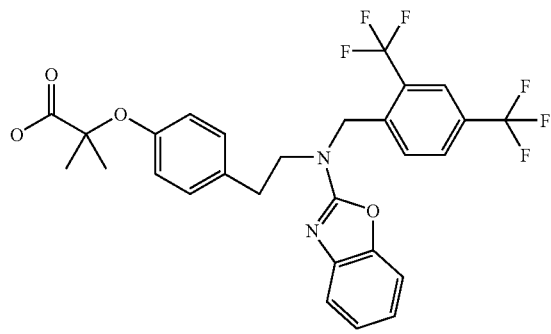

2-[4-(2-{1,3-Benzoxazol-2-yl[2,4-bis(trifluoromethyl)benzyl]amino}ethyl)phenoxy]-2-methylpropanoic acid Similarly prepared from methyl 2-[4-(2-{[2,4-bis(trifluoromethyl)benzyl]amino}ethyl)phenoxy]-2-methylpropanoate and 2-chlorobenzoxazole.

$^1$H NMR (CDCl$_3$) δ 7.89 (s, 1H), 7.69 (d, 1H, J=8.1), 7.48 (d, 1H, J=8.1), 7.42 (d, 1H, J=7.7), 7.24 (d, 1H, J=8.0), 7.17 (t, 1H, J=7.7), 7.04 (m, 3H), 6.81 (d, 2H, J=8.5), 4.87 (s, 2H), 3.70 (t, 2H, J=7.2), 2.92 (t, 2H, J=7.2), 1.53 (s, 6H). MS: m/z 567 (M+1).

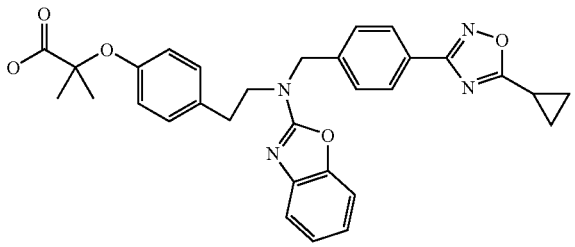

2-[4-(2-{1,3-Benzoxazol-2-yl[4-(5-cyclopropyl-1,2,4-oxadiazol-3-yl)benzyl]amino}ethyl)phenoxy]-2-methylpropanoic acid Similarly prepared from ethyl 2-[4-(2-{[4-(5-cyclopropyl-1,2,4-oxadiazol-3-yl)benzyl]amino}ethyl)phenoxy]-2-methylpropanoate and 2-chlorobenzoxazole.

$^1$H NMR (CDCl$_3$) δ 7.91 (d, 2H, J=8.1), 7.42 (d, 1H, J=7.6), 7.24 (m, 3H), 7.15 (t, 1H, J=7.6), 7.04 (t, 1H, J=7.6), 6.96 (d, 2H, J=8.5), 6.77 (d, 2H, J=8.5), 4.61 (s, 2H), 3.66 (t, 2H, J=7.2), 2.84 (t, 2H, J=7.2), 2.22 (m, 1H), 1.53 (s, 6H), 1.24 (m, 4H). MS: m/z 567 (M+1).

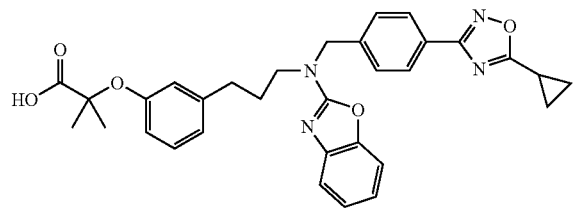

2-[3-(3-{1,3-Benzoxazol-2-yl[4-(5-cyclopropyl-1,2,4-oxadiazol-3-yl)benzyl]amino}propyl)phenoxy]-2-methylpropanoic acid Condensation of tert-butyl 2-[3-(3-{[4-(5-cyclopropyl-1,2,4-oxadiazol-3-yl)benzyl]amino}propyl)phenoxy]-2-methylpropanoate with 1.5 eq of 2-chlorobenzoxazole, as per general procedure E (conditions: 3 eq DIEA, THF, 100C, 8 hr), followed by standard TFA hydrolysis (general procedure 1) provided the title compound.

$^1$H NMR (CDCl$_3$) δ 7.96 (d, 2H, J=8.2), 7.44 (d, 1H, J=7.9), 7.29 (d, 2H, J=8.2), 7.27 (d, 1H, J=7.9), 7.20 (t, 1H, J=7.4), 7.12 (t, 1H, J=7.7), 7.08 (t, 1H, J=7.7), 6.75 (m, 3H), 4.75 (s, 2H), 3.46 (t, 2H, J=7.9), 2.56 (t, 2H, J=7.0), 2.26 (m, 1H), 1.92 (m, 2H), 1.63 (s, 6H), 1.26 (m, 4H). MS: m/z 553 (M+1).

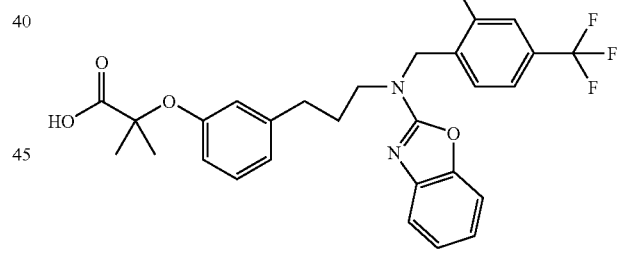

2-[3-(3-{1,3-Benzoxazol-2-yl[4-(5-cyclopropyl-1,2,4-oxadiazol-3-yl)benzyl]amino}propyl)phenoxy]-2-methylpropanoic acid Similarly prepared from tert-butyl 2-[3-(3-{[2,4-bis(trifluoromethyl)benzyl]amino}propyl)phenoxy]-2-methylpropanoate and 2-chlorobenzoxazole.

$^1$H NMR (CDCl$_3$) δ 7.93 (s, 1H), 7.71 (d, 1H, J=8.2), 7.46 (d, 1H, J=8.2) 7.38 (d, 1H, J=7.8), 7.19 (d, 1H, J=7.9), 7.16 (t, 1H, J=7.8), 7.09 (t, 1H, J=7.7), 7.01 (t, 1H, J=7.8), 6.76 (m, 3H), 4.96 (s, 2H), 3.49 (t, 2H, J=7.8), 2.59 (t, 2H, J=6.6), 1.95 (m, 2H), 1.57 (s, 6H). MS: m/z 581 (M+1).

The following 7 compounds were prepared using procedures similar to those described above.

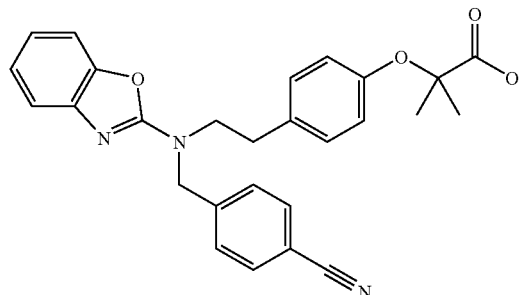

2-(4-{2-[1,3-benzoxazol-2-yl(4-cyanobenyl)amino]ethyl}phenoxy)-2-methylpropanoic acid MS: m/z 456.2 (M+1)

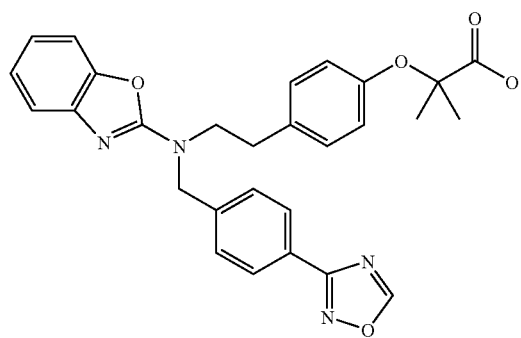

2-[4-(2-{1,3-benzoxazol-2-yl[4-(1,2,4-oxadiazol-3-yl)benzyl]amino}ethyl)phenoxy]-2-methylpropanoic acid

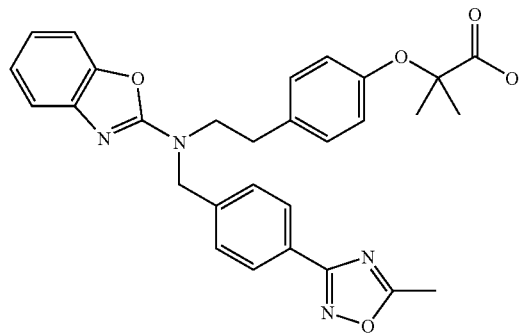

2-[4-(2-{1,3-benzoxazol-2-yl[4-(5-methyl-1,2,4-oxadiazol-3-yl)benzyl]amino}ethyl)phenoxy]-2-methylpropanoic acid

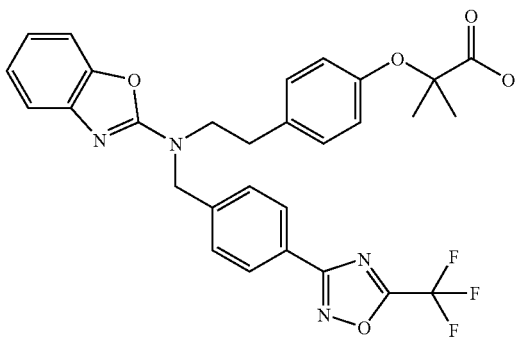

2-{4-[2-(1,3-benzoxazol-2-yl{4-[5-(trifluoromethyl)-1,2,4-oxadiazol-3-yl]benzyl}amino)ethyl]phenoxy}-2-methylpropanoic acid MS: m/z 566.9 (M+1)

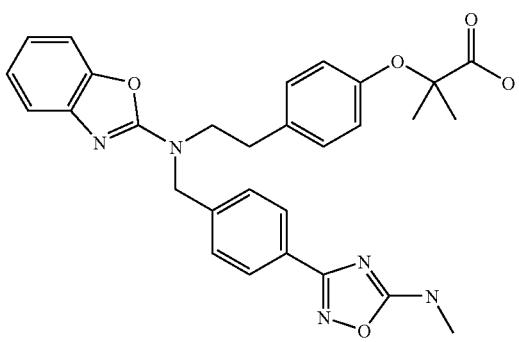

2-{4-[2-(1,3-benzoxazol-2-yl{4-[5-(methylamino)-1,2,4-oxadiazol-3-yl]benzyl}amino)ethyl]phenoxy}-2-methylpropanoic acid MS: m/z 528.2 (M+1)

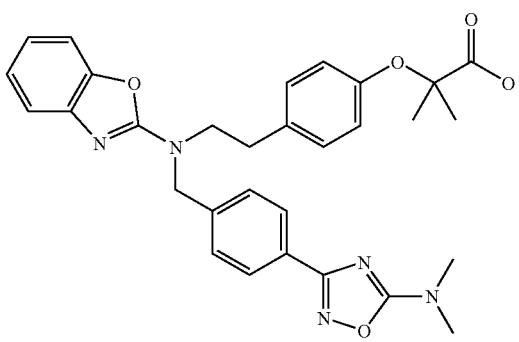

153

2-{4-[2-(1,3-benzoxazol-2-yl{4-[5-(dimethylamino)-1,2,4-oxadiazol-3-yl]benzyl}amino)ethyl]phenoxy}-2-methylpropanoic acid MS: m/z 542 (M+1)

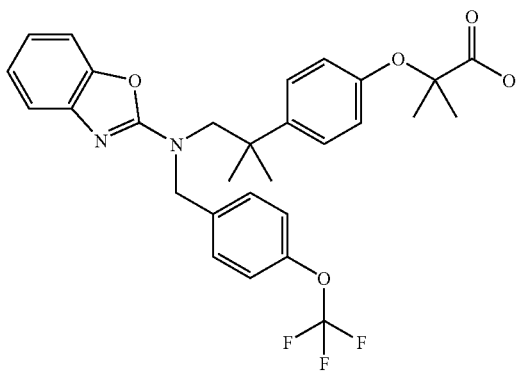

2-[4-(2-{1,3-benzoxazol-2-yl[4-(trifluoromethoxy)benzyl]amino}-1,1-dimethylethyl)phenoxy]-2-methylpropanoic acid MS: m/z 543.1 (M+1)

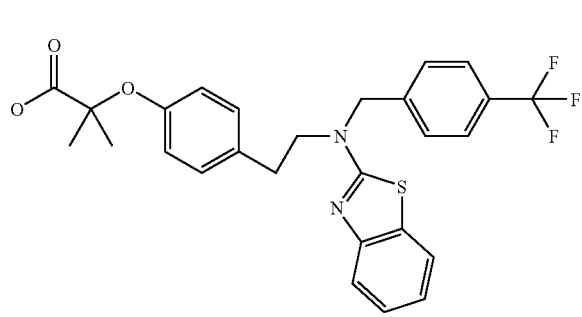

2-[4-(2-{1,3-Benzothiazol-2-yl[4-(trifluoromethyl)benzyl]amino}ethyl)phenoxy]-2-methylpropanoic acid Similarly, condensation of ethyl 2-methyl-2-[4-(2-{[4-(trifluoromethyl)benzyl]amino}ethyl)phenoxy]propanoate with 2-chlorobenzothiazole, followed by standard hydrolysis with NaOH afforded the title compound.

$^1$H NMR (CDCl$_3$) δ 7.56 (d, 2H, J=8.1), 7.52 (d, 2H, J=8.1), 7.30 (m, 3H), 7.05 (m, 3H), 6.85 (d, 2H, J=8.5), 4.65 (s, 2H), 3.64 (t, 2H, J=7.3), 2.91 (t, 2H, J=7.3), 1.54 (s, 6H). MS: m/z 515 (M+1).

154

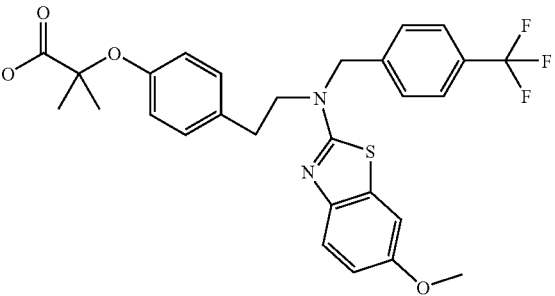

2-[4-(2-{(6-Methoxy-1,3-benzothiazol-2-yl)[4-(trifluoromethyl)benzyl]amino}ethyl)phenoxy]-2-methylpropanoic acid Similarly prepared from ethyl 2-methyl-2-[4-(2-{[4-(trifluoromethyl)benzyl]amino}ethyl)phenoxy]propanoate and 2-chloro-6-methoxy benzothiazole.

$^1$H NMR (CDCl$_3$) δ 7.52 (d, 2H, J=7.9), 7.46 (d, 1H, J=8.8), 7.29 (d, 2H, J=7.9), 7.10 (d, 1H, J=2.1), 7.04 (d, 2H, J=8.3), 6.88 (dd, 1H, J=8.8; 2.1), 6.84 (d, 2H, J=8.3), 4.62 (s, 2H), 3.79 (s, 3H), 3.61 (t, 2H, J=7.1), 2.90 (t, 2H, J=7.1), 1.54 (s, 6H).

2-[4-(2-{(6-Chloro-1,3-benzothiazol-2-yl)[4-(trifluoromethyl)benzyl]amino}ethyl)phenoxy]-2-methylpropanoic acid Similarly prepared from ethyl 2-methyl-2-[4-(2-{[4-(trifluoromethyl)benzyl]amino}ethyl)phenoxy]propanoate and 2,6-dichloro benzothiazole. $^1$H NMR (CDCl$_3$) δ 7.55 (d, 2H, J=8.0), 7.52 (d, 1H, J=2.0), 7.47 (d, 1H, J=8.0), 7.32 (d, 2H, J=8.0), 7.24 (dd, 1H, J=8.0; 2.0), 7.07 (d, 2H, J=8.6), 6.86 (d, 2H, J=8.6), 4.67 (s, 2H), 3.65 (t, 2H, J=7.2), 2.93 (t, 2H, J=7.2), 1.53 (s, 6H). MS: m/z 549 (M+1).

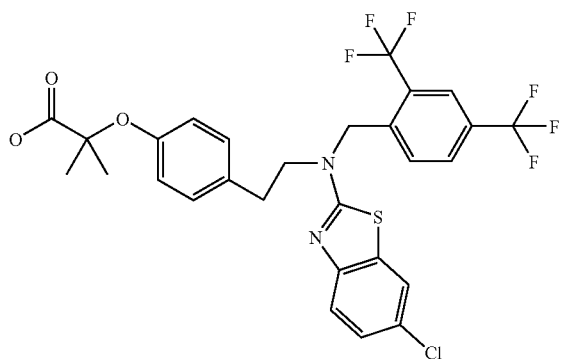

2-(4-{2-[[2,4-Bis(trifluoromethyl)benzyl](6-chloro-1,3-benzothiazol-2-yl)amino]ethyl}phenoxy)-2-methylpropanoic acid Similarly prepared from methyl 2-[4-(2-{[2,4-bis(trifluoromethyl)benzyl]amino}ethyl)phenoxy]-2-methylpropanoate and 2,6-dichloro benzothiazole.

$^1$H NMR (CDCl$_3$) δ 7.89 (s, 1H), 7.68 (d, 1H, J=8.1), 7.54 (d, 1H, J=2.1), 7.47 (d, 1H, J=8.1), 7.43 (d, 1H, J=8.6), 7.22 (dd, 1H, J=8.6; 2.1), 7.06 (d, 2H, J=8.5), 6.84 (d, 2H, J=8.5), 4.88 (s, 2H), 3.64 (t, 2H, J=7.4), 2.94 (t, 2H, J=7.4), 1.54 (s, 6H).

MS: m/z 617 (M+1).

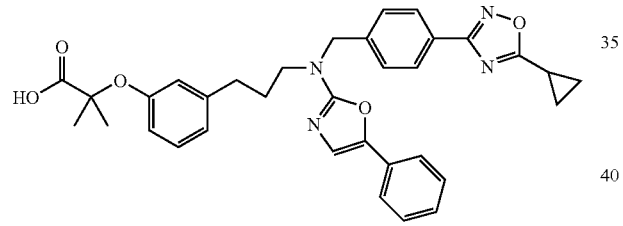

2-(3-{3-[[4-(5-Cyclopropyl-1,2,4-oxadiazol-3-yl)benzyl](5-phenyl-1,3-oxazol-2-yl)amino]propyl}phenoxy)-2-methylpropanoic acid Similarly prepared from tert-butyl 2-[3-(3-{[4-(5-cyclopropyl-1,2,4-oxadiazol-3-yl)benzyl]amino}propyl)phenoxy]-2-methylpropanoate and 2-chloro-5-phenyl-oxazole (ref. GB1552125).

$^1$H NMR (CDCl$_3$) δ 7.98 (d, 2H, J=8.1), 7.41–7.28 (m, 6H), 7.24–7.1 (m, 3H), 6.8–6.71 (m, 3H), 4.68 (s, 2H), 3.39 (broad t, 2H), 2.59 (broad t, 2H), 2.28–2.22 (m, 1H), 1.96–1.86 (m, 2H), 1.63 (s, 6H), 1.3–1.24 (m, 4H). MS: m/z 579 (M+1).

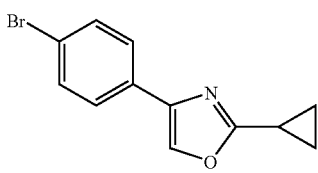

4-(4-bromophenyl)-2-cyclopropyl-1,3-oxazole

Step 1. To a slurry of sodium carbonate (9.00 g, 84.91 mmol) in DMF (100 ml) was added dropwise cyclopropane carboxylic acid (4.5 ml, 56.50 mmol). The mixture was stirred for 15 min and then treated with 2,4'-dibromoacetophenone (15.71 g, 56.52 mmol). After 3 h, the mixture was partitioned between Et$_2$O and water. The aqueous phase was extracted with Et$_2$O (4×125 ml). The combined organic phases were dried over MgSO$_4$ and concentrated in vacuo to yield 2-(4-bromophenyl)-2-oxoethyl cyclopropane carboxylate as a yellow solid (15.81 g, 98%).

$^1$H NMR (CDCl$_3$) δ 7.75 (d, 2H, J=8.5), 7.60 (d, 2H, J=8.6), 5.26 (s, 2H), 1.77 (m, 1H), 1.09–1.06 (m, 2H), 0.96–0.93 (m, 2H).

Step 2. To a mixture of 2-(4-bromophenyl)-2-oxoethyl cyclopropane carboxylate (6.00 g, 21.19 mmol) and acetamide (6.60 g, 111.73 mmol) was added BF$_3$/Et$_2$O (4 ml). The mixture was heated to 140C for 2.5 h. Upon cooling, water was added, and the mixture was extracted with Et$_2$O (4×125 ml). The combined organic phases were dried with MgSO$_4$ and concentrated in vacuo. The crude material was purified by flash chromatography (CH$_2$Cl$_2$/hexanes, 7:3) to provide the title compound as a yellow solid (3.61 g, 64%).

$^1$H NMR (CDCl$_3$) δ 7.71 (s, 1H), 7.54 (d, 2H, J=8.4), 7.47 (d, 2H, J=8.6), 2.08 (s, 1H), 1.11–1.00 (m, 4H).

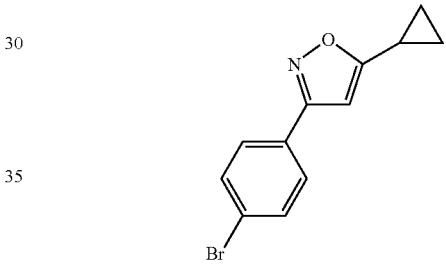

3-(4-bromophenyl)-5-cyclopropylisoxazole

Step 1. To a 0C solution of benzotriazole (5.05 g, 42.39 mmol) in CH$_2$Cl$_2$ (100 mL) was added dropwise triethylamine (9.0 ml, 64.57 mmol) followed by cyclopropyl carbonyl chloride (4.2 ml, 46.28 mmol). The mixture was stirred at rt for 1 h and then quenched with a solution of 2N aqueous HCl (75 ml). The organic phase was washed with 2 N HCl (2×75 mL) and water (100 ml), dried with MgSO$_4$ and concentrated in vacuo. The solid residue was washed with hexanes, filtered and dried to yield 1-(cyclopropylcarbonyl)-1H-1,2,3-benzotriazole as a white solid (5.92 g, 75%).

Step 2. To a –78C solution of LDA (generated from 8 ml of 2.5 M nBuLi and 2.1 ml of diisopropylamine) in THF (120 ml) was added dropwise, over 80 min, a solution a 4'-bromoacetophenone (2.98 g, 14.97 mmol) in THF (45 ml). The mixture continued to stir at –78C for 1 h, followed by addition of 1-(cyclopropylcarbonyl)-1H-1,2,3-benzotriazole (2.56 g, 13.65 mmol) in THF (45 ml). The mixture was warmed to rt overnight. The yellow mixture was poured into water and extracted with Et$_2$O (2×300 ml). The combined organic phases were washed with water, dried with MgSO$_4$, and concentrated in vacuo. The crude material was purified by flash chromatography (CH$_2$Cl$_2$/hexanes, 10:90 to 30:70) to yield 1-(4-bromophenyl)-3-cyclopropyl-1,3-propanedione as an orange solid (1.60 g, 44%).

¹H NMR (CDCl₃) δ 7.70 (d, 2H, J=8.6), 7.55 (d, 2H, J=8.4), 6.23 (s, 1H), 1.78 (m, 1H), 1.20–1.16 (m, 2H), 1.00–0.95 (m, 2H).

Step 3. To a solution of 1-(4-bromophenyl)-3-cyclopropyl-1,3-propanedione (2.60 g, 9.73 mmol) in anhydrous MeOH (80 ml) was added hydroxylamine hydrochloride (2.71 g, 39.00 mmol). The mixture was heated to reflux for 14 h. Upon cooling, the solution was poured into water, and extracted with CH₂Cl₂ (3×200 ml). The combined organic phases were dried with MgSO₄ and concentrated in vacuo. The regioisomers were separated by flash chromatography (CH₂Cl₂/hexanes, 10:90 to 40:60) to yield the title compound as a white solid (1.04 g, 40%).

¹H NMR (CDCl₃) δ 7.67 (d, 2H, J=8.5), 7.60 (d, 2H, J=8.5), 6.22 (s, 1H), 2.11 (m, 1H), 1.17–1.03 (m, 4H).

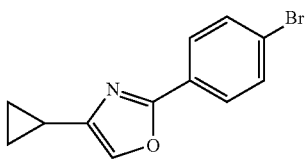

2-(4-bromophenyl)-4-cyclopropyl-1,3-oxazole

Step 1. To a cooled solution of cyclopropylmethyl ketone (7.0 ml, 70.65 mmol) in MeOH (40 mL) was added dropwise bromine (3.6 mL, 70.28 mmol) over a 2 h period. The mixture was stirred for 30 min at rt, followed by addition of water. The mixture was extracted with Et₂O (4×150 ml). The combined organic phases were washed with a solution of 10% aqueous Na₂CO₃, water and brine, dried with Na₂CO₃ and concentrated in vacuo. The crude material was purified by distillation in vacuo (44–47C) to yield 2-bromo-1-cyclopropylethanone (9.69 g, 85%).

¹H NMR (CDCl₃) δ 3.99 (s, 2H), 2.19 (m, 1H), 1.13–1.09 (m, 2H), 1.02–0.97 (m, 2H).

Step 2. To a solution of bromobenzoic acid (9.97 g, 49.60 mmol) in DMF (65 mL) was added Na₂CO₃ (7.90 g, 74.54 mmol). After stirring for 15 min, 2-bromo-1-cyclopropylethanone (9.69 g, 59.44 mmol) was added, and the mixture was stirred at rt for 12 h. Water was added, and the mixture was extracted with Et₂O (6×125 ml). The combined organic phases were dried with MgSO₄ and concentrated in vacuo. Recrystallization from EtOH yielded 2-cyclopropyl-2-oxoethyl 4-bromobenzoate as white needles (8.53 g, 61%).

¹H NMR (CDCl₃) δ 7.93 (d, 2H, J=8.8), 7.57 (d, 2H, J=8.8), 5.03 (s, 2H), 1.98 (m, 1H), 1.16–1.12 (m, 2H), 1.00–0.96 (m, 2H).

Step 3. To a mixture of 2-cyclopropyl-2-oxoethyl 4-bromobenzoate (4.51 g, 15.93 mmol) and acetamide (4.71 g, 79.74 mmol) was added BF₃/Et₂O (1 ml). The mixture was heated at 140C for 8 h. Upon cooling, the mixture was partitioned between water and Et₂O. The aqueous phase was extracted with Et₂O (1×125 ml). The combined organic phases were washed with Water and brine, dried with MgSO₄, and concentrated in vacuo. The crude material was purified by flash chromatography (CH₂Cl₂/hexanes, 30:70 to 50:50) to yield the title compound as a white crystalline solid (0.69 g, 16%).

¹H NMR (CDCl₃, 400 M): δ 7.84 (d, 2H, J=8.8), 7.53 (d, 2H, J=8.8), 7.40 (s, 1H), 1.81 (m, 1H), 0.91–0.86 (m, 2H), 0.81–0.77 (m, 2H).

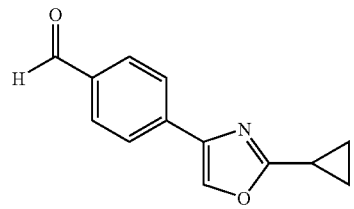

4-(2-Cyclopropyl-1,3-oxazol-4-yl)benzaldehyde

Step 1. To a solution of 4-(4-bromophenyl)-2-cyclopropyl-1,3-oxazole (1.78 g, 6.74 mmol) in NMP (25 mL) was added copper cyanide (4.22 g, 47.12 mmol). The mixture was heated to 185C for 4 h. Upon cooling, the mixture was poured into a 0C solution of 5% aqueous sodium cyanide (60 ml). The aqueous phase was extracted with Et₂O. The combined organic phases were washed with, 5% aqueous sodium cyanide, water, and brine, dried with MgSO₄ and concentrated in vacuo. The crude material was purified by flash chromatography (CH₂Cl₂/Hexanes, 2:3 to 10:0) to yield 4-(2-cyclopropy-1,3-oxazol-4-yl)benzonitrile as a yellow solid (1.00 g, 71%).

¹H NMR (CDCl₃) δ 7.82 (s, 1H), 7.77 (d, 2H, J=8.3), 7.64 (d, 2H, J=8.3), 2.10 (m, 1H), 1.13–1.03 (m, 4H).

Step 2. To a 0C solution of 4-(2-cyclopropyl-1,3-oxazol-4-yl)benzonitrile (0.984 g, 4.68 mmol) in anhydrous CH₂Cl₂ (3 ml) was added dropwise a 1M solution of DIBAL in CH₂Cl₂ (5.60 ml, 1.22 mmol). Upon completion of addition, the solution was warmed to 45C for 3 h. The solution was cooled and 10% aqueous H₂SO₄ was slowly added until pH<4. The mixture was stirred overnight at rt. The aqueous phase was extracted with CH₂Cl₂ (3×40 ml). The combined organic phases were dried with MgSO₄ and concentrated in vacuo. The crude material was purified by flash chromatography (EtOAc/hexanes, 1:4) to yield the title compound as a yellow solid (0.92 g, 92%).

¹H NMR (CDCl₃) δ 9.98 (s, 1H), 7.89–7.83 (m, 4H), 7.84 (s, 1H), 2.11 (m, 1H), 1.14–1.03 (m, 4H).

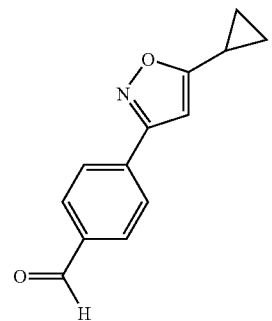

4-(3-cyclopropyl-5-isoxazolyl)benzaldehyde

Similarly prepared from 3-(4-bromophenyl)-5-cyclopropylisoxazole.

¹H NMR (CDCl₃) δ 10.03 (s, 1H), 7.93 (d+d, 4H), 6.25 (s, 1H), 2.08 (m, 1H), 1.11–1.01 (m, 4H).

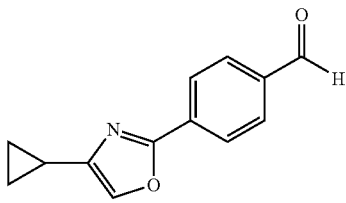

4-(4-Cyclopropyl-1,3-oxazol-2-yl)benzaldehyde

Similarly prepared from 2-(4-bromophenyl)-4-cyclopropyl-1,3-oxazole.

¹H NMR (CDCl₃) δ 10.03 (s, 1H), 8.14 (d, 2H, J=8.2), 7.92 (d, 2H, J=8.5), 7.47 (s, 1H), 1.84 (m, 1H), 0.93–0.80 (m, 4H).

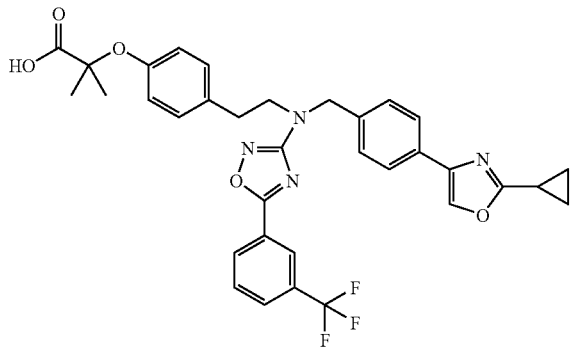

2-{4-[2-([4-(2-cyclopropyl-1,3-oxazol-4-yl)benzyl] {5-[3-(trifluoromethyl)phenyl]-1,2,4-oxadiazol-3-yl}amino)ethyl]phenoxy}-2-methylpropanoic acid Step 1. To a solution of 4-(2-cyclopropyl-1,3-oxazol-4-yl)benzaldehyde (0.318 g, 1.49 mmol) in MeOH (5 ml) was added tyramine (0.215 g, 1.57 mmol) and trimethylorthoformate (1.2 mL, 10.97 mmol). The resulting solid was redissolved in THF (3 ml) and allowed to stir for 12 h. Sodium borohydride (0.15 g, 3.94 mmol) was added and the mixture was stirred an additional 2 h. The reaction mixture was concentrated and partitioned between EtOAc and water. The aqueous phase was extracted with EtOAc and the combined organic phases were washed with brine, dried with MgSO₄, and concentrated in vacuo. The crude material was purified by flash chromatography (MeOH/CH₂Cl₂, 5:95 to 10:90) to yield 4-(2-{[4-(2-cyclopropyl-1,3-oxazol-4-yl)benzyl]amino}ethyl)phenol as a white solid (0.43 g, 85%).

¹H NMR (DMSO-d₆) δ 9.08 (s, 1H), 8.32 (s, 1H), 7.60 (d, 2H, J=8.1), 7.28 (d, 2H, J=7.9), 6.93 (d, 2H, J=8.3), 6.60 (d, 2H, J=8.3), 3.66 (s, 2H), 2.61–2.56 (m, 4H), 2.10 (m, 1H), 1.03–0.92 (m, 4H).

Step 2. To a warm solution of 4-(2-{[4-(2-cyclopropyl-1,3-oxazol-4-yl)benzyl]amino}ethyl)phenol (0.42 g, 1.25 mmol) in acetonitrile (6 ml) was added Cs₂CO₃ (1.34 g, 4.11 mmol) followed by ethyl-2-bromoisobutyrate (0.60 mL, 4.09 mmol). The mixture was heated at 80C for 20 h. Upon cooling, the mixture was partitioned between EtOAc and water. The aqueous phase was extracted with EtOAc (2×25 ml). The combined organic phases were dried with MgSO₄ and concentrated in vacuo. The crude material was purified by flash chromatography (MeOH/EtOAc, 2:98) to yield ethyl 2-[4-(2-{[4-(2-cyclopropyl-1,3-oxazol-4-yl)benzyl]amino}ethyl)phenoxy]-2-methylpropanoate (0.42 g, 74%).

¹H NMR (CDCl₃) δ 7.68 (s, 1H), 7.60 (d, 2H, J=8.1), 7.26 (d, 2H, J=8.1), 7.02 (d, 2H, J=8.4), 6.74 (d, 2H, J=8.5), 4.20 (q, 2H, J=7.2), 3.78 (s, 2H), 2.83 (t, 2H, J=7.1), 2.74 (t, 2H, J=6.5), 2.02 (m, 1H), 1.54 (s, 6H), 1.22 (t, 3H, J=5.5), 1.10–1.01 (m, 4H).

Step 3. To a 0C solution of ethyl 2-[4-(2-{[4-(2-cyclopropyl-1,3-oxazol-4-yl)benzyl]amino}ethyl)phenoxy]-2-methylpropanoate (0.42 g, 0.92 mmol) in anhydrous CH₂Cl₂ (9 ml) was added dropwise triethylamine (0.16 ml, 1.15 mmol) followed by a 3M solution of cyanogen bromide in CH₂Cl₂ (0.37 ml, 1.11 mmol). The mixture was stirred at rt for 2 h. The reaction mixture was concentrated in vacuo, and the residue was partitioned between CH₂Cl₂ and water. The aqueous phase was extracted with CH₂Cl₂ (2×20 ml). The combined organic phases were washed with brine, dried with MgSO₄, and concentrated in vacuo. The crude material was purified by flash chromatography (EtOAc/hexanes, 25:75 to 35:65) to yield ethyl 2-(4-(2-{cyano[4-(2-cyclopropyl-1,3-oxazo[4-yl)benzyl]amino}ethyl)phenoxy]-2-methylpropanoate (0.39 g, 89%).

¹H NMR (CDCl₃) δ 7.74 (s, 1H), 7.65 (d, 2H, J=8.1), 7.21 (d, 2H, J=8.1), 7.00 (d, 2H, J=8.6), 6.75 (d, 2H, J=8.5), 4.20 (q, 2H, J=7.1), 4.09 (s, 2H), 3.08 (t, 2H, J=7.1), 2.83 (t, 2H, J=7.8), 2.10 (m, 1H), 1.55 (s, 6H), 1.22 (t, 3H), 1.11–1.03 (m, 4H).

Step 4. To a solution of ethyl 2-[4-(2-{cyano[4-(2-cyclopropyl-1,3-oxazol-4-yl)benzyl]amino}ethyl)phenoxy]-2-methylpropanoate (0.38 g, 0.80 mmol) in DMF (2 ml) was added hydroxylamine hydrochloride (0.20 g, 2.94 mmol) followed by sodium acetate (2.88 g, 3.59 mmol). The mixture was stirred at rt for 12 h. The reaction mixture was partitioned between EtOAc and water. The aqueous phase was extracted with EtOAc (2×20 ml). The combined organic phases were washed with brine, dried with MgSO₄, and concentrated in vacuo to yield ethyl 2-[4-(2-{[(E)-amino(hydroxyimino)methyl][4-(2-cyclopropyl-1,3-oxazol-4-yl)benzyl]amino}ethyl)phenoxy]-2-methylpropanoate (0.46 g) which was used directly without purification.

¹H NMR (CDCl₃) δ 7.99 (s, 2H), 7.69 (s, 1H), 7.58 (d, 2H, J=8.1), 7.14 (d, 2H, J=8.1), 7.00 (d, 2H, J=8.5), 6.72 (d, 2H, J=8.5), 4.31 (s, 2H), 4.18 (q, 2H, J=7.1), 3.40 (t, 2H, J=7.1), 2.73 (t, 2H, J=7.2), 2.08 (m, 1H), 1.52 (s, 6H), 1.21 (t, 3H, J=7.3), 1.09–0.98 (m, 4H).

Step 5. To a cooled solution of ethyl 2-[4-(2-{[(E)-amino(hydroxyimino)methyl][4-(2-cyclopropyl-1,3-oxazol-4-yl)benzyl]amino}ethyl)phenoxy]-2-methylpropanoate (0.108 g, 0.21 mmol) in toluene (2 ml) was added triethylamine (0.028 mL, 0.20 mmol) dropwise. After 5 min, 3-(trifluoromethyl)benzoyl chloride (0.031 ml, 0.20 mmol) in toluene (0.1 ml) was added dropwise. The mixture was allowed to warm to rt over 2 h and then heated to 110C for 2 hr. Upon cooling, the mixture was filtered, and the solid was washed with EtOAc. The filtrate was concentrated in vacuo, and the resulting residue was partitioned between EtOAc and a solution of 0.5N aqueous HCl. The organic phase was washed with 0.5N aqueous HCl (1×), 0.5N aqueous NaOH (2×), and brine (1×), dried with Na₂SO₄ and concentrated in vacuo. The crude material was purified by flash chromatography (EtOAc/hexanes, 10:90 to 20:80) to yield ethyl 2-{4-[2-([4-(2-cyclopropyl-1,3-oxazol-4-yl)benzyl]{5-[3-(trifluoromethyl)phenyl]-1,2,4-oxadiazol-3-yl}amino)ethyl]phenoxy}-2-methylpropanoate (76 mg, 58%).

¹H NMR (CDCl₃) δ 8.33 (s, 1H), 8.24 (d, 1H, J=8.0), 7.79 (d, 2H, J=8.0), 7.69 (s, 1H), 7.62 (d, 2H, J=8.1), 7.24 (d, 2H, J=8.4), 7.02 (d, 2H, J=8.4), 6.74 (d, 2H, J=8.5), 4.55 (s, 2H), 4.20 (q, 2H, J=7.2), 3.54 (t, 2H, J=7.2), 2.83 (t, 2H, J=7.8), 2.09 (m, 1H), 1.52 (s, 6H), 1.22 (t, 3H, J=7.1), 1.10–1.01 (m, 4H).

Step 5. To a solution of ethyl 2-{4-[2-([4-(2-cyclopropyl-1,3-oxazol-4-yl)benzyl]{5-[3-(trifluoromethyl)phenyl]-1,2,4-oxadiazol-3-yl}amino)ethyl]phenoxy}-2-methylpropanoate (93 mg, 0.14 mmol) in anhydrous THF (1.5 ml) was added EtOH (0.4 ml), water (0.4 ml), and LiOH (31 mg, 1.28 mmol). The mixture was stirred at rt for 12 h. The reaction was quenched with a solution of saturated aqueous KH₂PO₄, and the aqueous phase was extracted with EtOAc (3×20 ml). The combined organic phases were dried with Na₂SO₄ and concentrated in vacuo to yield the title compound as a colorless solid (58 mg, 65%). ¹H NMR (CDCl₃) δ 8.34 (s, 1H), 8.26 (d, 1H, J=7.9), 7.80 (d, 1H, J=7.8), 7.65 (s, 1H), 7.62 (d, 1H, J=8.0), 7.40 (d, 2H, J=8.1), 6.92 (d, 2H, J=8.3), 6.81 (d, 2H, J=8.5), 6.65 (d, 2H, J=8.4), 4.53 (s, 2H), 3.63 (t, 2H, J=6.2), 2.92 (t, 2H, J=6.4), 2.21 (m, 1H), 1.58 (s, 6H), 1.19–1.06 (m, 4H). MS: m/z 633 (M+1).

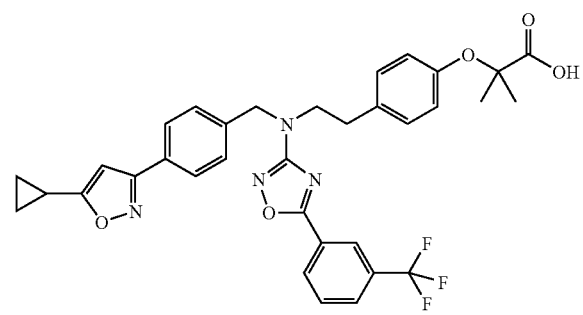

2-{4-[2-([4-(3-Cyclopropyl-5-isoxazolyl)benzyl]{5-[3-(trifluoromethyl)phenyl]-1,2,4-oxadiazol-3-yl}amino)ethyl]phenoxy}-2-methylpropanoic acid Similarly prepared from tyramine and 4-(3-cyclopropyl-5-isoxazolyl)benzaldehyde.

¹H NMR (CDCl₃) δ 8.33 (s, 1H), 8.25 (d, 1H, J=8), 7.80 (d, 1H, J=7.9), 7.65–7.61 (d+t, 3H), 7.20 (d, 2H, J=8.3), 6.98 (d, 2H, J=8.5), 6.76 (d, 2H, J=8.6), 6.17 (s, 1H), 4.58 (s, 2H), 3.62 (t, 2H, J=6.9), 2.89 (t, 2H, J=7.1), 2.05 (m, 1H), 1.53 (s, 6H), 1.10–1.00 (m, 4H).

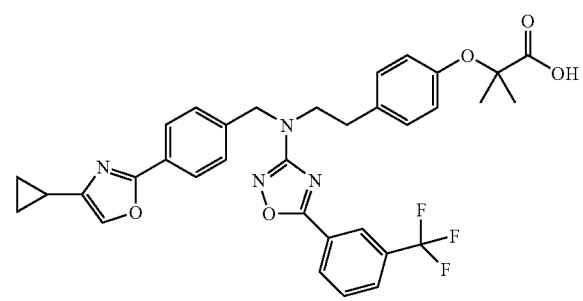

2-{4-[2-([4-(4-Cyclopropyl-1,3-oxazol-2-yl)benzyl]{5-[3-(trifluoromethyl)phenyl]-1,2,4-oxadiazol-3-yl}amino)ethyl]phenoxy}-2-methylpropanoic acid Similarly prepared from tyramine and 4-(4-cyclopropyl-1,3-oxazol-2-yl)benzaldehyde.

¹H NMR (CDCl₃) δ 8.34 (s, 1H), 8.26 (d, 1H, J=8.0), 7.81 (d, 1H, J=7.7), 7.74 (d, 2H, J=8.1), 7.64 (t, 1H, J=7.7), 7.38 (s, 1H), 6.99 (d, 2H, J=8.3), 6.83 (d, 2H, J=8.2), 6.68 (d, 2H, J=8.6), 4.56 (s, 2H), 3.62 (t, 2H, J=6.4), 2.92 (t, 2H, J=6.5), 1.87 (m, 1H), 1.58 (s, 6H), 0.93–0.80 (m, 4H). MS: m/z 633 (M+1).

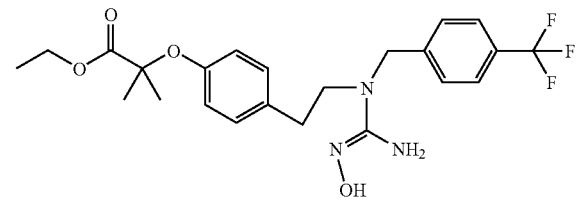

Ethyl 2-[4-(2-{[(E)-amino(hydroxyimino)methyl][4-(trifluoromethyl)benzyl]amino}ethyl)phenoxy]-2-methylpropanoate Step 1. A solution of ethyl 2-methyl-2-[4-(2-{[4-(trifluoromethyl)benzyl]amino}ethyl)phenoxy]propanoate (12 g; 29.34 mmol) and triethylamine (4.5 ml; 32.27 mmol) in 100 ml of dichloromethane was treated under nitrogen with cyanogen bromide (10.3 ml of a 3M solution in dichloromethane; 30.9 mmol). After 1.5 hr, additional triethylamine (2 ml) and cyanogen bromide (2.5 ml) were added and stirred another 30 minutes. The reaction mixture was concentrated and the residue partitioned between ethyl acetate and water. The organic phase was washed with water (three times) and brine, dried over sodium sulfate and concentrated. Purification by flash chromatography using ethyl acetate-hexane mixtures (5–40% gradient) afforded ethyl 2-[4-(2-{cyano[4-(trifluoromethyl)benzyl]amino}ethyl)phenoxy]-2-methylpropanoate (10.9 g; 85% yield).

¹H NMR (CDCl₃) δ 7.6 (d, 2H, J=8.1), 7.31 (d, 2H, J=8.1), 7.04 (d, 2H, J=8.5), 6.79 (d, 2H, J=8.5), 4.24 (q, 2H, J=7.2), 4.14 (s, 2H), 3.14 (t, 2H, J=7.4), 2.89 (t, 2H, J=7.4), 1.58 (s, 6H), 1.25 (t, 3H, J=7.2).

Step 2. A solution of the above intermediate (10.9 g; 25.28 mmol) in 80 ml of dry DMF was treated under nitrogen with hydroxylamine hydrochloride (6.32 g; 90.99 mmol) and sodium acetate (7.46 g; 90.99 mmol). After 14 hr, the reaction mixture was partitioned between ethyl acetate and 0.05N NaOH. The organic phase was washed with water (twice) and brine, dried over sodium sulfate and concentrated. Purification by flash chromatography using methanol-dichloromethane mixtures (2–20% gradient) afforded the title compound in good yield (~85% purity).

¹H NMR (CDCl₃) δ 7.58 (d, 2H, J=8.1), 7.35 (d, 2H, J=8.1), 7.05 (d, 2H, J=8.5), 6.8 (d, 2H, J=8.5), 4.4 (s, 2H), 4.28 (q, 2H, J=7.2), 3.39 (t, 2H, J=7.3), 2.80, t, 2H, J=7.3), 1.59 (s, 6H), 1.28 (t, 3H, J=7.2).

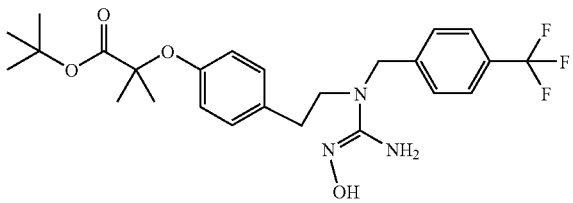

tert-Butyl 2-[4-(2-{[(E)-amino(hydroxyimino)methyl][4-(trifluoromethyl)benzyl]amino}ethyl)phenoxy]-2-methylpropanoate Similarly prepared from tert-butyl 2-methyl-2-[4-(2-{[4-(trifluoromethyl)benzyl]amino}ethyl)phenoxy]propanoate.

$^1$H NMR (CDCl$_3$) δ 7.55 (d, 2H, J=8), 7.32 (d, 2H, J=8), 7.01 (d, 2H, J=8.5), 6.78 (d, 2H, J=8.5), 4.34 (s, 2H), 3.32 (t, 2H, J=7.4), 2.80 (t, 2H, J=7.4), 1.53 (s, 6H), 1.43 (s, 9H).

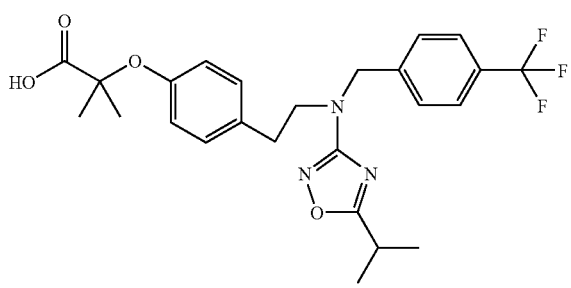

2-[4-(2-{(5-Isopropyl-1,2,4-oxadiazol-3-yl)[4-(trifluoromethyl)benzyl]amino}ethyl)phenoxy]-2-methylpropanoic acid Step 1. A solution of ethyl 2-[4-(2-{[(E)-amino(hydroxyimino)methyl][4-(trifluoromethyl)benzyl]amino}ethyl)phenoxy]-2-methylpropanoate (1 g; 2.14 mmol) and triethylamine (0.30 ml; 2.14 mmol) in 10 ml of dichloromethane was cooled in an ice bath and treated under nitrogen with isobutyryl chloride (0.20 ml; 1.93 mmol). The mixture was allowed to warm to rt. After 1 hr, 8 ml of toluene were added and the reaction mixture was heated to 110C under a reflux condenser. After 5 hr, it was partitioned between ethyl acetate and 0.5N HCl. The organic phase was washed with 0.5 N HCl (twice), 1N NaOH (three times) and brine, dried over sodium sulfate and concentrated. Purification by flash chromatography using ethyl acetate-hexane mixtures (5–50% gradient) afforded ethyl 2-[4-(2-{(5-isopropyl-1,2,4-oxadiazol-3-yl)[4-(trifluoromethyl)benzyl]amino}ethyl)phenoxy]-2-methylpropanoate (470 mg; 43% yield).

Step 2. The intermediate ester above (1 g) was hydrolyzed with NaOH as per general procedure H. Purification by radial chromatography using a 1–8% methanol-dichloromethane gradient, followed by crystallization from dichloromethane-hexane afforded the title compound as a white solid (0.80 g; 85% yield).

$^1$H NMR (CDCl$_3$) δ 7.52 (d, 2H, J=8.1), 7.29 (d, 2H, J=8.1), 7.01 (d, 2H, J=8.5), 6.81 (d, 2H, J=8.5), 4.5 (s, 2H), 3.49 (t, 2H, J=7.5), 3.06 (m, 1H), 2.80 (t, 2H, J=7.5), 1.54 (s, 6H), 1.33 (d, 6H, J=7.1).

2-[4-(2-{[5-(3-Chlorophenyl)-1,2,4-oxadiazol-3-yl][4-(trifluoromethyl)benzyl]amino}ethyl)phenoxy]-2-methylpropanoic acid Similarly prepared from ethyl 2-[4-(2-{[(E)-amino(hydroxyimino)methyl][4-(trifluoromethyl)benzyl]amino}ethyl)phenoxy]-2-methylpropanoate and 3-chlorobenzoyl chloride.

$^1$H NMR (CDCl$_3$) δ 8.03 (s, 1H), 7.92 (d, 1H, J=7.8), 7.54 (d, 2H, J=8.2), 7.51 (d, 1H, J=7.8), 7.41 (t, 1H, J=7.8), 7.32 (d, 2H, J=8.2), 7.06 (d, 2H, J=8.4), 6.84 (d, 2H, J=8.4), 4.57 (s, 2H), 3.58 (t, 2H, J=7.6), 2.87 (t, 2H, J=7.6), 1.55 (s, 6H).

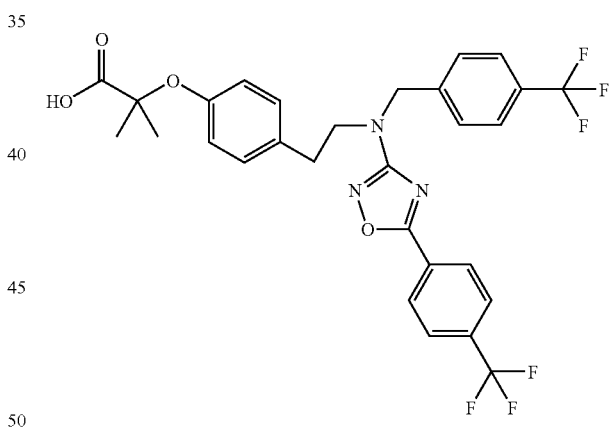

2-Methyl-2-{4-[2-([4-(trifluoromethyl)benzyl]{5-[4-(trifluoromethyl)phenyl]-1,2,4-oxadiazol-3-yl}amino)ethyl]phenoxy}propanoic acid Similarly prepared by condensation of tert-butyl 2-[4-(2-{[(E)-amino(hydroxyimino)methyl][4-(trifluoromethyl)benzyl]amino}ethyl)phenoxy]-2-methylpropanoate with 4-trifluoromethylbenzoyl chloride, followed by standard TFA hydrolysis.

$^1$H NMR (CDCl$_3$) δ 8.23 (d, 2H, J=8.1), 7.8 (d, 2H, J=8.1), 7.6 (d, 2H, J=8.1), 7.39 (d, 2H, J=8.1), 7.13 (d, 2H, J=8.5), 6.9 (d, 2H, J=8.5), 4.65 (s, 2H), 3.66 (t, 2H, J=7.7), 2.94 (t, 2H, J=7.7), 1.6 (s, 6H).

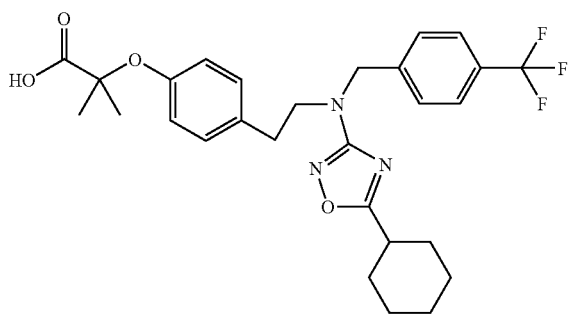

2-[4-(2-{(5-Cyclohexyl-1,2,4-oxadiazol-3-yl)[4-(trifluoromethyl)benzyl]amino}ethyl)phenoxy]-2-methylpropanoic acid Similarly prepared from tert-butyl 2-[4-(2-{[(E)-amino(hydroxyimino)methyl][4-(trifluoromethyl)benzyl]amino}ethyl)phenoxy]-2-methylpropanoate and cyclohexanecarbonyl chloride.

$^1$H NMR (CDCl$_3$) δ 7.58 (d, 2H, J=8.1), 7.35 (d, 2H, J=8.1), 7.09 (d, 2H, J=8.5), 6.88 (d, 2H, J=8.5), 4.56 (s, 2H), 3.55 (t, 2H, J=7.4), 2.85 (m, 3H), 2.09 (m, 2H), 1.85 (m, 2H), 1.65 (m, 2H), 1.6 (s, 6H), 1.38 (m, 4H).

The following 62 compounds were prepared using similar procedures to those described above.

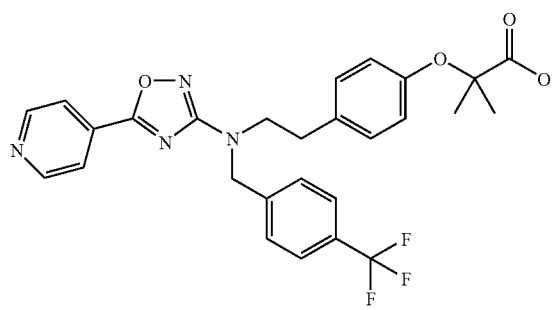

2-methyl-2-[4-(2-{(5-pyridin-4-yl-1,2,4-oxadiazol-3-yl)[4-(trifluoromethyl)benzyl]amino}ethyl)phenoxy]propanoic acid MS: m/z 527.0 (M+1)

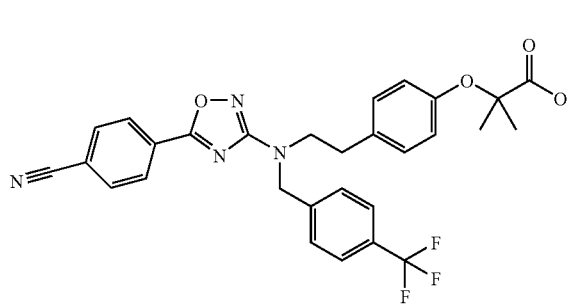

2-[4-(2-{[5-(4-cyanophenyl)-1,2,4-oxadiazol-3-yl][4-(trifluoromethyl)benzyl]amino}ethyl)phenoxy]-2-methylpropanoic acid MS: m/z 551 (M+1)

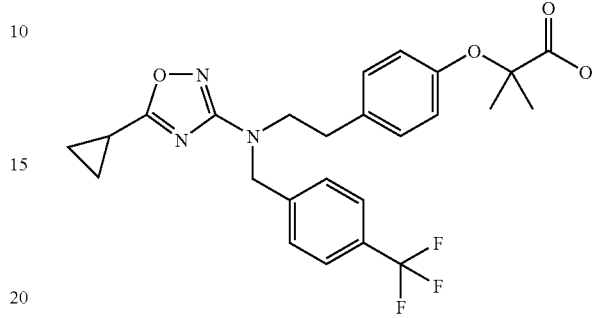

2-[4-(2-{(5-cyclopropyl-1,2,4-oxadiazol-3-yl)[4-(trifluoromethyl)benzyl]amino}ethyl)phenoxy]-2-methylpropanoic acid MS: m/z 490.1 (M+1)

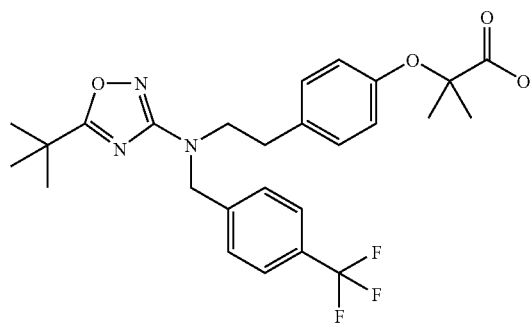

2-[4-(2-{(5-tert-butyl-1,2,4-oxadiazol-3-yl)[4-(trifluoromethyl)benzyl]amino}ethyl)phenoxy]-2-methylpropanoic acid MS: m/z 506.2 (M+1)

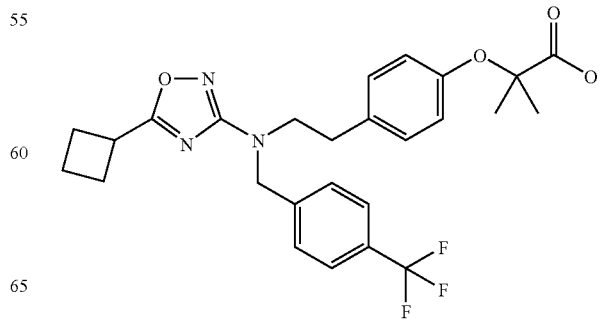

167

2-[4-(2-{(5-cyclobutyl-1,2,4-oxadiazol-3-yl)[4-(trifluoromethyl)benzyl]amino}ethyl)phenoxy]-2-methylpropanoic acid MS: m/z 504.3 (M+1)

168

2-methyl-2-[4-(2-{(5-thien-2-yl-1,2,4-oxadiazol-3-yl)[4-(trifluoromethyl)benzyl]amino}ethyl)phenoxy]propanoic acid MS: m/z 532.2 (M+1)

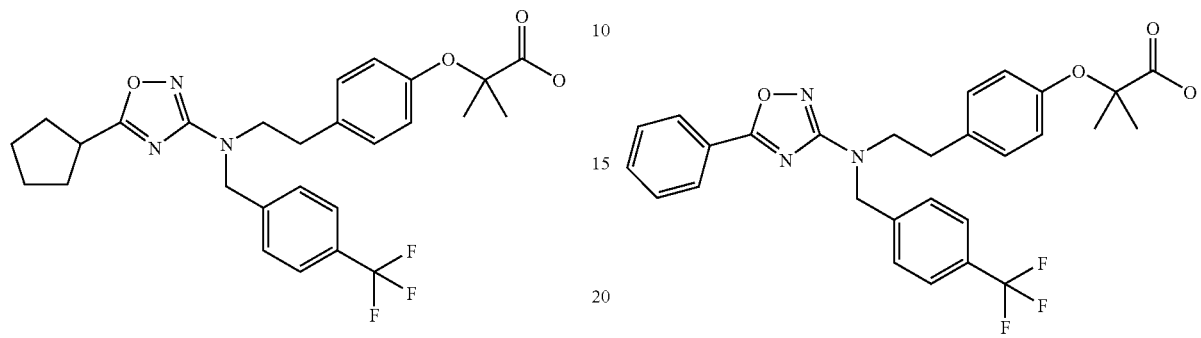

2-[4-(2-{(5-cyclopentyl-1,2,4-oxadiazol-3-yl)[4-(trifluoromethyl)benzyl]amino}ethyl)phenoxy]-2-methylpropanoic acid MS: m/z 518.3 (M+1)

2-methyl-2-[4-(2-{(5-phenyl-1,2,4-oxadiazol-3-yl)[4-(trifluoromethyl)benzyl]amino}ethyl)phenoxy]propanoic acid MS: m/z 526.2 (M+1)

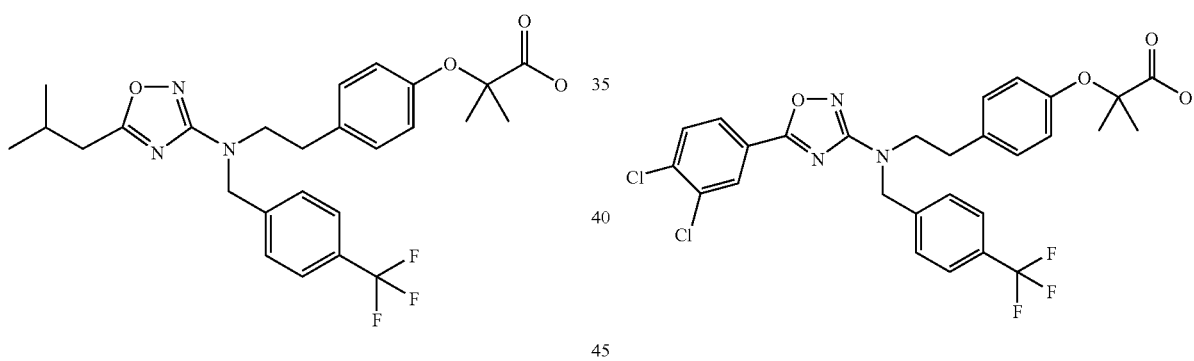

2-[4-(2-{(5-isobutyl-1,2,4-oxadiazol-3-yl)[4-(trifluoromethyl)benzyl]amino}ethyl)phenoxy]-2-methylpropanoic acid MS: m/z 506.3 (M+1)

2-[4-(2-{[5-(3,4-dichlorophenyl)-1,2,4-oxadiazol-3-yl][4-(trifluoromethyl)benzyl]amino}ethyl)phenoxy]-2-methylpropanoic acid MS: m/z 594 (M+1)

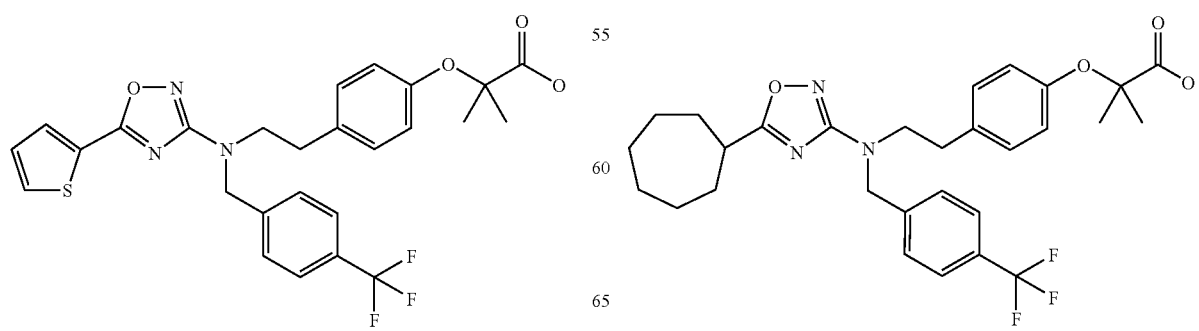

169

2-[4-(2-{(5-cycloheptyl-1,2,4-oxadiazol-3-yl)[4-(trifluoromethyl)benzyl]amino}ethyl)phenoxy]-2-methylpropanoic acid MS: m/z 544 (M−1)

170

2-methyl-2-[4-(2-{[5-(4-methylphenyl)-1,2,4-oxadiazol-3-yl][4-(trifluoromethyl)benzyl]amino}ethyl)phenoxy]propanoic acid MS: m/z 540.1 (M+1)

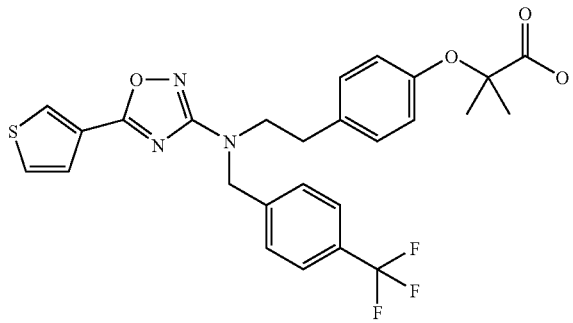

2-methyl-2-[4-(2-{(5-thien-3-yl-1,2,4-oxadiazol-3-yl)[4-(trifluoromethyl)benzyl]amino}ethyl)phenoxy]propanoic acid MS: m/z 529.8 (M−1)

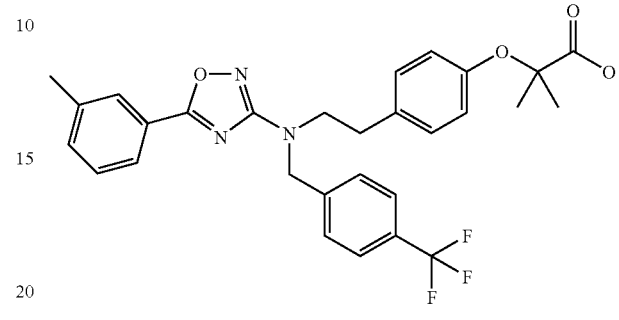

2-methyl-2-[4-(2-{[5-(3-methylphenyl)-1,2,4-oxadiazol-3-yl][4-(trifluoromethyl)benzyl]amino}ethyl)phenoxy]propanoic acid MS: m/z 540.1 (M+1)

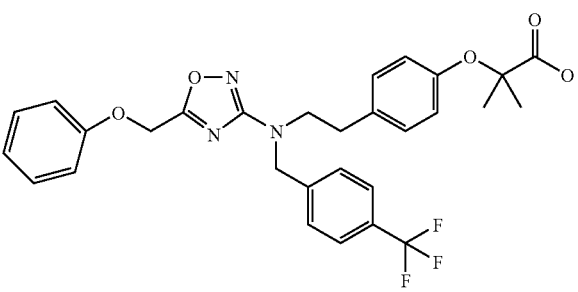

2-methyl-2-[4-(2-{[5-(phenoxymethyl)-1,2,4-oxadiazol-3-yl][4-(trifluoromethyl)benzyl]amino}ethyl)phenoxy]propanoic acid MS: m/z 556.1 (M+1)

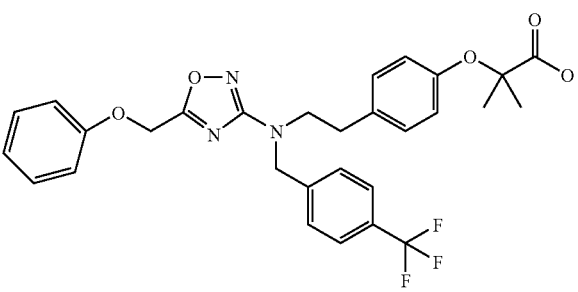

2-[4-(2-{(5-isopentyl-1,2,4-oxadiazol-3-yl)[4-(trifluoromethyl)benzyl]amino}ethyl)phenoxy]-2-methylpropanoic acid MS: m/z 520.2 (M+1)

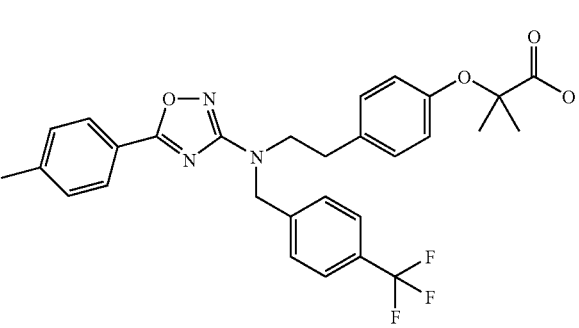

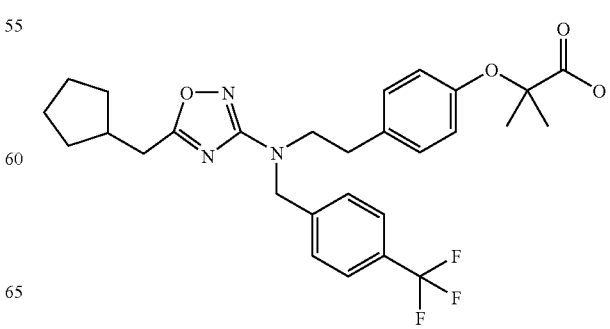

| 171 | 172 |
|---|---|
| 2-[4-(2-{[5-(cyclopentylmethyl)-1,2,4-oxadiazol-3-yl][4-(trifluoromethyl)benzyl]amino}ethyl)phenoxy]-2-methylpropanoic acid | 2-methyl-2-[4-(2-{[4-(trifluoromethyl)benzyl][5-(trifluoromethyl)-1,2,4-oxadiazol-3-yl]amino}ethyl)phenoxy]propanoic acid |

MS: m/z 532.2 (M+1)

MS: m/z 518.1 (M+1)

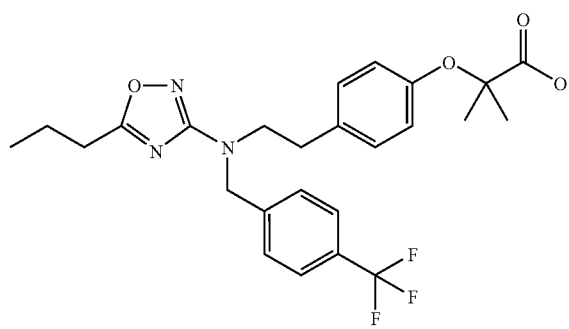

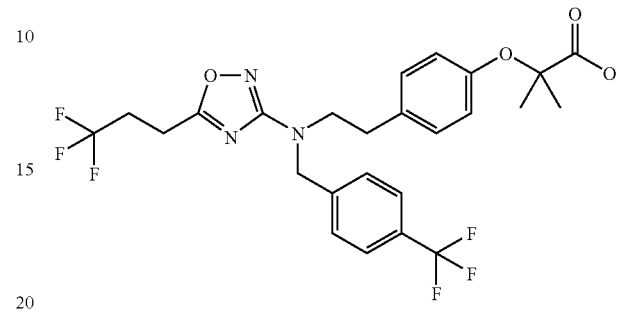

2-methyl-2-[4-(2-{(5-propyl-1,2,4-oxadiazol-3-yl)[4-(trifluoromethyl)benzyl]amino}ethyl)phenoxy]propanoic acid 2-methyl-2-[4-(2-{[4-(trifluoromethyl)benzyl][5-(3,3,3-trifluoropropyl)-1,2,4-oxadiazol-3-yl]amino}ethyl)phenoxy]propanoic acid MS: m/z 492.1 (M+1)

MS: m/z 546.1 (M+1)

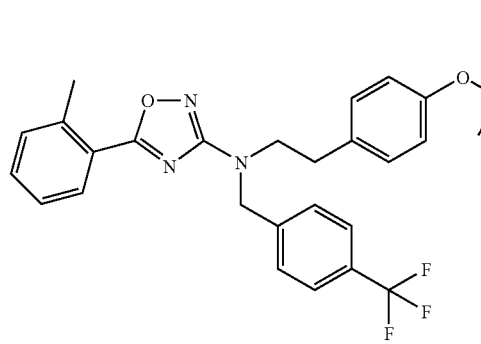

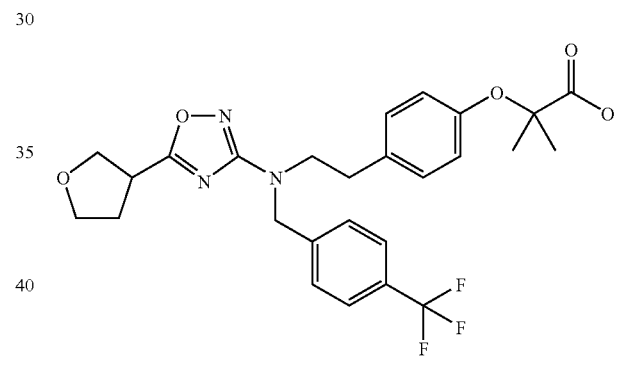

2-methyl-2-[4-(2-{[5-(2-methylphenyl)-1,2,4-oxadiazol-3-yl][4-(trifluoromethyl)benzyl]amino}ethyl)phenoxy]propanoic acid 2-methyl-2-[4-(2-{5-tetrahydrofuran-3-yl-1,2,4-oxadiazol-3-yl)[4-(trifluoromethyl)benzyl]amino}ethyl)phenoxy]propanoic acid MS: m/z 520.1 (M+1)

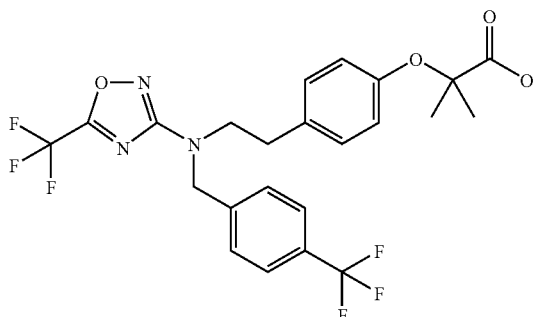

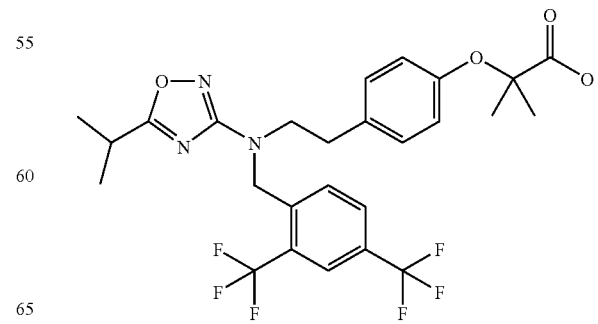

173

2-(4-{2-[[2,4-bis(trifluoromethyl)benzyl](5-isopropyl-1,2,4-oxadiazol-3-yl)amino]ethyl}phenoxy)-2-methylpropanoic acid

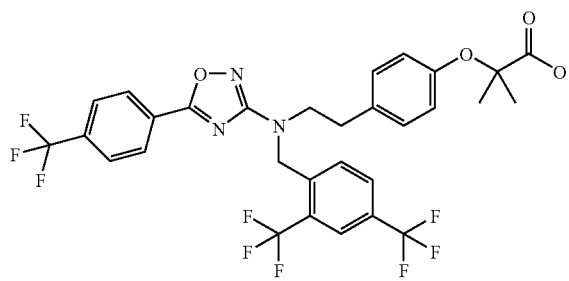

2-{4-[2-([2,4-bis(trifluoromethyl)benzyl]{5-[4-(trifluoromethyl)phenyl]-1,2,4-oxadiazol-3-yl}amino)ethyl]phenoxy}-2-methylpropanoic acid MS: m/z 661.8 (M+1)

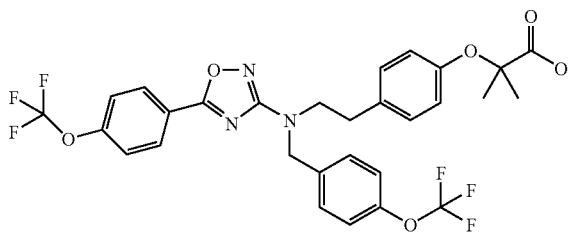

2-methyl-2-{4-[2-([4-(trifluoromethoxy)benzyl]{5-[4-(trifluoromethoxy)phenyl]-1,2,4-oxadiazol-3-yl}amino)ethyl]phenoxy}propanoic acid

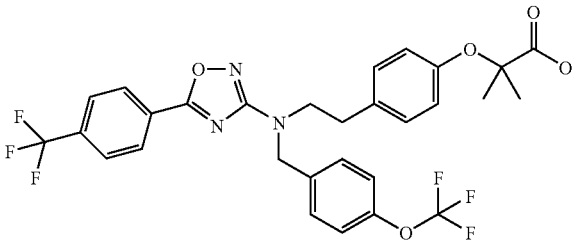

2-methyl-2-{4-[2-([4-trifluoromethoxy)benzyl]{5-[3-(trifluoromethyl)phenyl]-1,2,4-oxadiazol-3-yl}amino)ethyl]phenoxy}propanoic acid

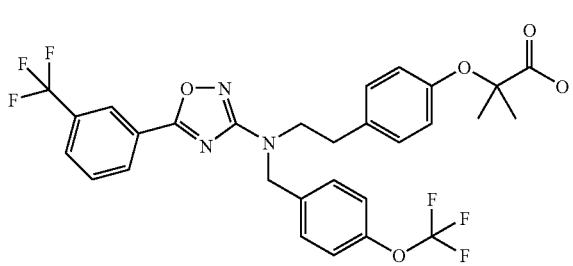

174

2-methyl-2-{4-[2-([4-(trifluoromethoxy)benzyl]{5-[4-(trifluoromethyl)phenyl]-1,2,4-oxadiazol-3-yl}amino)ethyl]phenoxy}propanoic acid

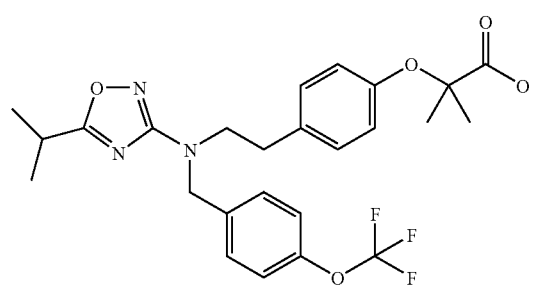

2-[4-(2-{(5-isopropyl-1,2,4-oxadiazol-3-yl)[4-(trifluoromethoxy)benzyl]amino}ethyl)phenoxy]-2-methylpropanoic acid

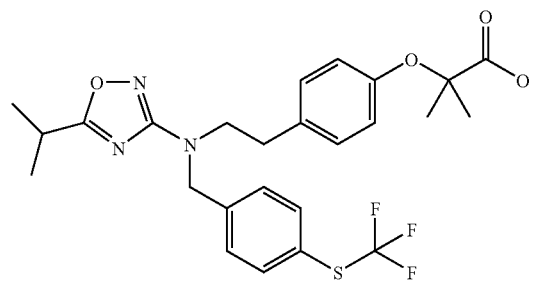

2-{4-[2-((5-isopropyl-1,2,4-oxadiazol-3-yl){4-[(trifluoromethyl)thio]benzyl}amino)ethyl]phenoxy}-2-methylpropanoic acid

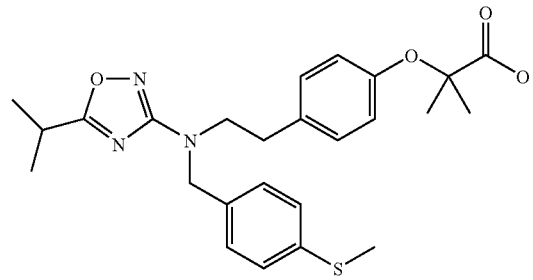

175

2-[4-(2-{(5-isopropyl-1,2,4-oxadiazol-3-yl)[4-(methylthio)benzyl]amino}ethyl)phenoxy]-2-methylpropanoic acid

176

2-methyl-2-[4-(2-{(5-{1-[(methylamino)carbonyl]piperidin-4-yl}-1,2,4-oxadiazol-3-yl)[4-(trifluoromethyl)benzyl]amino}ethyl)phenoxy]propanoic acid MS: m/z 590.1 (M+1)

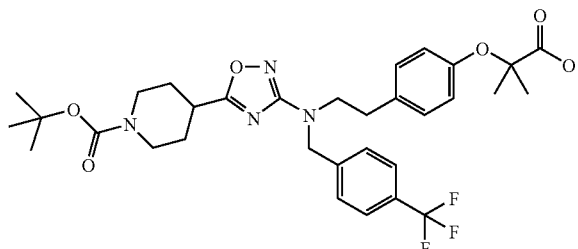

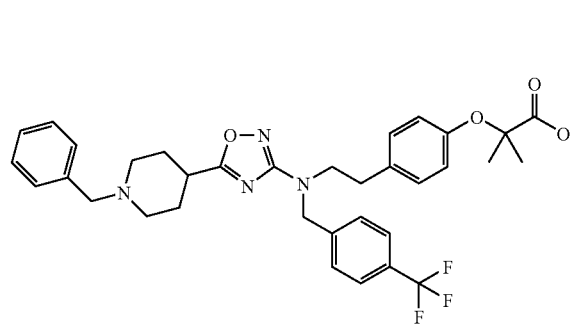

2-[4-(2-{{5-[1-(tert-butoxycarbonyl)piperidin-4-yl]-1,2,4-oxadiazol-3-yl}[4-(trifluoromethyl)benzyl]amino}ethyl)phenoxy]-2-methylpropanoic acid MS: m/z 633.2 (M+1)

2-[4-(2-{[5-(1-benzylpiperidin-4-yl)-1,2,4-oxadiazol-3-yl][4-(trifluoromethyl)benzyl]amino}ethyl)phenoxy]-2-methylpropanoic acid MS: m/z 623.2 (M+1)

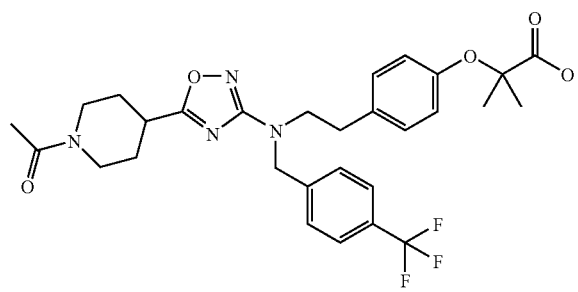

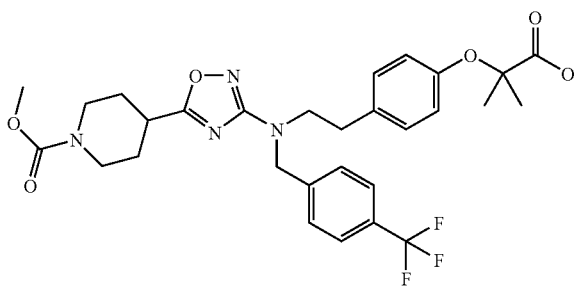

2-[4-(2-{[5-(1-acetylpiperidin-4-yl)-1,2,4-oxadiazol-3-yl][4-(trifluoromethyl)benzyl]amino}ethyl)phenoxy]-2-methylpropanoic acid MS: m/z 515.1 (M+1)

2-[4-(2-{{5-[1-(methoxycarbonyl)piperidin-4-yl]-1,2,4-oxadiazol-3-yl}[4-(trifluoromethyl)benzyl]amino}ethyl)phenoxy]-2-methylpropanoic acid MS: m/z 591.2 (M+1)

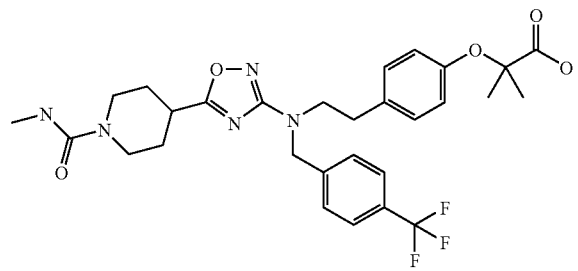

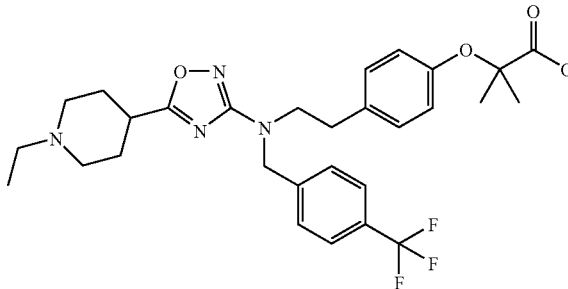

177

2-[4-(2-{[5-(1-ethylpiperidin-4-yl)-1,2,4-oxadiazol-3-yl][4-(trifluoromethyl)benzyl]amino}ethyl)phenoxy]-2-methylpropanoic acid MS: m/z 561.1 (M+1)

178

2-[4-(2-{{5-[1-(ethoxycarbonyl)piperidin-4-yl]-1,2,4-oxadiazol-3-yl}[4-(trifluoromethyl)benzyl]amino}ethyl)phenoxy]-2-methylpropanoic acid MS: m/z 605 (M+1)

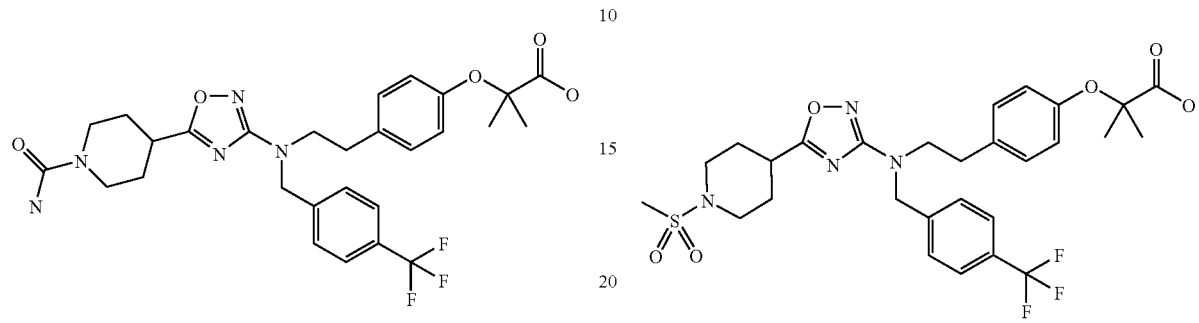

2-[4-(2-{{5-[1-(aminocarbonyl)piperidine-4-yl]-1,2,4-oxadiazol-3-yl}[4-(trifluoromethyl)benzyl]amino}ethyl)phenoxy]-2-methylpropanoic acid MS: m/z 576.2 (M+1)

2-methyl-2-[4-(2-{{5-[1-(methylsulfonyl)piperidin-4-yl]-1,2,4-oxadiazol-3-yl}[4-(trifluoromethyl)benzyl]amino}ethyl)phenoxy]propanoic acid

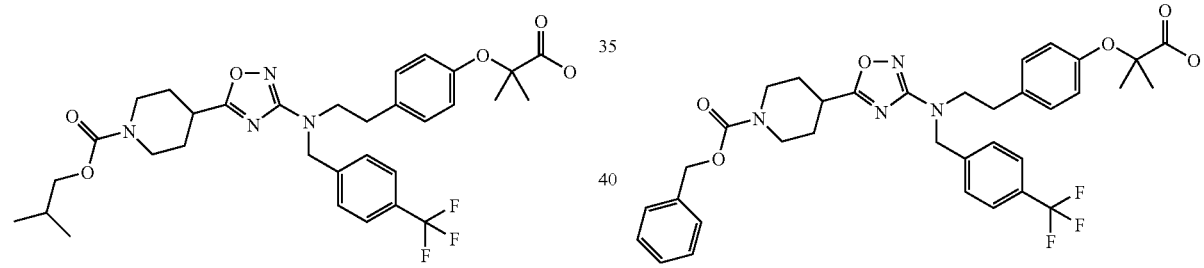

2-[4-(2-{{5-[1-(isobutoxycarbonyl)piperidin-4-yl]-1,2,4-oxadiazol-3-yl}[4-(trifluoromethyl)benzyl]amino}ethyl)phenoxy]-2-methylpropanoic acid MS: m/z 633 (M+1)

2-[4-(2-{(5-{1-[(benzyloxy)carbonyl]piperidin-4-yl}-1,2,4-oxadiazol-3-yl)[4-(trifluoromethyl)benzyl]amino}ethyl)phenoxy]-2-methylpropanoic acid MS: m/z 667 (M+1)

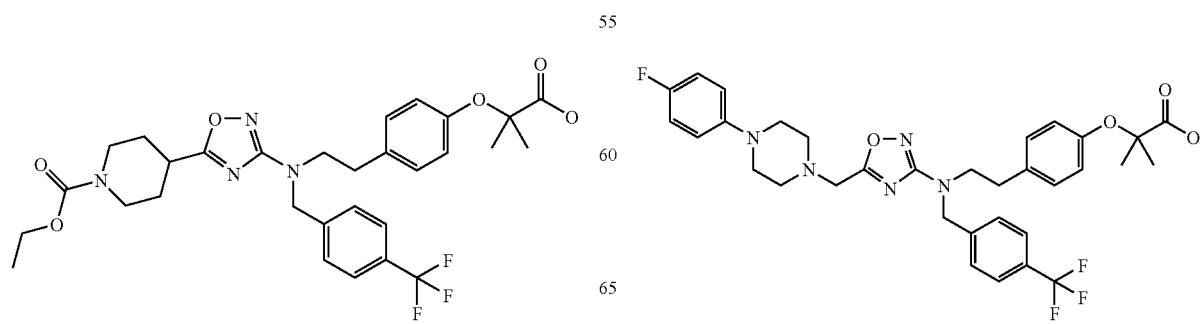

2-[4-(2-{(5-{[4-(4-fluorophenyl)piperazin-1-yl]methyl}-1,2,4-oxadiazol-3-yl)[4-(trifluoromethyl)benzyl]amino}ethyl)phenoxy]-2-methylpropanoic acid MS: m/z 640.1 (M−1)

2-methyl-2-{2-methyl-4-[2-([4-(trifluoromethoxy)benzyl]{5-[4-(trifluoromethyl)phenyl]-1,2,4-oxadiazol-3-yl}amino)ethyl]phenoxy}propanoic acid

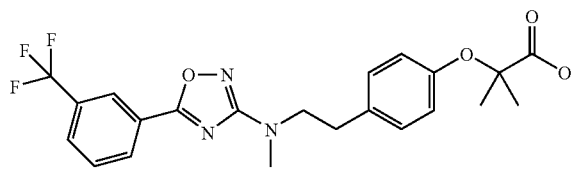

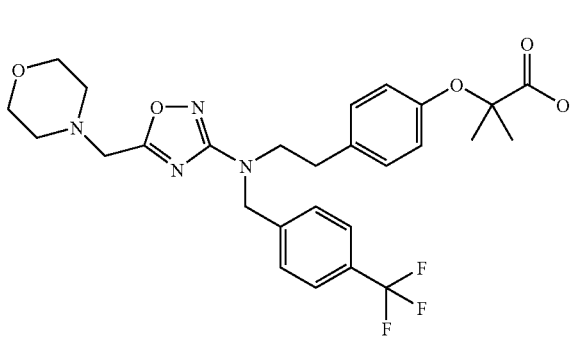

2-methyl-2-{4-[2-(methyl{5-[3-(trifluoromethyl)phenyl]-1,2,4-oxadiazol-3-yl}amino)ethyl]phenoxy}propanoic acid MS: m/z 506.2 (M+1)

2-methyl-2-[4-(2-{[5-(morpholin-4-ylmethyl)-1,2,4-oxadiazol-3-yl][4-(trifluoromethyl)benzyl]amino}ethyl)phenoxy]propanoic acid MS: m/z 549 (M+1)

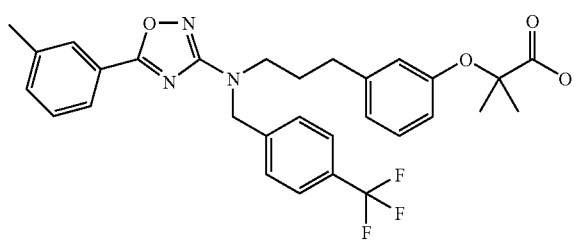

2-methyl-2-[3-(3-{[5-(2-methylphenyl)-1,2,4-oxadiazol-3-yl][4-(trifluoromethyl)benzyl]amino}propyl)phenoxy]propanoic acid

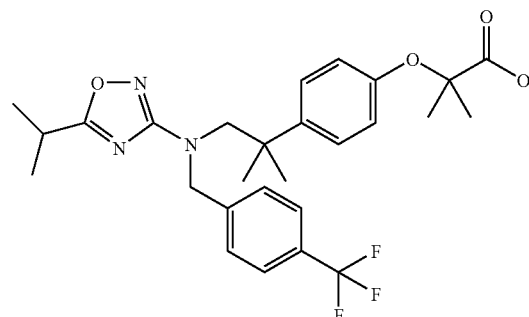

2-[4-(2-{(5-isopropyl-1,2,4-oxadiazol-3-yl)[4-(trifluoromethyl)benzyl]amino}-1,1-dimethylethyl)phenoxy]-2-methylpropanoic acid 2-methyl-2-[3-(3-{[5-(3-methylphenyl)-1,2,4-oxadiazol-3-yl][4-(trifluoromethyl)benzyl]amino}propyl)phenoxy]propanoic acid

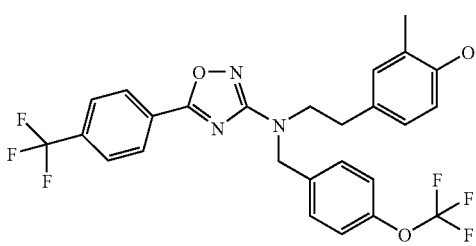

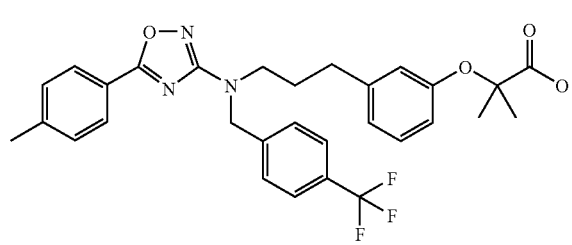

181

2-methyl-2-[3-(3-{[5-(4-methylphenyl)-1,2,4-oxadiazol-3-yl][4-(trifluoromethyl)benzyl]amino}propyl)phenoxy]propanoic acid

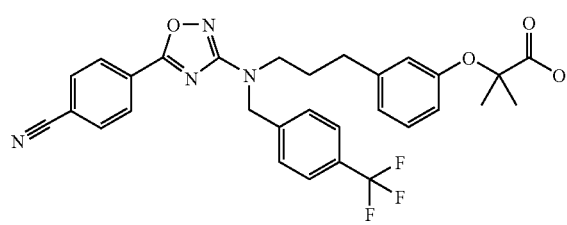

2-[3-(3-{[5-(4-cyanophenyl)-1,2,4-oxadiazol-3-yl][4-(trifluoromethyl)benzyl]amino}propyl)phenoxy]-2-methylpropanoic acid

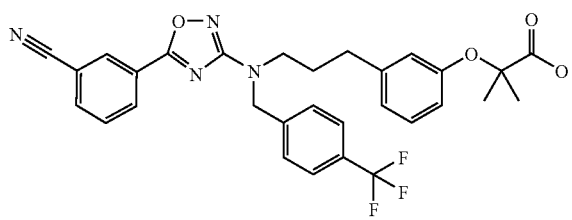

2-[3-(3-{[5-(3-cyanophenyl)-1,2,4-oxadiazol-3-yl][4-(trifluoromethyl)benzyl]amino}propyl)phenoxy]-2-methylpropanoic acid

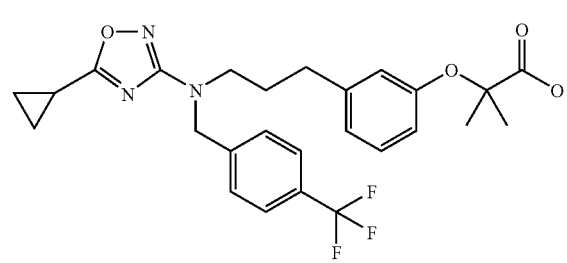

182

2-[3-(3-{(5-cyclopropyl-1,2,4-oxadiazol-3-yl)[4-(trifluoromethyl)benzyl]amino}propyl)phenoxy]-2-methylpropanoic acid

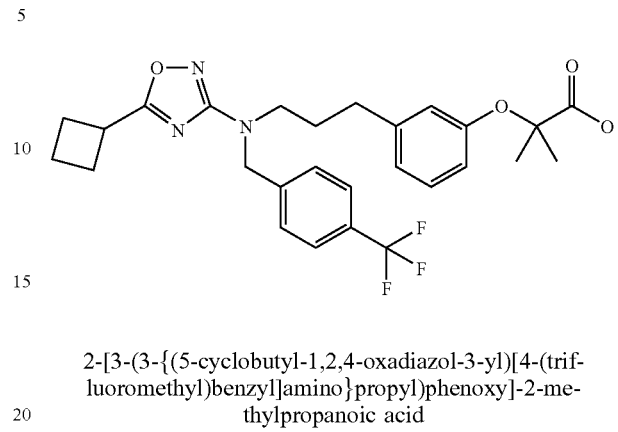

2-[3-(3-{(5-cyclobutyl-1,2,4-oxadiazol-3-yl)[4-(trifluoromethyl)benzyl]amino}propyl)phenoxy]-2-methylpropanoic acid 2-[3-(3-{(5-cyclopentyl-1,2,4-oxadiazol-3-yl)[4-(trifluoromethyl)benzyl]amino}propyl)phenoxy]-2-methylpropanoic acid

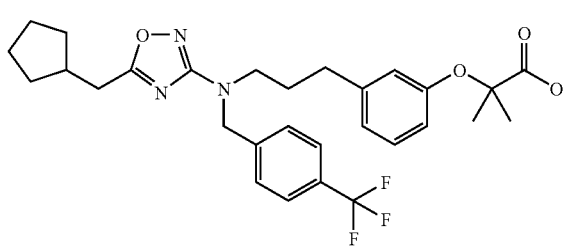

2-[3-(3-{[5-(cyclopentylmethyl)-1,2,4-oxadiazol-3-yl][4-(trifluoromethyl)benzyl]amino}propyl)phenoxy]-2-methylpropanoic acid

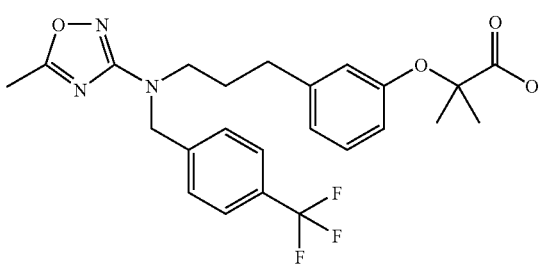

183

2-methyl-2-[3-(3-{(5-methyl-1,2,4-oxadiazol-3-yl)
[4-(trifluoromethyl)benzyl]amino}propyl)phenoxy]
propanoic acid

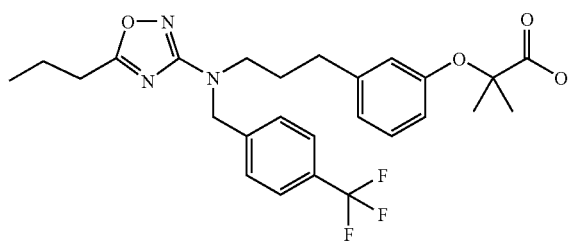

2-methyl-2-[3-(3-{(5-propyl-1,2,4-oxadiazol-3-yl)
[4-(trifluoromethyl)benzyl]amino}propyl)phenoxy]
propanoic acid

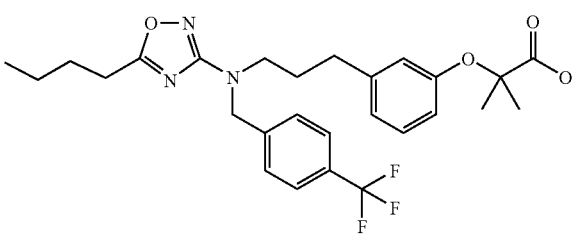

2-[3-(3-{(5-butyl-1,2,4-oxadiazol-3-yl)[4-(trifluo-
romethyl)benzyl]amino}propyl)phenoxy]-2-methyl-
propanoic acid

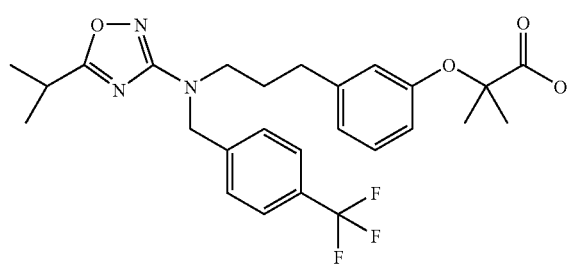

2-[3-(3-{(5-isopropyl-1,2,4-oxadiazol-3-yl)[4-(trif-
luoromethyl)benzyl]amino}propyl)phenoxy]-2-me-
thylpropanoic acid

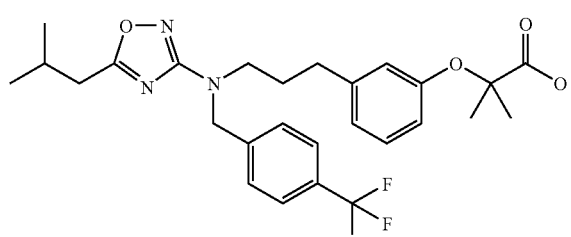

184

2-[3-(3-{(5-isobutyl-1,2,4-oxadiazol-3-yl)[4-(trifluo-
romethyl)benzyl]amino}propyl)phenoxy]-2-methyl-
propanoic acid

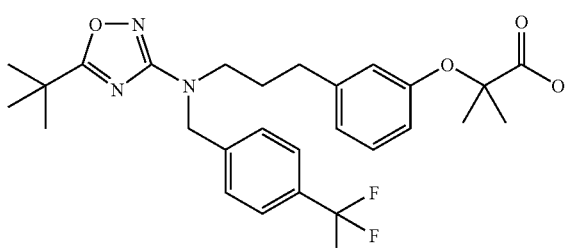

2-[3-(3-{(5-tert-butyl-1,2,4-oxadiazol-3-yl)[4-(trif-
luoromethyl)benzyl]amino}propyl)phenoxy]-2-me-
thylpropanoic acid

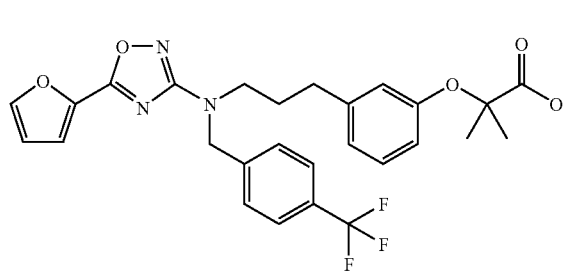

2-[3-(3-{[5-(2-furyl)-1,2,4-oxadiazol-3-yl][4-(trif-
luoromethyl)benzyl]amino}propyl)phenoxy]-2-me-
thylpropanoic acid

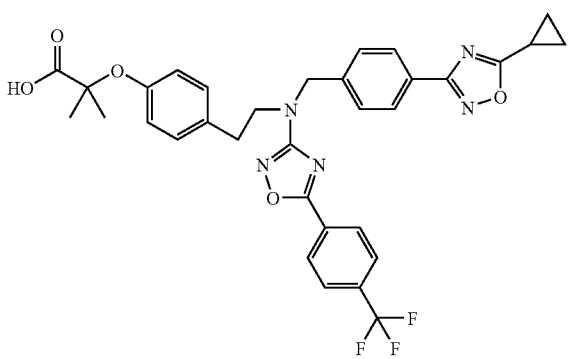

2-{4-[2-([4-(5-Cyclopropyl-1,2,4-oxadiazol-3-yl)
benzyl]{5-[4-(trifluoromethyl)phenyl]-1,2,4-oxadia-
zol-3-yl}amino)ethyl]phenoxy}-2-methylpropanoic
acid Similarly prepared from tert-butyl 2-[4-(2-{[4-(5-cyclo-
propyl-1,2,4-oxadiazol-3-yl)benzyl]amino}ethyl)phenoxy]-
2-methylpropanoate and 4-trifluoromethyl benzoyl chloride.

$^1$H NMR (CDCl$_3$) δ 8.21 (d, 2H, J=8.2), 7.9 (d, 2H,
J=8.2), 7.7 (d, 2H, J=8.2), 7.22 (d, 2H, J=8.2), 6.99 (d, 2H,

J=8.5), 6.78 (d, 2H, J=8.5), 4.61 (s, 2H), 3.64 (t, 2H, J=7.2), 2.92 (t, 2H, J=7.2), 2.28 (m, 1H), 1.57 (s, 6H), 1.30 (m, 4H).

The following 22 compounds were prepared using similar procedures to those described above.

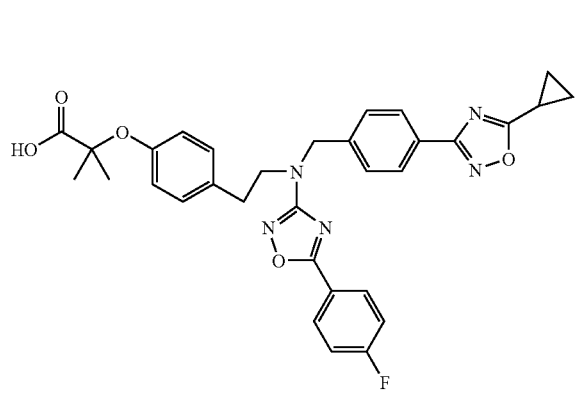

2-[4-(2-{[4-(5-Cyclopropyl-1,2,4-oxadiazol-3-yl)benzyl][5-(4-fluorophenyl)-1,2,4-oxadiazol-3-yl]amino}ethyl)phenoxy]-2-methylpropanoic acid Similarly prepared from tert-butyl 2-[4-(2-{[4-(5-cyclopropyl-1,2,4-oxadiazol-3-yl)benzyl]amino}ethyl)phenoxy]-2-methylpropanoate and 4-fluorobenzoyl chloride.

$^1$H NMR (CDCl$_3$) δ 8.13 (m, 2H), 7.94 (d, 2H, J=8.2), 7.26 (m, 4H), 7.04 (d, 2H, J=8.5), 6.83 (d, 2H, J=8.5), 4.63 (s, 2H), 3.65 (t, 2H, J=7.4), 2.94 (t, 2H, J=7.4), 2.31 (m, 1H), 1.61 (s, 6H), 1.32 (m, 4H).

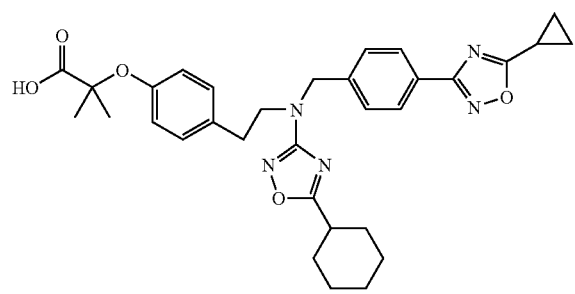

2-[4-(2-{(5-Cyclohexyl-1,2,4-oxadiazol-3-yl)[4-(5-cyclopropyl-1,2,4-oxadiazol-3-yl)benzyl]amino}ethyl)phenoxy]-2-methylpropanoic acid Similarly prepared from tert-butyl 2-[4-(2-{[4-(5-cyclopropyl-1,2,4-oxadiazol-3-yl)benzyl]amino}ethyl)phenoxy]-2-methylpropanoate and cyclohexanecarbonyl chloride. $^1$H NMR (CDCl$_3$) δ 7.87 (d, 2H, J=8.3), 7.17 (d, 2H, J=8.3), 6.95 (d, 2H, J=8.5), 6.76 (d, 2H, J=8.5), 4.52 (s, 2H), 3.53 (t, 2H, J=7.2), 2.83 (m, 3H), 2.28 (m, 1H), 2.06 (m, 2H), 1.83 (m, 2H), 1.65 (m, 2H), 1.57 (s, 6H), 1.32 (m, 8H).

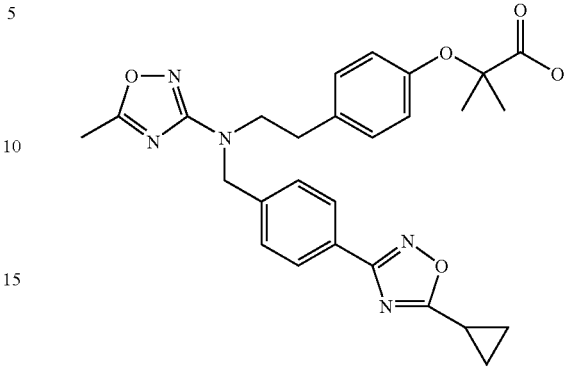

2-(4-{2-[[4-(5-cyclopropyl-1,2,4-oxadiazol-3-yl)benzyl](5-methyl-1,2,4-oxadiazol-3-yl)amino]ethyl}phenoxy)-2-methylpropanoic acid MS: m/z 504.3 (M+1).

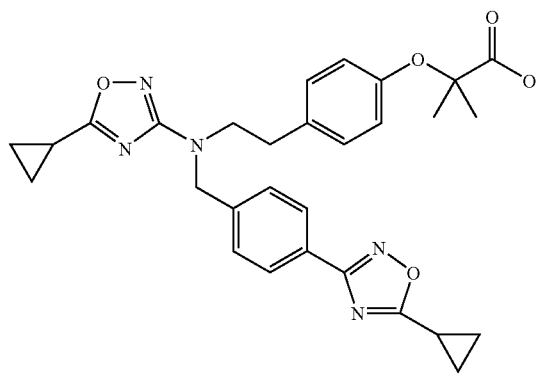

2-[4-(2-{(5-cyclopropyl-1,2,4-oxadiazol-3-yl)[4-(5-cyclopropyl-1,2,4-oxadiazol-3-yl)benzyl]amino}ethyl)phenoxy]-2-methylpropanoic acid MS: m/z 530.3 (M+1)

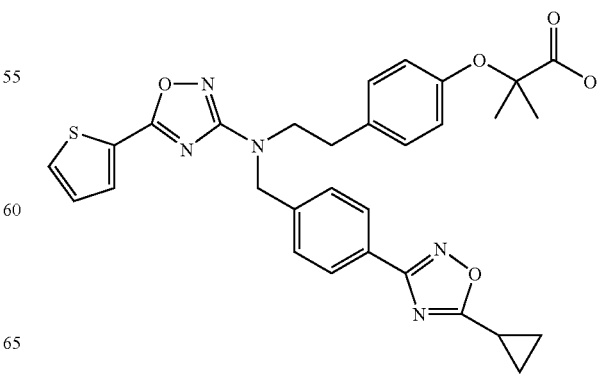

187

2-(4-{2-[[4-(5-cyclopropyl-1,2,4-oxadiazol-3-yl)
benzyl](5-thien-2-yl-1,2,4-oxadiazol-3-yl)amino]
ethyl}phenoxy)-2-methylpropanoic acid MS: m/z 572.2 (M+1)

188

2-(4-{2-[[4-(5-cyclopropyl-1,2,4-oxadiazol-3-yl)
benzyl](5-isobutyl-1,2,4-oxadiazol-3-yl)amino]
ethyl}phenoxy)-2-methylpropanoic acid MS: m/z 546.3 (M+1)

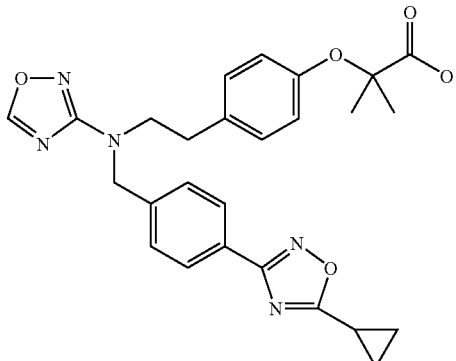

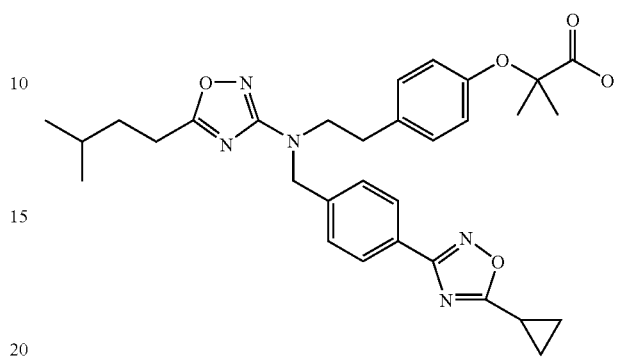

2-(4-{2-[[4-(5-cyclopropyl-1,2,4-oxadiazol-3-yl)
benzyl](1,2,4-oxadiazol-3-yl)amino]ethyl}phenoxy)-
2-methylpropanoic acid MS: m/z 490.2 (M+1)

2-(4-{2-[[4-(5-cyclopropyl-1,2,4-oxadiazol-3-yl)
benzyl](5-isopentyl-1,2,4-oxadiazol-3-yl)amino]
ethyl}phenoxy)-2-methylpropanoic acid MS: m/z 560.3 (M+1)

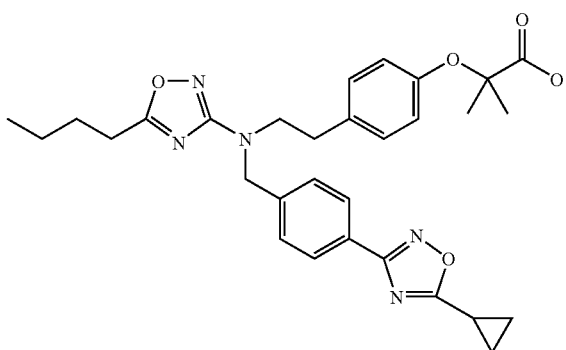

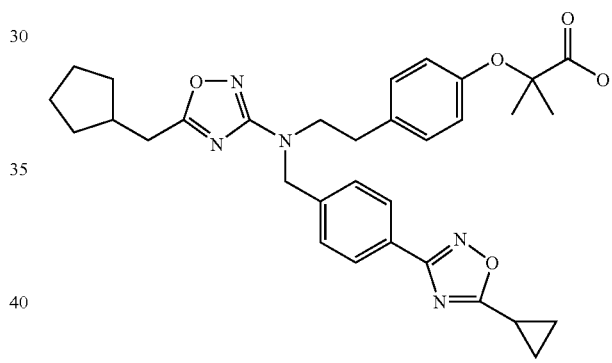

2-[4-(2-{(5-butyl-1,2,4-oxadiazol-3-yl)[4-(5-cyclo-
propyl-1,2,4-oxadiazol-3-yl)benzyl]amino}ethyl)
phenoxy]-2-methylpropanoic acid MS: m/z 546.3 (M+1)

2-[4-(2-{[5-(cyclopentylmethyl)-1,2,4-oxadiazol-3-
yl][4-(5-cyclopropyl-1,2,4-oxadiazol-3-yl)benzyl]
amino}ethyl)phenoxy]-2-methylpropanoic acid MS: m/z 572.3 (M+1)

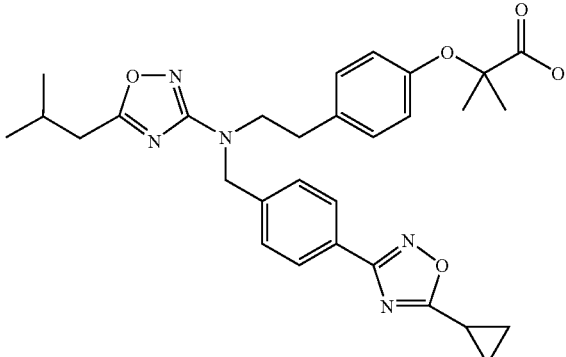

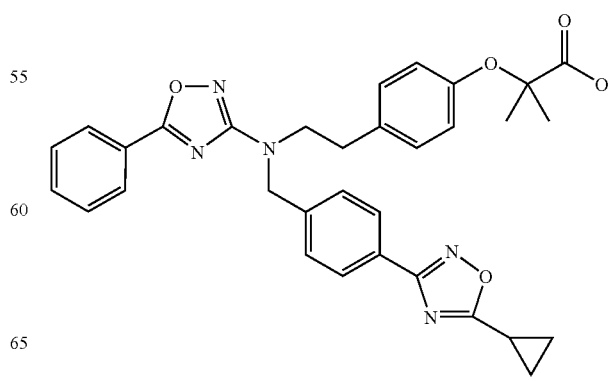

189

2-(4-{2-[[4-(5-cyclopropyl-1,2,4-oxadiazol-3-yl)benzyl](5-phenyl-1,2,4-oxadiazol-3-yl)amino]ethyl}phenoxy)-2-methylpropanoic acid MS: m/z 566.2 (M+1)

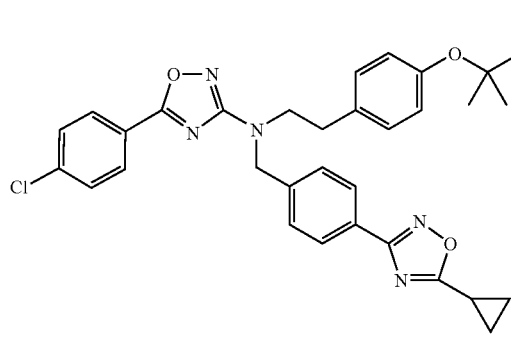

2-[4-(2-{[5-(4-chlorophenyl)-1,2,4-oxadiazol-3-yl][4-(5-cyclopropyl-1,2,4-oxadiazol-3-yl)benzyl]amino}ethyl)phenoxy]-2-methylpropanoic acid MS: m/z 600.2 (M+1)

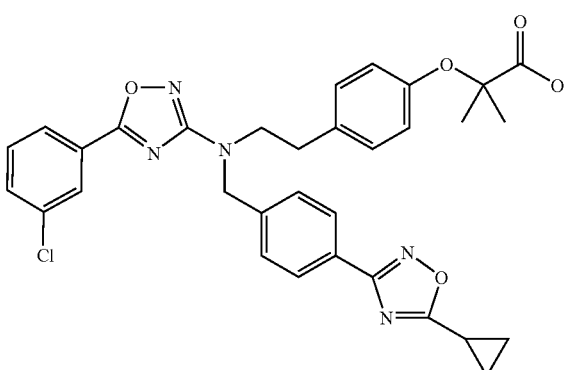

2-[4-(2-{[5-(3-chlorophenyl)-1,2,4-oxadiazol-3-yl][4-(5-cyclopropyl-1,2,4-oxadiazol-3-yl)benzyl]amino}ethyl)phenoxy]-2-methylpropanoic acid MS: m/z 600.2 (M+1)

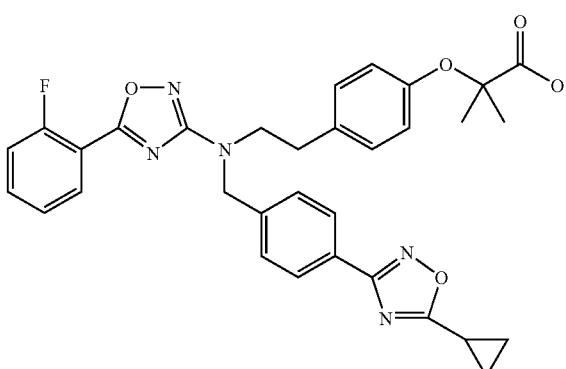

190

2-[4-(2-{[4-(5-cyclopropyl-1,2,4-oxadiazol-3-yl)benzyl][5-(2-fluorophenyl)-1,2,4-oxadiazol-3-yl]amino}ethyl)phenoxy]-2-methylpropanoic acid MS: m/z 584.3 (M+1)

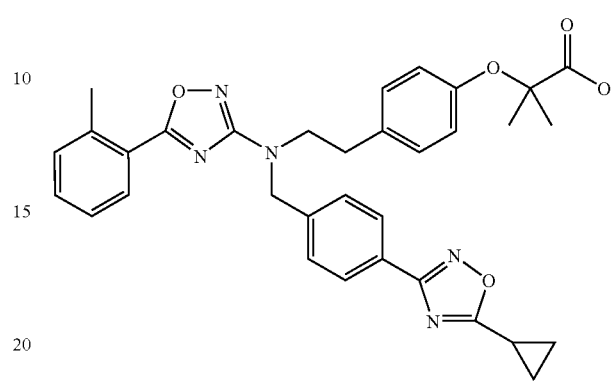

2-[4-(2-{[4-(5-cyclopropyl-1,2,4-oxadiazol-3-yl)benzyl][5-(2-methylphenyl)-1,2,4-oxadiazol-3-yl]amino}ethyl)phenoxy]-2-methylpropanoic acid MS: m/z 580.3 (M+1)

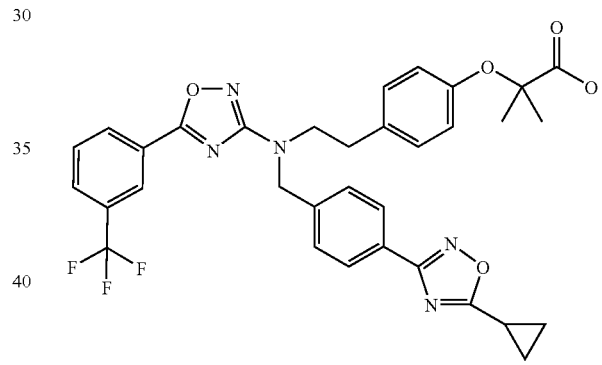

2-{4-[2-([4-(5-cyclopropyl-1,2,4-oxadiazol-3-yl)benzyl]{5-[3-(trifluoromethyl)phenyl]-1,2,4-oxadiazol-3-yl}amino)ethyl]phenoxy}-2-methylpropanoic acid MS: m/z 633.9 (M+1)

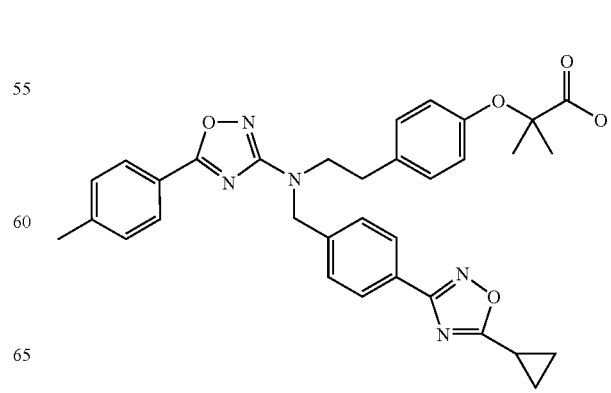

| 191 | 192 |
|---|---|
| 2-[4-(2-{[4-(5-cyclopropyl-1,2,4-oxadiazol-3-yl)benzyl][5-(4-methylphenyl)-1,2,4-oxadiazol-3-yl]amino}ethyl)phenoxy]-2-methylpropanoic acid | 2-{4-[2-([4-(5-cyclopropyl-1,2,4-oxadiazol-3-yl)benzyl]{5-[3-fluoro-4-(trifluoromethyl)phenyl]-1,2,4-oxadiazol-3-yl}amino)ethyl]phenoxy}-2-methyl-propanoic acid |

MS: m/z 577.6 (M−1)

MS: m/z 649.7 (M−1)

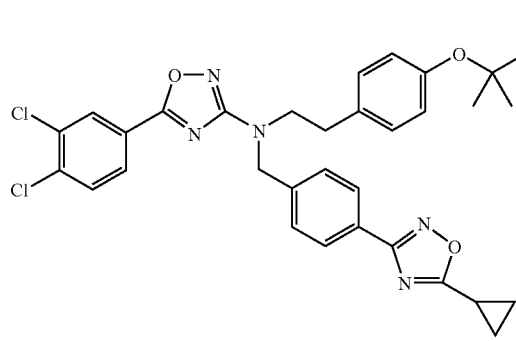

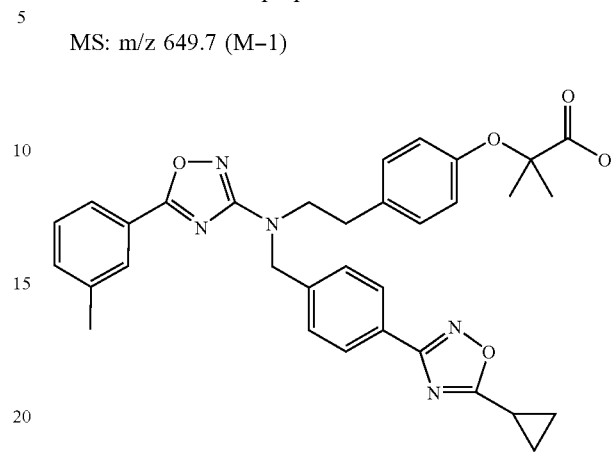

2-[4-(2-{[4-(5-cyclopropyl-1,2,4-oxadiazol-3-yl)benzyl][5-(3,4-dichlorophenyl)-1,2,4-oxadiazol-3-yl]amino}ethyl)phenoxy]-2-methylpropanoic acid 2-[4-(2-{[4-(5-cyclopropyl-1,2,4-oxadiazol-3-yl)benzyl][5-(3-methylphenyl)-1,2,4-oxadiazol-3-yl]amino}ethyl)phenoxy]-2-methylpropanoic acid MS: m/z 634.1 (M+1)

MS: m/z 580.2 (M+1)

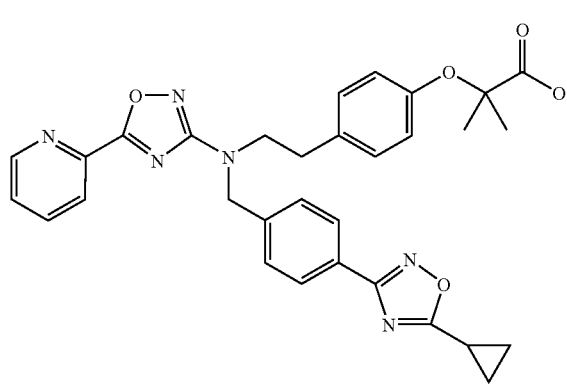

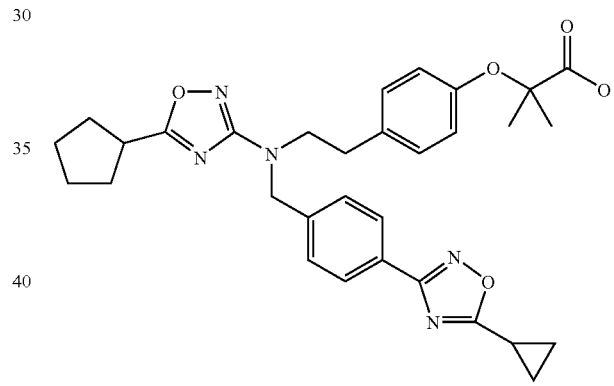

2-(4-{2-[[4-(5-cyclopropyl-1,2,4-oxadiazol-3-yl)benzyl](5-pyridin-2-yl-1,2,4-oxadiazol-3-yl)amino]ethyl}phenoxy)-2-methylpropanoic acid 2-[4-(2-{(5-cyclopentyl-1,2,4-oxadiazol-3-yl)[4-(5-cyclopropyl-1,2,4-oxadiazol-3-yl)benzyl]amino}ethyl)phenoxy]-2-methylpropanoic acid MS: m/z 567.2 (M+1)

MS: m/z 556.1 (M−1)

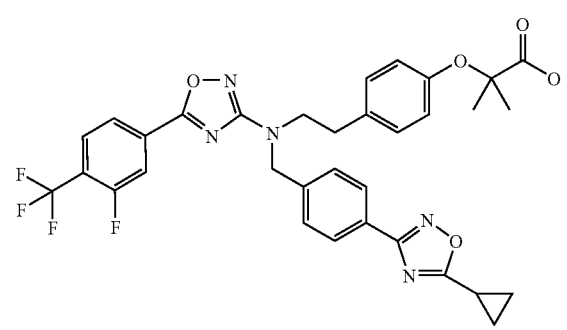

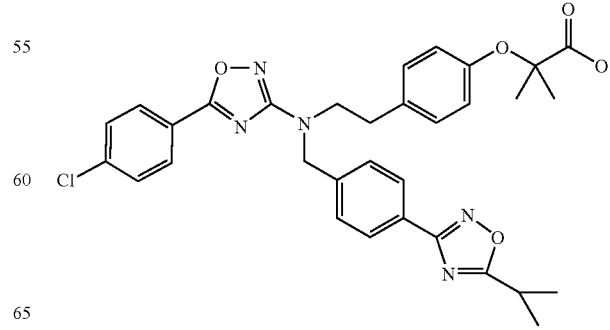

2-[4-(2-{[5-(4-chlorophenyl)-1,2,4-oxadiazol-3-yl][4-(5-isopropyl-1,2,4-oxadiazol-3-yl)benzyl]amino}ethyl)phenoxy]-2-methylpropanoic acid MS: m/z 602.1 (M+1)

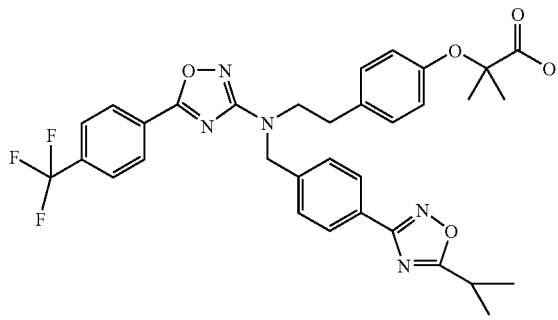

2-{4-[2-([4-(5-isopropyl-1,2,4-oxadiazol-3-yl)benzyl]{5-[4-(trifluoromethyl)phenyl]-1,2,4-oxadiazol-3-yl}amino)ethyl]phenoxy}-2-methylpropanoic acid MS: m/z 636.1 (M+1)

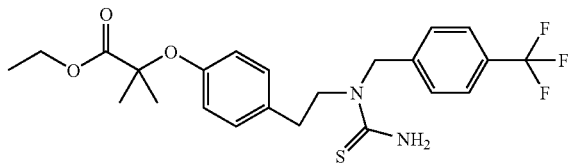

Ethyl 2-[4-(2-{(aminocarbonothioyl)[4-(trifluoromethyl)benzyl]amino}ethyl)phenoxy]-2-methylpropanoate A solution of ethyl 2-methyl-2-{[4-(2-([4-(trifluoromethyl)benzyl]amino}ethyl)phenoxy]propanoate (9 g; 22 mmol) and ammonium thiocyanate (1.67 g; 22 mmol) in 44 ml of xylene was heated at reflux for 12 hr. The mixture was concentrated and purified by flash chromatography using ethyl acetate-hexane mixtures (20–40% gradient) to afford the title compound (6.4 g; 62% yield).

$^1$H NMR (CDCl$_3$) δ 7.57 (d, 2H, J=7.9), 7.32 (d, 2H, J=7.6), 7.01 (d, 2H, J=8.), 6.78 (d, 2H, J=8.5), 4.20 (q, 2H, J=7.0), 3.73 (b, 2H), 2.89 (b, 2H), 1.54 (s, 6H), 1.23 (t, 3H, J=7.3).

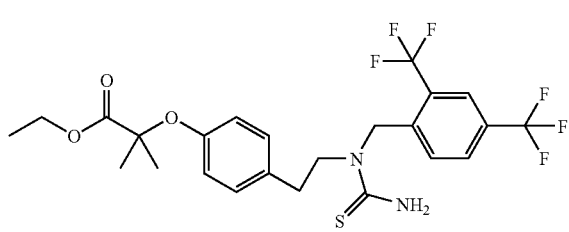

Ethyl 2-[4-(2-{(aminocarbonothioyl)[2,4-bis(trifluoromethyl)benzyl]amino}ethyl)phenoxy]-2-methylpropanoate Similarly prepared from ethyl 2-[4-(2-{[2,4-bis(trifluoromethyl)benzyl]amino}ethyl)phenoxy]-2-methylpropanoate.

$^1$H NMR (CDCl$_3$) δ 7.85 (s, 1H), 7.71 (d, 1H, J=7.7), 7.53 (b, 2H), 7.00 (d, 2H, J=7.9), 6.74 (d, 2H, J=8.1), 4.17 (q, 2H, J=6.9), 3.58 (b, 2H), 2.87 (b, 2H), 1.51 (s, 6H), 1.20 (t, 3H, J=7.0).

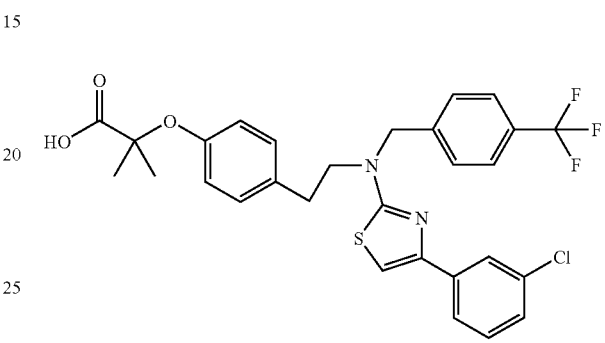

2-[4-(2-{[4-(3-Chlorophenyl)-1,3-thiazol-2-yl][4-(trifluoromethyl)benzyl]amino}ethyl)phenoxy]-2-methylpropanoic acid Step 1. A solution of ethyl 2-[4-(2-{(aminocarbonothioyl)[4-(trifluoromethyl)benzyl]amino}ethyl)phenoxy]-2-methylpropanoate (162 mg; 0.35 mmol) and 3-chlorophenacyl bromide (82 mg; 0.35 mmol) in EtOH (4 ml) was heated to reflux for 12 hr. Upon cooling the mixture was concentrated and the residue purified by flash chromatography using ethyl acetate-hexane mixtures (5–50% gradient) to afford ethyl 2-[4-(2-{[4-(3-chlorophenyl)-1,3-thiazol-2-yl][4-(trifluoromethyl)benzyl]amino}ethyl)phenoxy]-2-methylpropanoate (128 mg; 61% yield).

Step 2. The intermediate ester above was hydrolyzed with LiOH as per general procedure H. After standard aqueous workup the title compound was obtained in good yield.

$^1$H NMR (CD$_3$OD) δ 7.84 (s, 1H), 7.74 (d, 1H, J=7.7), 7.63 (d, 2H, J=8.1), 7.47 (d, 2H, J=8.0), 7.36–7.24 (m, 3H), 7.13 (d, 2H, J=8.2), 7.00 (s, 1H), 6.85 (d, 2H, J=8.4), 4.73 (s, 1H), 3.72 (t, 2H, J=7.2), 2.96 (t, 2H, J=7.4), 1.52 (s, 6H). MS: m/z 575 (M+1).

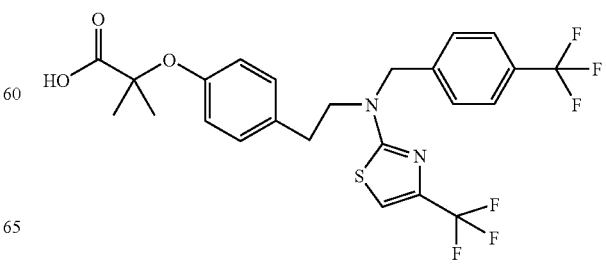

2-Methyl-2-[4-(2-{[4-(trifluoromethyl)benzyl][4-(trifluoromethyl)-1,3-thiazol-2-yl]amino}ethyl)phenoxy]propanoic acid Similarly prepared from ethyl 2-[4-(2-{(aminocarbonothioyl)[4-(trifluoromethyl)benzyl]amino}ethyl)phenoxy]-2-methylpropanoate and 3-bromo-1,1,1-trifluoroacetone.

$^1$H NMR (CD$_3$OD) δ 7.62 (d, 2H, J=8.1), 7.42 (d, 2H, J=8.0), 7.15 (s, 1H), 7.09 (d, 2H, J=8.4), 6.83 (d, 2H, J=8.4), 4.68 (s, 2H), 3.68 (t, 2H, J=7.2), 2.91 (t, 2H, J=7.3), 1.52 (s, 6H).

MS: m/z 533 (M+1).

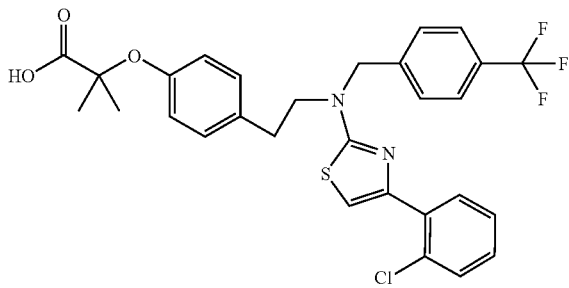

2-[4-(2-{[4-(2-Chlorophenyl)-1,3-thiazol-2-yl][4-(trifluoromethyl)benzyl]amino}ethyl)phenoxy]-2-methylpropanoic acid Similarly prepared from ethyl 2-[4-(2-{(aminocarbonothioyl)[4-(trifluoromethyl)benzyl]amino}ethyl)phenoxy]-2-methylpropanoate and 2-chlorophenacyl bromide.

$^1$H NMR (CD$_3$OD) δ 7.80 (d, 1H, J=7.5), 7.60 (d, 1H, J=8.0), 7.46–7.42 (m, 3H), 7.39–7.23 (m, 2H), 7.10 (d, 2H, J=8.4), 7.03 (s, 1H), 6.84 (d, 2H, J=8.3), 4.69 (s, 2H), 3.69 (t, 2H, J=7.0), 2.95 (t, 2H, J=7.1), 1.52 (s, 6H). MS: m/z 575 (M+1).

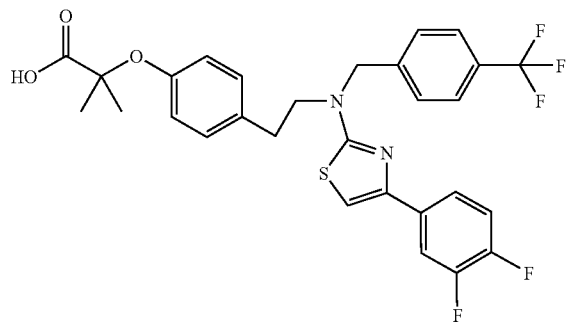

2-[4-(2-{[4-(3,4-Difluorophenyl)-1,3-thiazol-2-yl][4-(trifluoromethyl)benzyl]amino}ethyl)phenoxy]-2-methylpropanoic acid Similarly prepared from ethyl 2-[4-(2-{(aminocarbonothioyl)[4-(trifluoromethyl)benzyl]amino}ethyl)phenoxy]-2-methylpropanoate and 3,4-difluorophenacyl bromide.

$^1$H NMR (CD$_3$OD) δ 7.74–7.67 (m, 1H), 7.62 (d, 2H, J=8.1), 7.46 (d, 2H, J=8.0), 7.37–7.18 (m, 2H), 7.12 (d, 2H, J=8.4), 6.95 (s, 1H), 6.84 (d, 2H, J=8.4), 4.72 (s, 2H), 3.71 (t, 2H, J=7.2), 3.34 (t, 2H, J=7.2), 1.52 (s, 6H). MS: m/z 577 (M+1).

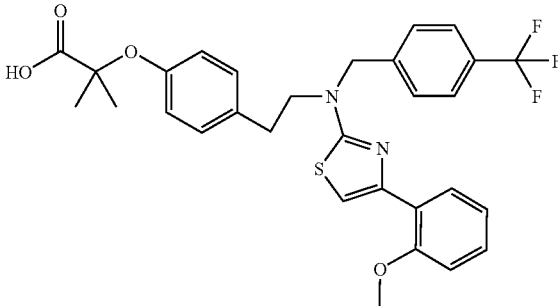

2-[4-(2-{[4-(2-Methoxyphenyl)-1,3-thiazol-2-yl][4-(trifluoromethyl)benzyl]amino}ethyl)phenoxy]-2-methylpropanoic acid Similarly prepared from ethyl 2-[4-(2-{(aminocarbonothioyl)[4-(trifluoromethyl)benzyl]amino}ethyl)phenoxy]-2-methylpropanoate and 2-methoxyphenacyl bromide.

$^1$H NMR (CD$_3$OD) δ 8.07 (d, 1H, J=7.8), 7.62 (d, 2H, J=8.0), 7.47 (d, 2H, J=8.0), 7.24 (t, 1H, J=7.4), 7.12 (d, 2H, J=8.4), 7.02–6.95 (m, 3H), 6.85 (d, 2H, J=8.4), 4.72 (s, 2H), 3.92 (s, 3H), 3.70 (t, 2H, J=7.1), 2.96 (t, 2H, J=7.1), 1.52 (s, 6H). MS: m/z 571 (M+1).

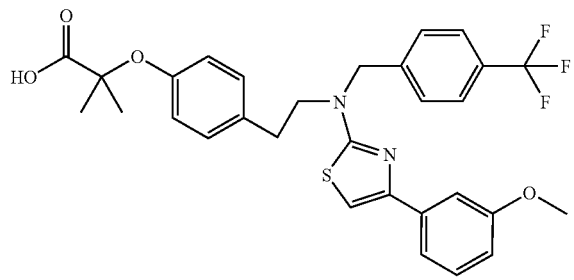

2-[4-(2-{[4-(3-methoxyphenyl)-1,3-thiazol-2-yl][4-(trifluoromethyl)benzyl]amino}ethyl)phenoxy]-2-methylpropanoic acid Similarly prepared from ethyl 2-[4-(2-{(aminocarbonothioyl)[4-(trifluoromethyl)benzyl]amino}ethyl)phenoxy]-2-methylpropanoate and 3-methoxyphenacyl bromide.

$^1$H NMR (CD$_3$OD) δ 7.63 (d, 2H, J=8.2), 7.48 (d, 2H, J=8.1), 7.43–7.40 (m, 2H), 7.28 (t, 1H, J=8.2), 7.15 (d, 2H, J=8.3), 6.86 (m, 3H), 4.74 (s, 2H), 3.83 (s, 3H), 3.73 (t, 2H, J=7.3), 2.97 (t, 2H, J=7.4), 1.55 (s, 6H). MS: m/z 571 (M+1).

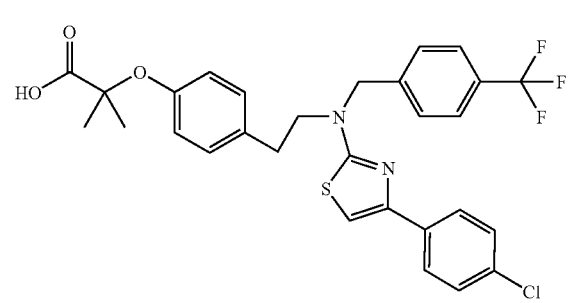

2-[4-(2-{[4-(4-Chlorophenyl)-1,3-thiazol-2-yl][4-(trifluoromethyl)benzyl]amino}ethyl)phenoxy]-2-methylpropanoic acid Similarly prepared from ethyl 2-[4-(2-{(aminocarbonothioyl)[4-(trifluoromethyl)benzyl]amino}ethyl)phenoxy]-2-methylpropanoate and 4-chlorophenacyl bromide.

¹H NMR (CD₃OD) δ 7.80 (d, 2H, J=8.4), 7.60 (d, 2H, J=8.1), 7.45 (d, 2H, J=8.0), 7.34 (d, 2H, J=8.4), 7.10 (d, 2H, J=8.4), 6.93 (s, 1H), 6.83 (d, 2H, J=8.4), 4.71 (s, 2H), 3.69 (t, 2H, J=7.2), 2.93 (t, 2H, J=7.3), 1.51 (s, 6H). MS: m/z 575 (M+1).

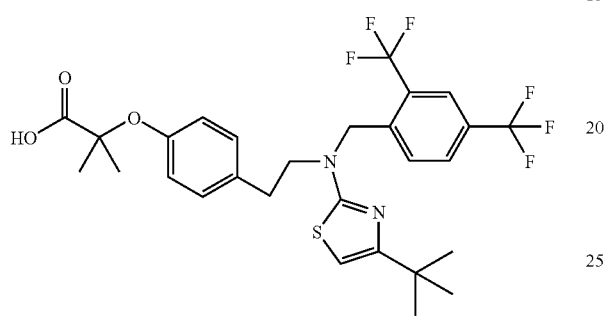

2-(4-{2-[[2,4-Bis(trifluoromethyl)benzyl](4-tert-butyl-1,3-thiazol-2-yl)amino]ethyl}phenoxy)-2-methylpropanoic acid Similarly prepared from ethyl 2-[4-(2-{(aminocarbonothioyl)[2,4-bis(trifluoromethyl)benzyl]amino}ethyl)phenoxy]-2-methylpropanoate and 1-bromopinacolone.

¹H NMR (CD₃OD) δ 7.96 (s, 1H), 7.85 (d, 1H, J=8.3), 7.59 (d, 1H, J=8.2), 7.13 (d, 2H, J=8.4), 6.86 (d, 2H, J=8.4), 6.23 (s, 1H), 4.82 (s, 2H), 3.72 (t, 2H, J=7.2), 3.00 (t, 2H, J=7.4), 1.56 (s, 6H), 1.22 (s, 9H). MS: m/z 589 (M+1).

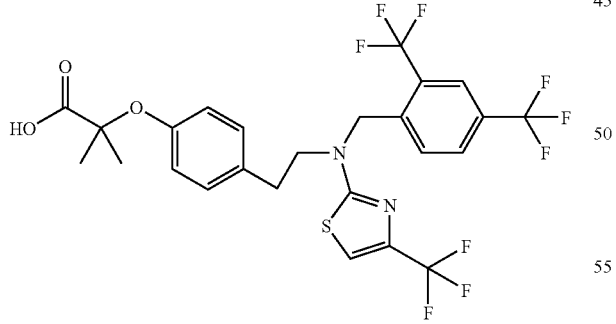

2-[4-(2-{[2,4-Bis(trifluoromethyl)benzyl][4-(trifluoromethyl)-1,3-thiazol-2-yl]amino}ethyl)phenoxy]-2-methylpropanoic acid Similarly prepared from ethyl 2-[4-(2-{(aminocarbonothioyl)[2,4-bis(trifluoromethyl)benzyl]amino}ethyl)phenoxy]-2-methylpropanoate and 3-bromo-1,1,1-trifluoroacetone.

¹H NMR (CD₃OD) δ 8.00 (s, 1H), 7.90 (d, 1H, J=8.1), 7.56 (d, 1H, J=8.3), 7.15 (s, 1H), 7.13 (d, 2H, J=8.3), 6.87 (d, 2H, J=8.4), 4.88 (s, 2H), 3.79 (t, 2H, J=7.0), 3.01 (t, 2H, J=7.0), 1.56 (s, 6H). MS: m/z 601 (M+1).

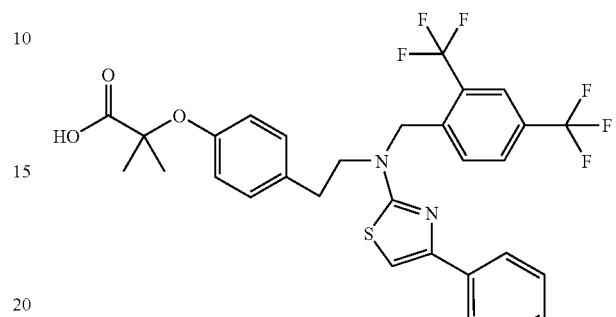

2-[4-(2-{[2,4-Bis(trifluoromethyl)benzyl][4-(2-chlorophenyl)-1,3-thiazol-2-yl]amino}ethyl)phenoxy]-2-methylpropanoic acid Similarly prepared from ethyl 2-[4-(2-{(aminocarbonothioyl)[2,4-bis(trifluoromethyl)benzyl]amino}ethyl)phenoxy]-2-methylpropanoate and 2-chlorophenacyl bromide.

¹H NMR (CD₃OD) δ 7.95 (s, 1H), 7.86 (d, 1H, J=8.0), 7.76 (d, 1H, J=8.1), 7.60 (d, 1H, J=8.2), 7.47 (d, 1H, J=8.0), 7.31–7.25 (m, 2H), 7.11 (m, 3H), 6.84 (d, 2H, J=8.3), 4.84 (s, 2H), 3.78 (t, 2H, J=7.0), 3.02 (t, 2H, J=7.0), 1.52 (s, 6H).

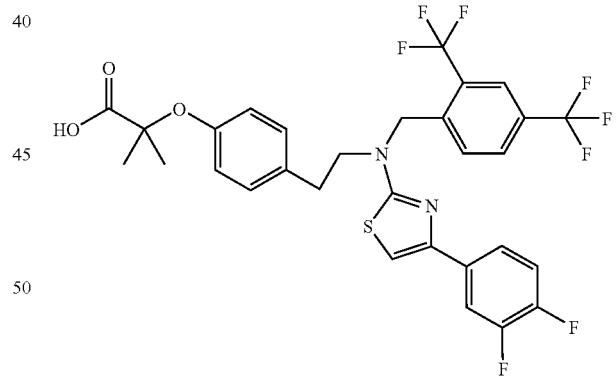

2-[4-(2-{[2,4-Bis(trifluoromethyl)benzyl][4-(3,4-difluorophenyl)-1,3-thiazol-2-yl]amino}ethyl)phenoxy]-2-methylpropanoic acid Similarly prepared from ethyl 2-[4-(2-{(aminocarbonothioyl)[2,4-bis(trifluoromethyl)benzyl]amino}ethyl)phenoxy]-2-methylpropanoate and 3,4-difluorophenacyl bromide.

¹H NMR (CD₃OD) δ 7.92 (s, 1H), 7.81 (d, 1H, J=8.0), 7.64–7.61 (m, 1H), 7.54 (d, 1H, J=8.3), 7.37–7.28 (m, 2H), 7.12 (d, 2H, J=8.4), 6.96 (s, 1H), 6.80 (d, 2H, J=8.3), 4.83 (s, 2H), 3.76 (t, 2H, J=7.2), 2.97 (t, 2H, J=7.0), 1.48 (s, 6H).

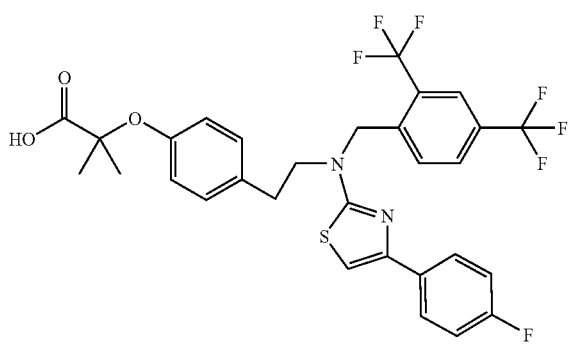

2-[4-(2-{[2,4-Bis(trifluoromethyl)benzyl][4-(4-fluorophenyl)-1,3-thiazol-2-yl]amino}ethyl)phenoxy]-2-methylpropanoic acid Similarly prepared from ethyl 2-[4-(2-{(aminocarbonothioyl)[2,4-bis(trifluoromethyl)benzyl]amino}ethyl)phenoxy]-2-methylpropanoate and 4-fluorophenacyl bromide.

$^1$H NMR (CD$_3$OD) δ 7.96 (s, 1H), 7.86–7.76 (m, 4H), 7.59 (d, 2H, J=8.2), 7.13 (d, 2H, J=8.4), 7.05 (t, 2H, J=8.7), 6.91 (s, 1H), 6.84 (d, 2H, J=8.4), 4.87 (s, 2H), 3.78 (t, 2H, J=7.0), 3.01 (t, 2H, J=7.1), 1.52 (s, 6H).

The following 9 compounds were prepared using similar procedures as those described above.

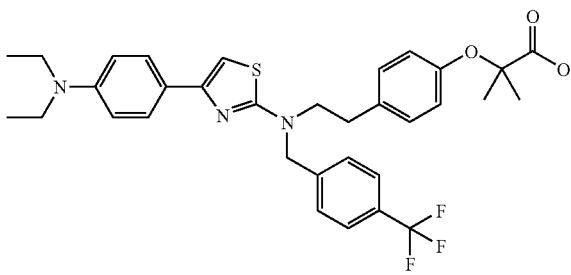

2-[4-(2-{{4-[4-(diethylamino)phenyl]-1,3-thiazol-2-yl}[4-(trifluoromethyl)benzyl]amino}ethyl)phenoxy]-2-methylpropanoic acid

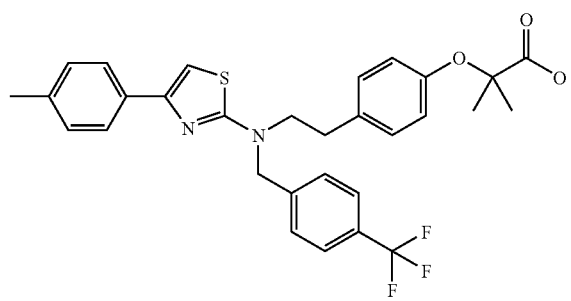

2-methyl-2-[4-(2-{[4-(4-methylphenyl)-1,3-thiazol-2-yl][4-(trifluoromethyl)benzyl]amino}ethyl)phenoxy]propanoic acid

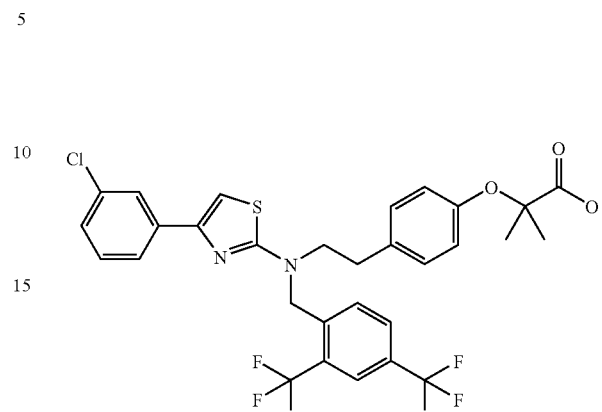

2-[4-(2-{[2,4-bis(trifluoromethyl)benzyl][4-(3-chlorophenyl)-1,3-thiazol-2-yl]amino}ethyl)phenoxy]-2-methylpropanoic acid

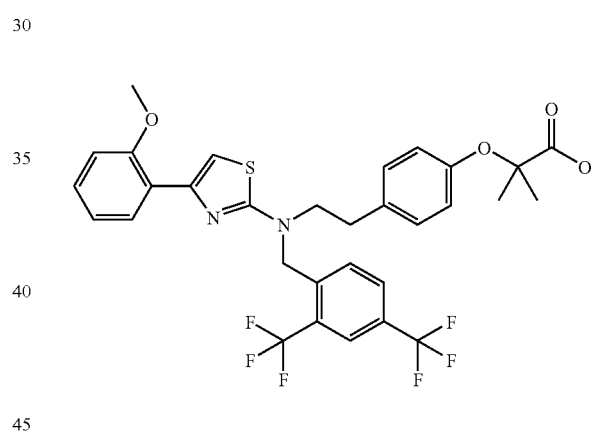

2-[4-(2-{[2,4-bis(trifluoromethyl)benzyl][4-(2-methoxyphenyl)-1,3-thiazol-2-yl]amino}ethyl)phenoxy]-2-methylpropanoic acid

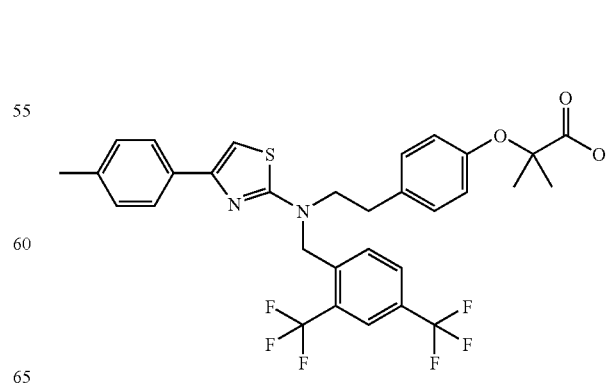

201

2-[4-(2-{[2,4-bis(trifluoromethyl)benzyl][4-(4-methylphenyl)-1,3-thiazol-2-yl]amino}ethyl)phenoxy]-2-methylpropanoic acid

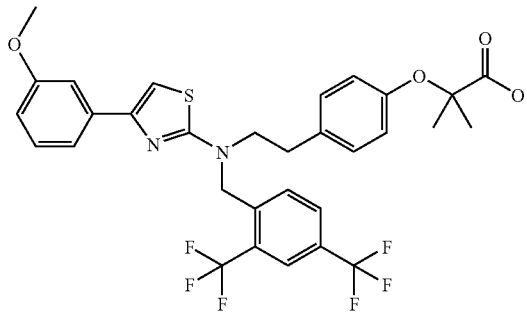

2-[4-(2-{[2,4-bis(trifluoromethyl)benzyl][4-(3-methoxyphenyl)-1,3-thiazol-2-yl]amino}ethyl)phenoxy]-2-methylpropanoic acid

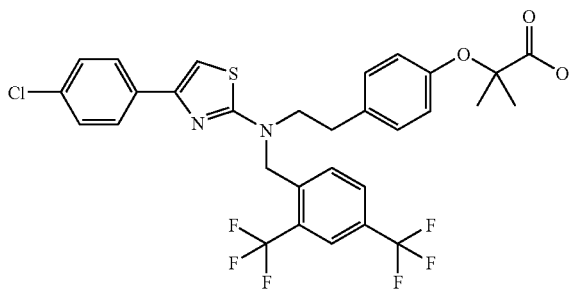

2-[4-(2-{[2,4-bis(trifluoromethyl)benzyl][4-(4-chlorophenyl)-1,3-thiazol-2-yl]amino}ethyl)phenoxy]-2-methylpropanoic acid

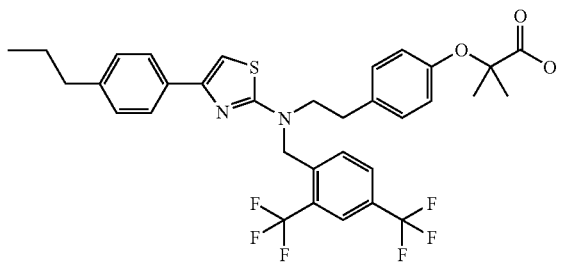

202

2-[4-(2-{[2,4-bis(trifluoromethyl)benzyl][4-(4-propylphenyl)-1,3-thiazol-2-yl]amino}ethyl)phenoxy]-2-methylpropanoic acid

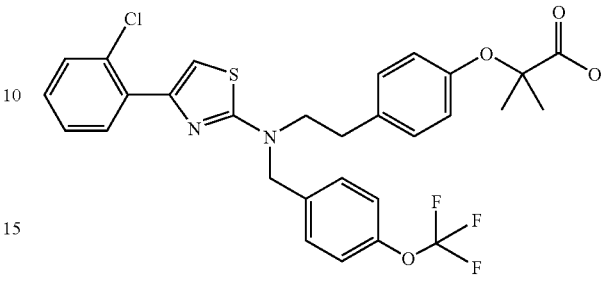

2-[4-(2-{[4-(2-chlorophenyl)-1,3-thiazol-2-yl][4-(trifluoromethoxy)benzyl]amino}ethyl)phenoxy]-2-methylpropanoic acid Binding Assay:

Compounds were tested for their ability to bind to hPPAR gamma, hPPARalpha or PPARdelta using a Scintillation Proximity Assay (SPA). The PPAR ligand-binding domain (LBD) was expressed in *E. coli* as polyHis tagged fusion proteins and purified. The LBD was then labeled with biotin and immobilized on streptavidin-modified scintillation proximity beads. The beads were then incubated with a constant amount of the appropriate radioligand (3H-BRL 49653 for PPARgamma, radiolabelled 2-(4-(2-(2,3-Ditritio-1-heptyl-3-(2,4-difluorophenyl)ureido)ethyl)phenoxy)-2-methylbutanoic acid for hPPAR alpha (see WO 00/08002) and labelled GW 2433 (see Brown, P. J et al. *Chem. Biol.*, 4, 909–918 (1997) for the structure and synthesis of this ligand) for PPAR delta) and variable concentrations of test compound, and after equilibration the radioactivity bound to the beads was measured by a scintillation counter. The amount of nonspecific binding, as assessed by control wells containing 50 μM of the corresponding unlabeled ligand, was subtracted from each data point. For each compound tested, plots of ligand concentration vs. CPM of radioligand bound were constructed and apparent KI values were estimated from nonlinear least squares fit of the data assuming simple competitive binding. The details of this assay have been reported elsewhere (see, Blanchard, S. G. et. al. Development of a Scintillation Proximity Assay for Peroxisome Proliferator-Activated Receptor gamma Ligand Binding Domain. *Anal. Biochem.*, 257, 112–119 (1998)).

Transfection Assay:

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., An antidiabetic thiazolidinedione is a high affinity ligand for peroxisome proliferator-activated receptor gamma (PPARgamma), *J. Biol. Chem.*, 270, 12953–6 (1995). The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and beta-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and beta-galactosidase activity. Alkaline phosphatase activity was corrected for transfection efficiency using the beta-galactosidase activity as an internal standard (see, for example, Kliewer, S. A., et. al. Cell 83, 813–819 (1995)). Rosiglitazone (BRL 49653) was used as a positive control in the hPPAR gamma assay. The positive control for PPAR delta assays was 2-{2-methyl-4-[({4-methyl-2-(trifluoromethyl)phenyl]-1,3-thiazol-5-yl}methyl)sulfanyl]phenoxy}acetic acid.

The positive control in the hPPARalpha transfection assay was 2-[4-(2-(3-(4-fluorophenyl)-1-heptylureido)ethyl)-phenoxy]-2-methylpropionic acid, which can be prepared as described in Brown, Peter J., et. al. *Synthesis* Issue 7, 778–782 (1997), or patent publication WO 9736579.

All of the above exemplified compounds of this invention are agonists of at least one hPPAR subtype as defined above on pages 5 and 6.

What is claimed is:

1. A compound of formula (1) or a pharmaceutically acceptable salt, acid isostere, or hydrolyzable ester thereof;

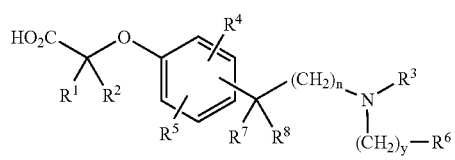

(1)

wherein
  $R^1$ and $R^2$ are independently hydrogen, F, $CF_3$, $C_{1-3}$alkyl, or $R^1$ and $R^2$ may together with the carbon atom to which they are attached form a 3 to 6-membered cycloalkyl ring;
  $R^4$ and $R^5$ are independently hydrogen, $C_{1-6}$alkyl, perfluoro$C_{1-6}$alkyl, $-OC_{1-3}$alkyl, perfluoroO$C_{1-6}$alkyl, halogen, or cyano;
  $R^7$ and $R^8$ are independently H, F, $CF_3$, or $C_{1-3}$alkyl, and the carbon to which $R^7$ and $R^8$ are bonded is attached to the benzene ring either meta or para to the depicted oxygen;
  n is 1 or 2;
  y is 1 or 2;
  $R^6$ is phenyl or a 5- or 6-membered heteroaryl group, where the phenyl or heteroaryl group is optionally substituted with 1, 2, or 3 moieties selected from the group consisting of $C_{1-6}$alkyl, halogen, perfluoro$C_{1-3}$alkyl, O$C_{1-3}$alkyl, perfluoroO$C_{1-3}$alkyl, S$C_{1-3}$alkyl, $SO_2C_{1-3}$alkyl, $SO_2C_{1-3}$perfluoroalkyl, SO$C_{1-3}$perfluoroalkyl, SO$C_{1-3}$alkyl, perfluoroS$C_{1-3}$alkyl, CN, and phenyl optionally substituted with one or two groups selected from halogen, $C_{1-3}$alkyl, O$C_{1-3}$alkyl, acetyl, CN, and perfluoro$C_{1-3}$alkyl, or
  $R^6$ is phenyl or a 5- or 6-membered heteroaryl group, where the phenyl or heteroaryl group is optionally substituted with 1, 2, or 3, 5— or 6—membered heteroaryl moieties optionally substituted with one group selected from $C_{1-3}$alkyl, $C_{3-6}$cycloalkyl, perfluoro$C_{1-3}$alkyl, NH$C_{1-3}$alkyl, and $N(C_{1-3}alkyl)_2$;
  $R^3$ is a 5- or 6-membered heteroaryl group optionally substituted by 1 or 2 moieties selected from the group consisting of halogen, $C_{1-6}$alkyl, perfluoro$C_{1-6}$alkyl, O$C_{1-3}$alkyl, and phenyl optionally substituted with one or two moieties selected from $C_{1-3}$alkyl, halogen, O$C_{1-3}$ alkyl, acetyl, CN, Operfluoro$C_{1-3}$alkyl, and perfluoro$C_{1-3}$alkyl, or
  $R^3$ is a 5— or 6—membered heteroaryl group optionally substituted by 1 or 2 moieties selected from the group consisting of
    5- or 6-membered heteroaryl optionally substituted with one or two moieties selected from $C_{1-3}$alkyl, halogen, O$C_{1-3}$alkyl, acetyl, CN, and perfluoro$C_{1-3}$ alkyl,
    hydroxy$C_{1-3}$alkyl, $C_{3-7}$cycloalkyl, cyano$C_{1-3}$alkyl, acetyl, nitro, $N(CH_3)_2$, $NHR^{21}$, piperidin-4-yl substituted at nitrogen with a moiety selected from $C_{1-5}$alkyl, benzyl, acetyl, $C(O)OC_{1-5}$alkyl, $C(O)$Obenzyl, $C(O)NH_2$, $C(O)NHC_{1-3}$alkyl, and $SO_2CH_3$,
    4-(4-fluorophenyl)piperazin-1-ylmethyl, morpholin-4-ylmethyl, tetrahydrofuran-3-yl, or two adjacent carbon atoms in the heteroaryl could be substituted to form a benzene ring thus forming a fused bicycle and wherein the resulting benzene ring is optionally substituted with one or two moieties selected from $C_{1-3}$alkyl, halogen, and perfluoro$C_{1-3}$alkyl; and
  $R^{21}$ is $C_{1-3}$alkyl, $-C(O)C_{1-3}$alkyl, $-C(O)OC_{1-3}$alkyl, or $SO_2CH_3$.

2. A compound according to claim 1 wherein $R^1$ and $R^2$ are independently hydrogen or $C_{1-3}$alkyl.

3. A compound according to claim 1 wherein $R^1$ and $R^2$ are both hydrogen or both methyl.

4. A compound according claim 2 wherein $R^4$ and $R^5$ are independently hydrogen, $C_{1-3}$alkyl, perfluoro$C_{1-3}$alkyl, $-OC_{1-3}$alkyl, perfluoroO$C_{1-3}$alkyl, halogen, or cyano.

5. A compound according to claim 4 wherein at least one of $R^4$ and $R^5$ are hydrogen.

6. A compound according to claim 5 wherein one of $R^4$ and $R^5$ is hydrogen and the other is not.

7. A compound according to claim 6 wherein the one of $R^4$ and $R^5$ that is not hydrogen is ortho to the depicted oxygen.

8. A compound according claim 5 wherein $R^7$ and $R^8$ are independently hydrogen or methyl.

9. A compound according to claim 5 wherein $R^7$ and $R^8$ are both hydrogen or both methyl.

10. A compound according to claim 9 wherein y is 1.

11. A compound according to claim 10 wherein $R^6$ is phenyl optionally substituted with 1 or 2 moieties selected from the group consisting of F, Cl, $CF_3$, $OCF_3$, and 5-membered nitrogen-containing heteroaryl optionally substituted with one group selected from $C_{1-3}$alkyl, $C_{3-6}$cycloalkyl, perfluoro$C_{1-3}$alkyl, NH$C_{1-3}$alkyl, and $N(C_{1-3}alkyl)_2$.

12. A compound according to claim 11 wherein $R^3$ is selected from the group consisting of pyrimidine, pyridine, pyridazine, pyrazine, 1,2,4-oxadiazole, oxazole, and thiazole; and $R^3$ is optionally substituted by a moiety selected from the group consisting of halogen, $C_{1-6}$alkyl, perfluoro$C_{1-6}$alkyl, phenyl optionally substituted with one or two moieties selected from $C_{1-3}$alkyl, halogen, O$C_{1-3}$alkyl, acetyl, CN, and perfluoro$C_{1-3}$alkyl, 5- or 6-membered heteroaryl optionally substituted with one or two moieties selected from $C_{1-3}$alkyl, halogen, $OC_{1-3}$alkyl, acetyl, CN, and perfluoro$C_{1-3}$alkyl,
hydroxy$C_{1-3}$alkyl, and $C_{3-7}$cycloalkyl, or $R^3$ may be substituted to form a fused bicycle selected from benzoxazole and benzothiazole.

13. A compound according to claim 12 wherein $R^3$ is a pyrimidine or a pyridine; and is optionally substituted by a moiety selected from the group consisting of halogen, $C_{1-6}$alkyl, perfluoro$C_{1-6}$alkyl, 5— or 6—-membered heteroaryl, hydroxy$C_{1-3}$alkyl, $C_{3-7}$cycloalkyl, and phenyl optionally substituted with one or two moieties selected from $C_{1-3}$alkyl, halogen, $OC_{1-3}$alkyl, acetyl, CN, and perfluoro$C_{1-3}$alkyl.

14. A compound according to claim 1 selected from the group consisting of:
- 2-(4-{2-[[2,4-Bis(trifluoromethyl)benzyl](5-ethylpyrimidin-2-yl)amino]ethyl}phenoxy)-2-methylpropanoic acid;
- 2-[4-(2-{(5-Ethylpyrimidin-2-yl)[4-(trifluoromethoxy)benzyl]amino}ethyl)phenoxy]-2-methylpropanoic acid;
- 2-[4-(2-{(5-Ethylpyrimidin-2-yl)[4-(trifluoromethyl)benzyl]amino}ethyl)phenoxy]-2-methylpropanoic acid;
- 2-[4-(2-{(5-Ethylpyrimidin-2-yl)[4-(trifluoromethyl)benzyl]amino}ethyl)-2-methoxyphenoxy]-2-methylpropanoic acid;
- 2-[2-Cyano-4-(2-{(5-ethylpyrimidin-2-yl)[4-(trifluoromethyl)benzyl]amino}ethyl)phenoxy]-2-methylpropanoic acid;
- 2-[4-(2-{(5-Ethylpyrimidin-2-yl)[3-(trifluoromethoxy)benzyl]amino}ethyl)phenoxy]-2-methylpropanoic acid;
- 2-[4-(2-{(5-Ethylpyrimidin-2-yl)[4-fluoro-2-(trifluoromethyl)benzyl]amino}ethyl)phenoxy]-2-methylpropanoic acid;
- 2-[4-{2-[(4-chlorobenzyl)(5-ethylpyrimidin-2-yl)amino]ethyl}phenoxy]-2-methylpropanoic acid;
- 2-[4-(2-{(5-Ethylpyrimidin-2-yl)[3-(trfluoromethyl)benzyl]amino}ethyl)phenoxy]-2-methylpropanoic acid;
- 2-[4-{2-[(5-Ethylpyrimidin-2-yl)[4-fluorobenzyl]amino]ethyl}phenoxy]-2-methylpropanoic acid;
- [4-(2-{(5-Ethylpyrimidin-2-yl)[4-(trifluoromethyl)benzyl]amino}ethyl)phenoxy]acetic acid;
- 2-[4-(2-{(5-Ethylpyrimidin-2-yl)[4-(5-isopropyl-1,2,4-oxadiazol-3-yl)benzyl]amino}ethyl)phenoxy]-2-methylpropanoic acid;
- [4-(2-{(5-Ethylpyrimidin-2-yl)[4-(trifluoromethoxy)benzyl]amino}ethyl)phenoxy]acetic acid;
- [4-(2-{(5-Ethylpyrimidin-2-yl)[4-(trifluoromethoxy)benzyl]amino}ethyl)-2-propylphenoxy]acetic acid;
- 5-Ethyl-N-{2-[3-propyl-4-(2H-tetraazol-5-ylmethoxy)phenyl]ethyl}-N-[4-(trifluoromethoxy)benzyl]pyrimidin-2-amine;
- 2-[4-(2(5-Ethylpyrimidin-2-yl)[4-(trifluoromethyl)benzyl]amino}-1,1-dimethylethyl)phenoxy]-2-methylpropanoic acid;
- 2-[4-(2-{(5-ethylpyrimidin-2-yl)[4-(trifluoromethoxy)benzyl]amino}-1,1-dimethylethyl)phenoxy]-2-methylpropanoic acid;
- [4-(2-{(5-ethylpyrimidin-2-yl)[4-(trifluoromethoxy)benzyl]amino}-1,1-dimethylethyl)phenoxy]acetic acid;
- 5-ethyl-N-{2-methyl-2-[4-(2H-tetraazol-5-ylmethoxy)phenyl]propyl}-N-[4-(trifluoromethoxy)benzyl]pyrimidin-2-amine;
- [2-Chloro-4-(2-{(5-ethylpyrimidin-2-yl)[4-(trifluoromethoxy)benzyl]amino}1,1-dimethylethyl)phenoxy]acetic acid;
- 2-[2-Chloro-4-(2-{(5-ethylpyrimidin-2-yl)[4-(trifluoromethoxy)benzyl]amino}1,1-dimethylethyl)phenoxy]-2-methylpropanoic acid;
- 2-[4-(2-{(5-Ethylpyrimidin-2-yl)[4-(trifluoromethoxy)benzyl]amino}1,1-dimethylethyl)-2-propylphenoxy]-2-methylpropanoic acid;
- [4-(2-{(5-Ethylpyrimidin-2-yl)[4-(trifluoromethoxy)benzyl]amino}-1,1-dimethylethyl)-2-propylphenoxy]acetic acid;
- 2-[4-(2-{(5-Ethylpyrimidin-2-yl)[4-(trifluoromethoxy)benzyl]amino}ethyl)-2-methylphenoxy]-2-methylpropanoic acid;
- 2-[2-Chloro-4-(2-{(5-Ethylpyrimidin-2-yl)[4-(trifluoromethoxy)benzyl]amino}ethyl)phenoxy]-2-methylpropanoic acid;
- 2-[4-(2-{(5-Ethylpyrimidin-2-yl)[4-(trifluoromethoxy)benzyl]amino}ethyl)-2-(trifluoromethyl)phenoxy]-2-methylpropanoic acid;
- [4-(2-{(5-Ethylpyrimidin-2-yl)[4-(trifluoromethoxy)benzyl]amino}ethyl)-2-methylphenoxy]acetic acid;
- [4-(2-{(5-Ethylpyrimidin-2-yl)[4-(trifluoromethyl)benzyl]amino}ethyl)-2-fluorophenoxy]acetic acid;
- [2-Chloro-4-(2-{(5-ethylpyrimidin-2-yl)[4-(trifluoromethoxy)benzyl]amino}ethyl)phenoxy]acetic acid;
- 2-[4-(2-{(5-Ethylpyridin-2-yl)[4-(trifluoromethyl)benzy]amino}ethyl)phenoxy]-2-methylpropanoic acid;
- 2-[4-(2-{(5-Ethylpyridin-2-yl)[4-(trifluoromethoxy)benzyl]amino}ethyl)phenoxy]-2-methylpropanoic acid;
- 2-[4-(2-{(5-Isopropylpyrdin-2-yl)[4-(trifluoromethyl)benzyl]amino}ethyl)phenoxy]-2-methylpropanoic acid;
- 2-[4-(2-{(5-Isopropylpyridin-2-yl)[4-(trifluoromethoxy)benzyl]amino}ethyl)phenoxy]-2-methylpropanoic acid;
- 2-Methyl-2-[4-(2-{[5-(2,2,2-trifluoroethyl)pyridin-2-yl][4-(trifluoromethoxy)benzyl]amino}ethyl)phenoxy]propanoic acid;
- 2-[4-(2-{[5-(Hydroxymethyl)pyridin-2-yl][4-(trifluoromethoxy)benzyl]amino}ethyl)phenoxy]-2-methylpropanoic acid;
- 2-[4-(3-{(5-Isopropylpyridin-2-yl)[4-(trifluoromethoxy)benzyl]amino}propyl)phenoxy]-2-methylpropanoic acid;
- 2-[4-(2-{[4-(2-Chlorophenyl)-1,3-thiazol-2-yl][4-(trifluoromethyl)benzyl]amino}ethyl)phenoxy]-2-methylpropanoic acid; and
- 2-[4-(2-{[4-(3,4-Difluorophenyl)-1,3-thiazol-2-yl][4-(trifluoromethyl)benzyl]amino}ethyl)phenoxy]-2-methylpropanoic acid;

or a pharmaceutically acceptable salt, acid isostere, or hydrolyzable ester thereof.

15. A compound according to claim 1 selected from the group consisting of: 2-[4-(2-{(5-ethylpyrimidin-2-yl)[4-(trifluoromethoxy)benzyl]amino}-1,1-dimethylethyl)phenoxy]-2-methylpropanoic acid; 2-[4-(2-{[4-(2-Chlorophenyl)-1,3-thiazol-2-yl][4-(trifluoromethyl)benzyl]amino}ethyl)phenoxy]-2-methylpropanoic acid; and 2-[4-(2-{[4-(3,4-Difluorophenyl)-1,3-thiazol-2-yl][4-(trifluoromethyl)benzyl]amino}ethyl)phenoxy]-2-methylpropanoic acid; or a pharmaceutically acceptable salt, acid isostere, or hydrolyzable ester thereof.

16. A compound of according to claim 1 wherein $R^1$ and $R_2$ are both hydrogen or both methyl; at least one of $R^4$ and $R^5$ are hydrogen; $R^7$ and $R^8$ are both hydrogen or both methyl; y is 1; $R^6$ is phenyl optionally substituted with 1 or 2 moieties selected from the group consisting of F, Cl, $CF_3$, $OCF_3$, 5-membered nitrogen-containing heteroaryl optionally substituted with one group selected from $C_{1-3}$alkyl, $C_{3-6}$cycloalkyl, perfluoro$C_{1-3}$alkyl, NH$C_{1-3}$alkyl, and N($C_{1-3}$ alkyl)$_2$; and $R^3$ is a thiazole, a pyrimidine, or a pyridine and is optionally substituted by a moiety selected from the group consisting of halogen, $C_{1-6}$alkyl, perfluoro$C_{1-6}$alkyl, 5—or6—membered heteroaryl, hydroxy$C_{1-3}$alkyl, $C_{3-7}$cycloalkyl, and phenyl optionally substituted with one or two moieties selected from $C_{1-3}$alkyl, halogen, O$C_{1-3}$alkyl, acetyl, CN, and perfluoro$C_{1-3}$alkyl.

17. A compound according to claim 1 wherein the compound is a hPPAR agonist.

18. A pharmaceutical composition comprising a compound according to claim 1.

* * * * *

UNITED STATES PATENT AND TRADEMARK OFFICE
CERTIFICATE OF CORRECTION

PATENT NO.      : 7,319,104 B2
APPLICATION NO. : 10/505333
DATED           : January 15, 2008
INVENTOR(S)     : Cadilla et al.

It is certified that error appears in the above-identified patent and that said Letters Patent is hereby corrected as shown below:

In the Claims:

Claim 4 (Column 204, Line 36) should read as follows:

-- 4. A compound according to claim 2 wherein $R^4$ and $R^5$ are --

Claim 8 (Column 204, Line 46) should read as follows:

-- 8. A compound according to claim 5 wherein $R^7$ and $R^8$ are --

Claim 14 (Column 205, Lines 56-58) should read as follows:

-- 2-[4-(2-{(5-Ethylpyrimidin-2-yl)[4-(trifluoromethyl)benzyl]amino-1, 1-dimethylethyl)phenoxy]-2-methylpropanoic acid; --

Claim 14 (Column 206, Lines 1-9) should read as follows:

-- [2-Chloro-4-(2-{(5-ethylpyrimidin-2-yl)[4-(trifluoromethoxy)benzyl]amino} -1, 1-dimethylethyl)phenoxy] acetic acid;
2-[2-Chloro-4-(2-{(5-ethylpyrimidin-2-yl)[4-(trifluoromethoxy)benzyl] amino}-1,1-dimethylethyl)phenoxy]-2-methylpropanoic acid;
2-[4-(2-{(5-Ethylpyrimidin-2-yl)[4-(trifluoromethoxy) benzyl]amino}-1, 1-dimethylethyl)-2-propylphenoxy]-2-methylpropanoic acid; --

UNITED STATES PATENT AND TRADEMARK OFFICE
CERTIFICATE OF CORRECTION

PATENT NO. : 7,319,104 B2
APPLICATION NO. : 10/505333
DATED : January 15, 2008
INVENTOR(S) : Cadilla et al.

It is certified that error appears in the above-identified patent and that said Letters Patent is hereby corrected as shown below:

Claim 16 (Column 206, Line 65) should read as follows:

-- 16. A compound according to claim 1 wherein $R^1$ and --

Signed and Sealed this

Twenty-second Day of July, 2008

JON W. DUDAS
*Director of the United States Patent and Trademark Office*